(12) United States Patent
Nakashima et al.

(10) Patent No.: US 8,252,781 B2
(45) Date of Patent: Aug. 28, 2012

(54) 1,2-DIAZETIDIN-3-ONE DERIVATIVES AND DRUGS CONTAINING SAME

(75) Inventors: Hisashi Nakashima, Higashimurayama (JP); Takaaki Araki, Higashimurayama (JP); Takahisa Ogamino, Higashimurayama (JP); Noriaki Gomi, Higashimurayama (JP); Yasushi Kaneko, Higashimurayama (JP); Kazutoyo Abe, Higashimurayama (JP); Tadaaki Ohgiya, Higashimurayama (JP)

(73) Assignee: Kowa Company, Ltd., Nagoya-shi (JP)

( * ) Notice: Subject to any disclaimer, the term of this patent is extended or adjusted under 35 U.S.C. 154(b) by 398 days.

(21) Appl. No.: 12/607,650

(22) Filed: Oct. 28, 2009

(65) Prior Publication Data

US 2010/0144694 A1 Jun. 10, 2010

Related U.S. Application Data

(60) Provisional application No. 61/109,332, filed on Oct. 29, 2008.

(51) Int. Cl.
*C07D 229/00* (2006.01)
*C07D 409/04* (2006.01)
*C07D 405/12* (2006.01)
*C07D 401/04* (2006.01)
*C07D 401/06* (2006.01)
*C07D 401/12* (2006.01)
*C07D 403/06* (2006.01)
*A61K 31/397* (2006.01)
*A61K 31/4427* (2006.01)
*A61K 31/498* (2006.01)
*A61P 9/12* (2006.01)
*A61P 3/10* (2006.01)
*A61P 3/04* (2006.01)
*A61P 3/06* (2006.01)

(52) U.S. Cl. ............ 514/210.02; 514/210.15; 540/202; 564/151; 564/310

(58) Field of Classification Search .................. 540/202; 514/210.02, 210.15
See application file for complete search history.

(56) References Cited

U.S. PATENT DOCUMENTS

| | | | |
|---|---|---|---|
| 4,826,971 A | 5/1989 | Skotnicki | |
| 2010/0075943 A1* | 3/2010 | Nakashima et al. | 514/210.02 |

FOREIGN PATENT DOCUMENTS

| | | |
|---|---|---|
| JP | 60-239420 A | 11/1985 |
| WO | 2004/037251 A1 | 5/2004 |
| WO | 2004/112779 A1 | 12/2004 |
| WO | 2005/046682 A1 | 5/2005 |
| WO | 2005/046685 A1 | 5/2005 |
| WO | 2005/108368 A1 | 11/2005 |
| WO | 2005/110992 A1 | 11/2005 |
| WO | 2006/000371 A2 | 1/2006 |
| WO | 2006/010546 A2 | 2/2006 |
| WO | 2006/040329 A1 | 4/2006 |
| WO | 2006/049952 A1 | 5/2006 |
| WO | 2006/051662 A1 | 5/2006 |
| WO | 2006/053024 A2 | 5/2006 |
| WO | 2006/055752 A2 | 5/2006 |
| WO | 2006/132197 A1 | 12/2006 |
| WO | 2006/132436 A1 | 12/2006 |
| WO | 2006/134467 A1 | 12/2006 |
| WO | 2007/003521 A2 | 1/2007 |
| WO | 2007/007688 A1 | 1/2007 |
| WO | 2007/029021 A1 | 3/2007 |
| WO | 2010/050191 A1 | 5/2010 |

OTHER PUBLICATIONS

Taylor, J. Am. Chem. Soc. 1981, 103, 7659-7660.*
E. Fahr et al.; "Die H-NMR-Spektroskopische Untersuchung Der N-Inversion in 1.2-Diazetidinonen", Tetrahedron Letters, No. 41, pp. 3605-3608, 1970, Pergamon Press. Printed in Great Britain.
Morioka, H. et al, "Differentiation of Friend Leukemia Cells Induced by b-. g-, d- and Aza-b-lactam, and Thiaziadine Compounds," Agric. Biol. Chem. vol. 50 (7), pp. 1757-1764, 1986.
Morton, N. et al, "Improved Lipid and Lipoprotein Profile, Hepatic Insulin Sensitivity, and Glucose Tolerance in 11b-Hydroxysteriod Dehydrogenase Type 1 Null Mice," The Journal of Biological Chemistry, vol. 276, No. 44, Nov. 2, 2001, pp. 41293-41300.
Masuzaki, H., et al, "Transgenic Amplification of Glucocorticoid Action in Adipose Tissue Causes High Blood Pressure in Mice," The Journal of Clinical Investigation, vol. 112, No. 1, Jul. 2003, pp. 83-90.
Bujalska, I.J., et al, "Expression Profiling of 11b-Hydroxysteriod Dehydrogenase Type-1 and Glucocorticoid-Target Genes in Subcutaneous and Omental Human Preadipocytes," Journal of Molecular Endocrinology, vol. 37, 2006, pp. 327-340.

(Continued)

*Primary Examiner* — Mark Berch
(74) *Attorney, Agent, or Firm* — Westerman, Hattori, Daniels & Adrian, LLP

(57) ABSTRACT

[Object]
It is to provide a novel compound useful for preventing and/or treating diseases that involves 11β-hydroxysteroid dehydrogenase 1 (in particular diabetes, insulin resistance, diabetes complication, obesity, dyslipidemia, hypertension, fatty liver, or metabolic syndrome).
[Means to Solve the Object]
A 1,2-diazetidin-3-one derivative represented by the following general formula (1) or salt thereof, or their solvate.

(1)

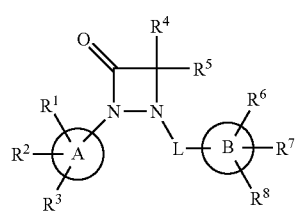

4 Claims, No Drawings

OTHER PUBLICATIONS

Kotelevtsev, Y., et al, 11Beta-hydroxysteriod Dehydrogenase Type 1 Knockout Mice Show Attenuated Glucocorticoid-Inducible Response and Resist Hyperglycemia on Obesity or Stress, 1997, pp. 14924-14929, PNAS, vol. 94.

Lindsay, R., "Subcutaneous Adipose 11b-Hydroxysteriod Dehydrogenase Type 1 Activity and Messenger Ribonecluic Acid Levels are Associated With Adiposity and Insulinema in Pima Indians and Caucasians," The Journal of Clinical Endocrinology and Metabolism, Jun. 2003, pp. 2738-2744, vol. 88.

Masuzaki, H., et al, "Molecular Condition of Metabolic Syndrome," Clinician 2004, pp. 1782-1787, vol. 30 No. 9.

Masuzaki, H., et al, "A Transgenic Model of Visceral Obesity and the Metabolic Syndrome," Science Magazine, Dec. 7, 2001, pp. 2166-2170, vol. 294.

Tomlinson, J.W., et al, "11b-Hydroxysteriod Dehydrogenase Type 1: A Tissue-Specific Regulator of Glucocorticoid Response," Endocrine Reviews, Oct. 2004, pp. 831-866, vol. 25 (5).

* cited by examiner ically, in cells, enzyme 11β-HSD2 is also present that converts an
1,2-DIAZETIDIN-3-ONE DERIVATIVES AND DRUGS CONTAINING SAME

TECHNICAL FIELD

The present invention relates to a novel 1,2-diazetidin-3-one derivative having an 11β-hydroxysteroid dehydrogenase 1-inhibitory activity and a medicine comprising the same.

BACKGROUND ART

11β-hydroxysteroid dehydrogenase (hereinafter, abbreviated as 11β-HSD)1 is an enzyme that converts in cells an inactive form of glucocorticoid (cortisone or 11-dehydrocorticosterone) into an active form of glucocorticoid (cortisol or 11β-corticosterone), and is found to be expressed on the liver, central nerves and the like as well as subcutaneous fat and visceral fat (non-patent documents 1 and 2). Meanwhile, in cells, enzyme 11β-HSD2 is also present that converts an active form of glucocorticoid into an inactivated form. An active form of glucocorticoid is converted in cells from inactive precursor by the action of 11β-HSD1, thereby exercises its effect. Glucocorticoid has been reported to be involved in adipocyte differentiation and to inhibit glycolipid metabolism that is helped by insulin (non-patent document 3). 11β-HSD1 activity and expression level in adipose tissues positively correlate with body-mass index (BMI) or insulin resistance (non-patent document 4). Further, it is reported that a transgenic mouse over-expressing 11β-HSD1 specifically in adipose tissues exhibits a phenotype comprising a combination of major factors of metabolic syndrome, such as visceral fat accumulation, insulin resistance, dyslipidemia, hypertension and fatty liver (non-patent documents 5 and 6). By contrast, it is reported that, in an 11β-HSD1 knockout mouse, an inactive form cannot be converted to an active form and as a result, the induction of the group of gluconeogenic enzymes attributable to the burden of high-fat food does not occur in the liver, which acts suppressively on hyperglycaemia due to obesity (non-patent document 7). It is also reported that decreased blood triglyceride, elevated HDL cholesterol, and improved insulin resistance were observed (non-patent document 8). From these findings, active form of glucocorticoid produced excessively by 11β-HSD1 is considered to cause the onset of a metabolic disease such as diabetes, insulin resistance, diabetes complication, obesity, dyslipidemia (hyperlipidemia), hypertension, and fatty liver, or a metabolic syndrome pathology which comprises a series of these metabolic diseases. Therefore, a selective inhibitor of 11β-HSD1 is believed to be useful for treating or preventing the above pathologies.

Heretofore, many compounds have been reported for the purpose of inhibiting 11β-HSD1 activity. The examples of reported compounds include compounds having a spiro structure (patent documents 1 to 4), adamantane derivative (patent document 5), sulfonamide derivative (patent document 6), pyrazole derivative (patent document 7), isooxazole derivative (patent document 8), triazole derivative (patent document 9), tetrazole derivative (patent document 10), pyridine derivative (patent document 11), pyrimidine derivative (patent document 12), piperidine derivative (patent document 13), pyridazine derivative (patent document 14), pyrrolidine derivative (patent document 15), thiazole derivative (patent document 16), thiophene derivative (patent document 17), lactam derivative (patent document 18) and the like.

On the other hand, 1,2-diazetidin-3-one skeleton related to the present invention is a skeleton which has not been much studied, and most of the documents disclosing the backbone are related to syntheses and reactions. Informations on bioactivity are fewer, and there are only descriptions that it is useful as an antifungal drug (patent document 19), useful as a differentiating agent for leukemia cells (non-patent document 9), and useful as an antitumor agent (patent document 20). Therefore, there is no description nor suggestion that a compound having 1,2-diazetidin-3-one skeleton inhibits 11β-HSD1 activity, and it has not been known at all that a 1,2-diazetidin-3-one skeleton compound is useful as an agent for preventing and/or treating diabetes, insulin resistance, diabetes complication, obesity, dyslipidemia, hypertension, fatty liver, or metabolic syndrome.

[Non-Patent document 1] J. Mol. Endocrinol., 37:327-340 (2006)
[Non-Patent document 2] Endcr. Rev., 25:831-866 (2004)
[Non-Patent document 3] Rinsho-i, vol. 30 No. 9: 1782-1787 (2004)
[Non-Patent document 4] J. Clin. Endocrinol. Metab., 88:2738-2744 (2003)
[Non-Patent document 5] Science 294:2166-2170 (2001)
[Non-Patent document 6] J. Clin. Invest. 112:83-90 (2003)
[Non-Patent document 7] Proc. Natl. Acad. Sci. USA, 94:14924-14929 (1997)
[Non-Patent document 8] J. Biol. Chem., 276:41293-41301 (2001)
[Non-Patent document 9] Agricultural and Biological Chemistry, 50:1757-1764 (1986)
[Patent document 1] WO2005/110992
[Patent document 2] WO2006/040329
[Patent document 3] WO2006/053024
[Patent document 4] WO2006/055752
[Patent document 5] WO2005/108368
[Patent document 6] WO2006/134467
[Patent document 7] WO2006/132436
[Patent document 8] WO2006/132197
[Patent document 9] WO2007/007688
[Patent document 10] WO2007/029021
[Patent document 11] WO2006/010546
[Patent document 12] WO2006/000371
[Patent document 13] WO2005/046685
[Patent document 14] WO2007/003521
[Patent document 15] WO2004/037251
[Patent document 16] WO2006/051662
[Patent document 17] WO2004/112779
[Patent document 18] WO2006/049952
[Patent document 19] U.S. Pat. No. 4,826,971
[Patent document 20] Japanese Laid-Open Patent Application No. 60-239420

DISCLOSURE OF THE INVENTION

The object of the present invention is to provide a novel compound that inhibits 11β-HSD1 selectively, and is useful as a medicine.

Problem to be Solved by the Invention

The present inventors made a keen study to find a compound that selectively inhibits 11β-HSD1. Consequently, the present inventors have found that a compound having 1,2-diazetidin-3-one skeleton represented by the following formula (1) is a compound that inhibits 11β-HSD1 selectively and thus completed the present invention. More specifically, the present invention relates to:

[1] a 1,2-diazetidin-3-one derivative represented by the following general formula (1) or salt thereof, or their solvate:

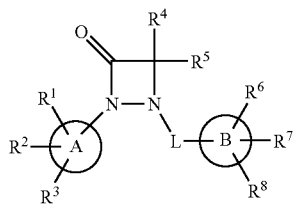

(1)

[wherein A ring represents a saturated $C_{3-10}$ carbocyclic group,
B ring represents a $C_{3-8}$ cycloalkyl group, $C_{3-8}$ cycloalkenyl group, $C_{6-14}$ aryl group or a 5- to 14-membered heteroaryl group,
$R^1$, $R^2$ and $R^3$ represent the same or different and are a hydrogen atom, halogen atom, hydroxyl group, carboxyl group, carbamoyl group or $C_{1-6}$ alkyl group,
$R^4$ and $R^5$ represent the same or different and are a hydrogen atom or $C_{1-6}$ alkyl group,
$R^6$, $R^7$ and $R^8$ represent the same or different and are a hydrogen atom, halogen atom, hydroxyl group, nitro group, cyano group, amino group (that may be substituted with a sulfonyl group or acyl group), $C_{1-6}$ alkyl group, halo $C_{1-6}$ alkyl group, $C_{1-6}$ alkoxy group (that may be substituted with a $C_{1-6}$ alkoxy group), $C_{6-10}$ aryl group, $C_{2-6}$ alkanoyloxy group, $C_{1-6}$ alkylthio group, $C_{1-6}$ alkylsulfinyl group or $C_{1-6}$ alkylsulfonyl group, or $R^6$ and $R^7$ may together form a $C_{1-3}$ alkylenedioxy group,
L represents a single bond, $C_{1-6}$ alkylene chain, $C_{2-6}$ alkenylene chain, —($C_{1-6}$ alkylene)-O—, —CO—X— or —SO$_2$—Y—,
X represents a single bond, —N($R^9$)—, —O—($C_{1-6}$ alkylene)-, —($C_{1-6}$ alkylene)-O—, —($C_{1-6}$ alkylene)-O—($C_{1-6}$ alkylene)- or —($C_{1-6}$ alkylene)-S—,
$R^9$ represents a hydrogen atom, $C_{1-6}$ alkyl group or acyl group, and
Y represents a single bond or $C_{1-6}$ alkylene chain];
[2] the 1,2-diazetidin-3-one derivative or salt thereof, or their solvate according to [1], wherein the saturated $C_{3-10}$ carbocyclic group in the A ring of general formula (1) is a "$C_{3-8}$ cycloalkyl group" or "$C_{4-10}$ cross-linked cyclic hydrocarbon group";
[3] the 1,2-diazetidin-3-one derivative or salt thereof, or their solvate according to [1] or [2], wherein the compound represented by general formula (1) is:
1-benzyl-4-methyl-2-(adamantan-2-yl)-1,2-diazetidin-3-one,
1-(4-chlorobenzyl)-4-methyl-2-(adamantan-2-yl)-1,2-diazetidin-3-one,
1-benzyl-4,4-dimethyl-2-(adamantan-2-yl)-1,2-diazetidin-3-one,
1-(4-chlorobenzyl)-4,4-dimethyl-2-(adamantan-2-yl)-1,2-diazetidin-3-one,
4,4-dimethyl-1-(4-methylbenzyl)-2-(adamantan-2-yl)-1,2-diazetidin-3-one,
1-(4-fluorobenzyl)-4,4-dimethyl-2-(adamantan-2-yl)-1,2-diazetidin-3-one,
1-(3,4-difluorobenzyl)-4,4-dimethyl-2-(adamantan-2-yl)-1,2-diazetidin-3-one,
1-(2,4-difluorobenzyl)-4,4-dimethyl-2-(adamantan-2-yl)-1,2-diazetidin-3-one,
1-(3,5-difluorobenzyl)-4,4-dimethyl-2-(adamantan-2-yl)-1,2-diazetidin-3-one,
1-(2,3-difluorobenzyl)-4,4-dimethyl-2-(adamantan-2-yl)-1,2-diazetidin-3-one,
1-(2,5-difluorobenzyl)-4,4-dimethyl-2-(adamantan-2-yl)-1,2-diazetidin-3-one,
1-(3-fluorobenzyl)-4,4-dimethyl-2-(adamantan-2-yl)-1,2-diazetidin-3-one,
1-(3,5-dimethoxybenzyl)-4,4-dimethyl-2-(adamantan-2-yl)-1,2-diazetidin-3-one,
1-(2-chlorobenzyl)-4,4-dimethyl-2-(adamantan-2-yl)-1,2-diazetidin-3-one,
1-(3-chlorobenzyl)-4,4-dimethyl-2-(adamantan-2-yl)-1,2-diazetidin-3-one,
4,4-dimethyl-1-(3-nitrobenzyl)-2-(adamantan-2-yl)-1,2-diazetidin-3-one,
4,4-dimethyl-1-(2-methylbenzyl)-2-(adamantan-2-yl)-1,2-diazetidin-3-one,
4,4-dimethyl-1-(4-nitrobenzyl)-2-(adamantan-2-yl)-1,2-diazetidin-3-one,
4,4-dimethyl-1-(3-methylbenzyl)-2-(adamantan-2-yl)-1,2-diazetidin-3-one,
1-(3-bromobenzyl)-4,4-dimethyl-2-(adamantan-2-yl)-1,2-diazetidin-3-one,
1-(3-iodobenzyl)-4,4-dimethyl-2-(adamantan-2-yl)-1,2-diazetidin-3-one,
4,4-dimethyl-2-(adamantan-2-yl)-1-[4-(trifluoromethyl)benzyl]-1,2-diazetidin-3-one,
1-(2,6-dichlorobenzyl)-4,4-dimethyl-2-(adamantan-2-yl)-1,2-diazetidin-3-one,
1-(2-fluorobenzyl)-4,4-dimethyl-2-(adamantan-2-yl)-1,2-diazetidin-3-one,
1-(2-bromobenzyl)-4,4-dimethyl-2-(adamantan-2-yl)-1,2-diazetidin-3-one,
1-(2-iodobenzyl)-4,4-dimethyl-2-(adamantan-2-yl)-1,2-diazetidin-3-one,
1-(2-chloro-5-fluorobenzyl)-4,4-dimethyl-2-(adamantan-2-yl)-1,2-diazetidin-3-one,
4,4-dimethyl-2-(adamantan-2-yl)-1-[2-(trifluoromethyl)benzyl]-1,2-diazetidin-3-one,
1-(2,3-dichlorobenzyl)-4,4-dimethyl-2-(adamantan-2-yl)-1,2-diazetidin-3-one,
1-(2,5-dichlorobenzyl)-4,4-dimethyl-2-(adamantan-2-yl)-1,2-diazetidin-3-one,
1-(2-chloro-4-fluorobenzyl)-4,4-dimethyl-2-(adamantan-2-yl)-1,2-diazetidin-3-one,
1-(2-chloro-6-fluorobenzyl)-4,4-dimethyl-2-(adamantan-2-yl)-1,2-diazetidin-3-one,
4,4-dimethyl-1-(2-nitrobenzyl)-2-(adamantan-2-yl)-1,2-diazetidin-3-one,
1-[4-fluoro-2-(trifluoromethyl)benzyl]-4,4-dimethyl-2-(adamantan-2-yl)-1,2-diazetidin-3-one,
1-(biphenyl-2-ylmethyl)-4,4-dimethyl-2-(adamantan-2-yl)-1,2-diazetidin-3-one,
1-(2-ethylbenzyl)-4,4-dimethyl-2-(adamantan-2-yl)-1,2-diazetidin-3-one,
1-(2-methoxybenzyl)-4,4-dimethyl-2-(adamantan-2-yl)-1,2-diazetidin-3-one,
1-(2,4-dichlorobenzyl)-4,4-dimethyl-2-(adamantan-2-yl)-1,2-diazetidin-3-one,
1-(4-bromobenzyl)-4,4-dimethyl-2-(adamantan-2-yl)-1,2-diazetidin-3-one,
1-(3-methoxybenzyl)-4,4-dimethyl-2-(adamantan-2-yl)-1,2-diazetidin-3-one,
1-(2,4-dimethylbenzyl)-4,4-dimethyl-2-(adamantan-2-yl)-1,2-diazetidin-3-one, 1-(2,5-dimethylbenzyl)-4,4-dimethyl-2-(adamantan-2-yl)-1,2-diazetidin-3-one,
1-(3-fluoro-2-methylbenzyl)-4,4-dimethyl-2-(adamantan-2-yl)-1,2-diazetidin-3-one,
1-(3)-chloro-2-fluorobenzyl)-4,4-dimethyl-2-(adamantan-2-yl)-1,2-diazetidin-3-one,
4,4-dimethyl-1-[2-(methylthio)benzyl]-2-(adamantan-2-yl)-1,2-diazetidin-3-one,
1-(1,3-benzodioxol-4-ylmethyl)-4,4-dimethyl-2-(adamantan-2-yl)-1,2-diazetidin-3-one,
4,4-dimethyl-1-(naphthalen-1-ylmethyl)-2-(adamantan-2-yl)-1,2-diazetidin-3-one,
4,4-dimethyl-1-(naphthalen-2-ylmethyl)-2-(adamantan-2-yl)-1,2-diazetidin-3-one,
trans-1-(2-chlorobenzyl)-2-(5-hydroxyadamantan-2-yl)-4,4-dimethyl-1,2-diazetidin-3-one,
trans-2-(5-hydroxyadamantan-2-yl)-4,4-dimethyl-1-[2-(trifluoromethyl)benzyl]-1,2-diazetidin-3-one,
trans-1-(2-chloro-5-fluorobenzyl)-2-(5-hydroxyadamantan-2-yl)-4,4-dimethyl-1,2-diazetidin-3-one,
1-(2-chlorobenzyl)-2-cyclohexyl-4,4-dimethyl-1,2-diazetidin-3-one,
2-cyclohexyl-1-(2,3-dichlorobenzyl)-4,4-dimethyl-1,2-diazetidin-3-one,
2-cyclohexyl-1-(2,5-dichlorobenzyl)-4,4-dimethyl-1,2-diazetidin-3-one,
1-(2-chloro-5-fluorobenzyl)-2-cyclohexyl-4,4-dimethyl-1,2-diazetidin-3-one,
1-(2-chloro-4-fluorobenzyl)-2-cyclohexyl-4,4-dimethyl-1,2-diazetidin-3-one,
1-(2-chlorobenzyl)-2-cyclooctyl-4,4-dimethyl-1,2-diazetidin-3-one,
2-cyclooctyl-1-(2,3-dichlorobenzyl)-4,4-dimethyl-1,2-diazetidin-3-one,
2-cyclooctyl-1-(2,5-dichlorobenzyl)-4,4-dimethyl-1,2-diazetidin-3-one,
1-(2-chloro-4-fluorobenzyl)-2-cyclooctyl-4,4-dimethyl-1,2-diazetidin-3-one,
1-(2-chloro-5-fluorobenzyl)-2-cyclooctyl-4,4-dimethyl-1,2-diazetidin-3-one,
2-(bicyclo[2.2.1]heptan-2-yl)-1-(2-chlorobenzyl)-4,4-dimethyl-1,2-diazetidin-3-one,
2-(bicyclo[2.2.1]heptan-2-yl)-1-(2,3-dichlorobenzyl)-4,4-dimethyl-1,2-diazetidin-3-one,
2-(bicyclo[2.2.1]heptan-2-yl)-1-(2,5-dichlorobenzyl)-4,4-dimethyl-1,2-diazetidin-3-one,
2-(bicyclo[2.2.1]heptan-2-yl)-1-(2-chloro-4-fluorobenzyl)-4,4-dimethyl-1,2-diazetidin-3-one,
2-(bicyclo[2.2.1]heptan-2-yl)-1-(2-chloro-5-fluorobenzyl)-4,4-dimethyl-1,2-diazetidin-3-one,
1-(2-chlorobenzyl)-2-cycloheptyl-4,4-dimethyl-1,2-diazetidin-3-one,
2-cycloheptyl-1-(2,3-dichlorobenzyl)-4,4-dimethyl-1,2-diazetidin-3-one,
2-cycloheptyl-1-(2,5-dichlorobenzyl)-4,4-dimethyl-1,2-diazetidin-3-one,
1-(2-chloro-4-fluorobenzyl)-2-cycloheptyl-4,4-dimethyl-1,2-diazetidin-3-one,
1-(2-chloro-5-fluorobenzyl)-2-cycloheptyl-4,4-dimethyl-1,2-diazetidin-3-one,
1-(cyclohexa-2-en-1-yl)-4,4-dimethyl-2-(adamantan-2-yl)-1,2-diazetidin-3-one,
1-cyclohexyl-4,4-dimethyl-2-(adamantan-2-yl)-1,2-diazetidin-3-one,
4-[2-(2-chlorobenzyl)-3,3-dimethyl-4-oxo-1,2-diazetidin-1-yl]adamantane-1-carboxamide,
4,4-dimethyl-1-(phenylcarbonyl)-2-(adamantan-2-yl)-1,2-diazetidin-3-one,
4,4-dimethyl-2-(adamantan-2-yl)-1-{[2-(trifluoromethyl)phenyl]carbonyl}-1,2-diazetidin-3-one,
1-[(4-bromophenyl)carbonyl]-4,4-dimethyl-2-(adamantan-2-yl)-1,2-diazetidin-3-one,
4,4-dimethyl-1-[(3-methylphenyl)carbonyl]-2-(adamantan-2-yl)-1,2-diazetidin-3-one,
1-[(3-bromophenyl)carbonyl]-4,4-dimethyl-2-(adamantan-2-yl)-1,2-diazetidin-3-one,
4,4-dimethyl-1-[(4-methylphenyl)carbonyl]-2-(adamantan-2-yl)-1,2-diazetidin-3-one,
4,4-dimethyl-1-[(2-methylphenyl)carbonyl]-2-(adamantan-2-yl)-1,2-diazetidin-3-one,
1-[(3,5-dichlorophenyl)carbonyl]-4,4-dimethyl-2-(adamantan-2-yl)-1,2-diazetidin-3-one,
1-[(2-fluorophenyl)carbonyl]-4,4-dimethyl-2-(adamantan-2-yl)-1,2-diazetidin-3-one,
1-[(2-bromophenyl)carbonyl]-4,4-dimethyl-2-(adamantan-2-yl)-1,2-diazetidin-3-one,
1-[(2-iodophenyl)carbonyl]-4,4-dimethyl-2-(adamantan-2-yl)-1,2-diazetidin-3-one,
1-[(2,5-dichlorophenyl)carbonyl]-4,4-dimethyl-2-(adamantan-2-yl)-1,2-diazetidin-3-one,
1-[(5-fluoro-2-methylphenyl)carbonyl]-4,4-dimethyl-2-(adamantan-2-yl)-1,2-diazetidin-3-one,
1-[(2-ethylphenyl)carbonyl]-4,4-dimethyl-2-(adamantan-2-yl)-1,2-diazetidin-3-one,
1-[(3-chlorophenyl)carbonyl]-4,4-dimethyl-2-(adamantan-2-yl)-1,2-diazetidin-3-one,
1-[(4-fluoro-2-trifluoromethylphenyl)carbonyl]-4,4-dimethyl-2-(adamantan-2-yl)-1,2-diazetidin-3-one,
1-(1,3-benzodioxol-5-ylcarbonyl)-4,4-dimethyl-2-(adamantan-2-yl)-1,2-diazetidin-3-one,
1-[(2-aminophenyl)carbonyl]-4,4-dimethyl-2-(adamantan-2-yl)-1,2-diazetidin-3-one,
1-[(2-hydroxyphenyl)carbonyl]-4,4-dimethyl-2-(adamantan-2-yl)-1,2-diazetidin-3-one,
1-[(4-aminophenyl)carbonyl]-4,4-dimethyl-2-(adamantan-2-yl)-1,2-diazetidin-3-one,
4,4-dimethyl-1-(naphthalen-1-ylcarbonyl)-2-(adamantan-2-yl)-1,2-diazetidin-3-one,
2-cyclohexyl-1-[(2,5-dimethylphenyl)carbonyl]-4,4-dimethyl-1,2-diazetidin-3-one,
1-[(3-chlorophenyl)carbonyl]-2-cyclooctyl-4,4-dimethyl-1,2-diazetidin-3-one,
2-cyclooctyl-4,4-dimethyl-1-[(3-methylphenyl)carbonyl]-1,2-diazetidin-3-one,
2-cyclooctyl-4,4-dimethyl-1-[(2-methylphenyl)carbonyl]-1,2-diazetidin-3-one,
1-[(2-aminophenyl)carbonyl]-2-cyclooctyl-4,4-dimethyl-1,2-diazetidin-3-one,
2-cyclooctyl-4,4-dimethyl-1-(naphthalen-1-ylcarbonyl)-1,2-diazetidin-3-one,
1-[(3-fluoro-2-methylphenyl)carbonyl]-4,4-dimethyl-2-(adamantan-2-yl)-1,2-diazetidin-3-one,
1-[(2,4-dimethylphenyl)carbonyl]-4,4-dimethyl-2-(adamantan-2-yl)-1,2-diazetidin-3-one,
1-[(2,5-dimethylphenyl)carbonyl]-4,4-dimethyl-2-(adamantan-2-yl)-1,2-diazetidin-3-one,
1-[(2-bromo-5-chlorophenyl)carbonyl]-4,4-dimethyl-2-(adamantan-2-yl)-1,2-diazetidin-3-one,
4,4-dimethyl-1-{[2-(methylthio)phenyl]carbonyl}-2-(adamantan-2-yl)-1,2-diazetidin-3-one,
2-cyclooctyl-4,4-dimethyl-1-{[2-(methylthio)phenyl]carbonyl}-1,2-diazetidin-3-one, 4,4-dimethyl-1-phenyl-2-(adamantan-2-yl)-1,2-diazetidin-3-one,
1-(4-aminophenyl)-4,4-dimethyl-2-(adamantan-2-yl)-1,2-diazetidin-3-one,
4,4-dimethyl-1-(2-nitrophenyl)-2-(adamantan-2-yl)-1,2-diazetidin-3-one,
1-(2-chlorophenyl)-4,4-dimethyl-2-(adamantan-2-yl)-1,2-diazetidin-3-one,
1-(3-chlorophenyl)-4,4-dimethyl-2-(adamantan-2-yl)-1,2-diazetidin-3-one,
4,4-dimethyl-1-(2-methylphenyl)-2-(adamantan-2-yl)-1,2-diazetidin-3-one,
4,4-dimethyl-1-(3-methylphenyl)-2-(adamantan-2-yl)-1,2-diazetidin-3-one,
1-(3,5-difluorophenyl)-4,4-dimethyl-2-(adamantan-2-yl)-1,2-diazetidin-3-one,
1-(1,3-benzodioxol-5-yl)-4,4-dimethyl-2-(adamantan-2-yl)-1,2-diazetidin-3-one,
1-(3-fluorophenyl)-4,4-dimethyl-2-(adamantan-2-yl)-1,2-diazetidin-3-one,
1-(4-fluorophenyl)-4,4-dimethyl-2-(adamantan-2-yl)-1,2-diazetidin-3-one,
1-(3,5-dichlorophenyl)-4,4-dimethyl-2-(adamantyl)-1,2-diazetidin-3-one,
1-(4-methoxyphenyl)-4,4-dimethyl-2-(adamantan-2-yl)-1,2-diazetidin-3-one,
1-(3-methoxyphenyl)-4,4-dimethyl-2-(adamantan-2-yl)-1,2-diazetidin-3-one,
1-(2-methoxyphenyl)-4,4-dimethyl-2-(adamantan-2-yl)-1,2-diazetidin-3-one,
1-(2,3-dichlorophenyl)-4,4-dimethyl-2-(adamantan-2-yl)-1,2-diazetidin-3-one,
1-(2,3-dimethylphenyl)-4,4-dimethyl-2-(adamantan-2-yl)-1,2-diazetidin-3-one,
1-(2,4-dichlorophenyl)-4,4-dimethyl-2-(adamantan-2-yl)-1,2-diazetidin-3-one,
1-(2,5-dichlorophenyl)-4,4-dimethyl-2-(adamantan-2-yl)-1,2-diazetidin-3-one,
1-(1-benzothiophen-3-yl)-4,4-dimethyl-2-(adamantan-2-yl)-1,2-diazetidin-3-one,
4,4-dimethyl-1-(naphthalen-1-yl)-2-(adamantan-2-yl)-1,2-diazetidin-3-one,
1-[4-(methoxymethoxy)phenyl]-4,4-dimethyl-2-(adamantan-2-yl)-1,2-diazetidin-3-one,
4,4-dimethyl-1-(4-hydroxyphenyl)-2-(adamantan-2-yl)-1,2-diazetidin-3-one,
1-[3-(methoxymethoxy)phenyl]-4,4-dimethyl-2-(adamantan-2-yl)-1,2-diazetidin-3-one,
1-[2-(methoxymethoxy)phenyl]-4,4-dimethyl-2-(adamantan-2-yl)-1,2-diazetidin-3-one,
1-(2-hydroxyphenyl)-4,4-dimethyl-2-(adamantan-2-yl)-1,2-diazetidin-3-one,
2-cyclooctyl-1-(2-methoxyphenyl)-4,4-dimethyl-1,2-diazetidin-3-one,
2-cyclooctyl-1-(2,3-dichlorophenyl)-4,4-dimethyl-1,2-diazetidin-3-one,
2-cyclooctyl-4,4-dimethyl-1-(naphthalen-1-yl)-1,2-diazetidin-3-one,
2-(bicyclo[2.2.1]heptan-2-yl)-1-(2-methoxyphenyl)-4,4-dimethyl-1,2-diazetidin-3-one,
2-(bicyclo[2.2.1]heptan-2-yl)-1-(2,3-dichlorophenyl)-4,4-dimethyl-1,2-diazetidin-3-one,
2-(bicyclo[2.2.1]heptan-2-yl)-4,4-dimethyl-1-(naphthalen-1-yl)-1,2-diazetidin-3-one,
trans-2-(5-hydroxyadamantan-2-yl)-4,4-dimethyl-1-phenyl-1,2-diazetidin-3-one,
trans-1-(2-chlorophenyl)-2-(5-hydroxyadamantan-2-yl)-4,4-dimethyl-1,2-diazetidin-3-one,
trans-2-(5-hydroxyadamantan-2-yl)-1-(4-methoxyphenyl)-4,4-dimethyl-1,2-diazetidin-3-one,
trans-1-(2,3-dichlorophenyl)-2-(5-hydroxyadamantan-2-yl)-4,4-dimethyl-1,2-diazetidin-3-one,
trans-1-(2-hydroxyphenyl)-2-(5-hydroxyadamantan-2-yl)-4,4-dimethyl-1,2-diazetidin-3-one,
trans-1-(4-aminophenyl)-2-(5-hydroxyadamantan-2-yl)-4,4-dimethyl-1,2-diazetidin-3-one,
trans-2-(5-hydroxyadamantan-2-yl)-4,4-dimethyl-1-(naphthalen-1-yl)-1,2-diazetidin-3-one,
trans-1-(4-fluoronaphthalen-1-yl)-2-(5-hydroxyadamantan-2-yl)-4,4-dimethyl-1,2-diazetidin-3-one,
cis-2-(5-hydroxyadamantan-2-yl)-1-(4-methoxyphenyl)-4,4-dimethyl-1,2-diazetidin-3-one,
cis-2-(5-hydroxyadamantan-2-yl)-4,4-dimethyl-1-(2-methylphenyl)-1,2-diazetidin-3-one,
cis-1-(2-hydroxyphenyl)-2-(5-hydroxyadamantan-2-yl)-4,4-dimethyl-1,2-diazetidin-3-one,
cis-1-(4-aminophenyl)-2-(5-hydroxyadamantan-2-yl)-4,4-dimethyl-1,2-diazetidin-3-one,
cis-2-(5-hydroxyadamantan-2-yl)-4,4-dimethyl-1-(naphthalen-1-yl)-1,2-diazetidin-3-one,
cis-2-(5-hydroxyadamantan-2-yl)-4,4-dimethyl-1-(naphthalen-2-yl)-1,2-diazetidin-3-one,
cis-1-(4-fluoronaphthalen-1-yl)-2-(5-hydroxyadamantan-2-yl)-4,4-dimethyl-1,2-diazetidin-3-one,
trans-2-(5-chloroadamantan-2-yl)-1-(2-methoxyphenyl)-4,4-dimethyl-1,2-diazetidin-3-one,
trans-2-(5-chloroadamantan-2-yl)-1-(2,3-dichlorophenyl)-4,4-dimethyl-1,2-diazetidin-3-one,
trans-2-(5-chloroadamantan-2-yl)-1-[2-(methoxymethoxy)phenyl]-4,4-dimethyl-1,2-diazetidin-3-one,
trans-2-(5-chloroadamantan-2-yl)-1-(2-hydroxyphenyl)-4,4-dimethyl-1,2-diazetidin-3-one,
trans-2-(5-chloroadamantan-2-yl)-4,4-dimethyl-1-(naphthalen-1-yl)-1,2-diazetidin-3-one,
trans-2-(5-chloroadamantan-2-yl)-1-(4-fluoronaphthalen-1-yl)-4,4-dimethyl-1,2-diazetidin-3-one,
cis-2-(5-chloroadamantan-2-yl)-1-(2,3-dichlorophenyl)-4,4-dimethyl-1,2-diazetidin-3-one,
cis-2-(5-chloroadamantan-2-yl)-4,4-dimethyl-1-(naphthalen-1-yl)-1,2-diazetidin-3-one,
1-(1,3-benzodioxol-4-yl)-4,4-dimethyl-2-(adamantan-2-yl)-1,2-diazetidin-3-one,
4,4-dimethyl-1-(3-phenylpropyl)-2-(adamantan-2-yl)-1,2-diazetidin-3-one,
4,4-dimethyl-1-[(E)-2-phenylethenyl]-2-(adamantan-2-yl)-1,2-diazetidin-3-one,
4,4-dimethyl-1-(2-phenylethyl)-2-(adamantan-2-yl)-1,2-diazetidin-3-one,
trans-4-[2-(naphthalen-1-yl)-3,3-dimethyl-4-oxo-1,2-diazetidin-1-yl]adamantane-1-carboxylic acid,
trans-4-[2-(naphthalen-1-yl)-3,3-dimethyl-4-oxo-1,2-diazetidin-1-yl]adamantane-1-carboxamide,
cis-4-[2-(naphthalen-1-yl)-3,3-dimethyl-4-oxo-1,2-diazetidin-1-yl]adamantane-1-carboxylic acid,
cis-4-[2-(naphthalen-1-yl)-3,3-dimethyl-4-oxo-1,2-diazetidin-1-yl]adamantane-1-carboxamide,
trans-4-[2-(2,3-dichlorophenyl)-3,3-dimethyl-4-oxo-1,2-diazetidin-1-yl]adamantane-1-carboxamide, or
cis-4-[2-(2,3-dichlorophenyl)-3,3-dimethyl-4-oxo-1,2-diazetidin-1-yl]adamantane-1-carboxamide;

[4] a pharmaceutical composition consisting of the 1,2-diazetidin-3-one derivative or salt thereof, or their solvate according to any one of [1] to [3], and a pharmaceutically acceptable carrier;

[5] an inhibitor of 11β-hydroxysteroid dehydrogenase 1, comprising the 1,2-diazetidin-3-one derivative or salt thereof, or their solvate according to any one of [1] to [3] as an active ingredient;

[6] an agent for preventing and/or treating diabetes, insulin resistance, diabetes complication, obesity, dyslipidemia, hypertension, fatty liver, or metabolic syndrome, which agent comprises the 1,2-diazetidin-3-one derivative or salt thereof, or their solvate according to any one of [1] to [3] as an active ingredient;

[7] use of the 1,2-diazetidin-3-one or salt thereof, or their solvate according to any one of [1] to [3] for producing a formulation for inhibiting 11β-hydroxysteroid dehydrogenase 1;

[8] use of the 1,2-diazetidin-3-one derivative or salt thereof, or their solvate according to any one of [1] to [3] for producing a formulation for preventing and/or treating diabetes, insulin resistance, diabetes complication, obesity, dyslipidemia, hypertension, fatty liver, or metabolic syndrome;

[9] a method for inhibiting 11β-hydroxysteroid dehydrogenase 1, which method comprises administering an effective amount of the 1,2-diazetidin-3-one derivative or salt thereof, or their solvate according to any one of [1] to [3]; and

[10] a method for preventing and/or treating diabetes, insulin resistance, diabetes complication, obesity, dyslipidemia, hypertension, fatty liver, or metabolic syndrome, which method comprises administering an effective amount of the 1,2-diazetidin-3-one derivative or salt thereof, or their solvate according to any one of [1] to [3].

Effect of the Invention

A 1,2-diazetidin-3-one derivative or salt thereof, or their solvate of the present invention shows a superior inhibitory effect of 11β-hydroxysteroid dehydrogenase 1, and is useful as an agent for preventing or treating a disease that involves 11β-hydroxysteroid dehydrogenase 1 (in particular, diabetes, insulin resistance, diabetes complication, obesity, dyslipidemia, hypertension, fatty liver, or metabolic syndrome).

BEST MODE FOR CARRYING OUT THE INVENTION

In the following, the present invention will be explained in detail.

1,2-diazetidin-3-one Derivative Represented by Formula (1)

Herein, "saturated carbocycle" means a monocyclic, cross-linked cyclic or spiro cyclic hydrocarbon group formed only with a single bond. Examples of "saturated $C_{3-10}$ carbocyclic group" specifically include a "$C_{3-8}$ cycloalkyl group", "$C_{4-10}$ cross-linked cyclic hydrocarbon group" and "$C_{5-10}$ spiro cyclic hydrocarbon group". Examples of "$C_{3-8}$ cycloalkyl group" include a cyclopropyl group, cyclobutyl group, cyclopentyl group, cyclohexyl group, cycloheptyl group and cyclooctyl group. Examples of "$C_{4-10}$ cross-linked cyclic hydrocarbon group" include a bicyclobutyl group, bicyclopentyl group, bicyclohexyl group, bicycloheptyl group, bicyclooctyl group, bicyclononyl group, bicyclodecyl group and adamantyl group. Examples of "$C_{5-10}$ spiro cyclic hydrocarbon group" include a spiropentyl group, spirohexyl group, spiroheptyl group, spirooctyl group, spirononyl group and spirodecyl group.

Herein, "cycloalkenyl" means a cyclic alkyl group, wherein one or more single bond constituting the ring has become a double bond. Therefore, examples of "$C_{3-8}$ cycloalkenyl group" include a monocyclic cycloalkenyl group having 3 to 8 carbons such as cyclopropenyl group, cyclobutenyl group, cyclopentenyl group, cyclohexenyl group, cyclohexane dienyl group, cycloheptenyl group and cyclooctenyl group.

Herein, "aryl" means a monocyclic or condensed ring aromatic hydrocarbon ring. Therefore, examples of "$C_{6-14}$ aryl group" include a phenyl group, naphthyl group (naphthalen-1-yl group, naphthalen-2-yl group), anthryl group, azulenyl group, fluorenyl group and phenanthryl group. Further, examples of "$C_{6-10}$ aryl group" include a phenyl group, naphthyl group (naphthalen-1-yl group, naphthalen-2-yl group) and azulenyl group.

Herein, "5- to 14-membered heteroaryl group" means a 5- to 14-membered monocyclic aromatic heterocyclic group or condensed aromatic heterocyclic group containing 1 to 4 heteroatoms selected from a nitrogen atom, oxygen atom and sulfur atom in addition to a carbon atom as atoms constituting the ring. Examples of monocyclic aromatic heterocyclic group include a 2-furyl group, 3-furyl group, 2-thienyl group, 3-thienyl group, pyrrol-1-yl group, pyrrol-2-yl group, pyrrol-3-yl group, pyridin-2-yl group, pyridin-3-yl group, pyridin-4-yl group, pyrazin-2-yl group, pyrimidin-2-yl group, pyrimidin-4-yl group, pyrimidin-5-yl group, pyridazin-3-yl group, pyridazin-4-yl group, imidazol-1-yl group, imidazol-2-yl group, imidazol-4-yl group, pyrazol-1-yl group, pyrazol-3-yl group, pyrazol-4-yl group, thiazol-2-yl group, thiazol-4-yl group, thiazol-5-yl group, oxazol-2-yl-group, oxazol-4-yl group, oxazol-5-yl group, isooxazol-3-yl group, isooxazol-4-yl group, isooxazol-5-yl group, 1,3,4-thiadiazol-2-yl group, 1,2,3-triazol-1-yl group, 1,2,3-triazol-4-yl group, 1,2,4-triazol-1-yl group, 1,2,4-triazol-3-yl group, 1,2,4-triazol-4-yl group, tetrazol-1-yl group and tetrazol-5-yl group. Examples of condensed aromatic heterocyclic group include a benzofuran-2-yl group, benzofuran-3-yl group, benzofuran-4-yl group, benzofuran-5-yl group, benzofuran-6-yl group, benzofuran-7-yl group, benzothiophen-2-yl group, benzothiophen-3-yl group, benzothiophen-4-yl group, benzothiophen-5-yl group, benzothiophen-6-yl group, benzothiophen-7-yl group, quinoxalin-2-yl group, quinoxalin-5-yl group, quinoxalin-6-yl group, indol-1-yl group, indol-2-yl group, indol-3-yl group, indol-4-yl group, indol-5-yl group, indol-6-yl group, indol-7-yl group, isoindol-1-yl group, isoindol-2-yl group, isoindol-4-yl group, isoindol-5-yl group, isobenzofuran-1-yl group, isobenzofuran-4-yl group, isobenzofuran-5-yl group, chromen-2-yl group, chromen-3-yl group, chromen-4-yl group, chromen-5-yl group, chromen-6-yl group, chromen-7-yl group, chromen-8-yl group, benzoimidazol-1-yl group, benzoimidazol-2-yl group, benzoimidazol-4-yl group, benzoimidazol-5-yl group, benzothiazol-2-yl group, benzothiazol-4-yl group, benzothiazol-5-yl group, benzooxazol-2-yl group, benzooxazol-4-yl group, benzooxazol-5-yl group, quinolin-2-yl group, quinolin-3-yl group, quinolin-4-yl group, quinolin-5-yl group, quinolin-6-yl group, quinolin-7-yl group, quinolin-8-yl group, isoquinolin-1-yl group, isoquinolin-3-yl group, isoquinolin-4-yl group, isoquinolin-5-yl group, isoquinolin-6-yl group, isoquinolin-7-yl group and isoquinolin-8-yl group.

Herein, a "halogen" represents a halogeno group, and examples include a fluorine atom, chlorine atom, bromine atom and iodine atom.

Herein "alkyl" means a straight-chained or branched-chained saturated hydrocarbon group. Therefore, examples of "$C_{1-6}$ alkyl group" include a methyl group, ethyl group, propyl group, isopropyl group, butyl group, isobutyl group, sec-butyl group, tert-butyl group, pentyl group, isopentyl group, neopentyl group, hexyl group and isohexyl group.

Herein, "sulfonyl" in "amino group (that may substituted with a sulfonyl group or acyl group)" means a group wherein a substituted or unsubstituted $C_{1-6}$ alkyl group is bound to a sulfonyl group ($SO_2$), or a group wherein a substituted or unsubstituted $C_{6-10}$ aryl group is bound to a sulfonyl group ($SO_2$). Therefore, examples of "sulfonyl group" include a methanesulfonyl group, ethanesulfonyl group, trifluoromethanesulfonyl group, benzenesulfonyl group, p-toluenesulfonyl group, p-fluorophenylsulfonyl group and 1-naphthalenesulfonyl group.

Herein, "acyl" means an aliphatic acyl group that may be branched, wherein a saturated or unsaturated hydrocarbon group is bound to a carbonyl group (CO) or aromatic acyl group. Examples of aliphatic acyl group include an acetyl group, propionyl group, butyryl group, isobutyryl group, valeryl group, isovaleryl group, pivaloyl group and hexanoyl group, acryloyl group, methacryloyl group or crotonoyl group. Further, examples of aromatic acyl group include an arylcarbonyl group such as a benzoyl group, α-naphthoyl group and β-naphthoyl group, halogenated arylcarbonyl group such as 2-bromobenzoyl group or 4-chlorobenzoyl group, alkylated arylcarbonyl group such as 2,4,6-trimethylbenzoyl group or 4-toluoyl group, alkoxycarbonylated arylcarbonyl group such as 2-(methoxycarbonyl)benzoyl group and arylated arylcarbonyl group such as 4-phenylbenzoyl group.

Herein, "amino group (that may be substituted with a sulfonyl group or acyl group)" means an unsubstituted amino group, or an amino group wherein 1 to 2 sulfonyl group or acyl group mentioned above which is same or different, is bound on a nitrogen atom, and examples include unsubstituted amino group, acylated amino groups such as acetylamino group, propionylamino group, butyrylamino group, valerylamino group, pivaloylamino group, hexanoylamino group, benzoylamino group or di(acetyl)amino group; sulfonylated amino groups such as methylsulfonylamino group, ethylsulfonylamino group, propylsulfonylamino group, butylsulfonylamino group, pentylsulfonylamino group, hexylsulfonylamino group, benzenesulfonylamino group, p-toluenesulfonylamino group, p-chlorobenzenesulfonylamino group, p-fluorobenzenesulfonylamino group and di(methylsulfonyl)amino group.

Herein, "haloalkyl" is an alkyl group substituted with one to the maximum number of substitutable halogen atoms, which is the same or different. Therefore, examples of "halo $C_{1-6}$ alkyl group" include a monofluoromethyl group, difluoromethyl group, trifluoromethyl group, monochloromethyl group, monobromomethyl group, monoiodomethyl group and 2,2,2-trifluoroethyl group.

Herein, "alkoxy" may be straight-chained or branched-chained alkoxy group. Therefore, examples of "$C_{1-6}$ alkoxy group" specifically include a methoxy group, ethoxy group, propoxy group, isopropoxy group, butoxy group, isobutoxy group, sec-butoxy group, tert-butoxy group, pentoxy group, isopentoxy group, neopentoxy group, hexyloxy group and isohexyloxy group.

Herein, "$C_{1-6}$ alkoxy group (that may be substituted with a $C_{1-6}$ alkoxy group)" means an unsubstituted $C_{1-6}$ alkoxy group or an $C_{1-6}$ alkoxy group substituted with a $C_{1-6}$ alkoxy group, and examples of a $C_{1-6}$ alkoxy group substituted with a $C_{1-6}$ alkoxy group include a methoxymethyloxy group, ethoxymethyloxy group and ethoxyethyloxy group.

Herein, "alkanoyloxy" means a group wherein an alkanoyl group (saturated aliphatic acyl group) is bound to an oxygen atom. Therefore, examples of "$C_{2-6}$ alkanoyloxy group" include an acetyloxy group, propionyloxy group, butyryloxy group, isobutyryloxy group, valeryloxy group, isovaleryloxy group, pivaloyloxy group and hexanoyloxy group.

Herein, "alkylthio" means a group wherein a straight-chained or branched-chained alkyl group is bound to a sulfur atom. Therefore, examples of "$C_{1-6}$ alkylthio group" include a methylthio group, ethylthio group, propylthio group, isopropylthio group, butylthio group, isobutylthio group, sec-butylthio group, tert-butylthio group, pentylthio group, isopentylthio group, neopentylthio group, hexylthio group and isohexylthio group.

Herein, "alkylsulfinyl" means a group wherein a straight-chained or branched-chained alkyl group is bound to a sulfinyl group (SO). Therefore, examples of "$C_{1-6}$ alkylsulfinyl group" include a methylsulfinyl group, ethylsulfinyl group, propylsulfinyl group, isopropylsulfinyl group, butylsulfinyl group, isobutylsulfinyl group, sec-butylsulfinyl group, tert-butylsulfinyl group, pentylsulfinyl group, isopentylsulfinyl group, neopentylsulfinyl group, hexylsulfinyl group and isohexylsulfinyl group.

Herein, "alkylsulfonyl" means a group wherein a straight-chained or branched-chained alkyl group is bound to a sulfonyl group ($SO_2$). Therefore, examples of "$C_{1-6}$ alkylsulfonyl group" include a methylsulfonyl group, ethylsulfonyl group, propylsulfonyl group, isopropylsulfonyl group, butylsulfonyl group, isobutylsulfonyl group, sec-butylsulfonyl group, tert-butylsulfonyl group, pentylsulfonyl group, isopentylsulfonyl group, neopentylsulfonyl group, hexylsulfonyl group and isohexylsulfonyl group.

Herein, "alkylene" means a divalent hydrocarbon chain having a straight-chain or branched-chain. Therefore, examples of "$C_{1-6}$ alkylene chain" include a methylene chain, ethylene chain, propylene chain, methylethylene chain, butylene chain, 1,2-dimethylethylene chain, pentylene chain, 1-methylbutylene chain, 2-methylbutylene chain and hexylene chain.

Herein, examples of "$C_{1-3}$ alkylenedioxy group" include a methylenedioxy group, ethylenedioxy group, 1,3-propylenedioxy group and 2,2-propylenedioxy group.

Herein, "alkenylene" means a divalent hydrocarbon chain having a straight-chain or branched-chain with a carbon-carbon double bond to any one or more sites on the bonds of the above alkyl chain. Therefore, examples of "$C_{2-6}$ alkenylene chain" include an ethenylene chain, propenylene chain, methylvinylene chain, butenylene chain, 1,2-dimethyl vinylene chain, pentenylene chain, 1-methylbutenylene chain, 2-methylbutenylene chain and hexenylene chain.

Herein, "—($C_{1-6}$ alkylene)-O—" means a chain wherein the above $C_{1-6}$ alkylene is bound to an oxygen atom, and examples include -(methylene)-O—, -(ethylene)-O—, -(propylene)-O—, -(butylene)-O—, -(pentylene)-O— and -(hexylene)-O—.

Herein, "—($C_{1-6}$ alkylene)-O—($C_{1-6}$ alkylene)-" means a chain wherein the above $C_{1-6}$ alkylene is bound to both ends of an oxygen atom, and examples include -(methylene)-O-(methylene)-, -(ethylene)-O-(ethylene)-, -(methylene)-O-(ethylene)-, -(ethylene)-O-(methylene)-, -(propylene)-O-(propylene)-, -(butylene)-O-(butylene)-, -(pentylene)-O-(pentylene)- and -(hexylene)-O-(hexylene)-.

Herein, "—($C_{1-6}$ alkylene)-S—" means a chain wherein the above $C_{1-6}$ alkylene is bound to a sulfur atom, and examples include -(methylene)-S—, -(ethylene)-S—, -(propylene)-S—, -(butylene)-S—, -(pentylene)-S— and -(hexylene)-S—.

In general formula (1), a saturated $C_{3-10}$ carbocyclic group of A ring is preferably a $C_{3-8}$ cycloalkyl group or $C_{4-10}$ cross-linked cyclic hydrocarbon group. $C_{3-8}$ cycloalkyl group is more preferably a cyclohexyl group, cycloheptyl group or cyclooctyl group. $C_{4-10}$ cross-linked cyclic hydrocarbon group is preferably a bicycloheptyl group (bicyclo[2.2.1]heptyl group, etc.) or tricyclodecyl group (adamantyl group, etc.).

In general formula (1), a $C_{3-8}$ cycloalkyl group of B ring is preferably a $C_{3-6}$ cycloalkyl group, and more preferably a cyclopropyl group or cyclohexyl group.

In general formula (1), a $C_{3-8}$ cycloalkenyl group of B ring is preferably a 2-cyclohexen-1-yl group.

In general formula (1), a $C_{6-14}$ aryl group of B ring is preferably a $C_{6-10}$ aryl group, and more preferably a phenyl group or naphthyl group (naphthalen-1-yl group, naphthalen-2-yl group, etc.).

In general formula (1), a 5- to 14-membered heteroaryl group of B ring is preferably a quinoxalinyl group (quinoxalin-2-yl group, etc.), benzothiophenyl group (benzothiophen-3-yl group, etc.) or pyridinyl group (pyridin-2-yl group, pyridin-3-yl group, pyridin-4-yl group, etc.).

In general formula (1), a halogen atom of $R^1$, $R^2$ and $R^3$ is preferably a fluorine atom or chlorine atom.

In general formula (1), a halogen atom of $R^6$, $R^7$ and $R^8$ is preferably a fluorine atom, chlorine atom, bromine atom or iodine atom.

In general formula (1), an amino group (that may be substituted with a sulfonyl group or acyl group) of $R^6$, $R^7$ and $R^8$ is preferably an unsubstituted amino group, acetylamino group, methylsulfonylamino group, p-fluorophenyl sulfonylamino group, or di(methylsulfonyl)amino group.

In general formula (1), a $C_{1-6}$ alkyl group of $R^6$, $R^7$ and $R^8$ is preferably a $C_{1-4}$ alkyl group, and more preferably a methyl group, ethyl group, or isopropyl group.

In general formula (1), a halo $C_{1-6}$ alkyl group of $R^6$, $R^7$ and $R^8$ is preferably a halo $C_{1-4}$ alkyl group, and more preferably a trifluoromethyl group.

In general formula (1), a $C_{1-6}$ alkoxy group (that may be substituted with a $C_{1-6}$ alkoxy group) of $R^6$, $R^7$ and $R^8$ is preferably a $C_{1-4}$ alkoxy group (that may be substituted with a $C_{1-4}$ alkoxy group), and more preferably a methoxy group and methoxymethyloxy group.

In general formula (1), a $C_{6-10}$ aryl group of $R^6$, $R^7$ and $R^8$ is preferably a phenyl group.

In general formula (1), a $C_{2-6}$ alkanoyloxy group of $R^6$, $R^7$ and $R^8$ is preferably a $C_{2-4}$ alkanoyloxy group, and more preferably an acetoxy group.

In general formula (1), a $C_{1-6}$ alkylthio group of $R^6$, $R^7$ and $R^8$ is preferably a $C_{1-4}$ alkylthio group, and more preferably a methylthio group.

In general formula (1), a $C_{1-6}$ alkyl sulfonyl group of $R^6$, $R^7$ and $R^8$ is preferably a $C_{1-4}$ alkylsulfonyl group, and more preferably a methylsulfonyl group.

In general formula (1), a $C_{1-3}$ alkylenedioxy group of $R^6$, $R^7$ and $R^8$ is preferably a methylenedioxy group or ethylenedioxy group.

In general formula (1), a $C_{1-6}$ alkylene chain of L is preferably a $C_{1-4}$ alkylene chain, and more preferably a methylene chain, ethylene chain or propylene chain.

In general formula (1), a $C_{2-6}$ alkenylene chain of L is preferably a $C_{2-4}$ alkenylene chain, and more preferably an ethenylene chain or propenylene chain.

In general formula (1), —($C_{1-6}$ alkylene)-O— of X is preferably —$CH_2$—O— or —$C(CH_3)_2$—O—.

In general formula (1), —($C_{1-6}$ alkylene)-O—($C_{1-6}$ alkylene)- of X is preferably —$CH_2$—O—$CH_2$—.

In general formula (1), —($C_{1-6}$ alkylene)-S— of X is preferably —$CH_2$—S—.

In general formula (1), $C_{1-6}$ alkylene chain of Y is preferably a $C_{1-4}$ alkylene chain, and more preferably a methylene chain.

As a 1,2-diazetidin-3-one derivative shown by general formula (1) of the present invention, a particularly preferred combination is a 1,2-diazetidin-3-one derivative, salt thereof, or their solvates wherein at least one of $R^4$ and $R^5$ is a methyl group, and L is a single bond, $C_{1-6}$ alkylene chain, $C_{1-6}$ alkenylene chain or —CO—.

As a 1,2-diazetidin-3-one derivative shown by general formula (1) of the present invention, the following compounds, pharmaceutically acceptable thereof, or their solvates are particularly preferred.

1-benzyl-4-methyl-2-(adamantan-2-yl)-1,2-diazetidin-3-one,
1-(4-chlorobenzyl)-4-methyl-2-(adamantan-2-yl)-1,2-diazetidin-3-one,
1-benzyl-4,4-dimethyl-2-(adamantan-2-yl)-1,2-diazetidin-3-one,
1-(4-chlorobenzyl)-4,4-dimethyl-2-(adamantan-2-yl)-1,2-diazetidin-3-one,
4,4-dimethyl-1-(4-methylbenzyl)-2-(adamantan-2-yl)-1,2-diazetidin-3-one,
1-(4-fluorobenzyl)-4,4-dimethyl-2-(adamantan-2-yl)-1,2-diazetidin-3-one,
1-(3,4-difluorobenzyl)-4,4-dimethyl-2-(adamantan-2-yl)-1,2-diazetidin-3-one,
1-(2,4-difluorobenzyl)-4,4-dimethyl-2-(adamantan-2-yl)-1,2-diazetidin-3-one,
1-(3,5-difluorobenzyl)-4,4-dimethyl-2-(adamantan-2-yl)-1,2-diazetidin-3-one,
1-(2,3-difluorobenzyl)-4,4-dimethyl-2-(adamantan-2-yl)-1,2-diazetidin-3-one,
1-(2,5-difluorobenzyl)-4,4-dimethyl-2-(adamantan-2-yl)-1,2-diazetidin-3-one,
1-(3-fluorobenzyl)-4,4-dimethyl-2-(adamantan-2-yl)-1,2-diazetidin-3-one,
1-(3,5-dimethoxybenzyl)-4,4-dimethyl-2-(adamantan-2-yl)-1,2-diazetidin-3-one,
1-(2-chlorobenzyl)-4,4-dimethyl-2-(adamantan-2-yl)-1,2-diazetidin-3-one,
1-(3-chlorobenzyl)-4,4-dimethyl-2-(adamantan-2-yl)-1,2-diazetidin-3-one,
4,4-dimethyl-1-(3-nitrobenzyl)-2-(adamantan-2-yl)-1,2-diazetidin-3-one,
4,4-dimethyl-1-(2-methylbenzyl)-2-(adamantan-2-yl)-1,2-diazetidin-3-one,
4,4-dimethyl-1-(4-nitrobenzyl)-2-(adamantan-2-yl)-1,2-diazetidin-3-one,
4,4-dimethyl-1-(3-methylbenzyl)-2-(adamantan-2-yl)-1,2-diazetidin-3-one,
1-(3-bromobenzyl)-4,4-dimethyl-2-(adamantan-2-yl)-1,2-diazetidin-3-one,
1-(3-iodobenzyl)-4,4-dimethyl-2-(adamantan-2-yl)-1,2-diazetidin-3-one,
4,4-dimethyl-2-(adamantan-2-yl)-1-[4-(trifluoromethyl)benzyl]-1,2-diazetidin-3-one, 1-(2,6-dichlorobenzyl)-4,4-dimethyl-2-(adamantan-2-yl)-1,2-diazetidin-3-one,
1-(2-fluorobenzyl)-4,4-dimethyl-2-(adamantan-2-yl)-1,2-diazetidin-3-one,
1-(2-bromobenzyl)-4,4-dimethyl-2-(adamantan-2-yl)-1,2-diazetidin-3-one,
1-(2-iodobenzyl)-4,4-dimethyl-2-(adamantan-2-yl)-1,2-diazetidin-3-one,
1-(2-chloro-5-fluorobenzyl)-4,4-dimethyl-2-(adamantan-2-yl)-1,2-diazetidin-3-one,
4,4-dimethyl-2-(adamantan-2-yl)-1-[2-(trifluoromethyl)benzyl]-1,2-diazetidin-3-one,
1-(2,3-dichlorobenzyl)-4,4-dimethyl-2-(adamantan-2-yl)-1,2-diazetidin-3-one,
1-(2,5-dichlorobenzyl)-4,4-dimethyl-2-(adamantan-2-yl)-1,2-diazetidin-3-one,
1-(2-chloro-4-fluorobenzyl)-4,4-dimethyl-2-(adamantan-2-yl)-1,2-diazetidin-3-one,
1-(2-chloro-6-fluorobenzyl)-4,4-dimethyl-2-(adamantan-2-yl)-1,2-diazetidin-3-one,
4,4-dimethyl-1-(2-nitrobenzyl)-2-(adamantan-2-yl)-1,2-diazetidin-3-one,
1-[4-fluoro-2-(trifluoromethyl)benzyl]-4,4-dimethyl-2-(adamantan-2-yl)-1,2-diazetidin-3-one,
1-(biphenyl-2-ylmethyl)-4,4-dimethyl-2-(adamantan-2-yl)-1,2-diazetidin-3-one,
1-(2-ethylbenzyl)-4,4-dimethyl-2-(adamantan-2-yl)-1,2-diazetidin-3-one,
1-(2-methoxybenzyl)-4,4-dimethyl-2-(adamantan-2-yl)-1,2-diazetidin-3-one,
1-(2,4-dichlorobenzyl)-4,4-dimethyl-2-(adamantan-2-yl)-1,2-diazetidin-3-one,
1-(4-bromobenzyl)-4,4-dimethyl-2-(adamantan-2-yl)-1,2-diazetidin-3-one,
1-(3-methoxybenzyl)-4,4-dimethyl-2-(adamantan-2-yl)-1,2-diazetidin-3-one,
1-(2,4-dimethylbenzyl)-4,4-dimethyl-2-(adamantan-2-yl)-1,2-diazetidin-3-one,
1-(2,5-dimethylbenzyl)-4,4-dimethyl-2-(adamantan-2-yl)-1,2-diazetidin-3-one,
1-(3-fluoro-2-methylbenzyl)-4,4-dimethyl-2-(adamantan-2-yl)-1,2-diazetidin-3-one,
1-(3)-chloro-2-fluorobenzyl)-4,4-dimethyl-2-(adamantan-2-yl)-1,2-diazetidin-3-one,
4,4-dimethyl-1-[2-(methylthio)benzyl]-2-(adamantan-2-yl)-1,2-diazetidin-3-one,
1-(1,3-benzodioxol-4-ylmethyl)-4,4-dimethyl-2-(adamantan-2-yl)-1,2-diazetidin-3-one,
4,4-dimethyl-1-(naphthalen-1-ylmethyl)-2-(adamantan-2-yl)-1,2-diazetidin-3-one,
4,4-dimethyl-1-(naphthalen-2-ylmethyl)-2-(adamantan-2-yl)-1,2-diazetidin-3-one,
trans-1-(2-chlorobenzyl)-2-(5-hydroxyadamantan-2-yl)-4,4-dimethyl-1,2-diazetidin-3-one,
trans-2-(5-hydroxyadamantan-2-yl)-4,4-dimethyl-1-[2-(trifluoromethyl)benzyl]-1,2-diazetidin-3-one,
trans-1-(2-chloro-5-fluorobenzyl)-2-(5-hydroxyadamantan-2-yl)-4,4-dimethyl-1,2-diazetidin-3-one,
1-(2-chlorobenzyl)-2-cyclohexyl-4,4-dimethyl-1,2-diazetidin-3-one,
2-cyclohexyl-1-(2,3-dichlorobenzyl)-4,4-dimethyl-1,2-diazetidin-3-one,
2-cyclohexyl-1-(2,5-dichlorobenzyl)-4,4-dimethyl-1,2-diazetidin-3-one,
1-(2-chloro-5-fluorobenzyl)-2-cyclohexyl-4,4-dimethyl-1,2-diazetidin-3-one,
1-(2-chloro-4-fluorobenzyl)-2-cyclohexyl-4,4-dimethyl-1,2-diazetidin-3-one,
1-(2-chlorobenzyl)-2-cyclo octyl-4,4-dimethyl-1,2-diazetidin-3-one,
2-cyclooctyl-1-(2,3-dichlorobenzyl)-4,4-dimethyl-1,2-diazetidin-3-one,
2-cyclooctyl-1-(2,5-dichlorobenzyl)-4,4-dimethyl-1,2-diazetidin-3-one,
1-(2-chloro-4-fluorobenzyl)-2-cyclooctyl-4,4-dimethyl-1,2-diazetidin-3-one,
1-(2-chloro-5-fluorobenzyl)-2-cyclooctyl-4,4-dimethyl-1,2-diazetidin-3-one,
2-(bicyclo[2.2.1]heptan-2-yl)-1-(2-chlorobenzyl)-4,4-dimethyl-1,2-diazetidin-3-one,
2-(bicyclo[2.2.1]heptan-2-yl)-1-(2,3-dichlorobenzyl)-4,4-dimethyl-1,2-diazetidin-3-one,
2-(bicyclo[2.2.1]heptan-2-yl)-1-(2,5-dichlorobenzyl)-4,4-dimethyl-1,2-diazetidin-3-one,
2-(bicyclo[2.2.1]heptan-2-yl)-1-(2-chloro-4-fluorobenzyl)-4,4-dimethyl-1,2-diazetidin-3-one,
2-(bicyclo[2.2.1]heptan-2-yl)-1-(2-chloro-5-fluorobenzyl)-4,4-dimethyl-1,2-diazetidin-3-one,
1-(2-chlorobenzyl)-2-cycloheptyl-4,4-dimethyl-1,2-diazetidin-3-one,
2-cycloheptyl-1-(2,3-dichlorobenzyl)-4,4-dimethyl-1,2-diazetidin-3-one,
2-cycloheptyl-1-(2,5-dichlorobenzyl)-4,4-dimethyl-1,2-diazetidin-3-one,
1-(2-chloro-4-fluorobenzyl)-2-cycloheptyl-4,4-dimethyl-1,2-diazetidin-3-one,
1-(2-chloro-5-fluorobenzyl)-2-cycloheptyl-4,4-dimethyl-1,2-diazetidin-3-one,
1-(cyclohexa-2-en-1-yl)-4,4-dimethyl-2-(adamantan-2-yl)-1,2-diazetidin-3-one,
1-cyclohexyl-4,4-dimethyl-2-(adamantan-2-yl)-1,2-diazetidin-3-one,
4-[2-(2-chlorobenzyl)-3,3-dimethyl-4-oxo-1,2-diazetidin-1-yl]adamantane-1-carboxamide,
4,4-dimethyl-1-(phenylcarbonyl)-2-(adamantan-2-yl)-1,2-diazetidin-3-one,
4,4-dimethyl-2-(adamantan-2-yl)-1-{[2-(trifluoromethyl)phenyl]carbonyl}-1,2-diazetidin-3-one,
1-[(4-bromophenyl)carbonyl]-4,4-dimethyl-2-(adamantan-2-yl)-1,2-diazetidin-3-one,
4,4-dimethyl-1-[(3-methylphenyl)carbonyl]-2-(adamantan-2-yl)-1,2-diazetidin-3-one,
1-[(3-bromophenyl)carbonyl]-4,4-dimethyl-2-(adamantan-2-yl)-1,2-diazetidin-3-one,
4,4-dimethyl-1-[(4-methylphenyl)carbonyl]-2-(adamantan-2-yl)-1,2-diazetidin-3-one,
4,4-dimethyl-1-[(2-methylphenyl)carbonyl]-2-(adamantan-2-yl)-1,2-diazetidin-3-one,
1-[(3,5-dichlorophenyl)carbonyl]-4,4-dimethyl-2-(adamantan-2-yl)-1,2-diazetidin-3-one,
1-[(2-fluorophenyl)carbonyl]-4,4-dimethyl-2-(adamantan-2-yl)-1,2-diazetidin-3-one,
1-[(2-bromophenyl)carbonyl]-4,4-dimethyl-2-(adamantan-2-yl)-1,2-diazetidin-3-one,
1-[(2-iodophenyl)carbonyl]-4,4-dimethyl-2-(adamantan-2-yl)-1,2-diazetidin-3-one,
1-[(2,5-dichlorophenyl)carbonyl]-4,4-dimethyl-2-(adamantan-2-yl)-1,2-diazetidin-3-one,
1-[(5-fluoro-2-methylphenyl)carbonyl]-4,4-dimethyl-2-(adamantan-2-yl)-1,2-diazetidin-3-one,
1-[(2-ethylphenyl)carbonyl]-4,4-dimethyl-2-(adamantan-2-yl)-1,2-diazetidin-3-one, 1-[(3-chlorophenyl)carbonyl]-4,4-dimethyl-2-(adamantan-2-yl)-1,2-diazetidin-3-one,
1-[(4-fluoro-2-trifluoromethylphenyl)carbonyl]-4,4-dimethyl-2-(adamantan-2-yl)-1,2-diazetidin-3-one,
1-(1,3-benzodioxol-5-ylcarbonyl)-4,4-dimethyl-2-(adamantan-2-yl)-1,2-diazetidin-3-one,
1-[(2-aminophenyl)carbonyl]-4,4-dimethyl-2-(adamantan-2-yl)-1,2-diazetidin-3-one,
1-[(2-hydroxyphenyl)carbonyl]-4,4-dimethyl-2-(adamantan-2-yl)-1,2-diazetidin-3-one,
1-[(4-aminophenyl)carbonyl]-4,4-dimethyl-2-(adamantan-2-yl)-1,2-diazetidin-3-one,
4,4-dimethyl-1-(naphthalen-1-ylcarbonyl)-2-(adamantan-2-yl)-1,2-diazetidin-3-one,
2-cyclohexyl-1-[(2,5-dimethylphenyl)carbonyl]-4,4-dimethyl-1,2-diazetidin-3-one,
1-[(3-chlorophenyl)carbonyl]-2-cyclooctyl-4,4-dimethyl-1,2-diazetidin-3-one,
2-cyclooctyl-4,4-dimethyl-1-[(3-methylphenyl)carbonyl]-1,2-diazetidin-3-one,
2-cyclooctyl-4,4-dimethyl-1-[(2-methylphenyl)carbonyl]-1,2-diazetidin-3-one,
1-[(2-aminophenyl)carbonyl]-2-cyclooctyl-4,4-dimethyl-1,2-diazetidin-3-one,
2-cyclooctyl-4,4-dimethyl-1-(naphthalen-1-ylcarbonyl)-1,2-diazetidin-3-one,
1-[(3-fluoro-2-methylphenyl)carbonyl]-4,4-dimethyl-2-(adamantan-2-yl)-1,2-diazetidin-3-one,
1-[(2,4-dimethylphenyl)carbonyl]-4,4-dimethyl-2-(adamantan-2-yl)-1,2-diazetidin-3-one,
1-[(2,5-dimethylphenyl)carbonyl]-4,4-dimethyl-2-(adamantan-2-yl)-1,2-diazetidin-3-one,
1-[(2-bromo-5-chlorophenyl)carbonyl]-4,4-dimethyl-2-(adamantan-2-yl)-1,2-diazetidin-3-one,
4,4-dimethyl-1-{[2-(methylthio)phenyl]carbonyl}-2-(adamantan-2-yl)-1,2-diazetidin-3-one,
2-cyclooctyl-4,4-dimethyl-1-{[2-(methylthio)phenyl]carbonyl}-1,2-diazetidin-3-one,
4,4-dimethyl-1-phenyl-2-(adamantan-2-yl)-1,2-diazetidin-3-one,
1-(4-aminophenyl)-4,4-dimethyl-2-(adamantan-2-yl)-1,2-diazetidin-3-one,
4,4-dimethyl-1-(2-nitrophenyl)-2-(adamantan-2-yl)-1,2-diazetidin-3-one,
1-(2-chlorophenyl)-4,4-dimethyl-2-(adamantan-2-yl)-1,2-diazetidin-3-one,
1-(3-chlorophenyl)-4,4-dimethyl-2-(adamantan-2-yl)-1,2-diazetidin-3-one,
4,4-dimethyl-1-(2-methylphenyl)-2-(adamantan-2-yl)-1,2-diazetidin-3-one,
4,4-dimethyl-1-(3-methylphenyl)-2-(adamantan-2-yl)-1,2-diazetidin-3-one,
1-(3,5-difluorophenyl)-4,4-dimethyl-2-(adamantan-2-yl)-1,2-diazetidin-3-one,
1-(1,3-benzodioxol-5-yl)-4,4-dimethyl-2-(adamantan-2-yl)-1,2-diazetidin-3-one,
1-(3-fluorophenyl)-4,4-dimethyl-2-(adamantan-2-yl)-1,2-diazetidin-3-one,
1-(4-fluorophenyl)-4,4-dimethyl-2-(adamantan-2-yl)-1,2-diazetidin-3-one,
1-(3,5-dichlorophenyl)-4,4-dimethyl-2-(adamantyl)-1,2-diazetidin-3-one,
1-(4-methoxyphenyl)-4,4-dimethyl-2-(adamantan-2-yl)-1,2-diazetidin-3-one,
1-(3-methoxyphenyl)-4,4-dimethyl-2-(adamantan-2-yl)-1,2-diazetidin-3-one,
1-(2-methoxyphenyl)-4,4-dimethyl-2-(adamantan-2-yl)-1,2-diazetidin-3-one,
1-(2,3-dichlorophenyl)-4,4-dimethyl-2-(adamantan-2-yl)-1,2-diazetidin-3-one,
1-(2,3-dimethylphenyl)-4,4-dimethyl-2-(adamantan-2-yl)-1,2-diazetidin-3-one,
1-(2,4-dichlorophenyl)-4,4-dimethyl-2-(adamantan-2-yl)-1,2-diazetidin-3-one,
1-(2,5-dichlorophenyl)-4,4-dimethyl-2-(adamantan-2-yl)-1,2-diazetidin-3-one,
1-(1-benzothiophen-3-yl)-4,4-dimethyl-2-(adamantan-2-yl)-1,2-diazetidin-3-one,
4,4-dimethyl-1-(naphthalen-1-yl)-2-(adamantan-2-yl)-1,2-diazetidin-3-one,
1-[4-(methoxymethoxy)phenyl]-4,4-dimethyl-2-(adamantan-2-yl)-1,2-diazetidin-3-one,
4,4-dimethyl-1-(4-hydroxyphenyl)-2-(adamantan-2-yl)-1,2-diazetidin-3-one,
1-[3-(methoxymethoxy)phenyl]-4,4-dimethyl-2-(adamantan-2-yl)-1,2-diazetidin-3-one,
1-[2-(methoxymethoxy)phenyl]-4,4-dimethyl-2-(adamantan-2-yl)-1,2-diazetidin-3-one,
1-(2-hydroxyphenyl)-4,4-dimethyl-2-(adamantan-2-yl)-1,2-diazetidin-3-one,
2-cyclooctyl-1-(2-methoxyphenyl)-4,4-dimethyl-1,2-diazetidin-3-one,
2-cyclooctyl-1-(2,3-dichlorophenyl)-4,4-dimethyl-1,2-diazetidin-3-one,
2-cyclooctyl-4,4-dimethyl-1-(naphthalen-1-yl)-1,2-diazetidin-3-one,
2-(bicyclo[2.2.1]heptan-2-yl)-1-(2-methoxyphenyl)-4,4-dimethyl-1,2-diazetidin-3-one,
2-(bicyclo[2.2.1]heptan-2-yl)-1-(2,3-dichlorophenyl)-4,4-dimethyl-1,2-diazetidin-3-one,
2-(bicyclo[2.2.1]heptan-2-yl)-4,4-dimethyl-1-(naphthalen-1-yl)-1,2-diazetidin-3-one,
trans-2-(5-hydroxyadamantan-2-yl)-4,4-dimethyl-1-phenyl-1,2-diazetidin-3-one,
trans-1-(2-chlorophenyl)-2-(5-hydroxyadamantan-2-yl)-4,4-dimethyl-1,2-diazetidin-3-one,
trans-2-(5-hydroxyadamantan-2-yl)-1-(4-methoxyphenyl)-4,4-dimethyl-1,2-diazetidin-3-one,
trans-1-(2,3-dichlorophenyl)-2-(5-hydroxyadamantan-2-yl)-4,4-dimethyl-1,2-diazetidin-3-one,
trans-1-(2-hydroxyphenyl)-2-(5-hydroxyadamantan-2-yl)-4,4-dimethyl-1,2-diazetidin-3-one,
trans-1-(4-aminophenyl)-2-(5-hydroxyadamantan-2-yl)-4,4-dimethyl-1,2-diazetidin-3-one,
trans-2-(5-hydroxyadamantan-2-yl)-4,4-dimethyl-1-(naphthalen-1-yl)-1,2-diazetidin-3-one,
trans-1-(4-fluoronaphthalen-1-yl)-2-(5-hydroxyadamantan-2-yl)-4,4-dimethyl-1,2-diazetidin-3-one,
cis-2-(5-hydroxyadamantan-2-yl)-1-(4-methoxyphenyl)-4,4-dimethyl-1,2-diazetidin-3-one,
cis-2-(5-hydroxyadamantan-2-yl)-4,4-dimethyl-1-(2-methylphenyl)-1,2-diazetidin-3-one,
cis-1-(2-hydroxyphenyl)-2-(5-hydroxyadamantan-2-yl)-4,4-dimethyl-1,2-diazetidin-3-one,
cis-1-(4-aminophenyl)-2-(5-hydroxyadamantan-2-yl)-4,4-dimethyl-1,2-diazetidin-3-one,
cis-2-(5-hydroxyadamantan-2-yl)-4,4-dimethyl-1-(naphthalen-1-yl)-1,2-diazetidin-3-one,
cis-2-(5-hydroxyadamantan-2-yl)-4,4-dimethyl-1-(naphthalen-2-yl)-1,2-diazetidin-3-one,
cis-1-(4-fluoronaphthalen-1-yl)-2-(5-hydroxyadamantan-2-yl)-4,4-dimethyl-1,2-diazetidin-3-one, trans-2-(5-chloroadamantan-2-yl)-1-(2-methoxyphenyl)-4,4-dimethyl-1,2-diazetidin-3-one,
trans-2-(5-chloroadamantan-2-yl)-1-(2,3-dichlorophenyl)-4,4-dimethyl-1,2-diazetidin-3-one,
trans-2-(5-chloroadamantan-2-yl)-1-[2-(methoxymethoxy)phenyl]-4,4-dimethyl-1,2-diazetidin-3-one,
trans-2-(5-chloroadamantan-2-yl)-1-(2-hydroxyphenyl)-4,4-dimethyl-1,2-diazetidin-3-one,
trans-2-(5-chloroadamantan-2-yl)-4,4-dimethyl-1-(naphthalen-1-yl)-1,2-diazetidin-3-one,
trans-2-(5-chloroadamantan-2-yl)-1-(4-fluoronaphthalen-1-yl)-4,4-dimethyl-1,2-diazetidin-3-one,
cis-2-(5-chloroadamantan-2-yl)-1-(2,3-dichlorophenyl)-4,4-dimethyl-1,2-diazetidin-3-one,
cis-2-(5-chloroadamantan-2-yl)-4,4-dimethyl-1-(naphthalen-1-yl)-1,2-diazetidin-3-one,
1-(1,3-benzodioxol-4-yl)-4,4-dimethyl-2-(adamantan-2-yl)-1,2-diazetidin-3-one,
4,4-dimethyl-1-(3-phenylpropyl)-2-(adamantan-2-yl)-1,2-diazetidin-3-one,
4,4-dimethyl-1-[(E)-2-phenylethenyl]-2-(adamantan-2-yl)-1,2-diazetidin-3-one,
4,4-dimethyl-1-(2-phenylethyl)-2-(adamantan-2-yl)-1,2-diazetidin-3-one,
trans-4-[2-(naphthalen-1-yl)-3,3-dimethyl-4-oxo-1,2-diazetidin-1-yl]adamantane-1-carboxylic acid,
trans-4-[2-(naphthalen-1-yl)-3,3-dimethyl-4-oxo-1,2-diazetidin-1-yl]adamantane-1-carboxamide,
cis-4-[2-(naphthalen-1-yl)-3,3-dimethyl-4-oxo-1,2-diazetidin-1-yl]adamantane-1-carboxylic acid,
cis-4-[2-(naphthalen-1-yl)-3,3-dimethyl-4-oxo-1,2-diazetidin-1-yl]adamantane-1-carboxamide,
trans-4-[2-(2,3-dichlorophenyl)-3,3-dimethyl-4-oxo-1,2-diazetidin-1-yl]adamantane-1-carboxamide, or
cis-4-[2-(2,3-dichlorophenyl)-3,3-dimethyl-4-oxo-1,2-diazetidin-1-yl]adamantane-1-carboxamide.

When an asymmetric carbon atom is present in the 1,2-diazetidin-3-one derivative shown by general formula (1) of the present invention, there exists an optical isomer, and the present invention encompasses all those optical isomers or any mixtures comprising racemate and the like.

The present invention also encompasses various hydrates or solvates of the 1,2-diazetidin-3-one derivative shown by general formula (1) or pharmaceutically acceptable acid-addition salt thereof, and a crystal polymorphic substance of the same.

Examples of pharmaceutically acceptable salt of the 1,2-diazetidin-3-one derivative shown by general formula (1) specifically include acid-addition salt treated with an inorganic acid (for example, a hydrochloric acid, hydrobromic acid, hydroiodic acid, sulfuric acid, nitric acid and phosphoric acid) or an organic acid (for example, a formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, p-toluenesulfonic acid, asparaginic acid and glutamic acid), and base-addition salt and the like treated with inorganic bases (alkali metals such as sodium and potassium; alkaline earth metals such as calcium and magnesium), or organic bases (trialkylamine).

Examples of solvates of the 1,2-diazetidin-3-one derivative shown by general formula (1) or pharmaceutically acceptable salt thereof include hydrates or various solvates (for example, a solvate with alcohol such as ethanol).

Preparation Method of a 1,2-diazetidin-3-one Derivative Represented by Formula (1), Salt thereof, or Their Solvate The 1,2-diazetidin-3-one derivative represented by the general formula (1), salt thereof, or their solvate of the present invention can be prepared by the following method or similar method.

1. Preparation Method of the Compound Represented by Formula (1), Salt thereof, or Their Solvate By reacting cyclic amines represented by general formula (II) and a reactive derivative represented by general formula (III), a 1,2-diazetidin-3-one derivative (I) of interest can be prepared.

The reaction path is shown by the following chemical formula.

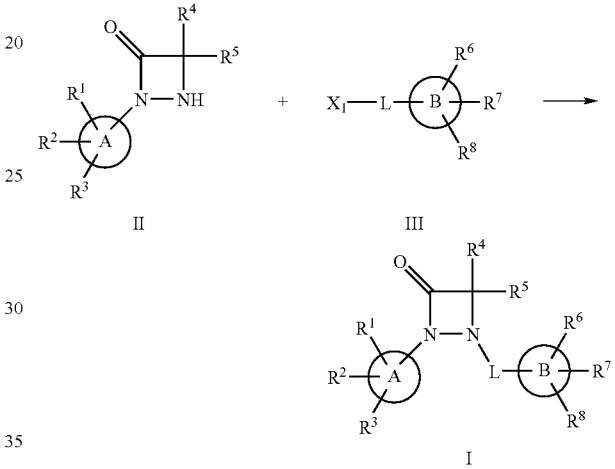

(wherein $R^1$, $R^2$, $R^3$, $R^4$, $R^5$, $R^6$, $R^7$, $R^8$, A ring, B ring and L show the same things as they show in the above, $X^1$ represents a hydroxyl group, formyl group or halogen atom)

The reaction of a reactive derivative (III) wherein L is a $C_{1-6}$ alkylene chain or $C_{1-6}$ alkenylene chain and $X^1$ is a halogen atom and a cyclic amine compound (II) can be conducted in a solvent, in the presence of a base. A solvent is not particularly limited, and for example, the followings can be used independently or in combination: 1,2-dichloroethane, chloroform, dichloromethane, ethyl acetate, isopropyl acetate, toluene, benzene, tetrahydrofuran, dioxane, acetonitrile, propionitrile and N,N-dimethylformamide. A base is not particularly limited, and for example, the followings can be used independently or in combination: organic bases such as pyridine, N,N-dimethylaminopyridine (DMAP), collidine, lutidine, 1,8-diazabicyclo[5.4.0]undecene (DBU), 1,5-diazabicyclo[4,3,0]nonene (DBN), 1,4-diazabicyclo[2.2.2]octane (DABCO), triethylamine, 2,6-di-t-butylpyridine, diisopropylethylamine, diisopropylpentylamine, N-methylmorpholine and trimethylamine; alkali metal hydrides such as lithium hydride, sodium hydride and potassium hydride; alkali metal hydroxides such as lithium hydroxide, sodium hydroxide and potassium hydroxide; alkali metal carbonates such as lithium carbonate, sodium carbonate, potassium carbonate and cesium carbonate; alkali metal bicarbonates such as sodium hydrogen carbonate and potassium hydrogen carbonate; lithium diisopropylamide, sodium diisopropylamide, potassium diisopropylamide, lithium hexamethyldisilazide, sodium hexamethyldisilazide, potassium hexamethyldisilazide, t-butoxysodium, t-butoxypotassium, n-butyllithium, s-butyllithium and t-butyllithium. The reaction condition varies depending on the materials used, but generally, the 1,2-diazetidin-3-one derivative (I) of interest is obtained by conducting the reaction at −20 to 150° C., preferably at 0 to 100° C. for 5 minutes to 48 hours, preferably for 2 hours to 24 hours. Further, the 1,2-diazetidin-3-one derivative (I) wherein L is a $C_{1-6}$ alkenylene chain can be also obtained by a technique of reductive amination of a cyclic amine compound (II), with an aldehyde derivative having a corresponding skeleton. Further, when L is a $C_{1-6}$ alkenylene chain, it can be converted to a corresponding $C_{1-6}$ alkylene chain by using a general catalytic hydrogenation reaction.

The reaction of a reactive derivative (III) wherein L is —CO—X— (with the proviso that X is a single bond, —($C_{1-6}$ alkylene)-O—, —($C_{1-6}$ alkylene)-O—($C_{1-6}$ alkylene)- or —($C_{1-6}$ alkylene)-S—), and $X^1$ is a halogen atom and a cyclic amine compound (II) can be conducted in a solvent, in the presence of a base. A solvent is not particularly limited, and for example, the followings can be used independently or in combination: tetrahydrofuran, toluene, dioxane, N,N-dimethylformamide, N-methylpyrrolidone, dichloromethane, chloroform, acetonitrile and propionitrile. A base is not particularly limited, and for example, the followings can be used independently or in combination: organic bases such as pyridine, DMAP, collidine, lutidine, DBU, DBN, DABCO, triethylamine, diisopropylethylamine, diisopropylpentylamine and trimethylamine; alkali metal hydrides such as lithium hydride, sodium hydride and potassium hydride; alkali metal hydroxides such as lithium hydroxide, sodium hydroxide and potassium hydroxide; alkali metal carbonates such as lithium carbonate, sodium carbonate, potassium carbonate and cesium carbonate. The reaction condition varies depending on the materials used, but generally, a 1,2-diazetidin-3-one derivative (I) of interest is obtained by conducting the reaction at −20 to 100° C., preferably at 15 to 80° C. for 5 minutes to 24 hours, preferably for 1 hour to 12 hours.

The reaction of a reactive derivative (III) wherein L is —CO—X— (with the proviso that X is a single bond, —($C_{1-6}$ alkylene)-O—, —($C_{1-6}$ alkylene)-O—($C_{1-6}$ alkylene)- or —($C_{1-6}$ alkylene)-S—) and $X^1$ is a hydroxyl group and a cyclic amine compound (II) can be conducted in a solvent, in the presence or absence of a base, in the presence or absence of a condensation accelerator using a condensation agent. A solvent is not particularly limited, and for example, the followings can be used: 1,2-dichloroethane, chloroform, dichloromethane, ethyl acetate, isopropyl acetate, toluene, benzene, tetrahydrofuran, dioxane, acetonitrile, propionitrile, N,N-dimethylformamide and N-methylpyrrolidone. A base is not particularly limited, and for example, the followings can be used: organic bases such as pyridine, DMAP, collidine, lutidine, DBU, DBN, DABCO, triethylamine, diisopropylethylamine, diisopropylpentylamine and trimethylamine; alkali metal hydrides such as lithium hydride, sodium hydride and potassium hydride; alkali metal hydroxides such as lithium hydroxide, sodium hydroxide and potassium hydroxide; alkali metal carbonates such as lithium carbonate, sodium carbonate, potassium carbonate and cesium carbonate; alkali metal bicarbonates such as sodium hydrogen carbonate and potassium hydrogen carbonate. A condensation accelerator is not particularly limited, and for example, the followings can be used: DMAP, 1-hydroxy-7-azabenzotriazole (HOAt), 1-hydroxybenzotriazole (HOBt), 3-hydroxy-3,4-dihydro-4-oxo-1,2,3-benzotriazole (HODhbt), N-hydroxy-5-norbornene-2,3-dicarboxyimide (HONB), pentafluorophenol (HOPfp), N-hydroxyphthalimide (HOPht) and N-hydroxysuccinimide (HOSu). A condensation agent is not particularly limited, and for example, the followings can be used: N,N'-dicyclohexylcarbodiimide (DCC), N,N'-diisopropylcarbodiimide (DIPCI), 1-ethyl-3-(3-dimethylaminopropyl) carbodiimide (WSCI), 1-ethyl-3-(3-dimethylaminopropyl) carbodiimide hydrochloride (WSC.HCl), diethyl cyanophosphate (DEPC), benzotriazol-1-yloxy-tris(dimethylamino)phosphonium hexafluorophosphate (BOP), benzotriazol-1-yloxy-tris(pyrrolidinylamino)phosphonium hexafluorophosphate (PyBOP) and 2-(1H-benzotriazol-1-yl)-1,1,3,3-tetramethyluronium tetrafluoroborate (TBTU). The reaction condition varies depending on the materials used, but generally, a 1,2-diazetidin-3-one derivative (I) of interest is obtained by conducting the reaction at −20 to 100° C., preferably at 0 to 40° C. for 5 minutes to 30 hours, preferably for 2 hours to 20 hours. Further, the carboxylic acid derivative (III) used herein, can be reacted with a cyclic amine compound (II) after inducing to an acid halide.

The reaction of a reactive derivative (III) wherein L is —$SO_2$—Y— and $X^1$ is a halogen atom and a cyclic amine compound (II) can be conducted in a solvent, in the presence of a base. A solvent is not particularly limited, and for example, the followings can be used independently or in combination: tetrahydrofuran, toluene, dioxane, N,N-dimethylformamide, N-methylpyrrolidone, dichloromethane, chloroform, acetonitrile and propionitrile. A base is not particularly limited, and for example, the followings can be used independently or in combination: organic bases such as pyridine, DMAP, collidine, lutidine, DBU, DBN, DABCO, triethylamine, diisopropylethylamine, diisopropylpentylamine and trimethylamine; alkali metal hydrides such as lithium hydride, sodium hydride and potassium hydride; alkali metal hydroxides such as lithium hydroxide, sodium hydroxide and potassium hydroxide; alkali metal carbonates such as lithium carbonate, sodium carbonate, potassium carbonate and cesium carbonate. The reaction condition varies depending on the materials used, but generally, a 1,2-diazetidin-3-one derivative (I) of interest is obtained by conducting the reaction at −20 to 100° C., preferably at 15 to 80° C. for 5 minutes to 24 hours, preferably for 5 hours to 12 hours.

The reaction of a reactive derivative (III) wherein L is a single bond and $X^1$ is a halogen atom and a cyclic amine compound (II) can be conducted in a solvent, in the presence or absence of a base, by applying a reaction technique of aryl halide and amines conducted in the presence of a metal catalyst. At that time, microwave irradiation can be carried out. A solvent is not particularly limited, and for example, the followings can be used independently or in combination: tetrahydrofuran, toluene, dioxane, N,N-dimethylformamide, N-methylpyrrolidone and water. A base is not particularly limited, and for example, the followings can be used: alkali metal hydrides such as lithium hydride, sodium hydride and potassium hydride; alkali metals such as metal lithium, metal sodium and metal potassium; alkali metal hydroxides such as lithium hydroxide, sodium hydroxide and potassium hydroxide; alkali metal carbonates such as lithium carbonate, sodium carbonate, potassium carbonate and cesium carbonate; lithium diisopropylamide, sodium diisopropylamide, potassium diisopropylamide, lithium hexamethyldisilazide, sodium hexamethyldisilazide, potassium hexamethyldisilazide, t-butoxysodium, t-butoxypotassium, n-butyllithium, s-butyllithium and t-butyllithium. As a metal catalyst, for example, palladium acetate (II), tris(dibenzylideneacetone) dipalladium (0), tris(dibenzylideneacetone)(chloroform)dipalladium (0), [1,1'-bis(diphenylphosphino)ferrocene] dichloropalladium (II), tetrakis(triphenylphosphine) palladium can be used independently, but ligands such as (2-biphenyl)di-t-butylphosphine and (2-biphenyl)dicyclohexylphosphine, trimethylphosphine, tri-t-butylphosphine can be used in combination. The reaction condition varies depending on the materials used, but generally, an intended substance is obtained by conducting the reaction at 0 to 180° C., preferably at 80 to 160° C. for 5 minutes to 72 hours, preferably for 10 minutes to 24 hours. When irradiating microwave, a 1,2-diazetidin-3-one derivative (I) of interest is obtained by conducting the reaction at 0 to 180° C., preferably at 80 to 120° C. for 1 minute to 12 hours, preferably for 1 minute to 2 hours.

Meanwhile, when $R^1$, $R^2$, $R^3$, $R^6$, $R^7$ and $R^8$ are hydroxyl group or amino group, each substituent thereof can be protected and deprotected with a commonly used protective group. Further, each hydroxyl group and amino group can be modified with the commonly used acylation and sulfonylation condition. When $R^6$, $R^7$ and $R^8$ are a nitro group, it can be converted into an amino group by using a general reduction reaction of a nitro group. Further, when $R^6$, $R^7$ and $R^8$ are a $C_{1-6}$ alkylthio group, the corresponding sulfur atom can be oxidized by using a general oxidation reaction of a sulfur atom.

2. Preparation Method of a Compound Represented by Formula (II) or Salt Thereof, or Their Solvate A cyclic amine compound (II) used in the above preparation method can be prepared by a method known in a reference, or similar method, for example according to the following reaction formula.

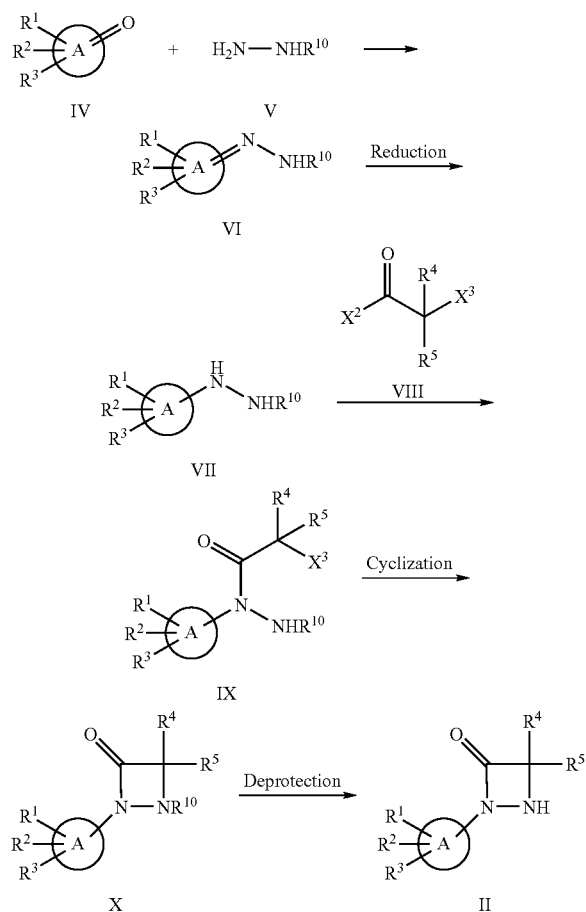

(wherein $R^1$, $R^2$, $R^3$, $R^4$, $R^5$ and A ring show the same things as they show in the above, $R^{10}$ is a protective group of an amino group, and $X^2$ and $X^3$ represent a halogen atom)

The reaction of a carbonyl compound (IV) and a hydrazine derivative (V) can be conducted in a solvent, in the presence or absence of an acid catalyst. A solvent is not particularly limited, and for example, the followings can be used independently or in combination: tetrahydrofuran, toluene, acetonitrile, methanol and ethanol. An acid catalyst is not particularly limited, and for example, the followings can be used: toluenesulfonic acid, aluminum trichloride, titanium tetrachloride, titanium tetraisopropoxide, scandium triflate and ytterbium triflate. The reaction condition varies depending on the materials used, but generally, an imine derivative (VI) is obtained by conducting the reaction at 0 to 150° C., preferably at 15 to 90° C. for 5 minutes to 24 hours, preferably for 30 minutes to 15 hours.

The reduction reaction of the compound obtained by the above method, imine derivative (VI), can be conducted in a solvent, in the presence of a reductant. A reductant is not particularly limited, and for example, sodium borohydride, sodium cyanoborohydride, sodium triacetoxyborohydride, lithium aluminium hydride, diborane and diisobutylaluminium hydride can be used. A solvent is not particularly limited, and for example, the followings can be used independently or in combination: tetrahydrofuran, diethylether, dioxane, toluene, dichloromethane, methanol and ethanol. Further, an acid can be used as an additive. An acid used is not particularly limited, and for example, acetic acid, toluenesulfonic acid, aluminium trichloride, titanium tetrachloride, titanium tetraisopropoxide, scandium triflate and ytterbium triflate can be used. The reaction condition varies depending on the materials used, but generally, a hydrazine derivative (VII) is obtained by conducting the reaction at −20 to 150° C., preferably at 15 to 60° C. for 5 minutes to 24 hours, preferably for 30 minutes to 15 hours.

The condensation reaction of the hydrazine derivative (VII) obtained by the above method and a reactive derivative (VIII) can be conducted in a solvent, in the presence or absence of a base. A solvent is not particularly limited, and for example, the followings can be used independently or in combination: tetrahydrofuran, toluene, dioxane, N,N-dimethylformamide, N-methylpyrrolidone, dichloromethane, chloroform, acetonitrile and propionitrile. A base is not particularly limited, and for example, the followings can be used independently or in combination: organic bases such as pyridine, DMAP, collidine, lutidine, DBU, DBN, DABCO, triethylamine, diisopropylethylamine, diisopropylpentylamine and trimethylamine; alkali metal hydrides such as lithium hydride, sodium hydride and potassium hydride; alkali metal hydroxides such as lithium hydroxide, sodium hydroxide and potassium hydroxide; alkali metal carbonates such as lithium carbonate, sodium carbonate, potassium carbonate and cesium carbonate; and sodium hydrogen carbonate. The reaction condition varies depending on the materials used, but generally, an amide derivative (IX) is obtained by conducting the reaction at −20 to 100° C., preferably at 15 to 80° C. for 5 minutes to 24 hours, preferably for 1 hour to 12 hours.

The cyclization reaction of an amide derivative (IX) obtained by the above method can be conducted in a solvent, in the presence of a base or acid. A solvent is not particularly limited, and for example, the followings can be used independently or in combination: tetrahydrofuran, toluene, dioxane, N,N-dimethylformamide, N-methylpyrrolidone, dichloromethane and acetonitrile. A base is not particularly limited, and for example, the followings can be used: alkali metal hydrides such as lithium hydride, sodium hydride and potassium hydride; alkali metal hydroxides such as lithium hydroxide, sodium hydroxide and potassium hydroxide; alkali metal carbonates such as lithium carbonate, sodium carbonate, potassium carbonate and cesium carbonate; sodium hydrogen carbonate, lithium diisopropylamide, sodium diisopropylamide, potassium diisopropylamide, lithium hexamethyldisilazide, sodium hexamethyldisilazide, potassium hexamethyldisilazide, t-butoxysodium, t-butoxypotassium, n-butyllithium, s-butyllithium and t-butyllithium. An acid is not particularly limited, and the followings can be used: hydrochloric acid, sulfuric acid, acetic acid, trifluoroacetic acid and p-toluenesulfonic acid. The reaction condition varies depending on the materials used, but generally, a cyclic compound (X) is obtained by conducting the reaction at −20 to 100° C., preferably at 0 to 80° C. for 5 minutes to 24 hours, preferably for 30 minutes to 12 hours.

The deprotection of the protective group $R^{10}$ of a cyclic compound (X) obtained by the above method is not particularly limited, but it can be conducted by referring to a method generally used as a deprotection condition of the protective group (Protective Groups in Organic Synthesis Third Edition, John Wiley & Sons, Inc.). The protective group is not particularly limited, and for example, the followings can be used: benzyl group, 9-fluorenylmethyloxycarbonyl group (Fmoc group), 2,2,2-trichloroethyloxycarbonyl group (Troc group), 2-trimethylsilylethyloxycarbonyl group (Teoc group), t-butyloxycarbonyl group (Boc group), allyloxycarbonyl group (Alloc group), vinyloxycarbonyl group, benzyloxycarbonyl group (Cbz group), p-methoxybenzyloxycarbonyl group, p-nitrobenzyloxycarbonyl group, allyl group, [2-(trimethylsilyl)ethoxy]methyl group (SEM group), 4-methoxybenzyl group, triphenylmethyl group, benzenesulfonyl group and o-nitrobenzenesulfonyl group. Among these, particularly, Fmoc group, Boc group and Cbz group are preferred.

A commercially available reagent may be used for the above compound (IV). Examples of the commercially available reagent include 2-adamantanone, 5-hydroxy-2-adamantanone, 5-chloro-2-adamantanone, cyclohexanone, cycloheptanone and cyclooctanone, bicyclo[2.2.1]heptan-2-one, but it is not limited to these.

The above compound (IV) can be prepared by a known method. For example, when A is an adamantane ring and any one of $R^1$, $R^2$ and $R^3$ is a methoxycarbonyl group, it may be referred to the method described in US Patent Publication No. US2006/0148871.

Further, a compound shown by formula (XI) among the compounds (I) can also be prepared by the following method, but it is not limited to this method.

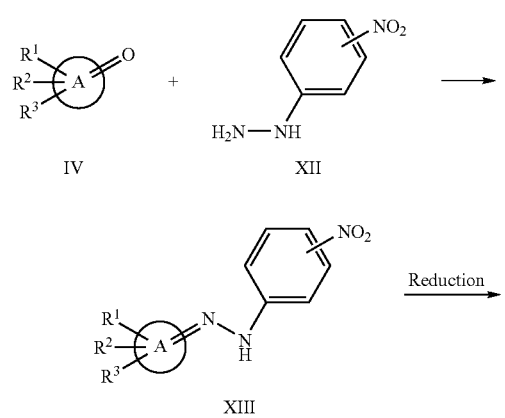

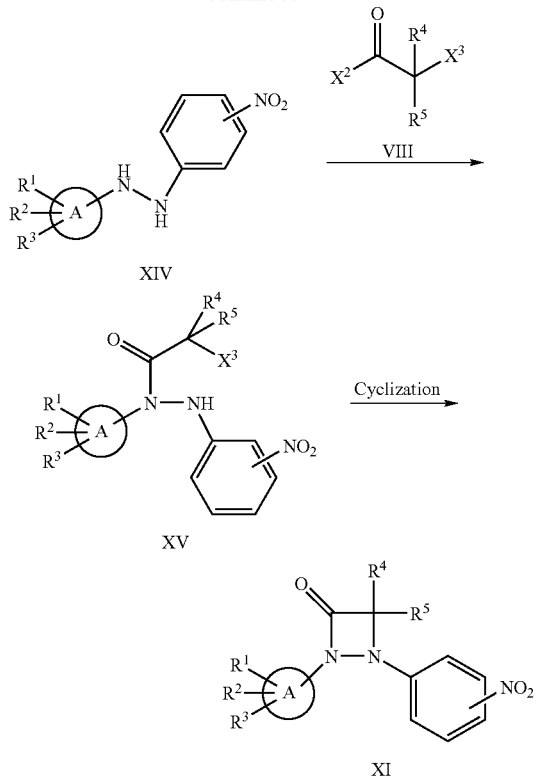

(wherein $R^1$, $R^2$, $R^3$, $R^4$, $R^5$ and A ring show the same things as they show in the above, and $X^2$ and $X^3$ represent a halogen atom)

The reaction of a carbonyl compound (IV) and hydrazine derivative (XII) can be conducted in a solvent, in the presence or absence of an acid catalyst. A solvent is not particularly limited, and for example, the followings can be used independently or in combination: tetrahydrofuran, toluene, acetonitrile, methanol and ethanol. An acid catalyst is not particularly limited, and for example, the followings can be used: toluenesulfonic acid, aluminium trichloride, titanium tetrachloride, titanium tetraisopropoxide, scandium triflate and ytterbium triflate. The reaction condition varies depending on the materials used, but generally, an imine derivative (XIII) is obtained by conducting the reaction at 0 to 150° C., preferably at 15 to 90° C. for 5 minutes to 24 hours, preferably for 30 minutes to 15 hours. As a hydrazine derivative (XII), those commercially available from Aldrich can be used.

The reduction reaction of the compound obtained by the above method, imine derivative (XIII), can be conducted in a solvent, in the presence of a reductant. A reductant is not particularly limited, and for example, sodium borohydride, sodium cyanoborohydride, sodium triacetoxyborohydride, lithium aluminium hydride, diborane, and diisobutylaluminium hydride can be used. A solvent is not particularly limited, and for example, the followings can be used independently or in combination: tetrahydrofuran, diethylether, dioxane, toluene, dichloromethane, methanol and ethanol. The reaction condition varies depending on the materials used, but generally, a hydrazine derivative (XIV) is obtained by conducting the reaction at −20 to 150° C., preferably at 15 to 60° C. for 5 minutes to 24 hours, preferably for 30 minutes to 15 hours.

The condensation reaction of a hydrazine derivative (XIV) obtained by the above method and a reactive derivative (VIII)

can be conducted in a solvent, in the presence or absence of a base. A solvent is not particularly limited, and for example, the followings can be used independently or in combination: tetrahydrofuran, toluene, dioxane, N,N-dimethylformamide, N-methylpyrrolidone, dichloromethane, chloroform, acetonitrile and propionitrile. A base is not particularly limited, and for example, the followings can be used: organic bases such as pyridine, DMAP, collidine, lutidine, DBU, DBN, DABCO, triethylamine, diisopropylethylamine, diisopropylpentylamine and trimethylamine; alkali metal hydrides such as lithium hydride, sodium hydride and potassium hydride; alkali metal hydroxides such as lithium hydroxide, sodium hydroxide and potassium hydroxide; alkali metal carbonates such as lithium carbonate, sodium carbonate, potassium carbonate and cesium carbonate; and sodium hydrogen carbonate. The reaction condition varies depending on the materials used, but generally, an amide derivative (XV) is obtained by conducting the reaction at −20 to 100° C., preferably at 15 to 80° C. for 5 minutes to 24 hours, preferably for 5 hours to 12 hours.

The cyclization reaction of the amide derivative (XV) obtained by the above method can be conducted in a solvent, in the presence of a base. A solvent is not particularly limited, and for example, the followings can be used independently or in combination: tetrahydrofuran, toluene, dioxane, N,N-dimethylformamide, N-methylpyrrolidone, dichloromethane and acetonitrile. A base is not particularly limited, and for example, the followings can be used: alkali metal hydrides such as lithium hydride, sodium hydride and potassium hydride; alkali metal hydroxides such as lithium hydroxide, sodium hydroxide and potassium hydroxide; alkali metal carbonates such as lithium carbonate, sodium carbonate, potassium carbonate and cesium carbonate; sodium hydrogen carbonate, lithium diisopropylamide, sodium diisopropylamide, potassium diisopropylamide, lithium hexamethyldisilazide, sodium hexamethyldisilazide, potassium hexamethyldisilazide, t-butoxysodium, t-butoxypotassium, n-butyllithium, s-butyllithium and t-butyllithium. The reaction condition varies depending on the materials used, but generally, a cyclic compound (XI) is obtained by conducting the reaction at −20 to 100° C., preferably at 15 to 80° C. for 5 minutes to 24 hours, preferably for 30 minutes to 12 hours. A nitro group, which is a substituent can be converted into an amino group by using a general reduction reaction of a nitro group. Further, an amino group thus obtained can be further modified under a general acylation and sulfonylation condition.

Further, a compound shown by formula (XVI) among the compounds (I) can be prepared by the following method, but it is not limited to this method.

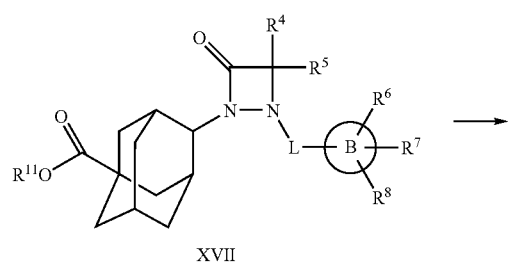

XVII

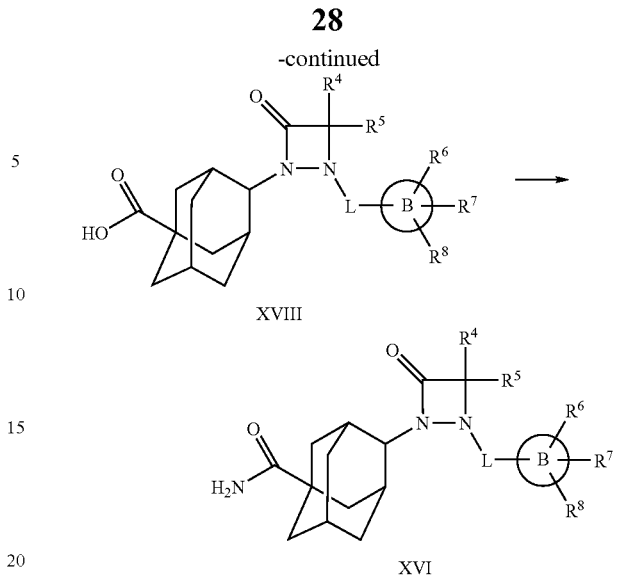

XVIII

XVI (wherein $R^4$, $R^5$, $R^6$, $R^7$, $R^8$, B ring and L show the same things as they show in the above, and $R^{11}$ represents a lower alkyl group)

By subjecting a carboxylic acid ester derivative (XVII) to a general hydrolysis reaction, a carboxylic acid derivative (XVIII) can be obtained. The reaction can be conducted in a solvent, in the presence of a base or acid. A solvent is not particularly limited, and for example, the followings can be used independently or in combination: tetrahydrofuran, dioxane, methanol, ethanol and water. A base is not particularly limited, and for example, the followings can be used: alkali metal hydroxides such as sodium hydroxide and potassium hydroxide; alkali metal carbonates such as lithium carbonate, sodium carbonate, potassium carbonate and cesium carbonate; and trimethylsilyloxy potassium. An acid is not particularly limited, and the followings can be used: hydrochloric acid, acetic acid, trifluoroacetic acid, boron tribromide and aluminium trichloride. The reaction condition varies depending on the materials used, but generally, an carboxylic acid derivative (XVIII) is obtained by conducting the reaction at −20 to 100° C., preferably at 15 to 80° C. for 5 minutes to 1 day, preferably for 30 minutes to 13 hours.

The dehydration-condensation reaction of a carboxylic acid derivative (XVIII) and ammonia can be conducted in a solvent, in the presence or absence of a base, in the presence or absence of a condensation accelerator, by using a condensation agent. A solvent is not particularly limited, and for example, the followings can be used independently or in combination: 1,2-dichloroethane, chloroform, dichloromethane, ethyl acetate, isopropyl acetate, toluene, benzene, tetrahydrofuran, dioxane, acetonitrile, propionitrile, N,N-dimethylformamide, N-methylpyrrolidone and water. A base is not particularly limited, and for example, the followings can be used: organic bases such as pyridine, DMAP, collidine, lutidine, DBU, DBN, DABCO, triethylamine, diisopropylethylamine, diisopropylpentylamine and trimethylamine; alkali metal hydrides such as lithium hydride, sodium hydride and potassium hydride; alkali metal hydroxides such as lithium hydroxide, sodium hydroxide and potassium hydroxide; alkali metal carbonates such as lithium carbonate, sodium carbonate, potassium carbonate and cesium carbonate; alkali metal bicarbonates such as sodium hydrogen carbonate and potassium hydrogen carbonate. A condensation accelerator is not particularly limited, and DMAP, HOAt, HOBt, HODhbt, HONB, HOPfp, HOPht and HOSu can be used. A condensation agent is not particularly limited, and for example, DCC, DIPCI, WSCI, WSC.HCl, DEPC, BOP, PyBOP and TBTU can be used. The reaction condition varies depending on the materials used, but generally, a compound of interest (XVI) is obtained by conducting the reaction at −20 to 100° C., preferably at 0 to 40° C. for 5 minutes to 1 day, preferably for 30 minutes to 12 hours. When $R^6$, $R^7$ and $R^8$ are hydroxyl group or amino group, each substituent thereof can be protected and deprotected with a commonly used protective group. Further, each hydroxyl group and amino group can be modified with a commonly used acylation and sulfonylation condition. When $R^6$, $R^7$ and $R^8$ are a nitro group, it can be converted into an amino group by using a general reduction reaction of a nitro group. When $R^6$, $R^7$ and $R^8$ are a $C_{1-6}$ alkylthio group, the corresponding sulfur atom can be oxidized by using a general oxidation reaction of a sulfur atom.

Further, a compound shown by formula (XIX) among the compounds (I) can be prepared by the following method, but it is not limited to this method.

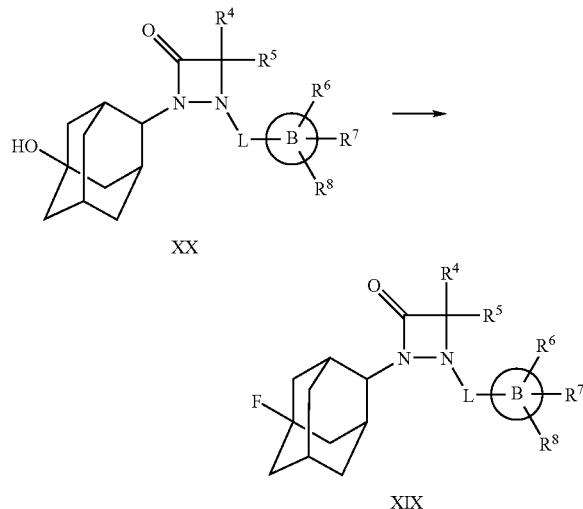

(wherein $R^4$, $R^5$, $R^6$, $R^7$, $R^8$, B ring and L show the same things as they show in the above)

By reacting a compound (XX) having a hydroxyl group on an adamantly group with a fluorinating agent, a compound of interest (XIX) can be obtained. The reaction can be conducted in a solvent, in the presence of a fluorinating agent. The fluorinating agent is not particularly limited, and for example, (diethylamino)sulfur trifluoride, potassium fluoride and pyridinium poly(hydrogen fluoride) can be used. A solvent is not particularly limited, and for example, the followings can be used independently or in combination: tetrahydrofuran, dioxane, diethylether, dichloromethane and chloroform. The reaction condition varies depending on the materials used, but generally, a compound of interest (XIX) of interest is obtained by conducting the reaction at −78 to 100° C., preferably at −10 to 50° C. for 5 minutes to 1 day, preferably for 1 hour to 12 hours. When $R^6$, $R^7$ and $R^8$ are hydroxyl group or amino group, each substituent thereof can be protected and deprotected with a commonly used protective group. Further, each hydroxyl group and amino group can be modified with a commonly used acylation and sulfonylation condition. When $R^6$, $R^7$ and $R^8$ are a nitro group, it can be converted into an amino group by using a general reduction reaction of a nitro group. When $R^6$, $R^7$ and $R^8$ are a $C_{1-6}$ alkylthio group, the corresponding sulfur atom can be oxidized by using a general oxidation reaction of a sulfur atom.

Further, a compound shown by formula (XXI) among the compounds (I) can be prepared by the following method, but it is not limited to this method.

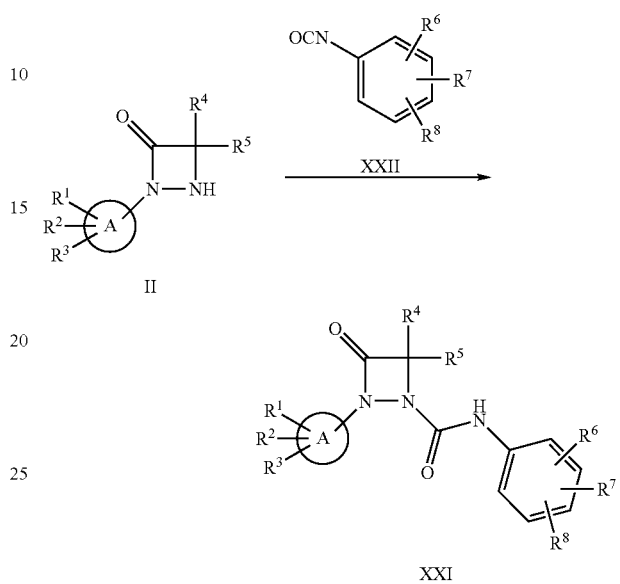

(wherein $R^1$, $R^2$, $R^3$, $R^4$, $R^5$, $R^6$, $R^7$, $R^8$ and A ring show the same things as they show in the above)

The reaction of an amine compound (II) and isocyanate (XXII) can be conducted in a solvent, in the presence of a base. A solvent is not particularly limited, and for example, the followings can be used independently or in combination: tetrahydrofuran, toluene, dioxane, N,N-dimethylformamide, N-methylpyrrolidone, dichloromethane, chloroform, acetonitrile and propionitrile. A base is not particularly limited, and for example, the followings can be used independently or in combination: organic bases such as pyridine, DMAP, collidine, lutidine, DBU, DBN, DABCO, triethylamine, diisopropylethylamine, diisopropylpentylamine and trimethylamine; alkali metal hydrides such as lithium hydride, sodium hydride and potassium hydride; alkali metal hydroxides such as lithium hydroxide, sodium hydroxide and potassium hydroxide; alkali metal carbonates such as lithium carbonate, sodium carbonate, potassium carbonate and cesium carbonate. The reaction condition varies depending on the materials used, but generally, a 1,2-diazetidin-3-one derivative (XXI) of interest is obtained by conducting the reaction at −20 to 100° C., preferably at 15 to 40° C. for 5 minutes to 24 hours, preferably for 1 hour to 12 hours. When $R^1$, $R^2$, $R^3$, $R^6$, $R^7$ and $R^8$ are a hydroxyl group or amino group, each substituent thereof can be protected and deprotected with a commonly used protective group. Further, each hydroxyl group and amino group can be modified with a commonly used acylation and sulfonylation condition. When $R^6$, $R^7$ and $R^8$ are a nitro group, it can be converted into an amino group by using a general reduction reaction of a nitro group. When $R^6$, $R^7$ and $R^8$ are a $C_{1-6}$ alkylthio group, the corresponding sulfur atom can be oxidized by using a general oxidation reaction of a sulfur atom.

Further, a compound shown by formula (XXIII) among the compounds (I) can be prepared by the following method, but it is not limited to this method.

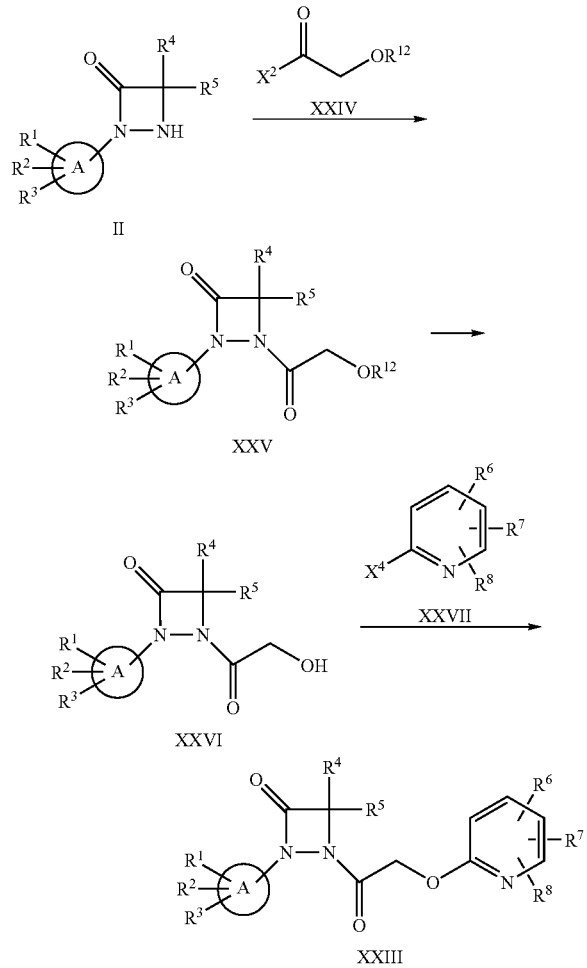

(wherein $R^1$, $R^2$, $R^3$, $R^4$, $R^5$, $R^6$, $R^7$, $R^8$, A ring and $X^2$ show the same things as they show in the above, $R^{12}$ represents a protective group, and $X^4$ represents a halogen atom)

The reaction of an amine compound (II) and a reactive derivative (XXIV) can be conducted in a solvent, in the presence of a base. A solvent is not particularly limited, and for example, the followings can be used independently or in combination: tetrahydrofuran, toluene, dioxane, N,N-dimethylformamide, N-methylpyrrolidone, dichloromethane, chloroform, acetonitrile and propionitrile. A base is not particularly limited, and for example, the followings can be used independently or in combination: organic bases such as pyridine, DMAP, collidine, lutidine, DBU, DBN, DABCO, triethylamine, diisopropylethylamine, diisopropylpentylamine and trimethylamine; alkali metal hydrides such as lithium hydride, sodium hydride and potassium hydride; alkali metal hydroxides such as lithium hydroxide, sodium hydroxide and potassium hydroxide; alkali metal carbonates such as lithium carbonate, sodium carbonate, potassium carbonate and cesium carbonate. The reaction condition varies depending on the materials used, but generally, a derivative (XXV) of interest is obtained by conducting the reaction at −20 to 100° C., preferably at 15 to 80° C. for 5 minutes to 24 hours, preferably for 1 hour to 12 hours. When $R^1$, $R^2$, $R^3$, $R^6$, $R^7$ and $R^8$ are a hydroxyl group or amino group, each substituent thereof can be protected and deprotected with a commonly used protective group. Further, each hydroxyl group and amino group can be modified with a commonly used acylation and sulfonylation condition. When $R^6$, $R^7$ and $R^8$ are a nitro group, it can be converted into an amino group by using a general reduction reaction of a nitro group. When $R^6$, $R^7$ and $R^8$ are a $C_{1-6}$ alkylthio group, the corresponding sulfur atom can be oxidized by using a general oxidation reaction of a sulfur atom.

The deprotection of the protective group $R^{12}$ of the cyclic compound (XXV) obtained by the above method is not particularly limited, and can be conducted by referring to a commonly used method as a deprotection condition of the protective group (Protective Groups in Organic Synthesis Third Edition, John Wiley & Sons, Inc.). The protective group is not particularly limited, and for example, methyl group, methoxymethyl group, benzyoxymethyl group, t-butyl group, allyl group and benzyl group can be used. Particularly, benzyl group is preferred.

The reaction of a cyclic compound (XXVI) obtained by the above method and a reactive derivative (XXVII) can be conducted in a solvent, in the presence of a base. A solvent is not particularly limited, and for example, the followings can be used independently or in combination: 1,2-dichloroethane, chloroform, dichloromethane, ethyl acetate, isopropyl acetate, toluene, benzene, tetrahydrofuran, dioxane, acetonitrile, propionitrile and N,N-dimethylformamide A base is not particularly limited, and for example, the followings can be used independently or in combination: organic bases such as pyridine, DMAP, collidine, lutidine, DBU, DBN, DABCO, triethylamine, 2,6-di-t-butylpyridine, diisopropylethylamine, diisopropylpentylamine, N-methylmorpholine and trimethylamine; alkali metal hydrides such as lithium hydride, sodium hydride and potassium hydride; alkali metal hydroxides such as lithium hydroxide, sodium hydroxide and potassium hydroxide; alkali metal carbonates such as lithium carbonate, sodium carbonate, potassium carbonate and cesium carbonate; metal bicarbonates such as sodium hydrogen carbonate and potassium hydrogen carbonate; lithium diisopropylamide, sodium diisopropylamide, potassium diisopropylamide, lithium hexamethyldisilazide, sodium hexamethyldisilazide, potassium hexamethyldisilazide, t-butoxysodium, t-butoxypotassium, n-butyllithium, s-butyllithium and t-butyllithium. The reaction condition varies depending on the materials used, but generally, a 1,2-diazetidin-3-one derivative (XXIII) of interest is obtained by conducting the reaction at −20 to 150° C., preferably at 0 to 80° C. for 5 minutes to 48 hours, preferably for 1 hour to 12 hours. When $R^1$, $R^2$, $R^3$, $R^6$, $R^7$ and $R^8$ are a hydroxyl group or amino group, each substituent thereof can be protected and deprotected with a commonly used protective group. Further, each hydroxyl group and amino group can be modified with a commonly used acylation and sulfonylation condition. When $R^6$, $R^7$ and $R^8$ are a nitro group, it can be converted into an amino group by using a general reduction reaction of a nitro group. When $R^6$, $R^7$ and $R^8$ are a $C_{1-6}$ alkylthio group, the corresponding sulfur atom can be oxidized by using a general oxidation reaction of a sulfur atom.

Further, a compound shown by formula (XXVIII) among the compounds (I) can be prepared by the following method, but it is not limited to this method.

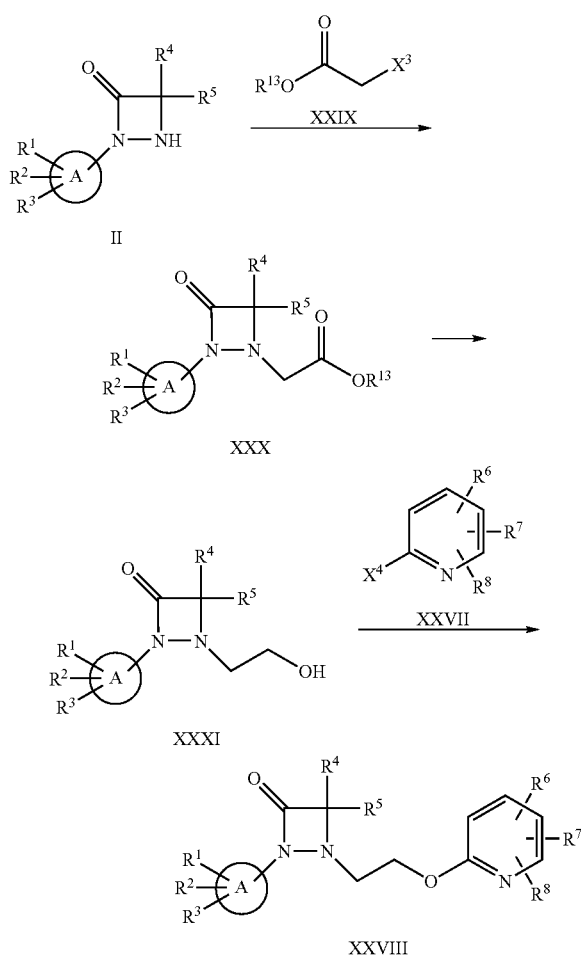

(wherein $R^1$, $R^2$, $R^3$, $R^4$, $R^5$, $R^6$, $R^7$, $R^8$, A ring, $X^3$ and $X^4$ show the same things as they show in the above, and $R^{13}$ represents a lower alkyl group).

The reaction of an amine compound (II) and a reactive derivative (XXIX) can be conducted in a solvent, in the presence of a base. A solvent is not particularly limited, and for example, the followings can be used independently or in combination: 1,2-dichloroethane, chloroform, dichloromethane, ethyl acetate, isopropyl acetate, toluene, benzene, tetrahydrofuran, dioxane, acetonitrile, propionitrile and N,N-dimethylformamide. A base is not particularly limited, and for example, the followings can be used independently or in combination: organic bases such as pyridine, DMAP, collidine, lutidine, DBU, DBN, DABCO, triethylamine, 2,6-di-t-butylpyridine, diisopropylethylamine, diisopropylpentylamine, N-methylmorpholine and trimethylamine; alkali metal hydrides such as lithium hydride, sodium hydride and potassium hydride; alkali metal hydroxides such as lithium hydroxide, sodium hydroxide and potassium hydroxide; alkali metal carbonates such as lithium carbonate, sodium carbonate, potassium carbonate and cesium carbonate; alkali metal bicarbonates such as sodium hydrogen carbonate and potassium hydrogen carbonate; lithium diisopropylamide, sodium diisopropylamide, potassium diisopropylamide, lithium hexamethyldisilazide, sodium hexamethyldisilazide, potassium hexamethyldisilazide, t-butoxysodium, t-butoxypotassium, n-butyllithium, s-butyllithium and t-butyllithium. The reaction condition varies depending on the materials used, but generally, a derivative of interest (XXX) is obtained by conducting the reaction at −20 to 150° C., preferably at 0 to 80° C. for 5 minutes to 48 hours, preferably for 1 hour to 24 hours. When $R^1$, $R^2$, $R^3$, $R^6$, $R^7$ and $R^8$ are hydroxyl group or amino group, each substituent thereof can be protected and deprotected with a commonly used protective group. Further, each hydroxyl group and amino group can be modified with a commonly used acylation and sulfonylation condition. When $R^6$, $R^7$ and $R^8$ are a nitro group, it can be converted into an amino group by using a general reduction reaction of a nitro group. When $R^6$, $R^7$ and $R^8$ are a $C_{1-6}$ alkylthio group, the corresponding sulfur atom can be oxidized by using a general oxidation reaction of a sulfur atom.

The reduction reaction of the obtained derivative (XXX) can be conducted in a solvent, in the presence of a reductant. A reductant is not particularly limited, and for example, the followings can be used: sodium borohydride, lithium borohydride, lithium aluminium hydride and diisobutylaluminium hydride. A solvent is not particularly limited, and for example, the followings can be used independently or in combination: tetrahydrofuran, diethylether, dioxane, toluene, dichloromethane, methanol, ethanol and water. The reaction condition varies depending on the materials used, but generally, a derivative of interest (XXXI) is obtained by conducting the reaction at −20 to 150° C., preferably at 15 to 60° C. for 5 minutes to 24 hours, preferably for 30 minutes to 10 hours.

The reaction of a derivative (XXXI) obtained by the above method and a reactive derivative (XXVII) can be conducted in a solvent, in the presence of a base. A solvent is not particularly limited, and for example, the followings can be used independently or in combination: 1,2-dichloroethane, chloroform, dichloromethane, ethyl acetate, isopropyl acetate, toluene, benzene, tetrahydrofuran, dioxane, acetonitrile, propionitrile and N,N-dimethylformamide A base is not particularly limited, and for example, the followings can be used independently or in combination: organic bases such as pyridine, DMAP, collidine, lutidine, DBU, DBN, DABCO, triethylamine, 2,6-di-t-butylpyridine, diisopropylethylamine, diisopropylpentylamine, N-methylmorpholine and trimethylamine; alkali metal hydrides such as lithium hydride, sodium hydride and potassium hydride; alkali metal hydroxides such as lithium hydroxide, sodium hydroxide and potassium hydroxide; alkali metal carbonates such as lithium carbonate, sodium carbonate, potassium carbonate and cesium carbonate; alkali metal bicarbonates such as sodium hydrogen carbonate and potassium hydrogen carbonate; lithium diisopropylamide, sodium diisopropylamide, potassium diisopropylamide, lithium hexamethyldisilazide, sodium hexamethyldisilazide, potassium hexamethyldisilazide, t-butoxysodium, t-butoxypotassium, n-butyllithium, s-butyllithium and t-butyllithium. The reaction condition varies depending on the materials used, but generally, a 1,2-diazetidin-3-one derivative (XXVIII) of interest is obtained by conducting the reaction at −20 to 150° C., preferably at 0 to 80° C. for 5 minutes to 48 hours, preferably for 1 hour to 12 hours. When $R^1$, $R^2$, $R^3$, $R^6$, $R^7$ and $R^8$ are hydroxyl group or amino group, each substituent thereof can be protected and deprotected with a commonly used protective group. Further, each hydroxyl group and amino group can be modified with a commonly used acylation and sulfonylation condition. When $R^6$, $R^7$ and $R^8$ are a nitro group, it can be converted into an amino group by using a general reduction reaction of a nitro group. When $R^6$, $R^7$ and $R^8$ are a $C_{1-6}$ alkylthio group, the corresponding sulfur atom can be oxidized by using a general oxidation reaction of a sulfur atom.

The intermediates and substances of interest obtained in each of the above reactions can be isolated and purified as desired by subjecting to a purification method that are used routinely in the field of organic synthetic chemistry, for example, filtration, neutralization, extraction, washing, drying, condensation, distillation, recrystallization, various types of chromatography and the like. Alternatively, the intermediates can be used for next reactions without a particular purification.

Further, various isomers can be isolated by applying a routine procedure utilizing the difference in physical-chemical property between the isomers. For example, a racemic mixture can be led to optically-pure isomers by a common racemic resolution method such as an optical resolution method comprising leading a mixture to diastereomeric salt with a common optically-active acid such as tartaric acid, or a method using optically-active column chromatography. Further, a diastereomeric mixture can be separated by a fractional crystallization, various types of chromatography or the like. Alternatively, an optically-active compound can be produced by using an appropriate optically-active material.

Embodiments of Use

The pharmaceutical composition of the present invention comprises the 1,2-diazetidin-3-one derivative shown by general formula (1), pharmaceutically acceptable salt thereof, or their solvate as an active ingredient. The compound of the present invention can be used independently, but generally, the compound is used in combination with a pharmaceutically acceptable carrier and/or diluent.

Examples of an administration form of a medicine that comprises 1,2-diazetidin-3-one derivative of the present invention or salt thereof, or their solvate as an active ingredient include an oral administration by a tablet, capsule, granules, powder, syrup or the like; or a parenteral administration by an intravenous injection, intramuscular injection, suppository, inhaler, percutaneous absorption, eye-drops, nasal preparation or the like. Further, to prepare a pharmaceutical formulation in such various forms, the active ingredient can be prepared independently or as a pharmaceutical composition where appropriate, by combining with other pharmaceutically acceptable carriers, specifically an excipient, binder, extender, disintegrant, surfactant, lubricant, dispersant, buffer, preservative, flavoring agent, flavor, coating agent, diluent or the like.

The dose of the medicine of the present invention varies depending on weight, age, sex, symptoms and the like of the patient, but generally, in a case of an adult, 1,2-diazetidin-3-one derivative represented by general formula (1) can be administered in an amount of 0.1 to 1000 mg, preferably 1 to 300 mg a day, as a single or several separate doses either orally or parenterally.

Examples

The present invention will be further described with reference to the following examples, while the scope of the present invention will not be limited to these examples.

Example 1

Preparation of 1-benzyl-2-(adamantan-2-yl)-1,2-diazetidin-3-one

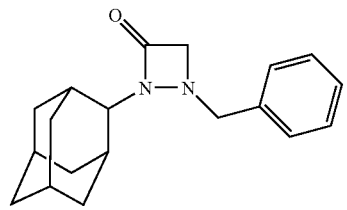

Process 1: Preparation of benzyl 2-(adamantan-2-ylidene)hydrazinecarboxylate

Under an argon atmosphere, a solution of 2-adamantanone (1.00 g, 6.70 mmol) in ethanol (40 mL) was added with benzylcarbazate (1.11 g, 6.70 mmol) at room temperature and the resultant was stirred at 80° C. for 12 hours. The reaction solution was concentrated in vacuo, and benzyl 2-(adamantan-2-ylidene)hydrazinecarboxylate (2.03 g, quant.) was obtained as a white crystalline powder.

$^1$H-NMR (400 MHz, CDCl$_3$) δ; 1.60-2.01 (m, 12H), 2.77 (s, 1H), 2.89 (s, 1H), 5.25 (s, 2H), 7.31-7.41 (m, 5H), 7.69 (s, 1H).

Process 2: Preparation of benzyl 2-(adamantan-2-yl)hydrazinecarboxylate

Under an argon atmosphere, a solution of benzyl 2-(adamantan-2-ylidene)hydrazinecarboxylate (1.60 g, 5.40 mmol) in tetrahydrofuran (54 mL) was added with sodium cyanoborohydride (370 mg, 5.90 mmol) at room temperature, to which a solution of p-toluenesulfonic acid monohydrate (190 mg, 1.00 mmol) in tetrahydrofuran (10 mL) was dropped. The resultant was stirred at the same temperature for 5 hours. The reaction solution was added with a saturated aqueous solution of sodium hydrogen carbonate and extracted with ethyl acetate. The organic layer was dried over anhydrous sodium sulfate, concentrated in vacuo, and benzyl 2-(adamantan-2-yl)hydrazinecarboxylate (1.54 g, 94.9%) was obtained as a white crystalline powder.

$^1$H-NMR (400 MHz, CDCl$_3$) δ; 1.30-2.09 (m, 13H), 2.54 (s, 1H), 3.13 (s, 1H), 3.90 (s, 1H), 5.24 (s, 2H), 6.20 (s, 1H), 7.32-7.39 (m, 5H).

Process 3: Preparation of benzyl 2-(2-chloroacetyl)-2-(adamantan-2-yl)hydrazinecarboxylate Under an argon atmosphere, a solution of 2-(adamantan-2-yl)hydrazinecarboxylate (800 mg, 2.66 mmol) in dichloromethane (30 mL) was added with sodium hydrogen carbonate (450 mg, 5.40 mmol) and chloroacetic acid chloride (300 mg, 2.66 mmol) were added at 0° C., and the resultant was stirred at room temperature for 3 hours. The reaction solution was added with water and extracted with chloroform. The organic layer was dried over anhydrous sodium sulfate, concentrated in vacuo, and benzyl 2-(2-chloroacetyl)-2-(adamantan-2-yl)hydrazinecarboxylate (726 mg, 72.4%) was obtained as a white crystalline powder.

$^1$H-NMR (400 MHz, CDCl$_3$) δ; 1.56-1.93 (m, 12H), 2.29-2.54 (m, 2H), 3.98 (d, J=13.8 Hz, 1H), 4.17 (d, J=13.8 Hz, 1H), 4.33 (s, 1H), 5.22 (s, 2H), 6.90 (s, 1H), 7.29-7.40 (m, 5H).

Process 4: Preparation of benzyl 2-(adamantan-2-yl)-3-oxo-1,2-diazetidine-1-carboxylate Under an argon atmosphere, a solution of benzyl 2-(2-chloroacetyl)-2-(adamantan-2-yl)hydrazinecarboxylate (726 mg, 1.93 mmol) in tetrahydrofuran (20 mL) was added at 0° C. with potassium-t-butoxide (238 mg, 2.12 mmol), and the resultant was stirred at the same temperature for 1 hour. The reaction solution was added with a saturated aqueous solution of ammonium chloride, and extracted with ethyl acetate. The organic layer was dried over anhydrous sodium sulfate, concentrated in vacuo, the obtained residue was purified using silica gel chromatography (hexane:ethyl acetate=3:1), and benzyl 2-(adamantan-2-yl)-3-oxo-1,2-diazetidine-1-carboxylate (463 mg, 70.4%) was obtained as a colorless oil.

$^1$H-NMR (400 MHz, CDCl$_3$) δ; 1.47-2.04 (m, 12H), 2.17 (s, 1H), 2.44 (s, 1H), 4.00 (s, 1H), 4.58 (s, 2H), 5.18 (s, 2H), 7.35-7.37 (m, 5H).

Process 5: Preparation of 2-(adamantan-2-yl)-1,2-diazetidin-3-one

A solution of benzyl 2-(adamantan-2-yl)-3-oxo-1,2-diazetidine-1-carboxylate (100 mg, 0.29 mmol) in tetrahydrofuran (5 mL) was added with 10% palladium carbon (catalyst amount), and under a hydrogen atmosphere, the resultant was stirred at room temperature for 10 hours. The reaction solution was filtered using celite, concentrated in vacuo, and the obtained residue was purified using silica gel chromatography (hexane:ethyl acetate=1:1), and 2-(adamantan-2-yl)-1,2-diazetidin-3-one (34.0 mg, 56.8%) was obtained as a colorless oil.

$^1$H-NMR (400 MHz, CDCl$_3$) δ; 1.46-2.10 (m, 12H), 2.55 (s, 2H), 3.40 (s, 1H), 4.25 (s, 2H).

Process 6: Preparation of 1-benzyl-2-(adamantan-2-yl)-1,2-diazetidin-3-one

Under an argon atmosphere, a solution of 2-(adamantan-2-yl)-1,2-diazetidin-3-one (10.2 mg, 0.05 mmol) in N,N-dimethylformamide (1 mL), potassium carbonate (28.0 mg, 0.100 mmol) and benzyl bromide (35.0 mg, 0.100 mmol) were added at room temperature, and the resultant was stirred at the same temperature for 24 hours. The reaction solution was added with water and extracted with diethyl ether. The organic layer was dried over anhydrous sodium sulfate, concentrated in vacuo, the obtained residue was purified using Preparative Thin-Layer chromatography (hexane:ethyl acetate=2:1), and the title compound (7.60 mg, 48.6%) was obtained as a colorless oil.

$^1$H-NMR (400 MHz, CDCl$_3$) δ; 1.56-1.91 (m, 10H), 2.17-2.26 (m, 2H), 2.40 (s, 1H), 2.48 (s, 1H), 3.50 (d, J=12.0 Hz, 1H), 3.59 (d, J=13.7 Hz, 1H), 3.76 (s, 1H), 4.12 (d, J=13.7 Hz, 1H), 4.38 (d, J=12.0 Hz, 1H), 7.30-7.35 (m, 5H).

IR (ATR); 2917, 1736, 1322, 731 cm$^{-1}$.

EI-MS m/z; 296 (M$^+$).

Example 2

Preparation of 1-(4-chlorobenzyl)-2-(adamantan-2-yl)-1,2-diazetidin-3-one

4-Chlorobenzylbromide was used in place of benzyl bromide for a similar reaction and treatment as Process 6 of Example 1, and the title compound was obtained as a white amorphous solid.

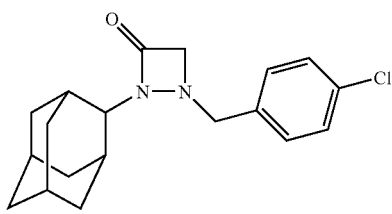

$^1$H-NMR (400 MHz, CDCl$_3$) δ; 1.55-1.88 (m, 10H), 2.13-2.24 (m, 2H), 2.38 (s, 1H), 2.48 (s, 1H), 3.50 (d, J=11.9 Hz, 1H), 3.54 (d, J=13.5 Hz, 1H), 3.76 (s, 1H), 4.12 (d, J=13.5 Hz, 1H), 4.33 (d, J=11.9 Hz, 1H), 7.26 (d, J=8.1 Hz, 2H), 7.31 (d, J=8.1 Hz, 2H).

IR (ATR); 2915, 2852, 1736, 1322, 1100, 714 cm$^{-1}$.

EI-MS m/z; 330 (M$^+$).

Example 3

Preparation of 1-(4-methylbenzyl)-2-(adamantan-2-yl)-1,2-diazetidin-3-one

4-Methylbenzyl bromide was used in place of benzyl bromide for a similar reaction and treatment as Process 6 of Example 1, and the title compound was obtained as a white amorphous solid.

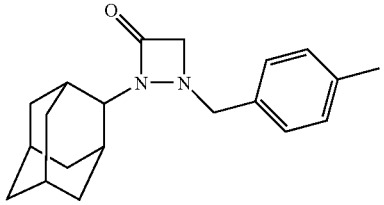

$^1$H-NMR (400 MHz, CDCl$_3$) δ; 1.52-1.91 (m, 10H), 2.16-2.19 (m, 1H), 2.22-2.26 (m, 1H), 2.34 (s, 3H), 2.40 (s, 1H), 2.49 (s, 1H), 3.45 (d, J=11.7 Hz, 1H), 3.57 (d, J=13.7 Hz, 1H), 3.77 (s, 1H), 4.09 (d, J=13.7 Hz, 1H), 4.34 (d, J=11.7 Hz, 1H), 7.14 (d, J=7.8 Hz, 2H), 7.20 (d, J=7.8 Hz, 2H).

IR (ATR); 2908, 1757, 1288, 1230, 774 cm$^{-1}$.

EI-MS m/z; 310 (M$^+$).

Example 4

Preparation of 1-(4-methoxybenzyl)-2-(adamantan-2-yl)-1,2-diazetidin-3-one

4-Methoxybenzyl bromide was used in place of benzyl bromide for a similar reaction and treatment as Process 6 of Example 1, and the title compound was obtained as a white amorphous solid.

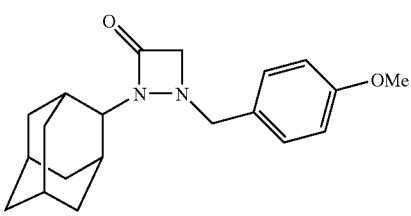

$^1$H-NMR (400 MHz, CDCl$_3$) δ; 1.59-1.90 (m, 10H), 2.14-2.25 (m, 2H), 2.40 (s, 1H), 2.48 (s, 1H), 3.43 (d, J=11.6 Hz, 1H), 3.58 (d, J=13.5 Hz, 1H), 3.76 (s, 1H), 3.81 (s, 3H), 4.07 (d, J=13.5 Hz, 1H), 4.30 (d, J=11.6 Hz, 1H), 6.87 (d, J=8.6 Hz, 2H), 7.24 (d, J=8.6 Hz, 2H).

IR (ATR); 2912, 2852, 1758, 1511, 1248, 1039, 775 cm$^{-1}$.

EI-MS m/z; 326 (M$^+$).

Example 5

Preparation of 1-(4-fluorobenzyl)-2-(adamantan-2-yl)-1,2-diazetidin-3-one

4-Fluorobenzyl bromide was used in place of benzyl bromide for a similar reaction and treatment as Process 6 of Example 1, and the title compound was obtained as a white amorphous solid.

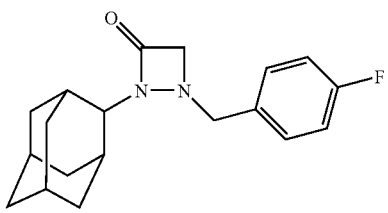

$^1$H-NMR (400 MHz, CDCl$_3$) δ; 1.64-1.91 (m, 10H), 2.13-2.25 (m, 2H), 2.38 (s, 1H), 2.47 (s, 1H), 3.47 (d, J=12.1 Hz, 1H), 3.54 (d, J=13.5 Hz, 1H), 3.75 (s, 1H), 4.11 (d, J=13.5 Hz, 1H), 4.32 (d, J=12.1 Hz, 1H), 7.03 (t, J=8.6 Hz, 2H), 7.29 (dd, J=5.7, 8.6 Hz, 2H).
IR (ATR); 2912, 1758, 1731, 1510, 1223, 823 cm$^{-1}$.
EI-MS m/z; 314 (M$^+$).

Example 6

Preparation of 2-(adamantan-2-yl)-1-[4-(trifluoromethyl)benzyl]-1,2-diazetidin-3-one 4-Trifluoromethylbenzyl bromide was used in place of benzyl bromide for a similar reaction and treatment as Process 6 of Example 1, and the title compound was obtained as a white amorphous solid.

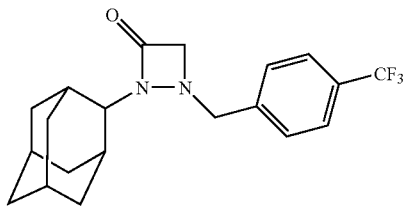

$^1$H-NMR (400 MHz, CDCl$_3$) δ; 1.60-1.93 (m, 10H), 2.14-2.25 (m, 2H), 2.38 (s, 1H), 2.47 (s, 1H), 3.54 (d, J=12.4 Hz, 1H), 3.58 (d, J=13.5 Hz, 1H), 3.76 (s, 1H), 4.16 (d, J=13.5 Hz, 1H), 4.42 (d, J=12.4 Hz, 1H), 7.45 (d, J=8.1 Hz, 2H), 7.60 (d, J=8.1 Hz, 2H).
IR (ATR); 2915, 1758, 1742, 1325, 1166, 1118, 1066, 733 cm$^{-1}$.
EI-MS m/z; 364 (M$^+$).

Example 7

Preparation of 1-(4-nitrobenzyl)-2-(adamantan-2-yl)-1,2-diazetidin-3-one

4-Nitrobenzyl bromide was used in place of benzyl bromide for a similar reaction and treatment as Process 6 of Example 1, and the title compound was obtained as a pale yellow crystalline powder.

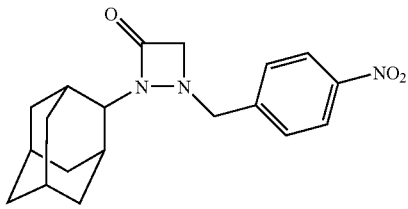

$^1$H-NMR (400 MHz, CDCl$_3$) δ; 1.60-1.90 (m, 10H), 2.14-2.25 (m, 2H), 2.36 (s, 1H), 2.48 (s, 1H), 3.52 (d, J=12.7 Hz, 1H), 3.64 (d, J=13.5 Hz, 1H), 3.76 (s, 1H), 4.20 (d, J=13.5 Hz, 1H), 4.44 (d, J=12.7 Hz, 1H), 7.51 (d, J=8.6 Hz, 2H), 8.20 (d, J=8.6 Hz, 2H).
IR (ATR); 2911, 1736, 1524, 1344, 734 cm$^{-1}$.
EI-MS m/z; 341 (M$^+$).

Example 8

Preparation of 1-benzyl-4-methyl-2-(adamantan-2-yl)-1,2-diazetidin-3-one

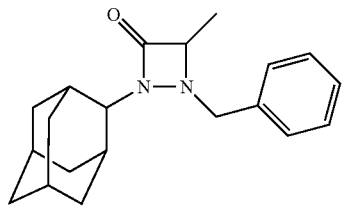

Process 1: Preparation of t-butyl 2-(adamantan-2-ylidene)hydrazinecarboxylate t-Butyl carbazate was used in place of benzylcarbazate for a similar reaction and treatment as Process 1 of Example 1, and t-butyl 2-(adamantan-2-ylidene)hydrazinecarboxylate was obtained as a colorless oil.
$^1$H-NMR (400 MHz, CDCl$_3$) δ; 1.51 (s, 9H), 1.60-2.01 (m, 12H), 2.74 (s, 1H), 2.90)s, 1H), 7.44 (s, 1H).

Process 2: Preparation of t-butyl 2-(adamantan-2-yl)hydrazinecarboxylate t-Butyl 2-(adamantan-2-ylidene)hydrazinecarboxylate was used for a similar reaction and treatment as Process 2 of Example 1, and t-butyl 2-(adamantan-2-yl)hydrazinecarboxylate was obtained as a colorless oil.
$^1$H-NMR (400 MHz, CDCl$_3$) δ; 1.42 (s, 9H), 1.66-2.06 (m, 13H), 2.51 (s, 1H), 3.02 (s, 1H), 3.83 (s, 1H), 6.30 (s, 1H).

Process 3: Preparation of t-butyl 2-(2-chloropropanoyl)-2-(adamantan-2-yl)hydrazinecarboxylate 2-Chloropropionyl chloride was used in place of chloroacetic acid chloride for a similar reaction and treatment as Process 3 of Example 1, and t-butyl 2-(2-chloropropanoyl)-2-(adamantan-2-yl)hydrazinecarboxylate was obtained as a colorless oil.

¹H-NMR (400 MHz, CDCl₃) δ; 1.49 (s, 9H), 1.54-2.02 (m, 16H), 2.33 (s, 1H), 4.36 (s, 1H), 4.52 (m, 1H), 6.72 (s, 1H).

Process 4: Preparation of 2-(adamantan-2-yl)-4-methyl-1,2-diazetidin-3-one

A solution of t-butyl 2-(2-chloropropanoyl)-2-(adamantan-2-yl)hydrazinecarboxylate (200 mg, 0.560 mmol) in dichloromethane (3 mL) was added with trifluoroacetic acid (3 mL) at room temperature, and the resultant was stirred at the same temperature for 1 hour. The reaction solution was concentrated, and the obtained residue was purified using silica gel chromatography (hexane:ethyl acetate=1:1), 2-(adamantan-2-yl)-4-methyl-1,2-diazetidin-3-one (66.3 mg, 53.7%) was obtained as a colorless oil.

¹H-NMR (400 MHz, CDCl₃) δ; 1.48 (d, J=7.1 Hz, 3H), 1.63-2.05 (m, 12H), 2.26 (s, 1H), 2.39 (s, 1H), 3.74 (s, 1H), 4.44 (q, J=7.1 Hz, 1H).

Process 5: Preparation of 1-benzyl-4-methyl-2-(adamantan-2-yl)-1,2-diazetidin-3-one 2-(Adamantan-2-yl)-4-methyl-1,2-diazetidin-3-one was used for a similar reaction and treatment as Process 6 of Example 1, and the title compound was obtained as a colorless oil.

¹H-NMR (400 MHz, CDCl₃) δ; 1.13 (d, J=7.1 Hz, 3H), 1.64-1.90 (m, 10H), 2.17-2.27 (m, 2H), 2.41 (s, 1H), 2.47 (s, 1H), 3.53 (d, J=11.7 Hz, 1H), 3.67 (q, J=7.1 Hz, 1H), 3.74 (s, 1H), 4.34 (d, J=11.7 Hz, 1H), 7.29-7.35 (m, 5H).

IR (ATR); 2909, 2853, 1752, 1452, 731 cm⁻¹.

EI-MS m/z; 310 (M⁺).

Example 9

Preparation of 1-(4-chlorobenzyl)-4-methyl-2-(adamantan-2-yl)-1,2-diazetidin-3-one Except using 4-chlorobenzyl bromide in place of benzyl bromide, similar reaction and treatment were carried out as Process 2 of Example 8, and the title compound was obtained as a colorless oil.

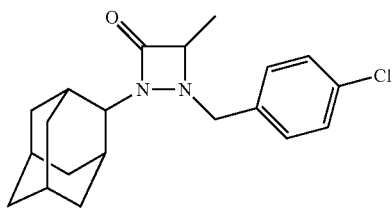

¹H-NMR (400 MHz, CDCl₃) δ; 1.15 (d, J=7.1 Hz, 3H), 1.62-1.90 (m, 10H), 2.15-2.24 (m, 2H), 2.40 (s, 1H), 2.45 (s, 1H), 3.51 (d, J=12.0 Hz, 1H), 3.62 (q, J=7.1 Hz, 1H), 3.72 (s, 1H), 4.30 (d, J=12.0 Hz, 1H), 7.28 (d, J=8.8 Hz, 2H), 7.31 (d, J=8.8 Hz, 2H).

IR (ATR); 2909, 2853, 1752, 1491, 756 cm⁻¹.

EI-MS m/z; 345 (M⁺).

Example 10

Preparation of 1-benzyl-4-(propan-2-yl)-2-(adamantan-2-yl)-1,2-diazetidin-3-one

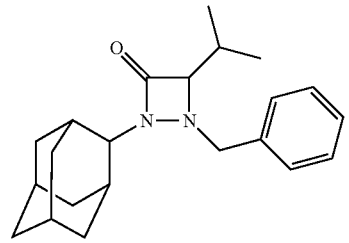

Process 1: Preparation of benzyl 2-(2-bromo-3-methylbutanoyl)-2-(adamantan-2-yl)hydrazinecarboxylate 2-Bromoisovaleryl chloride was used in place of chloroacetic acid chloride for a similar reaction and treatment as Process 3 of Example 1, and benzyl 2-(2-bromo-3-methylbutanoyl)-2-(adamantan-2-yl)hydrazinecarboxylate was obtained as a colorless oil.

¹H-NMR (400 MHz, CDCl₃) δ; 0.91 (d, J=6.8 Hz, 3H), 1.06 (d, J=6.8 Hz, 3H), 1.55-2.30 (m, 15H), 3.99 (d, J=9.5 Hz, 1H), 4.38 (s, 1H), 5.20 (s, 2H), 6.87 (s, 1H), 7.36-7.40 (m, 5H).

Process 2: Preparation of benzyl 2-(adamantan-2-yl)-4-(propan-2-yl)-3-oxo-1,2-diazetidine-1-carboxylate Benzyl 2-(2-bromo-3-methylbutanoyl)-2-(adamantan-2-yl)hydrazinecarboxylate was used for a similar reaction and treatment as Process 4 of Example 1, and benzyl 2-(adamantan-2-yl)-4-(propan-2-yl)-3-oxo-1,2-diazetidine-1-carboxylate was obtained as a colorless oil.

¹H-NMR (400 MHz, CDCl₃) δ; 1.09 (d, J=6.8 Hz, 3H), 1.11 (d, J=6.8 Hz, 3H), 1.55-0.80 (m, 10H), 21.98-2.02 (m, 1H), 2.22-2.17 (m, 2H), 2.30 (s, 1H), 2.58 (s, 1H), 4.02 (s, 1H), 4.23 (d, J=7.1 Hz, 1H), 5.12 (d, J=12.2 Hz, 1H), 5.21 (d, J=12.2 Hz, 1H), 7.34-7.37 (m, 5H).

Process 3: Preparation of 2-(adamantan-2-yl)-4-(propan-2-yl)-1,2-diazetidin-3-one Benzyl 2-(adamantan-2-yl)-4-(propan-2-yl)-3-oxo-1,2-diazetidine-1-carboxylate was used for a similar reaction and treatment as Process 5 of Example 1, and 2-(adamantan-2-yl)-4-(propan-2-yl)-1,2-diazetidin-3-one was obtained as a colorless oil.

¹H-NMR (400 MHz, CDCl₃) δ; 1.04 (d, J=6.8 Hz, 3H), 1.07 (d, J=6.8 Hz, 3H), 1.62-2.38 (m, 15H), 3.73 (s, 1H), 4.15 (d, J=7.1 Hz, 1H).

Process 4: Preparation of 1-benzyl-4-(propan-2-yl)-2-(adamantan-2-yl)-1,2-diazetidin-3-one 2-(Adamantan-2-yl)-4-(propan-2-yl)-1,2-diazetidin-3-one was used for a similar reaction and treatment as Process 6 of Example 1, and the title compound was obtained as a white crystalline powder.

¹H-NMR (400 MHz, CDCl₃) δ; 0.68 (d, J=6.8 Hz, 3H), 0.73 (d, J=6.8 Hz, 3H), 1.57-1.87 (m, 11H), 2.17-2.27 (m, 2H), 2.38-2.42 (m, 2H), 3.44-3.51 (m, 2H), 3.71 (s, 1H), 4.27 (d, J=11.6 Hz, 1H), 7.28-7.33 (m, 5H).
IR (ATR); 2913, 2851, 1753, 1742, 737 cm⁻¹.
EI-MS m/z; 338 (M⁺).

Example 11

Preparation of 4-butyl-2-(adamantan-2-yl)-1-[2-(trifluoromethyl)benzyl]-1,2-diazetidin-3-one

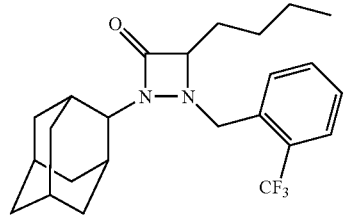

Process 1: Preparation of benzyl 2-(2-bromo-hexanoyl)-2-(adamantan-2-yl)hydrazinecarboxylate 2-Bromohexanoyl bromide was used in place of chloroacetic acid chloride for a similar reaction and treatment as Process 3 of Example 1, and benzyl 2-(2-bromo-hexanoyl)-2-(adamantan-2-yl)hydrazinecarboxylate was obtained as a colorless oil.
¹H-NMR (400 MHz, CDCl₃) δ; 0.82-0.95 (m, 3H), 1.22-2.36 (m, 20H), 4.26 (t, J=7.0 Hz, 1H), 4.37 (s, 1H), 5.20 (s, 2H), 6.65-6.89 (m, 1H), 7.34-7.38 (m, 5H).

Process 2: Preparation of benzyl 2-(adamantan-2-yl)-4-butyl-3-oxo-1,2-diazetidine-1-carboxylate Benzyl 2-(2-bromo-hexanoyl)-2-(adamantan-2-yl)hydrazinecarboxylate was used for a similar reaction and treatment as Process 4 of Example 1, and benzyl 2-(adamantan-2-yl)-4-butyl-3-oxo-1,2-diazetidine-1-carboxylate was obtained as a colorless oil.
¹H-NMR (400 MHz, CDCl₃) δ; 0.88 (t, J=7.9 Hz, 3H), 1.32-2.13 (m, 18H), 2.28 (s, 1H), 2.57 (s, 1H), 4.01 (s, 1H), 4.57 (t, J=7.4 Hz, 1H), 5.13 (d, J=12.0 Hz, 1H), 5.22 (d, J=12.0 Hz, 1H), 7.34-7.40 (m, 5H).

Process 3: Preparation of 2-(adamantan-2-yl)-4-butyl-1,2-diazetidin-3-one

Benzyl 2-(adamantyl-2-yl)-4-butyl-3-oxo-1,2-diazetidine-1-carboxylate was used for a similar reaction and treatment as Process 5 of Example 1, and 2-(adamantan-2-yl)-4-butyl-1,2-diazetidin-3-one was obtained as a colorless oil.
¹H-NMR (400 MHz, CDCl₃) δ; 0.92 (t, J=7.8 Hz, 3H), 1.35-1.47 (m, 4H), 1.63-2.40 (m, 17H), 3.73 (s, 1H), 4.37 (t, J=7.9 Hz, 1H).

Process 4: Preparation of 4-butyl-2-(adamantan-2-yl)-1-[2-(trifluoromethyl)benzyl]-1,2-diazetidin-3-one 2-(Adamantan-2-yl)-4-butyl-1,2-diazetidin-3-one and 2-(trifluoromethyl)benzyl bromide were used for a similar reaction and treatment as Process 6 of Example 1, and the title compound was obtained as a white crystalline powder.
¹H-NMR (400 MHz, CDCl₃) δ 0.73 (t, J=7.0 Hz, 3H), 1.18-0.99 (m, 4H), 1.93-1.52 (m, 12H), 2.28-2.15 (m, 2H), 2.44-2.38 (m, 2H), 3.65 (t, J=6.5 Hz, 1H), 3.70 (br, 1H), 3.83 (d, J=13.2 Hz, 1H), 4.39 (d, J=13.2 Hz, 1H), 7.40 (t, J=7.6 Hz, 1H), 7.54 (t, J=7.6 Hz, 1H), 7.66 (d, J=7.8 Hz, 1H), 7.76 (d, J=7.8 Hz, 1H).

Example 12

Preparation of 1-benzyl-4,4-dimethyl-2-(adamantan-2-yl)-1,2-diazetidin-3-one

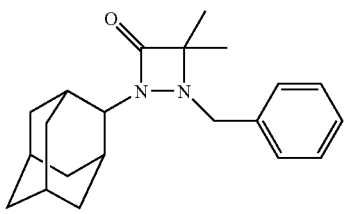

Process 1: Preparation of benzyl 2-(2-bromoisobutyryl)-2-(adamantan-2-yl)hydrazinecarboxylate 2-Bromoisobutyryl bromide was used in place of chloroacetic acid chloride for a similar reaction and treatment as Process 3 of Example 1, and benzyl 2-(2-bromoisobutyryl)-2-(adamantan-2-yl)hydrazinecarboxylate was obtained as a colorless oil.
¹H-NMR (400 MHz, CDCl₃) δ 1.58 (s, 6H), 1.62-1.98 (m, 13H), 2.37 (s, 1H), 4.17-4.37 (m, 1H), 5.09-5.27 (m, 2H), 6.79-7.00 (m, 1H), 7.34-7.38 (m, 5H).

Process 2: Preparation of benzyl 2-(adamantan-2-yl)-4,4-dimethyl-3-oxo-1,2-diazetidine-1-carboxylate Benzyl 2-(2-bromoisobutyryl)-2-(adamantan-2-yl)hydrazinecarboxylate was used for a similar reaction and treatment as Process 4 of Example 1, and benzyl 2-(adamantan-2-yl)-4,4-dimethyl-3-oxo-1,2-diazetidine-1-carboxylate was obtained as a colorless oil.
¹H-NMR (400 MHz, CDCl₃) δ; 1.49 (s, 6H), 1.62-2.03 (m, 12H), 2.38 (s, 2H), 4.02 (s, 1H), 5.18 (s, 2H), 7.34-7.41 (m, 5H).

Process 3: Preparation of 2-(adamantan-2-yl)-4,4-dimethyl-1,2-diazetidin-3-one

Benzyl 2-(adamantan-2-yl)-4,4-dimethyl-3-oxo-1,2-diazetidine-1-carboxylate was used for a similar reaction and treatment as Process 5 of Example 1, and 2-(adamantan-2-yl)-4,4-dimethyl-1,2-diazetidin-3-one was obtained as a colorless oil.
¹H-NMR (400 MHz, CDCl₃) δ; 1.41 (s, 3H), 1.55 (s, 3H), 1.63-2.13 (m, 13H), 2.54 (s, 1H), 3.71 (s, 1H), 3.97 (s, 1H).

Process 4: Preparation of 1-benzyl-4,4-dimethyl-2-(adamantan-2-yl)-1,2-diazetidin-3-one 2-(Adamantan-2-yl)-4,4-dimethyl-1,2-diazetidin-3-one was used for a similar reaction and treatment as Process 6 of Example 1, and the title compound was obtained as a white crystalline powder.

$^1$H-NMR (400 MHz, CDCl$_3$) δ; 1.25 (s, 3H), 1.38 (s, 3H), 1.53-1.89 (m, 10H), 2.13-2.14 (m, 1H), 2.29-2.32 (m, 2H), 2.39 (s, 1H), 3.57 (s, 1H), 3.87 (d, J=13.9 Hz, 1H), 4.15 (d, J=13.9 Hz, 1H), 7.24-7.40 (m, 5H).

EI-MS m/z; 324 (M$^+$).

Example 13

Preparation of 1-(4-chlorobenzyl)-4,4-dimethyl-2-(adamantan-2-yl)-1,2-diazetidin-3-one 2-(Adamantan-2-yl)-4,4-dimethyl-1,2-diazetidin-3-one prepared in Process 3 of Example 12, and 4-chlorobenzyl bromide were used for a similar reaction and treatment as Process 6 of Example 1, and the title compound was obtained as a white crystalline powder.

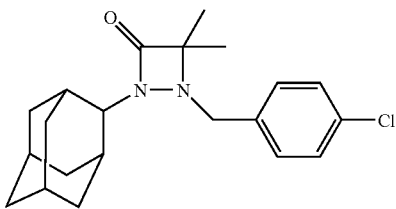

$^1$H-NMR (400 MHz, CDCl$_3$) δ; 1.24 (s, 3H), 1.37 (s, 3H), 1.57-1.89 (m, 10H), 2.12-2.14 (m, 1H), 2.29-2.35 (m, 2H), 2.37 (s, 1H), 3.57 (s, 1H), 3.84 (d, J=13.9 Hz, 1H), 4.10 (d, J=13.9 Hz, 1H), 7.28 (d, J=8.6 Hz, 2H), 7.33 (d, J=8.6 Hz, 2H).

EI-MS m/z; 359 (M$^+$).

Example 14

Preparation of 4,4-dimethyl-1-(4-methylbenzyl)-2-(adamantan-2-yl)-1,2-diazetidin-3-one 2-(Adamantan-2-yl)-4,4-dimethyl-1,2-diazetidin-3-one and 4-methylbenzyl bromide were used for a similar reaction and treatment as Process 6 of Example 1, and the title compound was obtained as a white crystalline powder.

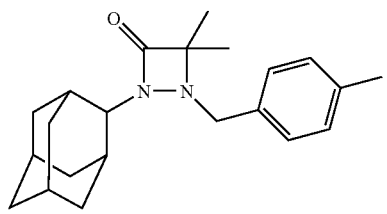

$^1$H-NMR (400 MHz, CDCl$_3$) δ; 1.25 (s, 3H), 1.37 (s, 3H), 1.57-1.89 (m, 10H), 2.13-2.16 (m, 1H), 2.30-2.40 (m, 6H), 3.58 (s, 1H), 3.82 (d, J=13.7 Hz, 1H), 4.12 (d, J=13.7 Hz, 1H), 7.11 (d, J=7.8 Hz, 2H), 7.26 (d, J=7.8 Hz, 2H).

IR (ATR); 2909, 2853, 1751, 808 cm$^{-1}$.

EI-MS m/z; 338 (M$^+$).

Example 15

Preparation of 1-(4-fluorobenzyl)-4,4-dimethyl-2-(adamantan-2-yl)-1,2-diazetidin-3-one 2-(Adamantan-2-yl)-4,4-dimethyl-1,2-diazetidin-3-one and 4-fluorobenzyl bromide were used for a similar reaction and treatment as Process 6 of Example 1, and the title compound was obtained as a white crystalline powder.

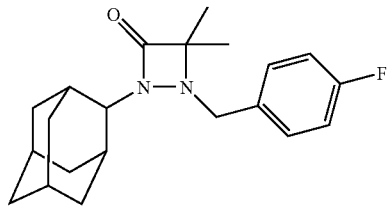

$^1$H-NMR (400 MHz, CDCl$_3$) δ; 1.24 (s, 3H), 1.37 (s, 3H), 1.55-1.89 (m, 10H), 2.07-2.11 (m, 1H), 2.20-2.28 (, 2H), 2.38 (s, 1H), 3.56 (s, 1H), 3.85 (d, J=13.7 Hz, 1H), 4.13 (d, J=13.7 Hz, 1H), 7.00 (t, J=8.8 Hz, 2H), 7.37 (dd, J=5.8, 8.8 Hz, 2H).

IR (ATR); 2924, 2905, 1743, 1731, 1510, 1224, 811 cm$^{-1}$.

EI-MS m/z; 342 (M$^+$).

Example 16

Preparation of 1-(3,4-difluorobenzyl)-4,4-dimethyl-2-(adamantan-2-yl)-1,2-diazetidin-3-one 2-(Adamantan-2-yl)-4,4-dimethyl-1,2-diazetidin-3-one and 3,4-difluorobenzyl bromide were used for a similar reaction and treatment as Process 6 of Example 1, and the title compound was obtained as a white crystalline powder.

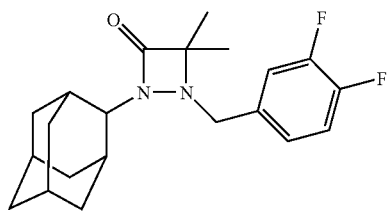

$^1$H-NMR (400 MHz, CDCl$_3$) δ; 1.24 (s, 3H), 1.39 (s, 3H), 1.58-1.90 (m, 10H), 2.12 (d, J=12.7 Hz, 1H), 2.25 (d, J=12.7 Hz, 1H), 2.30 (s, 1H), 2.36 (s, 1H), 3.57 (s, 1H), 3.83 (d, J=14.0 Hz, 1H), 4.08 (d, J=14.0 Hz, 1H), 7.08-7.14 (m, 2H), 7.27 (t, J=9.2 Hz, 1H).

IR (ATR); 2908, 1725, 1520, 1291, 1206, 774 cm$^{-1}$.

EI-MS m/z; 360 (M$^+$).

Example 17

Preparation of 1-(2,4-difluorobenzyl)-4,4-dimethyl-2-(adamantan-2-yl)-1,2-diazetidin-3-one 2-(Adamantan-2-yl)-4,4-dimethyl-1,2-diazetidin-3-one and 2,4-difluorobenzyl bromide were used for a similar reaction and treatment as Process 6 of Example 1, and the title compound was obtained as a white crystalline powder.

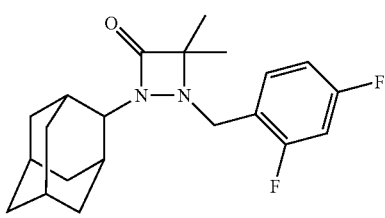

¹H-NMR (400 MHz, CDCl₃) δ; 1.27 (s, 3H), 1.38 (s, 3H), 1.58-1.89 (m, 10H), 2.11 (d, J=12.2 Hz, 1H), 2.26 (d, J=12.2 Hz, 1H), 2.28 (s, 1H), 2.39 (s, 1H), 3.60 (s, 1H), 3.97 (d, J=14.2 Hz, 1H), 4.02 (d, J=14.2 Hz, 1H), 6.76-6.81 (m, 1H), 6.87 (dt, J=1.7, 8.4 Hz, 1H), 7.55 (q, J=7.8 Hz, 1H).

IR (ATR); 2916, 1733, 1506, 1276, 1139, 962 cm⁻¹.

FAB-MS m/z; 361 (M+H)⁺.

Example 18

Preparation of 1-(3,5-difluorobenzyl)-4,4-dimethyl-2-(adamantan-2-yl)-1,2-diazetidin-3-one 2-(Adamantan-2-yl)-4,4-dimethyl-1,2-diazetidin-3-one and 3,5-difluorobenzyl bromide were used for a similar reaction and treatment as Process 6 of Example 1, and the title compound was obtained as a white crystalline powder.

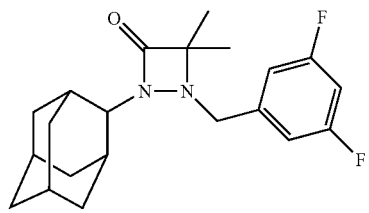

¹H-NMR (400 MHz, CDCl₃) δ; 1.25 (s, 3H), 1.42 (s, 3H), 1.60-1.90 (m, 10H), 2.13 (d, J=12.6 Hz, 1H), 2.25 (d, J=12.6 Hz, 1H), 2.33 (d, J=13.3 Hz, 2H), 3.58 (s, 1H), 3.86 (d, J=14.5 Hz, 1H), 4.11 (d, J=14.5 Hz, 1H), 6.68-6.73 (m, 1H), 6.94-6.96 (m, 2H).

IR (ATR); 2909, 1733, 1593, 1113, 850 cm⁻¹.

FAB-MS m/z; 361 (M+H)⁺.

Example 19

Preparation of 1-(2,3-difluorobenzyl)-4,4-dimethyl-2-(adamantan-2-yl)-1,2-diazetidin-3-one 2-(Adamantan-2-yl)-4,4-dimethyl-1,2-diazetidin-3-one and 2,3-difluorobenzyl bromide were used for a similar reaction and treatment as Process 6 of Example 1, and the title compound was obtained as a white crystalline powder.

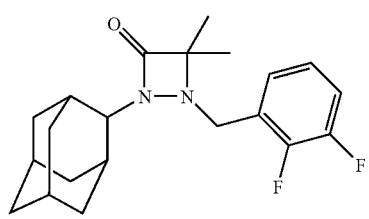

¹H-NMR (400 MHz, CDCl₃) δ; 1.28 (s, 3H), 1.40 (s, 3H), 1.60-1.90 (m, 10H), 2.12 (d, J=12.7 Hz, 1H), 2.26 (d, J=12.7 Hz, 1H), 2.28 (s, 1H), 2.39 (s, 1H), 3.61 (s, 1H), 4.02 (d, J=14.6 Hz, 1H), 4.08 (d, J=14.6 Hz, 1H), 7.05-7.10 (m, 2H), 7.31-7.34 (m, 1H).

IR (ATR); 2915, 1734, 1487, 1280, 781 cm⁻¹.

FAB-MS m/z; 361 (M+H)⁺.

Example 20

Preparation of 1-(2,5-difluorobenzyl)-4,4-dimethyl-2-(adamantan-2-yl)-1,2-diazetidin-3-one 2-(Adamantan-2-yl)-4,4-dimethyl-1,2-diazetidin-3-one and 2,5-difluorobenzyl bromide were used for a similar reaction and treatment as Process 6 of Example 1, and the title compound was obtained as a white crystalline powder.

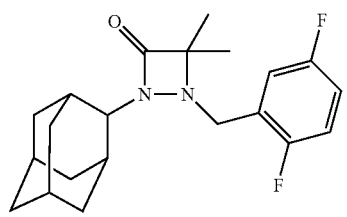

¹H-NMR (400 MHz, CDCl₃) δ; 1.26 (s, 3H), 1.42 (s, 3H), 1.58-1.90 (m, 10H), 2.13 (d, J=12.8 Hz, 1H), 2.26 (d, J=12.8 Hz, 1H), 2.30 (s, 1H), 2.38 (s, 1H), 3.62 (s, 1H), 3.99 (d, J=14.8 Hz, 1H), 4.04 (d, J=14.8 Hz, 1H), 6.89-7.02 (m, 2H), 7.29-7.33 (m, 1H).

IR (ATR); 2917, 1735, 1492, 1237, 818 cm⁻¹.

FAB-MS m/z; 361 (M+H)⁺.

Example 21

Preparation of 1-(2,6-difluorobenzyl)-4,4-dimethyl-2-(adamantan-2-yl)-1,2-diazetidin-3-one 2-(Adamantan-2-yl)-4,4-dimethyl-1,2-diazetidin-3-one and 2,6-difluorobenzyl bromide were used for a similar reaction and treatment as Process 6 of Example 1, and the title compound was obtained as a white crystalline powder.

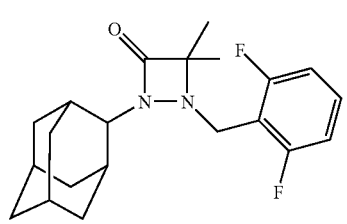

¹H-NMR (400 MHz, CDCl₃) δ; 1.36 (s, 3H), 1.43 (s, 3H), 1.52-1.87 (m, 10H), 1.99 (d, J=13.1 Hz, 1H), 2.05 (s, 1H), 2.28 (d, J=13.1 Hz, 1H), 2.45 (s, 1H), 3.56 (s, 1H), 3.99 (d, J=13.5 Hz, 1H), 4.03 (d, J=13.5 Hz, 1H), 6.85-6.91 (m, 2H), 7.21-7.29 (m, 1H).

IR (ATR); 2910, 1743, 1470, 1046, 797 cm⁻¹.

FAB-MS m/z; 361 (M+H)⁺.

Example 22

Preparation of 1-(3-fluorobenzyl)-4,4-dimethyl-2-(adamantan-2-yl)-1,2-diazetidin-3-one 2-(Adamantan-2-yl)-4,4-dimethyl-1,2-diazetidin-3-one and 3-fluorobenzyl bromide were used for a similar reaction and treatment as Process 6 of Example 1, and the title compound was obtained as a white crystalline powder.

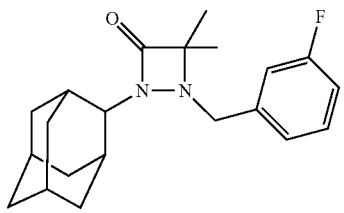

$^1$H-NMR (400 MHz, CDCl$_3$) δ; 1.25 (s, 3H), 1.40 (s, 3H), 1.57-1.90 (m, 10H), 2.13 (d, J=13.2 Hz, 1H), 2.27 (d, J=13.2 Hz, 1H), 2.31 (s, 1H), 2.37 (s, 1H), 3.58 (s, 1H), 3.87 (d, J=14.0 Hz, 1H), 4.14 (d, J=14.0 Hz, 1H), 6.92-6.97 (m, 1H), 7.15 (d, J=8.0 Hz, 1H), 7.25-7.30 (m, 1H).

IR (ATR); 2918, 1732, 1335 1254, 782 cm$^{-1}$.

FAB-MS m/z; 343 (M+H)$^+$.

Example 23

Preparation of 1-(3,5-dimethoxybenzyl)-4,4-dimethyl-2-(adamantan-2-yl)-1,2-diazetidin-3-one 2-(Adamantan-2-yl)-4,4-dimethyl-1,2-diazetidin-3-one and 3,5-dimethoxybenzyl bromide were used for a similar reaction and treatment as Process 6 of Example 1, and the title compound was obtained as a white crystalline powder.

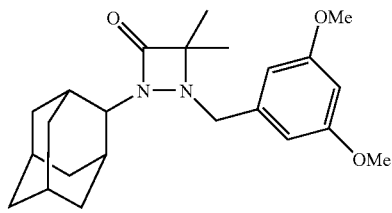

$^1$H-NMR (400 MHz, CDCl$_3$) δ; 1.25 (s, 3H), 1.39 (s, 3H), 1.59-1.89 (m, 10H), 2.15 (d, J=12.6 Hz, 1H), 2.27 (d, J=12.6 Hz, 1H), 2.36 (d, J=15.6 Hz, 2H), 3.60 (s, 1H), 3.79 (s, 6H), 3.81 (d, J=14.5 Hz, 1H), 4.12 (d, J=14.5 Hz, 1H), 6.35 (t, J=2.2 Hz, 1H), 6.56 (d, J=2.2 Hz, 2H).

IR (ATR); 2916, 1740, 1598, 1202, 1145, 829 cm$^{-1}$.

EI-MS m/z; 384 (M$^+$).

Example 24

Preparation of 4,4-dimethyl-2-(adamantan-2-yl)-1-[3-(trifluoromethyl)benzyl]-1,2-diazetidin-3-one 2-(Adamantan-2-yl)-4,4-dimethyl-1,2-diazetidin-3-one and 3-(trifluoromethyl)benzyl bromide were used for a similar reaction and treatment as Process 6 of Example 1, and the title compound was obtained as a colorless oil.

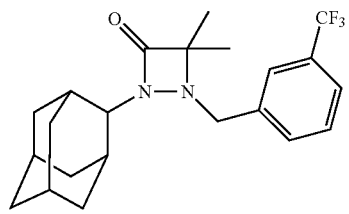

$^1$H-NMR (400 MHz, CDCl$_3$) δ; 1.24 (s, 3H), 1.39 (s, 3H), 1.53-1.90 (m, 10H), 2.14 (d, J=13.1 Hz, 1H), 2.27 (d, J=13.1 Hz, 1H), 2.29 (s, 1H), 2.35 (s, 1H), 3.56 (s, 1H), 3.95 (d, J=14.2 Hz, 1H), 4.19 (d, J=14.2 Hz, 1H), 7.44 (t, J=7.7 Hz, 1H), 7.52 (t, J=7.7 Hz, 1H), 7.59 (t, J=7.7 Hz, 1H), 7.69 (s, 1H).

IR (ATR); 2911, 1728, 1328, 1165, 1126, 1076 cm$^{-1}$.

EI-MS m/z; 392 (M$^+$).

Example 25

Preparation of 1-[3-fluoro-5-(trifluoromethyl)benzyl]-4,4-dimethyl-2-(adamantan-2-yl)-1,2-diazetidin-3-one 2-(Adamantan-2-yl)-4,4-dimethyl-1,2-diazetidin-3-one and 3-fluoro-5-(trifluoromethyl)benzyl bromide were used for a similar reaction and treatment as Process 6 of Example 1, and the title compound was obtained as a colorless oil.

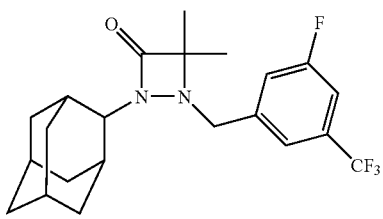

$^1$H-NMR (400 MHz, CDCl$_3$) δ; 1.25 (s, 3H), 1.41 (s, 3H), 1.57-1.91 (m, 10H), 2.13 (d, J=12.9 Hz, 1H), 2.26 (d, J=12.9 Hz, 1H), 2.32 (s, 2H), 3.57 (s, 1H), 3.95 (d, J=14.4 Hz, 1H), 4.17 (d, J=14.4 Hz, 1H), 7.23 (d, J=8.3 Hz, 1H), 7.35 (d, J=9.3 Hz, 1H), 7.47 (s, 1H).

IR (ATR); 2918, 1737, 1340, 1144, 868 cm$^{-1}$.

EI-MS m/z; 410 (M$^+$).

Example 26

Preparation of 1-[3,5-bis(trifluoromethyl)benzyl]-4,4-dimethyl-2-(adamantan-2-yl)-1,2-diazetidin-3-one 2-(Adamantan-2-yl)-4,4-dimethyl-1,2-diazetidin-3-one and 3,5-bis(trifluoromethyl)benzyl bromide were used for a similar reaction and treatment as Process 6 of Example 1, and the title compound was obtained as a white crystalline powder.

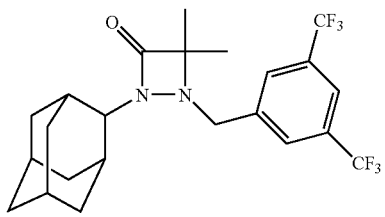

¹H-NMR (400 MHz, CDCl₃) δ; 1.25 (s, 3H), 1.41 (s, 3H), 1.53-1.91 (m, 10H), 2.13 (d, J=13.2 Hz, 1H), 2.26 (d, J=13.2 Hz, 1H), 2.30 (s, 2H), 3.55 (s, 1H), 4.04 (d, J=14.6 Hz, 1H), 4.23 (d, J=14.6 Hz, 1H), 7.79 (s, 1H), 7.88 (s, 2H).
IR (ATR); 2914, 1748, 1278, 1166, 1130, 897 cm⁻¹.
EI-MS m/z; 460 (M⁺).

Example 27

Preparation of 1-(2-chlorobenzyl)-4,4-dimethyl-2-(adamantan-2-yl)-1,2-diazetidin-3-one 2-(Adamantan-2-yl)-4,4-dimethyl-1,2-diazetidin-3-one and 2-chlorobenzyl bromide were used for a similar reaction and treatment as Process 6 of Example 1, and the title compound was obtained as a white crystalline powder.

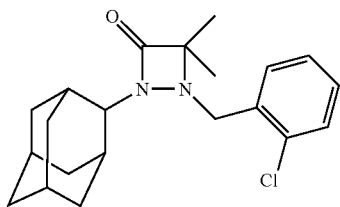

¹H-NMR (400 MHz, CDCl₃) δ; 1.23 (s, 3H), 1.46 (s, 3H), 1.57-1.90 (m, 10H), 2.13 (d, J=13.0 Hz, 1H), 2.26 (s, 1H), 2.29 (d, J=13.0 Hz, 1H), 2.41 (s, 1H), 3.62 (s, 1H), 4.07 (d, J=15.2 Hz, 1H), 4.15 (d, J=15.2 Hz, 1H), 7.17-7.30 (m, 2H), 7.34 (dd, J=1.5, 7.8 Hz, 1H), 7.64 (d, J=7.6 Hz, 1H).
EI-MS m/z; 358 (M⁺).

Example 28

Preparation of 1-(3-chlorobenzyl)-4,4-dimethyl-2-(adamantan-2-yl)-1,2-diazetidin-3-one 2-(Adamantan-2-yl)-4,4-dimethyl-1,2-diazetidin-3-one and 3-chlorobenzyl bromide were used for a similar reaction and treatment as Process 6 of Example 1, and the title compound was obtained as a white crystalline powder.

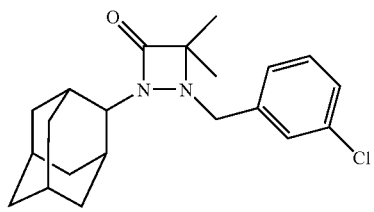

¹H-NMR (400 MHz, CDCl₃) δ; 1.25 (s, 3H), 1.40 (s, 3H), 1.56-1.90 (m, 10H), 2.13 (d, J=12.6 Hz, 1H), 2.25 (d, J=12.6 Hz, 1H), 2.30 (s, 1H), 2.36 (s, 1H), 3.57 (s, 1H), 3.85 (d, J=14.0 Hz, 1H), 4.12 (d, J=14.0 Hz, 1H), 7.23-7.27 (m, 3H), 7.42 (s, 1H).
IR (ATR); 2908, 1734, 1334, 1078, 783 cm⁻¹.
EI-MS m/z; 358 (M⁺).

Example 29

Preparation of 4,4-dimethyl-1-(3-nitrobenzyl)-2-(adamantan-2-yl)-1,2-diazetidin-3-one 2-(Adamantan-2-yl)-4,4-dimethyl-1,2-diazetidin-3-one and 3-nitrobenzyl bromide were used for a similar reaction and treatment as Process 6 of Example 1, and the title compound was obtained as a yellow oil.

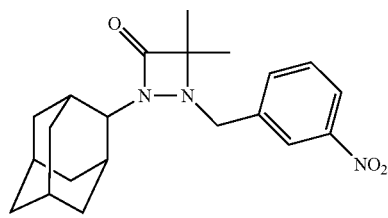

¹H-NMR (400 MHz, CDCl₃) δ; 1.26 (s, 3H), 1.42 (s, 3H), 1.57-1.91 (m, 10H), 2.12-2.16 (m, 3H), 2.25-2.35 (m, 1H), 3.58 (s, 1H), 4.01 (d, J=14.4 Hz, 1H), 4.21 (d, J=14.4 Hz, 1H), 7.51 (t, J=7.8 Hz, 1H), 7.75 (d, J=7.8 Hz, 1H), 8.13 (d, J=7.8 Hz, 1H), 8.30 (s, 1H).
IR (ATR); 2909, 1749, 1529, 1349, 755 cm⁻¹.
EI-MS m/z; 369 (M⁺).

Example 30

Preparation of 4,4-dimethyl-1-(2-methylbenzyl)-2-(adamantan-2-yl)-1,2-diazetidin-3-one 2-(Adamantan-2-yl)-4,4-dimethyl-1,2-diazetidin-3-one and 2-methylbenzyl bromide were used for a similar reaction and treatment as Process 6 of Example 1, and the title compound was obtained as a white crystalline powder.

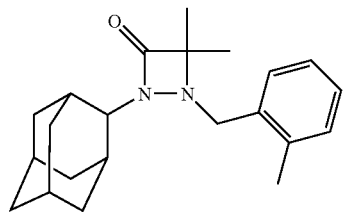

¹H-NMR (400 MHz, CDCl₃) δ; 1.26 (s, 3H), 1.44-1.48 (m, 4H), 1.60-1.87 (m, 9H), 2.04-2.07 (m, 2H), 2.27-2.42 (m, 5H), 3.54 (s, 1H), 3.94 (d, J=14.2 Hz, 1H), 4.00 (d, J=14.2 Hz, 1H), 7.12-7.26 (m, 3H), 7.45 (m, 1H).
IR (ATR); 2890, 1731, 1474, 1334, 743 cm⁻¹.
EI-MS m/z; 338 (M⁺).

Example 31

Preparation of 4,4-dimethyl-1-(4-nitrobenzyl)-2-(adamantan-2-yl)-1,2-diazetidin-3-one 2-(Adamantan-2-yl)-4,4-dimethyl-1,2-diazetidin-3-one and 4-nitrobenzyl bromide were used for a similar reaction and treatment as Process 6 of Example 1, and the title compound was obtained as a yellow crystalline powder.

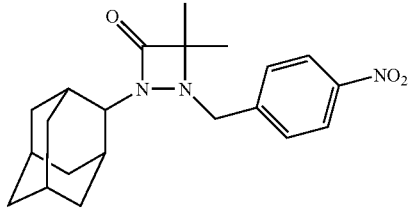

¹H-NMR (400 MHz, CDCl₃) δ; 1.24 (s, 3H), 1.40 (s, 3H), 1.56-1.91 (m, 10H), 2.12-2.35 (m, 4H), 3.59 (s, 1H), 4.00 (d, J=14.6 Hz, 1H), 4.22 (d, J=14.6 Hz, 1H), 7.60 (d, J=8.8 Hz, 2H), 8.19 (d, J=8.8 Hz, 2H).

IR (ATR); 2913, 1731, 1522, 1345, 732 cm⁻¹.

EI-MS m/z; 369 (M⁺).

Example 32

Preparation of 4,4-dimethyl-1-(3-methylbenzyl)-2-(adamantan-2-yl)-1,2-diazetidin-3-one 2-(Adamantan-2-yl)-4,4-dimethyl-1,2-diazetidin-3-one and 3-methylbenzyl bromide were used for a similar reaction and treatment as Process 6 of Example 1, and the title compound was obtained as a white crystalline powder.

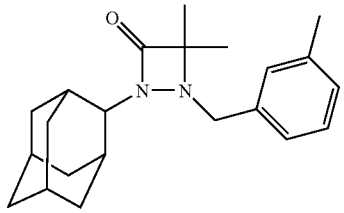

¹H-NMR (400 MHz, CDCl₃) δ; 1.25 (s, 3H), 1.39 (s, 3H), 1.57-1.89 (m, 10H), 2.14 (d, J=12.0 Hz, 1H), 2.21-2.39 (m, 6H), 3.57 (s, 1H), 3.84 (d, J=13.6 Hz, 1H), 4.12 (d, J=13.6 Hz, 1H), 7.04-7.08 (m, 1H), 7.18-7.19 (m, 3H).

IR (ATR); 2910, 1749, 1335, 780 cm⁻¹.

EI-MS m/z; 338 (M⁺).

Example 33

Preparation of 1-(3-bromobenzyl)-4,4-dimethyl-2-(adamantan-2-yl)-1,2-diazetidin-3-one 2-(Adamantan-2-yl)-4,4-dimethyl-1,2-diazetidin-3-one and 3-bromobenzyl bromide were used for a similar reaction and treatment as Process 6 of Example 1, and the title compound was obtained as a colorless oil.

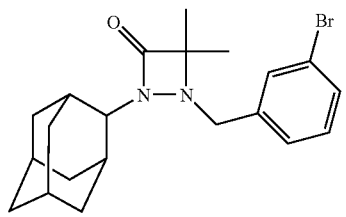

¹H-NMR (400 MHz, CDCl₃) δ; 1.25 (s, 3H), 1.40 (s, 3H), 1.56-1.90 (m, 10H), 2.13 (d, J=12.7 Hz, 1H), 2.25-2.36 (m, 3H), 3.56 (s, 1H), 3.85 (d, J=13.9 Hz, 1H), 4.12 (d, J=13.9 Hz, 1H), 7.18 (t, 7.8 Hz, 1H), 7.31 (d, J=7.8 Hz, 1H), 7.39 (d, J=7.8 Hz, 1H), 7.57 (s, 1H).

IR (ATR); 2908, 1750, 1247, 779 cm⁻¹.

EI-MS m/z; 402 (M⁺).

Example 34

Preparation of 1-(4-t-butylbenzyl)-4,4-dimethyl-2-(adamantan-2-yl)-1,2-diazetidin-3-one 2-(Adamantan-2-yl)-4,4-dimethyl-1,2-diazetidin-3-one and 4-t-butylbenzyl bromide were used for a similar reaction and treatment as Process 6 of Example 1, and the title compound was obtained as a white crystalline powder.

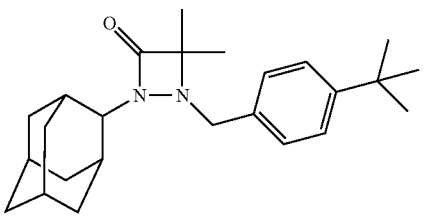

¹H-NMR (270 MHz, CDCl₃) δ; 1.28 (s, 3H), 1.31 (s, 9H), 1.40 (s, 3H), 1.47-1.87 (m, 10H), 2.09-2.39 (m, 4H), 3.55 (s, 1H), 3.87 (d, J=20.0 Hz, 1H), 4.10 (d, J=20.0 Hz, 1H), 7.27-7.36 (m, 4H).

IR (ATR); 2912, 1766, 1752, 823 cm⁻¹.

EI-MS m/z; 380 (M⁺).

Example 35

Preparation of 1-(3-iodobenzyl)-4,4-dimethyl-2-(adamantan-2-yl)-1,2-diazetidin-3-one 2-(Adamantan-2-yl)-4,4-dimethyl-1,2-diazetidin-3-one and 3-iodobenzyl bromide were used for a similar reaction and treatment as Process 6 of Example 1, and the title compound was obtained as a colorless oil.

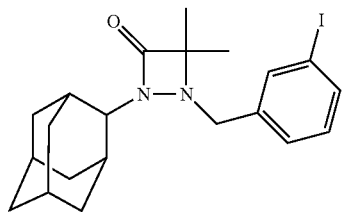

¹H-NMR (400 MHz, CDCl₃) δ; 1.25 (s, 3H), 1.39 (s, 3H), 1.55-1.90 (m, 10H), 2.12 (d, 12.2 Hz, 1H), 2.25-2.35 (m, 3H), 3.55 (s, 1H), 3.82 (d, J=14.0 Hz, 1H), 4.09 (d, J=14.0 Hz, 1H), 7.05 (t, J=7.8 Hz, 1H), 7.35 (d, J=7.8 Hz, 1H), 7.59 (d, J=7.8, 1H), 7.77 (s, 1H).

IR (ATR); 2907, 1748, 778 cm⁻¹.

EI-MS m/z; 450 (M⁺).

Example 36

Preparation of 4,4-dimethyl-2-(adamantan-2-yl)-1-[4-(trifluoromethyl)benzyl]-1,2-diazetidin-3-one 2-(Adamantan-2-yl)-4,4-dimethyl-1,2-diazetidin-3-one and 4-(trifluoromethyl)benzyl bromide were used for a similar reaction and treatment as Process 6 of Example 1, and the title compound was obtained as a white crystalline powder.

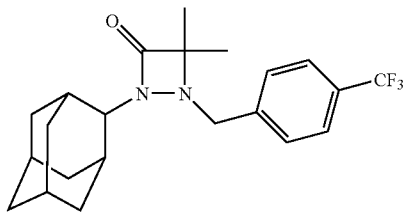

¹H-NMR (400 MHz, CDCl₃) δ; 1.25 (s, 6H), 1.39 (s, 3H), 1.55-1.90 (m, 10H), 1.23 (d, J=12.7 Hz, 1H), 2.25-2.37 (m, 3H), 3.58 (s, 1H), 3.94 (d, J=14.2 Hz, 1H), 4.19 (d, 14.2 Hz, 1H), 7.53 (d, J=8.0 Hz, 2H), 7.58 (d, J=8.0 Hz, 2H).

IR (ATR); 2917, 1743, 1731, 1322, 1161, 1129, 1069, 826 cm⁻¹.

EI-MS m/z; 392 (M⁺).

Example 37

Preparation of 1-(2,6-dichlorobenzyl)-4,4-dimethyl-2-(adamantan-2-yl)-1,2-diazetidin-3-one 2-(Adamantan-2-yl)-4,4-dimethyl-1,2-diazetidin-3-one and 2,6-dichlorobenzyl bromide were used for a similar reaction and treatment as Process 6 of Example 1, and the title compound was obtained as a white crystalline powder.

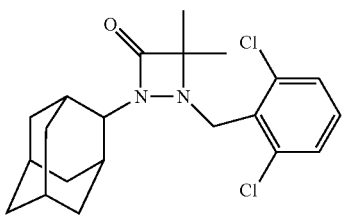

¹H-NMR (400 MHz, CDCl₃) δ; 1.07 (d, J=12.4 Hz, 1H), 1.38-1.82 (m, 17H), 2.32 (d, J=13.2 Hz, 1H), 2.48 (s, 1H), 3.45 (s, 1H), 4.12 (d, J=13.7 Hz, 1H), 4.25 (d, 13.7 Hz, 1H), 7.14-7.18 (m, 1H), 7.31 (d, J=8.1 Hz, 2H).

IR (ATR); 2929, 1746, 1434, 1323, 1190, 1086, 784, 762 cm⁻¹.

EI-MS m/z; 393 (M⁺).

Example 38

Preparation of 1-(2-fluorobenzyl)-4,4-dimethyl-2-(adamantan-2-yl)-1,2-diazetidin-3-one 2-(Adamantan-2-yl)-4,4-dimethyl-1,2-diazetidin-3-one and 2-fluorobenzyl bromide were used for a similar reaction and treatment as Process 6 of Example 1, and the title compound was obtained as a white crystalline powder.

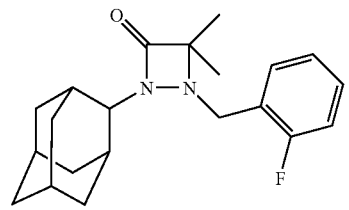

¹H-NMR (400 MHz, CDCl₃) δ; 1.27 (s, 3H), 1.40 (s, 3H), 1.57-1.89 (m, 10H), 2.13 (d, J=12.2 Hz, 1H), 2.27 (d, J=12.2 Hz, 1H), 2.29 (s, 1H), 2.41 (s, 1H), 3.61 (s, 1H), 4.05 (s, 2H), 7.02 (t, J=8.7 Hz, 1H), 7.11 (t, J=7.4 Hz, 1H), 7.21-7.25 (m, 1H), 7.56 (t, J=7.4 Hz, 1H).

IR (ATR); 2917, 1732, 1333, 1229, 1098, 756 cm⁻¹.

EI-MS m/z; 342 (M⁺).

Example 39

Preparation of 1-(2-bromobenzyl)-4,4-dimethyl-2-(adamantan-2-yl)-1,2-diazetidin-3-one 2-(Adamantan-2-yl)-4,4-dimethyl-1,2-diazetidin-3-one and 2-bromobenzyl bromide were used for a similar reaction and treatment as Process 6 of Example 1, and the title compound was obtained as a white crystalline powder.

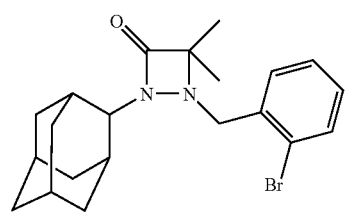

¹H-NMR (400 MHz, CDCl₃) δ; 1.23 (s, 3H), 1.47 (s, 3H), 1.57-1.90 (m, 10H), 2.13 (d, J=12.8 Hz, 1H), 2.29 (d, J=12.8 Hz, 1H), 2.24 (s, 1H), 2.41 (s, 1H), 3.62 (s, 1H), 4.06 (d, J=15.3 Hz, 1H), 4.12 (d, J=15.3 Hz, 1H), 7.11 (t, J=7.8 Hz, 1H), 7.29 (t, J=7.8 Hz, 1H), 7.54 (d, J=7.8 Hz, 1H), 7.64 (d, J=7.8 Hz, 1H).

IR (ATR); 2911, 1761, 1244, 1025, 762 cm⁻¹.

EI-MS m/z; 402 (M⁺).

Example 40

Preparation of 1-(2-iodobenzyl)-4,4-dimethyl-2-(adamantan-2-yl)-1,2-diazetidin-3-one 2-(Adamantan-2-yl)-4,4-dimethyl-1,2-diazetidin-3-one and 2-iodobenzyl bromide were used for a similar reaction and treatment as Process 6 of Example 1, and the title compound was obtained as a white crystalline powder.

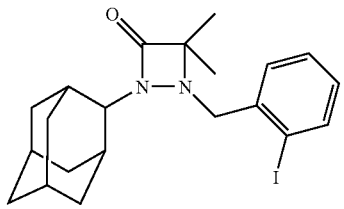

$^1$H-NMR (400 MHz, CDCl$_3$) δ; 1.24 (s, 3H), 1.48 (s, 3H), 1.54-1.89 (m, 10H), 2.12 (d, J=12.6 Hz, 1H), 2.20 (s, 1H), 2.29 (d, J=12.6 Hz, 1H), 2.41 (s, 1H), 3.60 (s, 1H), 3.99 (d, J=15.1 Hz, 1H), 4.05 (d, J=15.1 Hz, 1H), 6.96 (t, J=6.8 Hz, 1H), 7.32 (t, J=7.8 Hz, 1H), 7.59 (d, J=6.8 Hz, 1H), 7.82 (d, J=7.8 Hz, 1H).

IR (ATR); 2915, 1740, 1327, 1015, 764 cm$^{-1}$.

EI-MS m/z; 450 (M$^+$).

Example 41

Preparation of 1-(2-chloro-5-fluorobenzyl)-4,4-dimethyl-2-(adamantan-2-yl)-1,2-diazetidin-3-one 2-(Adamantan-2-yl)-4,4-dimethyl-1,2-diazetidin-3-one and 2-chloro-5-fluorobenzyl bromide were used for a similar reaction and treatment as Process 6 of Example 1, and the title compound was obtained as a white crystalline powder.

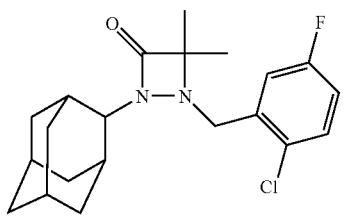

$^1$H-NMR (270 MHz, CDCl$_3$) δ; 1.22 (s, 3H), 1.48 (s, 3H), 1.53-1.87 (m, 10H), 2.05-2.38 (m, 4H), 3.63 (s, 1H), 4.02 (d, J=23.2 Hz, 1H), 4.11 (d, J=23.2 Hz, 1H), 6.88-6.95 (m, 1H), 7.26-7.33 (m, 1H), 7.39-7.43 (dd, J=14.2, 3.9 Hz, 1H).

IR (ATR); 2910, 1761, 1473, 1245, 1150, 1077, 817 cm$^{-1}$.

EI-MS m/z; 376 (M$^+$).

Example 42

Preparation of 4,4-dimethyl-2-(adamantan-2-yl)-1-[2-(trifluoromethyl)benzyl]-1,2-diazetidin-3-one 2-(Adamantan-2-yl)-4,4-dimethyl-1,2-diazetidin-3-one and 2-(trifluoromethyl)benzyl bromide were used for a similar reaction and treatment as Process 6 of Example 1, and the title compound was obtained as a white crystalline powder.

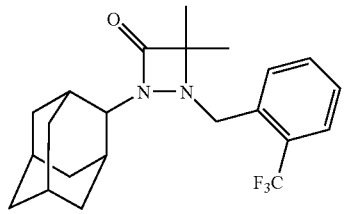

$^1$H-NMR (400 MHz, CDCl$_3$) δ; 1.19 (s, 3H), 1.49-1.91 (m, 13H), 2.13-2.38 (m, 4H), 3.60 (s, 1H), 4.14-4.23 (m, 2H), 7.36 (t, J=7.5 Hz, 1H), 7.53 (t, J=7.5 Hz, 1H), 7.64 (d, J=7.5 Hz, 1H), 7.95 (d, J=7.5 Hz, 1H).

IR (ATR); 2911, 1755, 1455, 1312, 1160, 1119, 1037, 771 cm$^{-1}$.

EI-MS m/z; 392 (M$^+$).

Example 43

Preparation of 1-(2,3-dichlorobenzyl)-4,4-dimethyl-2-(adamantan-2-yl)-1,2-diazetidin-3-one 2-(Adamantan-2-yl)-4,4-dimethyl-1,2-diazetidin-3-one and 2,3-dichlorobenzyl bromide were used for a similar reaction and treatment as Process 6 of Example 1, and the title compound was obtained as a white crystalline powder.

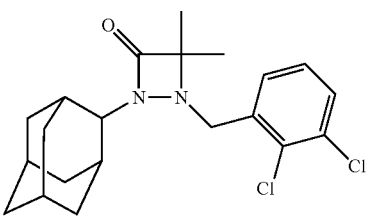

$^1$H-NMR (400 MHz, CDCl$_3$) δ; 1.24 (s, 3H), 1.46 (s, 3H), 1.58-1.90 (m, 10H), 2.11-2.23 (m, 3H), 2.39 (s, 1H), 3.62 (s, 1H), 4.08 (d, J=15.6 Hz, 1H), 4.17 (d, J=15.6 Hz, 1H), 7.20 (t, J=7.8 Hz, 1H), 7.37-7.39 (m, 1H), 7.57-7.59 (m, 1H).

IR (ATR); 2916, 1736, 784 cm$^{-1}$.

EI-MS m/z; 392 (M$^+$).

Example 44

Preparation of 1-(2,5-dichlorobenzyl)-4,4-dimethyl-2-(adamantan-2-yl)-1,2-diazetidin-3-one 2-(Adamantan-2-yl)-4,4-dimethyl-1,2-diazetidin-3-one and 2,5-dichlorobenzyl bromide were used for a similar reaction and treatment as Process 6 of Example 1, and the title compound was obtained as a white crystalline powder.

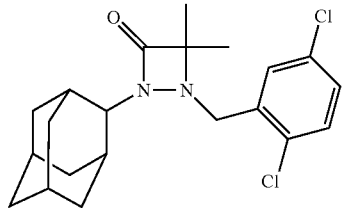

¹H-NMR (400 MHz, CDCl₃) δ; 1.23 (s, 3H), 1.48 (s, 3H), 1.66-1.91 (m, 10H), 2.12-2.37 (m, 4H), 3.62 (s, 1H), 4.02 (d, J=15.4 Hz, 1H), 4.11 (d, J=15.4 Hz, 1H), 7.18 (dd, J=8.3, 2.2 Hz, 1H), 7.27-7.29 (m, 1H), 7.66 (d, J=2.2 Hz, 1H).

IR (ATR); 2909, 1753, 1464, 1244, 1092, 1043, 812 cm⁻¹.

EI-MS m/z; 392 (M⁺).

Example 45

Preparation of 1-(2-chloro-4-fluorobenzyl)-4,4-dimethyl-2-(adamantan-2-yl)-1,2-diazetidin-3-one 2-(Adamantan-2-yl)-4,4-dimethyl-1,2-diazetidin-3-one and 2-chloro-4-fluorobenzyl bromide were used for a similar reaction and treatment as Process 6 of Example 1, and the title compound was obtained as a white crystalline powder.

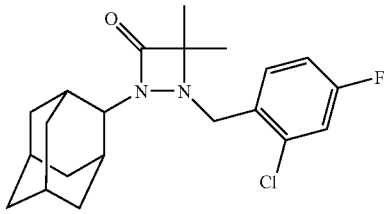

¹H-NMR (400 MHz, CDCl₃) δ; 1.23 (s, 3H), 1.43 (s, 3H), 1.58-1.90 (m, 10H), 2.12 (d, J=12.9 Hz, 1H), 2.25-2.29 (m, 2H), 2.39 (s, 1H), 3.61 (s, 1H), 4.01 (d, 15.1 Hz, 1H), 4.10 (d, J=15.1 Hz, 1H), 6.96-7.01 (m, 1H), 7.11 (dd, J=8.4, 2.7 Hz, 1H), 7.62-7.65 (m, 1H).

IR (ATR); 2909, 1752, 1604, 1490, 1232, 906, 857, 753 cm⁻¹.

EI-MS m/z; 376 (M⁺).

Example 46

Preparation of 1-(2-chloro-6-fluorobenzyl)-4,4-dimethyl-2-(adamantan-2-yl)-1,2-diazetidin-3-one 2-(Adamantan-2-yl)-4,4-dimethyl-1,2-diazetidin-3-one and 2-chloro-6-fluorobenzyl bromide were used for a similar reaction and treatment as Process 6 of Example 1, and the title compound was obtained as a white crystalline powder.

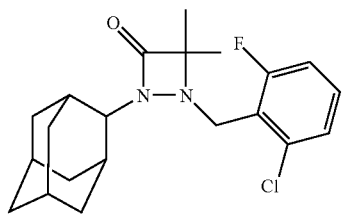

¹H-NMR (400 MHz, CDCl₃) δ; 1.24-1.27 (m, 1H), 1.43 (s, 3H), 1.48 (s, 3H), 1.56-1.91 (m, 11H), 2.31 (m, 1H), 2.46 (s, 1H), 3.49 (s, 1H), 4.08 (s, 2H), 6.96-7.00 (m, 1H), 7.19-7.22 (m, 2H).

IR (ATR); 2910, 1746, 1453, 1240, 784 cm⁻¹.

EI-MS m/z; 376 (M⁺).

Example 47

Preparation of 4,4-dimethyl-1-(2-nitrobenzyl)-2-(adamantan-2-yl)-1,2-diazetidin-3-one 2-(Adamantan-2-yl)-4,4-dimethyl-1,2-diazetidin-3-one and 2-nitrobenzyl bromide were used for a similar reaction and treatment as Process 6 of Example 1, and the title compound was obtained as a yellow oil.

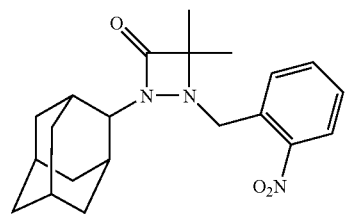

¹H-NMR (400 MHz, CDCl₃) δ; 1.23 (s, 3H), 1.40 (s, 3H), 1.47-1.93 (m, 10H), 2.03-2.14 (m, 2H), 2.26-2.31 (m, 2H), 3.50 (s, 1H), 4.27 (d, J=15.6 Hz, 1H), 4.36 (d, J=15.6 Hz, 1H), 7.43 (t, J=7.8 Hz, 1H), 7.57 (dt, J=7.8 1.2 Hz, 1H), 7.73 (d, J=7.8 Hz, 1H), 7.88 (dt, J=7.8, 1.2 Hz, 1H).

IR (ATR); 2909, 1750, 1527, 1361, 729 cm⁻¹.

EI-MS m/z; 369 (M⁺).

Example 48

Preparation of 1-[4-fluoro-2-(trifluoromethyl)benzyl]-4,4-dimethyl-2-(adamantan-2-yl)-1,2-diazetidin-3-one 2-(Adamantan-2-yl)-4,4-dimethyl-1,2-diazetidin-3-one and 4-fluoro-2-(trifluoromethyl)benzyl bromide were used for a similar reaction and treatment as Process 6 of Example 1, and the title compound was obtained as a colorless oil.

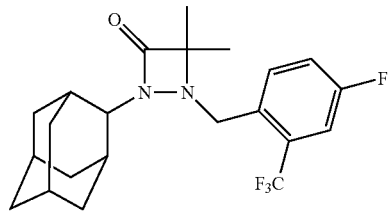

¹H-NMR (270 MHz, CDCl₃) δ; 1.19 (s, 3H), 1.48 (s, 3H), 1.58-1.86 (m, 10H), 2.11-2.36 (m, 4H), 3.59 (s, 1H), 4.14 (s, 2H), 7.22-7.26 (m, 1H), 7.36 (dd, J=9.2, 4.0 Hz, 1H), 7.93-7.98 (m, 1H).

IR (ATR); 2910, 1748, 750, 702 cm⁻¹.

EI-MS m/z; 410 (M⁺).

Example 49

Preparation of 1-(biphenyl-2-ylmethyl)-4,4-dimethyl-2-(adamantan-2-yl)-1,2-diazetidin-3-one 2-(Adamantan-2-yl)-4,4-dimethyl-1,2-diazetidin-3-one and 2-phenylbenzyl bromide were used for a similar reaction and treatment as Process 6 of Example 1, and the title compound was obtained as a colorless oil.

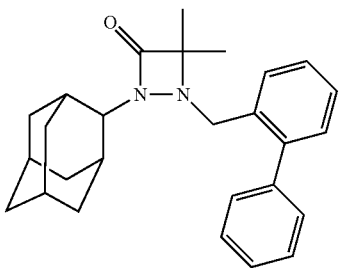

¹H-NMR (400 MHz, CDCl₃) δ; 0.98 (s, 3H), 1.34 (s, 3H), 1.52-1.85 (m, 10H), 2.03-2.20 (m, 3H), 2.33 (s, 1H), 3.47 (s, 1H), 3.78 (d, J=14.2 Hz, 1H), 4.06 (d, J=14.2 Hz, 1H), 7.22-7.44 (m, 8H), 7.22-7.26 (m, 1H), 7.36 (dd, J=9.2, 4.0 Hz, 1H), 7.72-7.74 (m, 1H).

IR (ATR); 2911, 1755, 1316, 1216, 1163, 1048, 907, 743 cm⁻¹.

EI-MS m/z; 400 (M⁺).

Example 50

Preparation of 1-(2-ethylbenzyl)-4,4-dimethyl-2-(adamantan-2-yl)-1,2-diazetidin-3-one 2-(Adamantan-2-yl)-4,4-dimethyl-1,2-diazetidin-3-one and 2-ethylbenzyl bromide were used for a similar reaction and treatment as Process 6 of Example 1, and the title compound was obtained as a colorless oil.

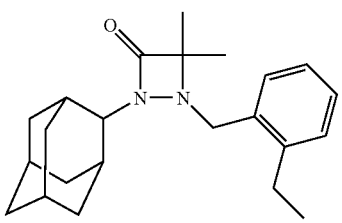

¹H-NMR (400 MHz, CDCl₃) δ; 1.22 (t, J=7.6 Hz, 3H), 1.27 (s, 3H), 1.45 (s, 3H), 1.65-1.75 (m, 7H), 1.82-1.88 (m, 3H), 2.07-2.11 (m, 2H), 2.28 (d, J=12.9 Hz, 1H), 2.42 (s, 1H), 2.71 (q, J=7.6 Hz, 2H), 3.54 (s, 1H), 3.99 (d, J=14.2 Hz, 1H), 4.03 (d, J=14.2 Hz, 1H), 7.13-7.24 (m, 3H), 7.49 (d, J=7.6 Hz, 1H).

IR (ATR); 2908, 1751, 1452, 758 cm⁻¹.

EI-MS m/z; 352 (M⁺).

Example 51

Preparation of 1-(2-methoxybenzyl)-4,4-dimethyl-2-(adamantan-2-yl)-1,2-diazetidin-3-one 2-(Adamantan-2-yl)-4,4-dimethyl-1,2-diazetidin-3-one and 2-methoxybenzyl bromide were used for a similar reaction and treatment as Process 6 of Example 1, and the title compound was obtained as a colorless oil.

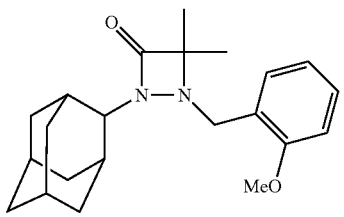

¹H-NMR (400 MHz, CDCl₃) δ; 1.21 (s, 3H), 1.45 (s, 3H), 1.53-1.89 (m, 10H), 2.15 (d, J=14.4 Hz, 1H), 2.28 (s, 2H), 2.43 (s, 1H), 3.63 (s, 1H), 3.83 (s, 3H), 3.98 (d, J=14.9 Hz, 1H), 4.05 (d, J=14.9 Hz, 1H), 6.84 (d, J=8.3 Hz, 1H), 6.93 (t, J=7.6 Hz, 1H), 7.20-7.24 (m, 1H), 7.52 (d, J=7.6 Hz, 1H).

IR (ATR); 2909, 1749, 1243, 754 cm⁻¹.

EI-MS m/z; 354 (M⁺).

Example 52

Preparation of 1-(2,4-dichlorobenzyl)-4,4-dimethyl-2-(adamantan-2-yl)-1,2-diazetidin-3-one 2-(Adamantan-2-yl)-4,4-dimethyl-1,2-diazetidin-3-one and 2,4-dichlorobenzyl bromide were used for a similar reaction and treatment as Process 6 of Example 1, and the title compound was obtained as a colorless oil.

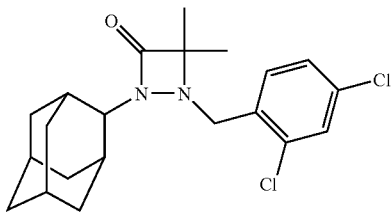

¹H-NMR (400 MHz, CDCl₃) δ; 1.22 (s, 3H), 1.44 (s, 3H), 1.58-1.90 (m, 10H), 2.12 (d, J=12.7 Hz, 1H), 2.26 (s, 2H), 2.39 (s, 1H), 3.61 (s, 1H), 4.01 (d, J=15.1 Hz, 1H), 4.10 (d, J=15.1 Hz, 1H), 7.24 (dd, J=8.3, 2.2 Hz, 1H), 7.37 (d, J=2.2 Hz, 1H), 7.60 (d, J=8.3 Hz, 1H).

IR (ATR); 2910, 1752, 1468, 755 cm⁻¹.

EI-MS m/z; 393 (M⁺).

Example 53

Preparation of 1-(4-bromobenzyl)-4,4-dimethyl-2-(adamantan-2-yl)-1,2-diazetidin-3-one 2-(Adamantan-2-yl)-4,4-dimethyl-1,2-diazetidin-3-one and 4-bromobenzyl bromide were used for a similar reaction and treatment as Process 6 of Example 1, and the title compound was obtained as a white crystalline powder.

63

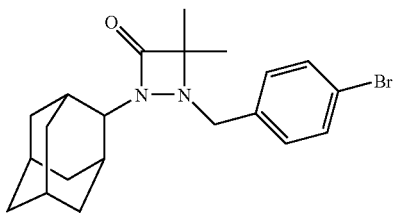

¹H-NMR (400 MHz, CDCl₃) δ; 1.24 (s, 3H), 1.38 (s, 3H), 1.53-1.90 (m, 10H), 2.15 (d, J=11.7 Hz, 1H), 2.24-2.37 (m, 3H), 3.57 (s, 1H), 3.83 (d, J=13.9 Hz, 1H), 4.09 (d, J=13.9 Hz, 1H), 7.28 (d, J=8.6 Hz, 2H), 7.44 (d, J=8.6 Hz, 2H).

IR (ATR); 2922, 1769, 1246, 1217, 809, 772 cm⁻¹.

EI-MS m/z; 402 (M⁺).

Example 54

Preparation of 1-(3-methoxybenzyl)-4,4-dimethyl-2-(adamantan-2-yl)-1,2-diazetidin-3-one 2-(Adamantan-2-yl)-4,4-dimethyl-1,2-diazetidin-3-one and 3-methoxybenzyl bromide were used for a similar reaction and treatment as Process 6 of Example 1, and the title compound was obtained as a white crystalline powder.

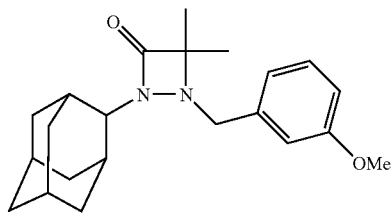

¹H-NMR (400 MHz, CDCl₃) δ; 1.25 (s, 3H), 1.42 (s, 3H), 1.57-1.89 (m, 10H), 2.13-2.17 (m, 1H), 2.28 (d, J=13.4 Hz, 1H), 2.32-2.39 (m, 2H), 3.59 (s, 1H), 3.81 (s, 3H), 3.85 (d, J=13.9 Hz, 1H), 4.15 (d, J=13.9 Hz, 1H), 6.79 (dd, J=8.1, 2.2 Hz, 1H), 6.95-6.97 (m, 2H), 7.22 (d, J=8.1 Hz, 1H).

IR (ATR); 2907, 1743, 1604, 1267, 1176, 1043, 780 cm⁻¹.

EI-MS m/z; 354 (M⁺).

Example 55

Preparation of 1-(2,4-dimethylbenzyl)-4,4-dimethyl-2-(adamantan-2-yl)-1,2-diazetidin-3-one 2-(Adamantan-2-yl)-4,4-dimethyl-1,2-diazetidin-3-one and 2,4-dimethylbenzyl bromide were used for a similar reaction and treatment as Process 6 of Example 1, and the title compound was obtained as a white crystalline powder.

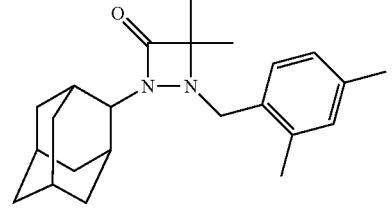

64

¹H-NMR (400 MHz, CDCl₃) δ; 1.25 (s, 3H), 1.43-1.50 (m, 4H), 1.56-1.74 (m, 6H), 1.82-1.87 (m, 3H), 2.07-2.13 (m, 2H), 2.26-2.34 (m, 7H), 2.42 (s, 1H), 3.55 (s, 1H), 3.90 (d, J=13.9 Hz, 1H), 3.97 (d, J=13.9 Hz, 1H), 6.94-6.96 (m, 2H), 7.32 (d, J=8.3 Hz, 1H).

IR (ATR); 2909, 1750, 816, 754 cm⁻¹.

EI-MS m/z; 352 (M⁺).

Example 56

Preparation of 1-(2,5-dimethylbenzyl)-4,4-dimethyl-2-(adamantan-2-yl)-1,2-diazetidin-3-one 2-(Adamantan-2-yl)-4,4-dimethyl-1,2-diazetidin-3-one and 2,5-dimethylbenzyl bromide were used for a similar reaction and treatment as Process 6 of Example 1, and the title compound was obtained as a white crystalline powder.

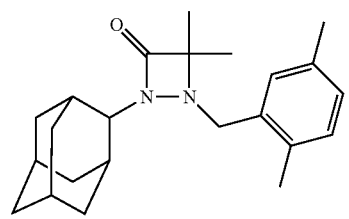

¹H-NMR (400 MHz, CDCl₃) δ; 1.27 (s, 3H), 1.43-1.47 (m, 4H), 1.57-1.72 (m, 6H), 1.82-1.87 (m, 3H), 2.08-2.12 (m, 2H), 2.27-2.33 (m, 7H), 2.41 (s, 1H), 3.53 (s, 1H), 3.90 (d, J=14.2 Hz, 1H), 3.96 (d, J=14.2 Hz, 1H), 6.96 (d, J=7.8 Hz, 1H), 7.02 (d, J=7.8 Hz, 1H), 7.26 (s, 1H).

IR (ATR); 2901, 1732, 1328, 808, 755 cm⁻¹.

EI-MS m/z; 352 (M⁺).

Example 57

Preparation of 1-(2,3-dimethylbenzyl)-4,4-dimethyl-2-(adamantan-2-yl)-1,2-diazetidin-3-one 2-(Adamantan-2-yl)-4,4-dimethyl-1,2-diazetidin-3-one and 2,3-dimethylbenzyl bromide were used for a similar reaction and treatment as Process 6 of Example 1, and the title compound was obtained as a white crystalline powder.

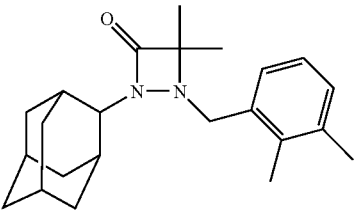

¹H-NMR (400 MHz, CDCl₃) δ; 1.26 (s, 3H), 1.44-1.47 (m, 4H), 1.55-1.71 (m, 6H), 1.81-1.87 (m, 3H), 2.07-2.10 (m, 2H), 2.25-2.34 (m, 7H), 2.42 (s, 1H), 3.52 (s, 1H), 3.95-4.03 (m, 2H), 7.01-7.11 (m, 2H), 7.28-7.31 (m, 1H).

IR (ATR); 2904, 1730, 1473, 1334, 777 cm⁻¹.

EI-MS m/z; 352 (M⁺).

Example 58

Preparation of 1-(3-fluoro-2-methylbenzyl)-4,4-dimethyl-2-(adamantan-2-yl)-1,2-diazetidin-3-one 2-(Adamantan-2-yl)-4,4-dimethyl-1,2-diazetidin-3-one and 3-fluoro-2-methylbenzyl bromide were used for a similar reaction and treatment as Process 6 of Example 1, and the title compound was obtained as a white crystalline powder.

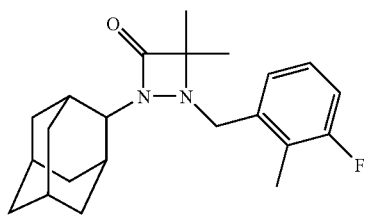

$^1$H-NMR (400 MHz, CDCl$_3$) δ; 1.26 (s, 3H), 1.40-1.49 (m, 4H), 1.57-1.65 (m, 6H), 1.82-1.88 (m, 3H), 2.06-2.11 (m, 2H), 2.28-2.33 (m, 4H), 2.40 (s, 1H), 3.53 (s, 1H), 3.95 (d, J=14.4 Hz, 1H), 4.00 (d, J=14.4 Hz, 1H), 6.94 (t, J=8.8 Hz, 1H), 7.08-7.13 (m, 1H), 7.24 (d, J=7.6 Hz, 1H).
IR (ATR); 2905, 1731, 1472, 1334, 1240, 783 cm$^{-1}$.
EI-MS m/z; 356 (M$^+$).

Example 59

Preparation of 1-(3-chloro-2-fluorobenzyl)-4,4-dimethyl-2-(adamantan-2-yl)-1,2-diazetidin-3-one 2-(Adamantan-2-yl)-4,4-dimethyl-1,2-diazetidin-3-one and 3-chloro-2-fluorobenzyl bromide were used for a similar reaction and treatment as Process 6 of Example 1, and the title compound was obtained as a white crystalline powder.

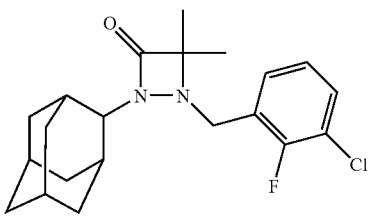

$^1$H-NMR (400 MHz, CDCl$_3$) δ; 1.25 (s, 3H), 1.40 (s, 3H), 1.56-1.90 (m, 10H), 2.13 (d, J=12.7 Hz, 1H), 2.25-2.36 (m, 3H), 3.57 (s, 1H), 3.87 (d, J=14.2 Hz, 1H), 4.12 (d, J=14.2 Hz, 1H), 7.23-7.25 (m, 2H), 7.41 (s, 1H).
IR (ATR); 2908, 1733, 1334, 783 cm$^{-1}$.
EI-MS m/z; 376 (M$^+$).

Example 60

Preparation of 4,4-dimethyl-1-[2-(methylthio)benzyl]-2-(adamantan-2-yl)-1,2-diazetidin-3-one 2-(Adamantan-2-yl)-4,4-dimethyl-1,2-diazetidin-3-one and 2-(methylthio)benzyl bromide were used for a similar reaction and treatment as Process 6 of Example 1, and the title compound was obtained as a white crystalline powder.

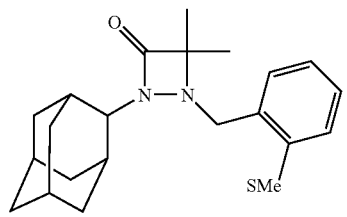

$^1$H-NMR (400 MHz, CDCl$_3$) δ; 1.25 (s, 3H), 1.45 (s, 3H), 1.54-1.76 (m, 7H), 1.82-1.88 (m, 3H), 2.09-2.31 (m, 3H), 2.43-2.52 (m, 4H), 3.60 (s, 1H), 4.00 (d, J=14.4 Hz, 1H), 4.10 (d, J=14.4 Hz, 1H), 7.11-7.29 (m, 3H), 7.53 (d, J=7.3 Hz, 1H).
IR (ATR); 2910, 1748, 747 cm$^{-1}$.
EI-MS m/z; 370 (M$^+$).

Example 61

Preparation of 1-(1,3-benzodioxol-4-ylmethyl)-4,4-dimethyl-2-(adamantan-2-yl)-1,2-diazetidin-3-one 2-(Adamantan-2-yl)-4,4-dimethyl-1,2-diazetidin-3-one and 2,3-(methylenedioxy)benzyl bromide were used for a similar reaction and treatment as Process 6 of Example 1, and the title compound was obtained as a white crystalline powder.

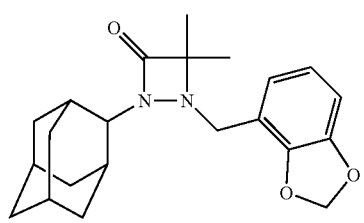

$^1$H-NMR (270 MHz, CDCl$_3$) δ; 1.29 (s, 3H), 1.39 (s, 3H), 1.61-1.87 (m, 10H), 2.10-2.40 (m, 4H), 3.62 (s, 1H), 3.92 (d, J=20.4 Hz, 1H), 4.02 (d, J=20.4 Hz, 1H), 5.95 (s, 2H), 6.72-6.84 (m, 2H), 7.01 (d, J=11.2 Hz, 1H).
IR (ATR); 2915, 1742, 1457, 1246, 1060, 928, 774 cm$^{-1}$.
EI-MS m/z; 368 (M$^+$).

Example 62

Preparation of 1-(1,3-benzodioxol-5-ylmethyl)-4,4-dimethyl-2-(adamantan-2-yl)-1,2-diazetidin-3-one 2-(Adamantan-2-yl)-4,4-dimethyl-1,2-diazetidin-3-one and 3,4-(methylenedioxy)benzyl bromide were used for a similar reaction and treatment as Process 6 of Example 1, and the title compound was obtained as a brown oil.

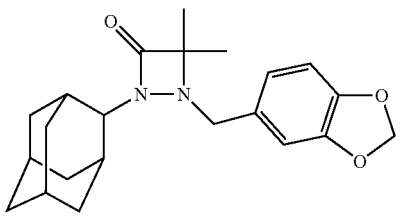

$^1$H-NMR (400 MHz, CDCl$_3$) δ; 1.27 (s, 3H), 1.38 (s, 3H), 1.60-1.89 (m, 10H), 2.11-2.14 (m, 1H), 2.25-2.39 (m, 3H), 3.58 (s, 1H), 3.78 (d, J=13.7 Hz, 1H), 4.05 (d, J=13.7 Hz, 1H), 5.94 (s, 1H), 5.95 (s, 1H), 6.74 (d, J=7.8 Hz, 1H), 6.81 (d, J=7.8 Hz, 1H), 6.93 (s, 1H).

IR (ATR); 2908, 1730, 1491, 1444, 1250, 1039, 930, 811 cm$^{-1}$.

Example 63

Preparation of 4,4-dimethyl-1-(naphthalen-1-ylmethyl)-2-(adamantan-2-yl)-1,2-diazetidin-3-one 2-(Adamantan-2-yl)-4,4-dimethyl-1,2-diazetidin-3-one and 1-(bromomethyl)naphthalene were used for a similar reaction and treatment as Process 6 of Example 1, and the title compound was obtained as a colorless oil.

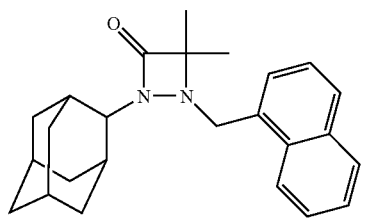

$^1$H-NMR (270 MHz, CDCl$_3$) δ; 1.28 (s, 3H), 1.48 (s, 3H), 1.54-1.87 (m, 10H), 2.05-2.14 (m, 2H), 2.29-2.34 (m, 1H), 2.46 (s, 1H), 3.62 (s, 1H), 4.40-4.52 (m, 2H), 7.39-7.56 (m, 3H), 7.64 (d, J=10.6 Hz, 1H), 7.77 (d, J=12.0 Hz, 1H), 7.84-7.88 (m, 1H), 8.17 (d, J=10.6 Hz, 1H).

IR (ATR); 2908, 1749, 1241, 793, 776 cm$^{-1}$.

EI-MS m/z; 374 (M$^+$).

Example 64

Preparation of 4,4-dimethyl-1-(naphthalen-2-ylmethyl)-2-(adamantan-2-yl)-1,2-diazetidin-3-one 2-(Adamantan-2-yl)-4,4-dimethyl-1,2-diazetidin-3-one and 2-(bromomethyl)naphthalene were used for a similar reaction and treatment as Process 6 of Example 1, and the title compound was obtained as a white crystalline powder.

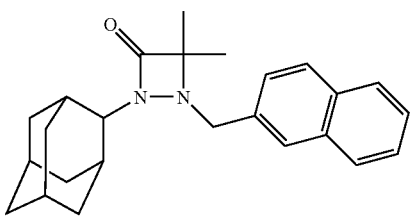

$^1$H-NMR (270 MHz, CDCl$_3$) δ; 1.27 (s, 3H), 1.39 (s, 3H), 1.51-1.91 (m, 10H), 2.16-2.43 (m, 4H), 3.64 (s, 1H), 4.02 (d, J=20.3 Hz, 1H), 4.32 (d, J=20.3 Hz, 1H), 7.43-7.55 (m, 3H), 7.78-7.82 (m, 4H).

IR (ATR); 2904, 1770, 819, 736 cm$^{-1}$

FAB-MS m/z; 374 (M$^+$)..

Example 65

Preparation of trans-1-(2-chlorobenzyl)-2-(5-hydroxyadamantan-2-yl)-4,4-dimethyl-1,2-diazetidin-3-one

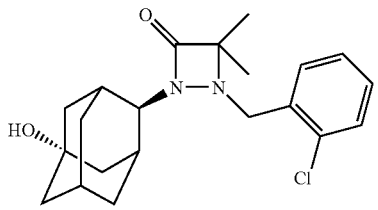

Process 1: Preparation of benzyl 2-(5-hydroxyadamantan-2-ylidene)hydrazinecarboxylate 5-Hydroxy-2-adamantanone was used in place of 2-adamantanone for a similar reaction and treatment as Process 1 of Example 1, and benzyl 2-(5-hydroxyadamantan-2-ylidene)hydrazinecarboxylate was obtained as a colorless oil.

$^1$H-NMR (400 MHz, CDCl$_3$) δ; 1.58-1.99 (m, 11H), 2.31 (s, 1H), 2.92 (s, 1H), 3.03 (s, 1H), 5.24 (s, 2H), 7.33-7.42 (m, 5H), 7.66 (br, 1H).

Process 2: Preparation of benzyl trans-2-(5-hydroxyadamantan-2-yl)hydrazinecarboxylate Benzyl 2-(5-hydroxyadamantan-2-ylidene)hydrazinecarboxylate was used for a similar reaction and treatment as Process 2 of Example 1, the resultant two geometric isomers were separated using silica gel chromatography, and benzyl trans-2-(5-hydroxyadamantan-2-yl)hydrazinecarboxylate was obtained as a colorless amorphous solid.

$^1$H-NMR (400 MHz, CDCl$_3$) δ; 1.31 (d, J=12.0 Hz, 2H), 1.72 (d, J=6.6 Hz, 7H), 2.00-2.08 (m, 5H), 3.11 (s, 1H), 3.93 (br, 1H), 5.13 (s, 2H), 6.24 (br, 1H), 7.30-7.39 (m, 5H).

Process 3: Preparation of benzyl trans-2-(2-bromoisobutyryl)-2-(5-hydroxyadamantan-2-yl)hydrazinecarboxylate Benzyl trans-2-(5-hydroxyadamantan-2-yl)hydrazinecarboxylate and 2-bromoisobutyryl bromide were used for a similar reaction and treatment as Process 3 of Example 1, and benzyl trans-2-(2-bromoisobutyryl)-2-(5-hydroxyadamantan-2-yl)hydrazinecarboxylate was obtained as a colorless oil.

$^1$H-NMR (400 MHz, CDCl$_3$) δ; 1.48 (d, J=11.7 Hz, 2H), 1.60-1.95 (m, 16H), 2.14-2.22 (m, 2H), 2.58 (br, 1H), 4.11 (br, 0.4H), 4.31 (br, 0.6H), 5.07-5.30 (m, 2H), 7.34-7.37 (m, 5H).

Process 4: Preparation of benzyl trans-2-(5-hydroxyadamantan-2-yl)-4,4-dimethyl-3-oxo-1,2-diazetidine-1-carboxylate Benzyl trans-2-(2-bromoisobutyryl)-2-(5-hydroxyadamantan-2-yl)hydrazinecarboxylate was used for a similar reaction and treatment as Process 4 of Example 1, and benzyl trans-2-(5-hydroxyadamantan-2-yl)-4,4-dimethyl-3-oxo-1,2-diazetidine-1-carboxylate was obtained as a colorless amorphous solid.

¹H-NMR (400 MHz, CDCl₃) δ; 1.43-1.97 (m, 11H), 1.49 (s, 6H), 2.15 (s, 1H), 2.58 (s, 2H), 3.94 (s, 1H), 5.18 (s, 2H), 7.34-7.39 (m, 5H).

Process 5: Preparation of trans-2-(5-hydroxyadamantan-2-yl)-4,4-dimethyl-1,2-diazetidin-3-one Benzyl trans-2-(5-hydroxyadamantan-2-yl)-4,4-dimethyl-3-oxo-1,2-diazetidine-1-carboxylate was used for a similar reaction and treatment as Process 5 of Example 1, and trans-2-(5-hydroxyadamantan-2-yl)-4,4-dimethyl-1,2-diazetidin-3-one was obtained as a pale yellow amorphous solid.

¹H-NMR (400 MHz, CDCl₃) δ; 1.49-2.05 (m, 18H), 2.17 (s, 1H), 2.57 (br, 1H), 3.64 (s, 1H), 3.88 (br, 1H).

Process 6: Preparation of trans-1-(2-chlorobenzyl)-2-(5-hydroxyadamantan-2-yl)-4,4-dimethyl-1,2-diazetidin-3-one trans-2-(5-Hydroxyadamantan-2-yl)-4,4-dimethyl-1,2-diazetidin-3-one and 2-chlorobenzyl bromide were used for a similar reaction and treatment as Process 6 of Example 1, and the title compound was obtained as a colorless oil.

¹H-NMR (400 MHz, CDCl₃) δ; 1.26 (s, 3H), 1.46 (s, 3H), 1.49-1.74 (m, 9H), 2.12 (d, J=13.0 Hz, 1H), 2.19 (s, 1H), 2.21 (d, J=13.0 Hz, 1H), 2.43 (s, 1H), 2.58 (s, 1H), 3.53 (s, 1H), 4.06 (d, J=15.0 Hz, 1H), 4.15 (d, J=15.0 Hz, 1H), 7.18-7.31 (m, 2H), 7.35 (d, J=7.6 Hz, 1H), 7.62 (d, J=7.6 Hz, 1H).

IR (ATR); 3676, 2923, 1736, 1354, 1116, 750 cm⁻¹.

EI-MS m/z; 374 (M⁺).

Example 66

Preparation of trans-2-(5-hydroxyadamantan-2-yl)-4,4-dimethyl-1-[2-(trifluoromethyl)benzyl]-1,2-diazetidin-3-one 2-(Trifluoromethyl)benzyl bromide was used in place of 2-chlorobenzyl bromide for a similar reaction and treatment as Process 6 of Example 65, and the title compound was obtained as a colorless oil.

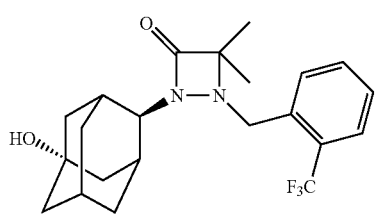

¹H-NMR (400 MHz, CDCl₃) δ; 1.21 (s, 3H), 1.49 (s, 3H), 1.51-1.77 (m, 9H), 2.06 (d, J=13.2 Hz, 1H), 2.19 (s, 1H), 2.21 (d, J=13.2 Hz, 1H), 2.48 (s, 1H), 2.54 (s, 1H), 3.51 (s, 1H), 4.19 (s, 2H), 7.37 (t, J=7.6 Hz, 1H), 7.53 (t, J=7.6 Hz, 1H), 7.65 (d, J=7.6 Hz, 1H), 7.93 (d, J=7.6 Hz, 1H).

IR (ATR); 2927, 1736, 1313, 1161, 1115, 771 cm⁻¹.

EI-MS m/z; 408 (M⁺).

Example 67

Preparation of trans-1-(2-chloro-5-fluorobenzyl)-2-(5-hydroxyadamantan-2-yl)-4,4-dimethyl-1,2-diazetidin-3-one 2-Chloro-5-fluorobenzyl bromide was used in place of 2-chlorobenzyl bromide for a similar reaction and treatment as Process 6 of Example 65, and the title compound was obtained as a colorless amorphous solid.

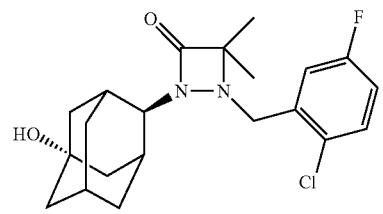

¹H-NMR (400 MHz, CDCl₃) δ; 1.24 (s, 3H), 1.48 (s, 3H), 1.52-1.78 (m, 9H), 2.05 (d, J=12.9 Hz, 1H), 2.18-2.21 (m, 2H), 2.49 (s, 1H), 2.56 (s, 1H), 3.55 (s, 1H), 4.03 (d, J=15.6 Hz, 1H), 4.12 (d, J=15.6 Hz, 1H), 6.93 (dt, J=3.0, 8.2 Hz, 1H), 7.32 (dd, J=5.1, 8.8 Hz, 1H), 7.40 (dd, J=2.9, 9.5 Hz, 1H).

IR (ATR); 3650, 2925, 1736, 1474, 1264, 1115, 756 cm⁻¹.

EI-MS m/z; 392 (M⁺).

Example 68

Preparation of 1-(2-chlorobenzyl)-2-cyclohexyl-4,4-dimethyl-1,2-diazetidin-3-one

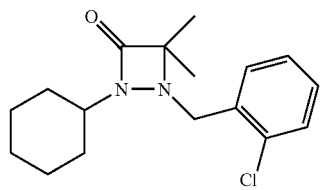

Process 1: Preparation of benzyl 2-cyclohexylidene hydrazinecarboxylate

Cyclohexanone was used in place of 2-adamantanone for a similar reaction and treatment as Process 1 of Example 1, and benzyl 2-cyclohexylidene hydrazinecarboxylate was obtained as a pale yellow crystalline powder.

¹H-NMR (400 MHz, CDCl₃) δ; 1.62-1.74 (m, 6H), 2.20 (t, J=6.0 Hz, 2H), 2.37 (t, J=6.2 Hz, 2H), 5.24 (s, 2H), 7.32-7.41 (m, 5H), 7.68 (s, 1H).

Process 2: Preparation of benzyl 2-cyclohexylhydrazinecarboxylate

Benzyl 2-cyclohexylidenehydrazinecarboxylate was used for a similar reaction and treatment as Process 2 of Example 1, and benzyl 2-cyclohexylhydrazinecarboxylate was obtained as a white crystalline powder.

¹H-NMR (400 MHz, CDCl₃) δ; 1.13-2.12 (m, 10H), 3.13-3.22 (m, 1H), 5.25 (dd, J=12.1, 14.3 Hz, 2H), 6.38 (d, J=6.8 Hz, 1H), 6.66 (s, 1H), 7.35-7.40 (m, 5H).

Process 3: Preparation of benzyl 2-(2-bromoisobutyryl)-2-cyclohexylhydrazinecarboxylate Benzyl 2-cyclohexylhydrazinecarboxylate and 2-bromoisobutyryl bromide were used for a similar reaction and treatment as Process 3 of Example 1, and benzyl 2-(2-bromoisobutyryl)-2-cyclohexylhydrazinecarboxylate was obtained as a white oil.

$^1$H-NMR (400 MHz, CDCl$_3$) δ; 1.05-2.04 (m, 10H), 2.01 (s, 3H), 2.08 (s, 3H), 4.11 (s, 1H), 5.17 (s, 2H), 7.00 (br, 1H), 7.34-7.36 (m, 5H).

Process 4: Preparation of benzyl 2-cyclohexyl-4,4-dimethyl-3-oxo-1,2-diazetidine-1-carboxylate Benzyl 2-(2-bromoisobutyryl)-2-cyclohexylhydrazinecarboxylate was used for a similar reaction and treatment as Process 4 of Example 1, and benzyl 2-cyclohexyl-4,4-dimethyl-3-oxo-1,2-diazetidine-1-carboxylate was obtained as a pale yellow oil.

$^1$H-NMR (400 MHz, CDCl$_3$) δ; 1.14-1.28 (m, 3H), 1.43-1.81 (m, 5H), 1.46 (s, 6H), 2.03-2.06 (m, 2H), 3.54 (dt, J=3.8, 11.8 Hz, 1H), 5.21 (s, 2H), 7.34-7.40 (m, 5H).

Process 5: Preparation of 2-cyclohexyl-4,4-dimethyl-1,2-diazetidin-3-one

Benzyl 2-(2-bromoisobutyryl)-2-cyclohexylhydrazinecarboxylate was used for a similar reaction and treatment as Process 5 of Example 1, and 2-cyclohexyl-4,4-dimethyl-1,2-diazetidin-3-one was obtained as a pale yellow oil.

$^1$H-NMR (400 MHz, CDCl$_3$) δ; 1.12-1.92 (m, 10H), 1.47 (s, 6H), 3.56 (dt, J=3.8, 11.1 Hz, 1H), 3.92 (br, 1H).

Process 6: Preparation of 1-(2-chlorobenzyl)-2-cyclohexyl-4,4-dimethyl-1,2-diazetidin-3-one 2-Cyclohexyl-4,4-dimethyl-1,2-diazetidin-3-one and 2-chlorobenzyl bromide were used for a similar reaction and treatment as Process 6 of Example 1, and the title compound was obtained as a pale yellow oil.

$^1$H-NMR (400 MHz, CDCl$_3$) δ; 1.07-1.21 (m, 3H), 1.30 (s, 3H), 1.33-1.42 (m, 1H), 1.37 (s, 3H), 1.55-1.62 (m, 1H), 1.73-1.85 (m, 3H), 1.94-2.02 (m, 2H), 3.12 (tt, J=3.8, 11.7 Hz, 1H), 4.03 (d, J=15.0 Hz, 1H), 4.12 (d, J=15.0 Hz, 1H), 7.18-7.29 (m, 2H), 7.36 (dd, J=1.5, 7.8 Hz, 1H), 7.63 (dd, J=1.5, 7.8 Hz, 1H).

IR (ATR); 2934, 1762, 1649, 1446, 1335, 1051, 755 cm$^{-1}$.

FAB-MS m/z; 307 (M+H)$^+$.

Example 69

Preparation of 2-cyclohexyl-1-(2,3-dichlorobenzyl)-4,4-dimethyl-1,2-diazetidin-3-one 2-Cyclohexyl-4,4-dimethyl-1,2-diazetidin-3-one prepared in Process 5 of Example 68, and 2,3-dichlorobenzyl bromide were used for a similar reaction and treatment as Process 6 of Example 1, and the title compound was obtained as a pale yellow oil.

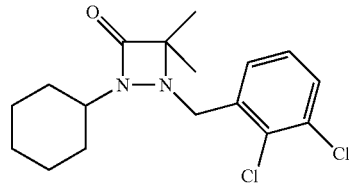

$^1$H-NMR (400 MHz, CDCl$_3$) δ; 1.08-1.21 (m, 3H), 1.29 (s, 3H), 1.35-1.45 (m, 1H), 1.38 (s, 3H), 1.59-1.60 (m, 1H), 1.74-1.85 (m, 3H), 1.94-2.03 (m, 2H), 3.13 (tt, J=3.7, 11.7 Hz, 1H), 4.04 (d, J=15.4 Hz, 1H), 4.15 (d, J=15.4 Hz, 1H), 7.19-7.25 (m, 1H), 7.36 (dd, J=1.5, 8.0 Hz, 1H), 7.58 (d, J=8.0 Hz, 1H).

IR (ATR); 2934, 1763, 1650, 1451, 1333, 1154, 1047, 777 cm$^{-1}$.

FAB-MS m/z; 341 (M+H)$^+$.

Example 70

Preparation of 2-cyclohexyl-1-(2,5-dichlorobenzyl)-4,4-dimethyl-1,2-diazetidin-3-one 2-Cyclohexyl-4,4-dimethyl-1,2-diazetidin-3-one and 2,5-dichlorobenzyl bromide were used for a similar reaction and treatment as Process 6 of Example 1, and the title compound was obtained as a pale yellow oil.

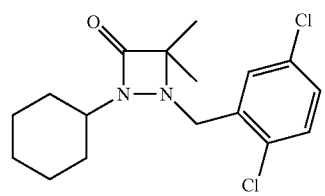

$^1$H-NMR (400 MHz, CDCl$_3$) δ; 1.06-1.22 (m, 3H), 1.29 (s, 3H), 1.35-1.45 (m, 1H), 1.39 (s, 3H), 1.56-1.64 (m, 1H), 1.71-1.84 (m, 3H), 1.94-2.03 (m, 2H), 3.15 (tt, J=3.8, 11.7 Hz, 1H), 3.99 (d, J=15.5 Hz, 1H), 4.08 (d, J=15.5 Hz, 1H), 7.19 (dd, J=2.4, 8.6 Hz, 1H), 7.25-7.34 (m, 1H), 7.66 (d, J=2.4 Hz, 1H).

IR (ATR); 2933, 1763, 1650, 1464, 1333, 1093, 812 cm$^{-1}$.

FAB-MS m/z; 341 (M+H)$^+$.

Example 71

Preparation of 1-(2-chloro-5-fluorobenzyl)-2-cyclohexyl-4,4-dimethyl-1,2-diazetidin-3-one 2-Cyclohexyl-4,4-dimethyl-1,2-diazetidin-3-one and 2-chloro-5-fluorobenzyl bromide were used for a similar reaction and treatment as Process 6 of Example 1, and the title compound was obtained as a colorless oil.

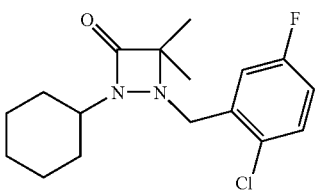

¹H-NMR (400 MHz, CDCl₃) δ; 1.06-1.23 (m, 3H), 1.29 (s, 3H), 1.36-1.45 (m, 1H), 1.39 (s, 3H), 1.58-1.62 (m, 1H), 1.75-1.84 (m, 3H), 1.94-2.04 (m, 2H), 3.18 (tt, J=3.7, 11.7 Hz, 1H), 3.99 (d, J=15.6 Hz, 1H), 4.10 (d, J=15.6 Hz, 1H), 6.93 (dt, J=2.9, 8.2 Hz, 1H), 7.32 (dd, J=5.1, 8.8 Hz, 1H), 7.41 (dd, J=2.9, 9.8 Hz, 1H).

IR (ATR); 2935, 1763, 1651, 1470, 1266, 1050, 813 cm⁻¹.

FAB-MS m/z; 325 (M+H)⁺.

Example 72

Preparation of 1-(2-chloro-4-fluorobenzyl)-2-cyclohexyl-4,4-dimethyl-1,2-diazetidin-3-one 2-Cyclohexyl-4,4-dimethyl-1,2-diazetidin-3-one and 2-chloro-4-fluorobenzyl bromide were used for a similar reaction and treatment as Process 6 of Example 1, and the title compound was obtained as a colorless oil.

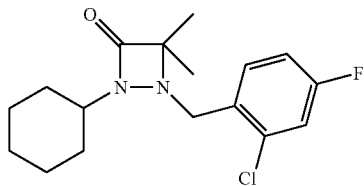

¹H-NMR (400 MHz, CDCl₃) δ; 1.08-1.20 (m, 3H), 1.30 (s, 3H), 1.35 (s, 3H), 1.36-1.43 (m, 1H), 1.51-1.60 (m, 1H), 1.73-1.83 (m, 3H), 1.93-2.01 (m, 2H), 3.11 (tt, J=3.7, 11.5 Hz, 1H), 3.98 (d, J=14.8 Hz, 1H), 4.07 (d, J=14.8 Hz, 1H), 6.99 (dt, J=2.6, 8.5 Hz, 1H), 7.12 (dd, J=2.6, 8.5 Hz, 1H), 7.62 (dd, J=6.2, 8.5 Hz, 1H).

IR (ATR); 2934, 1763, 1605, 1491, 1233, 1043, 906 cm⁻¹.

FAB-MS m/z; 325 (M+H)⁺.

Example 73

Preparation of 1-(2-chlorobenzyl)-2-cyclooctyl-4,4-dimethyl-1,2-diazetidin-3-one

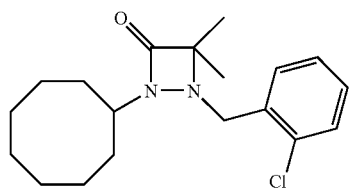

Process 1: Preparation of benzyl 2-cyclooctylidenehydrazinecarboxylate

Cyclooctanone was used in place of 2-adamantanone for a similar reaction and treatment as Process 1 of Example 1, and benzyl 2-cyclooctylidenehydrazinecarboxylate was obtained as a white crystalline powder.

¹H-NMR (400 MHz, CDCl₃) δ; 1.43-1.56 (m, 6H), 1.69-1.78 (m, 4H), 2.28 (t, J=6.3 Hz, 2H), 2.45 (t, J=6.3 Hz, 2H), 5.24 (s, 2H), 7.33-7.42 (m, 5H), 7.70 (s, 1H).

Process 2: Preparation of benzyl 2-cyclooctylhydrazinecarboxylate

Benzyl 2-cyclooctylidenehydrazinecarboxylate was used for a similar reaction and treatment as Process 2 of Example 1, and benzyl 2-cyclooctylhydrazinecarboxylate was obtained as a white crystalline powder.

¹H-NMR (400 MHz, CDCl₃) δ; 1.41-2.05 (m, 14H), 3.40-3.47 (m, 1H), 5.26 (s, 2H), 6.35 (d, J=6.8 Hz, 1H), 6.63 (s, 1H), 7.36-7.42 (m, 5H).

Process 3: Preparation of benzyl 2-(2-bromoisobutyryl)-2-cyclooctylhydrazinecarboxylate Benzyl 2-cyclooctylhydrazinecarboxylate and 2-bromoisobutyryl bromide were used for a similar reaction and treatment as Process 3 of Example 1, and benzyl 2-(2-bromoisobutyryl)-2-cyclooctylhydrazinecarboxylate was obtained as a pale yellow oil.

¹H-NMR (400 MHz, CDCl₃) δ; 1.55-2.01 (m, 20H), 4.50 (br, 1H), 5.18 (s, 2H), 6.91 (br, 1H), 7.29-7.37 (m, 5H).

Process 4: Preparation of benzyl 2-cyclooctyl-4,4-dimethyl-3-oxo-1,2-diazetidine-1-carboxylate Benzyl 2-(2-bromoisobutyryl)-2-cyclooctylhydrazinecarboxylate was used for a similar reaction and treatment as Process 4 of Example 1, and benzyl 2-cyclooctyl-4,4-dimethyl-3-oxo-1,2-diazetidine-1-carboxylate was obtained as a pale yellow oil.

¹H-NMR (400 MHz, CDCl₃) δ; 1.46 (s, 6H), 1.49-2.04 (m, 14H), 3.76 (quint, J=6.8 Hz, 1H), 5.20 (s, 2H), 7.30-7.40 (m, 5H).

Process 5: Preparation of 2-cyclooctyl-4,4-dimethyl-1,2-diazetidin-3-one

Benzyl 2-cyclooctyl-4,4-dimethyl-3-oxo-1,2-diazetidine-1-carboxylate was used for a similar reaction and treatment as Process 5 of Example 1, and 2-cyclooctyl-4,4-dimethyl-1,2-diazetidin-3-one was obtained as a pale yellow oil.

¹H-NMR (400 MHz, CDCl₃) δ; 1.46-1.89 (m, 20H), 3.78 (quint, 1H), 3.80 (br, 1H).

Process 6: Preparation of 1-(2-chlorobenzyl)-2-cyclooctyl-4,4-dimethyl-1,2-diazetidin-3-one 2-Cyclooctyl-4,4-dimethyl-1,2-diazetidin-3-one and 2-chlorobenzyl bromide were used for a similar reaction and treatment as Process 6 of Example 1, and the title compound was obtained as a colorless oil.

¹H-NMR (400 MHz, CDCl₃) δ; 1.29-1.52 (m, 8H), 1.33 (s, 3H), 1.36 (s, 3H), 1.63-1.76 (m, 3H), 1.87-2.00 (m, 2H), 2.04-2.13 (m, 1H), 3.15-3.22 (m, 1H), 4.04 (s, 2H), 7.19-7.27 (m, 2H), 7.36 (d, J=7.6 Hz, 1H), 7.62 (d, J=7.6 Hz, 1H).

IR (ATR); 2924, 1759, 1468, 1276, 1051, 753 cm⁻¹.

EI-S m/z; 334 (M⁺).

Example 74

Preparation of 2-cyclooctyl-1-(2,3-dichlorobenzyl)-4,4-dimethyl-1,2-diazetidin-3-one 2-Cyclooctyl-4,4-dimethyl-1,2-diazetidin-3-one prepared in Process 5 of Example 73 and 2,3-dichlorobenzyl bromide were used for a similar reaction and treatment as Process 6 of Example 1, and the title compound was obtained as a colorless oil.

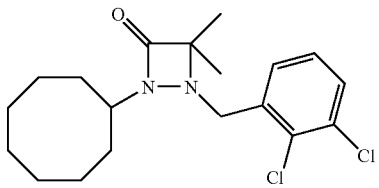

$^1$H-NMR (400 MHz, CDCl$_3$) δ; 1.29-1.53 (m, 8H), 1.32 (s, 3H), 1.38 (s, 3H), 1.63-1.78 (m, 3H), 1.88-2.00 (m, 2H), 2.04-2.13 (m, 1H), 3.16-3.23 (m, 1H), 4.04 (d, J=15.0 Hz, 1H), 4.09 (d, J=15.0 Hz, 1H), 7.21 (t, J=7.8 Hz, 1H), 7.40 (dd, J=1.5, 7.8 Hz, 1H), 7.55 (d, J=7.8 Hz, 1H).
IR (ATR); 2925, 1760, 1422, 1275, 1048, 779 cm$^{-1}$.
EI-MS m/z; 368 (M$^+$).

Example 75

Preparation of 2-cyclooctyl-1-(2,5-dichlorobenzyl)-4,4-dimethyl-1,2-diazetidin-3-one 2-Cyclooctyl-4,4-dimethyl-1,2-diazetidin-3-one and 2,5-dichlorobenzyl bromide were used for a similar reaction and treatment as Process 6 of Example 1, and the title compound was obtained as a colorless oil.

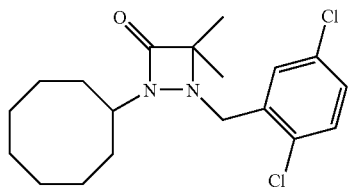

$^1$H-NMR (400 MHz, CDCl$_3$) δ; 1.30-1.55 (m, 8H), 1.33 (s, 3H), 1.39 (s, 3H), 1.64-1.78 (m, 3H), 1.89-2.00 (m, 2H), 2.03-2.12 (m, 1H), 3.17-3.24 (m, 1H), 3.98 (d, J=14.9 Hz, 1H), 4.02 (d, J=14.9 Hz, 1H), 7.19 (dd, J=2.4, 8.5 Hz, 1H), 7.30 (d, J=8.5 Hz, 1H), 7.65 (d, J=2.4 Hz, 1H).
IR (ATR); 2925, 1759, 1464, 1275, 1092, 813 cm$^{-1}$.
EI-MS m/z; 368 (M$^+$).

Example 76

Preparation of 1-(2-chloro-4-fluorobenzyl)-2-cyclooctyl-4,4-dimethyl-1,2-diazetidin-3-one 2-Cyclooctyl-4,4-dimethyl-1,2-diazetidin-3-one and 2-chloro-4-fluorobenzyl bromide were used for a similar reaction and treatment as Process 6 of Example 1, and the title compound was obtained as a colorless crystalline powder.

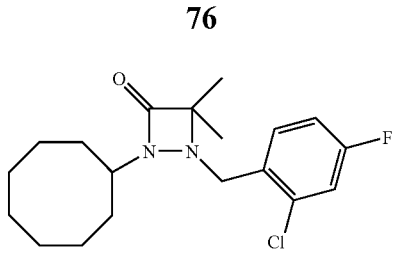

$^1$H-NMR (400 MHz, CDCl$_3$) δ; 1.29-1.55 (m, 8H), 1.33 (s, 3H), 1.35 (s, 3H), 1.61-1.78 (m, 3H), 1.86-1.99 (m, 2H), 2.03-2.12 (m, 1H), 3.15-3.21 (m, 1H), 3.97 (d, J=14.4 Hz, 1H), 4.02 (d, J=14.4 Hz, 1H), 6.99 (dt, J=2.5, 8.3 Hz, 1H), 7.13 (dd, J=2.5, 8.5 Hz, 1H), 7.60 (dd, J=6.2, 8.5 Hz, 1H).
IR (ATR); 2926, 1746, 1494, 1231, 1048, 891 cm$^{-1}$.
EI-MS m/z; 352 (M$^+$).

Example 77

Preparation of 1-(2-chloro-5-fluorobenzyl)-2-cyclooctyl-4,4-dimethyl-1,2-diazetidin-3-one 2-Cyclooctyl-4,4-dimethyl-1,2-diazetidin-3-one and 2-chloro-5-fluorobenzyl bromide were used for a similar reaction and treatment as Process 6 of Example 1, and the title compound was obtained as a colorless oil.

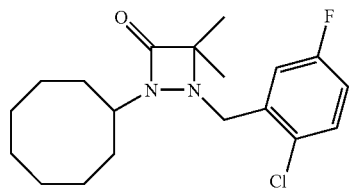

$^1$H-NMR (400 MHz, CDCl$_3$) δ; 1.28-1.56 (m, 8H), 1.32 (s, 3H), 1.39 (s, 3H), 1.65-1.78 (m, 3H), 1.89-2.00 (m, 2H), 2.10-2.13 (m, 1H), 3.21-3.28 (m, 1H), 3.99 (d, J=14.9 Hz, 1H), 4.04 (d, J=14.9 Hz, 1H), 6.93 (dt, J=2.9, 8.3 Hz, 1H), 7.32 (dd, J=5.3, 8.9 Hz, 1H), 7.40 (dd, J=3.2, 9.5 Hz, 1H).
IR (ATR); 2926, 1760, 1471, 1267, 1148, 1051, 812 cm$^{-1}$.
EI-MS m/z; 352 (M$^+$).

Example 78

Preparation of 2-(bicyclo[2.2.1]heptan-2-yl)-1-(2-chlorobenzyl)-4,4-dimethyl-1,2-diazetidin-3-one

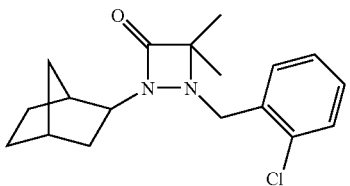

Process 1: Preparation of benzyl 2-(bicyclo[2.2.1]heptan-2-ylidene)hydrazinecarboxylate Bicyclo[2.2.1]-2-heptanone was used in place of 2-adamantanone for a similar reaction and treatment as Process 1 of Example 1, and benzyl 2-(bicyclo[2.2.1]heptan-2-ylidene)hydrazinecarboxylate was obtained as a pale yellow oil.

¹H-NMR (400 MHz, CDCl₃) δ; 1.24-1.53 (m, 4H), 1.65-1.82 (m, 3H), 2.03-2.11 (m, 1H), 2.58 (s, 1H), 2.98 (s, 2H), 5.23 (s, 2H), 7.33-7.40 (m, 6H).

Process 2: Preparation of benzyl 2-(bicyclo[2.2.1]heptan-2-yl)hydrazinecarboxylate Benzyl 2-(bicyclo[2.2.1]heptan-2-ylidene)hydrazinecarboxylate was used for a similar reaction and treatment as Process 2 of Example 1, and benzyl 2-(bicyclo[2.2.1]heptan-2-yl)hydrazinecarboxylate was obtained as a pale yellow crystalline powder.

¹H-NMR (400 MHz, CDCl₃) δ; 1.08-2.68 (m, 10H), 3.52-3.62 (m, 1H), 5.26 (s, 2H), 5.50-6.75 (m, 2H), 7.35-7.39 (m, 5H).

Process 3: Preparation of benzyl 2-(bicyclo[2.2.1]heptan-2-yl)-2-(2-bromoisobutyryl)hydrazinecarboxylate Benzyl 2-(bicyclo[2.2.1]heptan-2-yl)hydrazinecarboxylate and 2-bromoisobutyryl bromide were used for a similar reaction and treatment as Process 3 of Example 1, and benzyl 2-(bicyclo[2.2.]heptan-2-yl)-2-(2-bromoisobutyryl)hydrazinecarboxylate was obtained as a white crystalline powder.

¹H-NMR (400 MHz, CDCl₃) δ; 1.09-2.20 (m, 15H), 2.76-2.80 (m, 1H), 4.43-4.58 (m, 1H), 5.17 (s, 2H), 6.94-7.02 (m, 1H), 7.28-7.44 (m, 5H).

Process 4: Preparation of benzyl 2-(bicyclo[2.2.1]heptan-2-yl)-4,4-dimethyl-3-oxo-1,2-diazetidine-1-carboxylate Benzyl 2-(bicyclo[2.2.1]heptan-2-yl)-2-(2-bromoisobutyryl)hydrazinecarboxylate was used for a similar reaction and treatment as Process 4 of Example 1, and benzyl 2-(bicyclo[2.2.1]heptan-2-yl)-4,4-dimethyl-3-oxo-1,2-diazetidine-1-carboxylate was obtained as a pale yellow oil.

¹H-NMR (400 MHz, CDCl₃) δ; 1.32 (s, 2H), 1.43-1.64 (m, 4H), 1.47 (s, 3H), 1.53 (s, 3H), 1.81-1.89 (m, 1H), 2.26 (s, 1H), 2.56 (s, 1H), 4.01-4.06 (m, 1H), 5.16 (d, J=12.2 Hz, 1H), 5.12 (d, J=12.2 Hz, 1H), 7.33-7.41 (m, 5H).

Process 5: Preparation of 2-(bicyclo[2.2.1]heptan-2-yl)-4,4-dimethyl-1,2-diazetidin-3-one Benzyl 2-(bicyclo[2.2.1]heptan-2-yl)-4,4-dimethyl-3-oxo-1,2-diazetidine-1-carboxylate was used for a similar reaction and treatment as Process 5 of Example 1, and 2-(bicyclo[2.2.1]heptan-2-yl)-4,4-dimethyl-1,2-diazetidin-3-one was obtained as a pale yellow oil.

¹H-NMR (400 MHz, CDCl₃) δ; 1.30-1.85 (m, 14H), 2.26 (s, 1H), 2.48 (s, 1H), 3.80-3.90 (m, 2H).

Process 6: Preparation of 2-(bicyclo[2.2.1]heptan-2-yl)-1-(2-chlorobenzyl)-4,4-dimethyl-1,2-diazetidin-3-one 2-(Bicyclo[2.2.1]heptan-2-yl)-4,4-dimethyl-1,2-diazetidin-3-one and 2-chlorobenzyl bromide were used for a similar reaction and treatment as Process 6 of Example 1, and the title compound was obtained as a colorless oil.

¹H-NMR (400 MHz, CDCl₃) δ; 1.19-1.56 (m, 11H), 1.70-1.83 (m, 2H), 2.00-2.39 (m, 3H), 3.44-3.63 (m, 1H), 3.99-4.15 (m, 2H), 7.18-7.25 (m, 1H), 7.35 (d, J=7.6 Hz, 1H), 7.65 (d, J=7.3 Hz, 1H).

IR (ATR); 2962, 1736, 1469, 1346, 1052, 758 cm⁻¹.
EI-MS m/z; 318 (M⁺).

Example 79

Preparation of 2-(bicyclo[2.2.1]heptan-2-yl)-1-(2,3-dichlorobenzyl)-4,4-dimethyl-1,2-diazetidin-3-one 2-(Bicyclo[2.2.1]heptan-2-yl)-4,4-dimethyl-1,2-diazetidin-3-one prepared in Process 5 of Example 78 and 2,3-dichlorobenzyl bromide were used for a similar reaction and treatment as Process 6 of Example 1, and the title compound was obtained as a colorless oil.

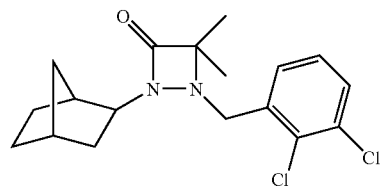

¹H-NMR (400 MHz, CDCl₃) δ; 1.21-1.56 (m, 11H), 1.64-1.83 (m, 2H), 2.00-2.40 (m, 3H), 3.43-3.63 (m, 1H), 4.02-4.13 (m, 2H), 7.20 (t, J=7.8 Hz, 1H), 7.39 (d, J=7.1 Hz, 1H), 7.59 (d, J=7.8 Hz, 1H).

IR (ATR); 2959, 1753, 1421, 1338, 1180, 1046, 779 cm⁻¹.
EI-MS m/z; 352 (M⁺).

Example 80

Preparation of 2-(bicyclo[2.2.1]heptan-2-yl)-1-(2,5-dichlorobenzyl)-4,4-dimethyl-1,2-diazetidin-3-one 2-(Bicyclo[2.2.1]heptan-2-yl)-4,4-dimethyl-1,2-diazetidin-3-one and 2,5-dichlorobenzyl bromide were used for a similar reaction and treatment as Process 6 of Example 1, and the title compound was obtained as a colorless oil.

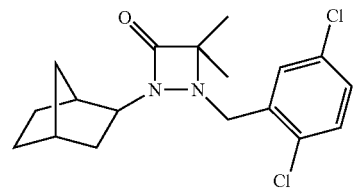

¹H-NMR (400 MHz, CDCl₃) δ; 1.21-1.57 (m, 11H), 1.70-1.86 (m, 2H), 2.01-2.43 (m, 3H), 3.41-3.63 (m, 1H), 3.95-4.10 (m, 2H), 7.19 (dd, J=2.6, 8.5 Hz, 1H), 7.29 (d, J=8.5 Hz, 1H), 7.68 (s, 1H).

IR (ATR); 2959, 1753, 1464, 1339, 1092, 1042, 812 cm⁻¹.
EI-MS m/z; 352 (M⁺).

Example 81

Preparation of 2-(bicyclo[2.2.1]heptan-2-yl)-1-(2-chloro-4-fluorobenzyl)-4,4-dimethyl-1,2-diazetidin-3-one 2-(Bicyclo[2.2.1]heptan-2-yl)-4,4-dimethyl-1,2-diazetidin-3-one and 2-chloro-4-fluorobenzyl bromide were used for a similar reaction and treatment as Process 6 of Example 1, and the title compound was obtained as a colorless oil.

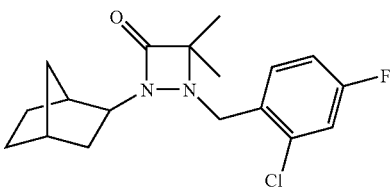

¹H-NMR (400 MHz, CDCl₃) δ; 1.19-1.53 (m, 11H), 1.67-1.83 (m, 2H), 2.00-2.37 (m, 3H), 3.40-3.61 (m, 1H), 3.95-4.10 (m, 2H), 6.99 (dt, J=2.6, 8.3 Hz, 1H), 7.11 (dd, J=2.4, 8.6 Hz, 1H), 7.61-7.66 (m, 1H).
IR (ATR); 2958, 1753, 1605, 1491, 1232, 1042, 906, 857 cm⁻¹.
EI-MS m/z; 336 (M⁺).

Example 82

Preparation of 2-(bicyclo[2.2.1]heptan-2-yl)-1-(2-chloro-5-fluorobenzyl)-4,4-dimethyl-1,2-diazetidin-3-one 2-(Bicyclo[2.2.1]heptan-2-yl)-4,4-dimethyl-1,2-diazetidin-3-one and 2-chloro-5-fluorobenzyl bromide were used for a similar reaction and treatment as Process 6 of Example 1, and the title compound was obtained as a colorless oil.

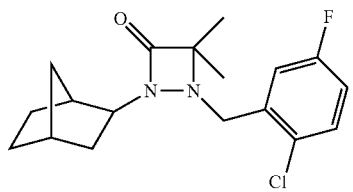

¹H-NMR (400 MHz, CDCl₃) δ; 1.21-1.57 (m, 11H), 1.64-1.86 (m, 2H), 2.01-2.43 (m, 3H), 3.42-3.63 (m, 1H), 3.96-4.11 (m, 2H), 6.92 (dt, J=5.0, 8.2 Hz, 1H), 7.31 (dd, J=5.0, 8.8 Hz, 1H), 7.43 (d, J=9.5 Hz, 1H).
IR (ATR); 2958, 1754, 1471, 1265, 1148, 1049, 813 cm⁻¹.
EI-MS m/z; 336 (M⁺).

Example 83

Preparation of 1-(2-chlorobenzyl)-2-cycloheptyl-4,4-dimethyl-1,2-diazetidin-3-one

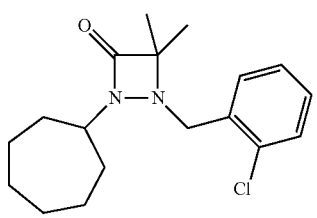

Process 1: Preparation of benzyl 2-cycloheptylhydrazinecarboxylate

Benzyl 2-cycloheptylidene hydrazinecarboxylate obtained by using Cycloheptanone in place of 2-adamantanone for a similar reaction and treatment as Process 1 of Example 1, was used for a similar reaction and treatment as Process 2 of Example 1, and benzyl 2-cycloheptylhydrazinecarboxylate was obtained as a white crystalline powder.
¹H-NMR (400 MHz, CDCl₃) δ; 1.40-2.07 (m, 12H), 3.32 (s, 1H), 5.25 (dd, J=12.0, 15.6 Hz, 2H), 6.57 (d, J=6.6 Hz, 1H), 6.84 (s, 1H), 7.36-7.41 (m, 5H).

Process 2: Preparation of benzyl 2-(2-bromoisobutyryl)-2-cycloheptylhydrazine carboxylate Benzyl 2-cycloheptylhydrazinecarboxylate and 2-bromoisobutyryl bromide were used for a similar reaction and treatment as Process 3 of Example 1, and benzyl 2-(2-bromoisobutyryl)-2-cycloheptylhydrazinecarboxylate was obtained as a yellow oil.
¹H-NMR (400 MHz, CDCl₃) δ; 1.47-2.13 (m, 12H), 2.02 (s, 3H), 2.09 (s, 3H), 4.41 (br, 1H), 5.18 (s, 2H), 7.00 (br, 1H), 7.30-7.38 (m, 5H).

Process 3: Preparation of benzyl 2-cycloheptyl-4,4-dimethyl-3-oxo-1,2-diazetidine-1-carboxylate Benzyl 2-(2-bromoisobutyryl)-2-cycloheptylhydrazinecarboxylate was used for a similar reaction and treatment as Process 4 of Example 1, and benzyl 2-cycloheptyl-4,4-dimethyl-3-oxo-1,2-diazetidine-1-carboxylate was obtained as a pale yellow oil.
¹H-NMR (270 MHz, CDCl₃) δ; 1.33-2.10 (m, 12H), 1.49 (s, 6H), 3.63-3.73 (m, 1H), 5.20 (s, 2H), 7.33-7.42 (m, 5H).

Process 4: Preparation of 2-cycloheptyl-4,4-dimethyl-1,2-diazetidin-3-one

2-Cycloheptyl-4,4-dimethyl-1,2-diazetidin-3-one was used for a similar reaction and treatment as Process 5 of Example 1, and 2-cycloheptyl-4,4-dimethyl-1,2-diazetidin-3-one was obtained as a colorless oil.
¹H-NMR (400 MHz, CDCl₃) δ; 1.41-1.99 (m, 18H), 3.73 (sept, J=4.7 Hz, 1H), 3.84 (br, 1H).

Process 5: Preparation of 1-(2-chlorobenzyl)-2-cycloheptyl-4,4-dimethyl-1,2-diazetidin-3-one 2-Cycloheptyl-4,4-dimethyl-1,2-diazetidin-3-one and 2-chlorobenzyl bromide were used for a similar reaction and treatment as Process 6 of Example 1, and the title compound was obtained as a colorless oil.
¹H-NMR (270 MHz, CDCl₃) δ; 1.21-1.43 (m, 6H), 1.36 (s, 3H), 1.40 (s, 3H), 1.56-1.73 (m, 3H), 1.96-2.06 (m, 3H), 3.15-3.26 (m, 1H), 4.02 (d, J=14.9 Hz, 1H), 4.09 (d, J=14.9 Hz, 1H), 7.17-7.28 (m, 2H), 7.35 (dd, J=1.8, 7.4 Hz, 1H), 7.62 (dd, J=1.8, 7.4 Hz, 1H).
IR (ATR); 2927, 1759, 1464, 1268, 1051, 755 cm⁻¹.
EI-MS m/z; 320 (M⁺).

Example 84

Preparation of 2-cycloheptyl-1-(2,3-dichlorobenzyl)-4,4-dimethyl-1,2-diazetidin-3-one 2-Cycloheptyl-4,4-dimethyl-1,2-diazetidin-3-one prepared in Process 4 of Example 83 and 2,3-dichlorobenzyl bromide were used for a similar reaction and treatment as Process 6 of Example 1, and the title compound was obtained as a colorless oil.

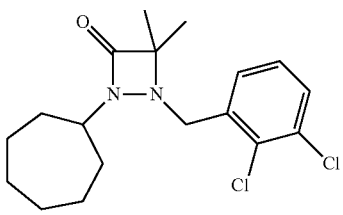

¹H-NMR (400 MHz, CDCl₃) δ; 1.24-1.49 (m, 6H), 1.31 (s, 3H), 1.37 (s, 3H), 1.60-1.71 (m, 3H), 1.99-2.06 (m, 3H), 3.18-3.26 (m, 1H), 4.04 (d, J=15.4 Hz, 1H), 4.12 (d, J=15.4 Hz, 1H), 7.21 (t, J=7.8 Hz, 1H), 7.40 (dd, J=1.5, 8.0 Hz, 1H), 7.57 (d, J=7.8 Hz, 1H).
IR (ATR); 2928, 1760, 1422, 1267, 1047, 778 cm⁻¹.
EI-MS m/z; 354 (M⁺).

Example 85

Preparation of 2-cycloheptyl-1-(2,5-dichlorobenzyl)-4,4-dimethyl-1,2-diazetidin-3-one 2-Cycloheptyl-4,4-dimethyl-1,2-diazetidin-3-one and 2,5-dichlorobenzyl bromide were used for a similar reaction and treatment as Process 6 of Example 1, and the title compound was obtained as a colorless oil.

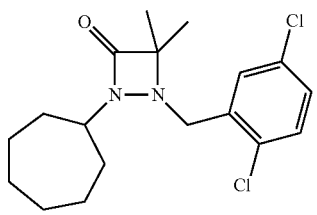

¹H-NMR (400 MHz, CDCl₃) δ; 1.23-1.55 (m, 6H), 1.31 (s, 3H), 1.39 (s, 3H), 1.58-1.73 (m, 3H), 1.98-2.06 (m, 3H), 3.19-3.26 (m, 1H), 3.99 (d, J=15.4 Hz, 1H), 4.05 (d, J=15.4 Hz, 1H), 7.19 (dd, J=2.3, 8.5 Hz, 1H), 7.29 (d, J=8.5 Hz, 1H), 7.66 (d, J=2.3 Hz, 1H).
IR (ATR); 2928, 1761, 1463, 1266, 1091, 1043, 813 cm⁻¹.
EI-MS m/z; 354 (M⁺).

Example 86

Preparation of 1-(2-chloro-4-fluorobenzyl)-2-cycloheptyl-4,4-dimethyl-1,2-diazetidin-3-one 2-Cycloheptyl-4,4-dimethyl-1,2-diazetidin-3-one and 2-chloro-4-fluorobenzyl bromide were used for a similar reaction and treatment as Process 6 of Example 1, and the title compound was obtained as a colorless oil.

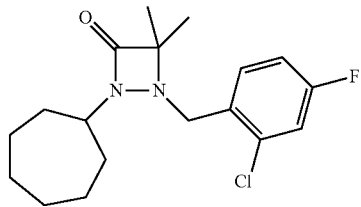

¹H-NMR (270 MHz, CDCl₃) δ; 1.24-1.49 (m, 6H), 1.31 (s, 3H), 1.35 (s, 3H), 1.60-1.72 (m, 3H), 1.97-2.06 (m, 3H), 3.15-3.26 (m, 1H), 3.97 (d, J=14.7 Hz, 1H), 4.05 (d, J=14.7 Hz, 1H), 6.99 (dt, J=2.6, 8.6 Hz, 1H), 7.12 (dd, J=2.6, 8.6 Hz, 1H), 7.61 (dd, J=6.2, 8.6 Hz, 1H).
IR (ATR); 2929, 1760, 1491, 1233, 1043, 906, 858 cm⁻¹.
EI-MS m/z; 338 (M⁺).

Example 87

Preparation of 1-(2-chloro-5-fluorobenzyl)-2-cycloheptyl-4,4-dimethyl-1,2-diazetidin-3-one 2-Cycloheptyl-4,4-dimethyl-1,2-diazetidin-3-one and 2-chloro-5-fluorobenzyl bromide were used for a similar reaction and treatment as Process 6 of Example 1, and the title compound was obtained as a colorless oil.

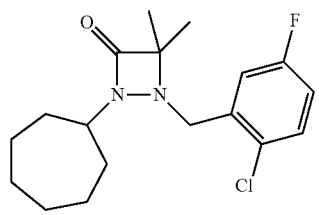

¹H-NMR (270 MHz, CDCl₃) δ; 1.25-1.50 (m, 6H), 1.30 (s, 3H), 1.39 (s, 3H), 1.61-1.71 (m, 3H), 2.02-2.07 (m, 3H), 3.21-3.32 (m, 1H), 3.99 (d, J=15.5 Hz, 1H), 4.07 (d, J=15.5 Hz, 1H), 6.93 (dt, J=3.0, 8.2 Hz, 1H), 7.32 (dd, J=5.3, 8.8 Hz, 1H), 7.41 (dd, J=3.2, 9.7 Hz, 1H).
IR (ATR); 2929, 1760, 1469, 1265, 1148, 1050, 812 cm⁻¹.
EI-MS m/z; 338 (M⁺).

Example 88

Preparation of 4,4-dimethyl-1-(pyridin-2-ylmethyl)-2-(adamantan-2-yl)-1,2-diazetidin-3-one 2-(Adamantan-2-yl)-4,4-dimethyl-1,2-diazetidin-3-one prepared in Process 3 of Example 12, and 2-(bromomethyl)pyridine hydrobromide were used for a similar reaction and treatment as Process 6 of Example 1, and the title compound was obtained as a pale yellow crystalline powder.

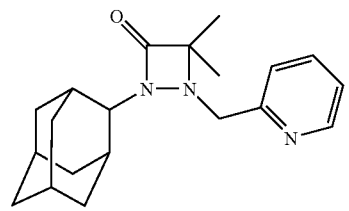

¹H-NMR (400 MHz, CDCl₃) δ; 1.28 (s, 3H), 1.45 (s, 3H), 1.50-1.89 (m, 10H), 2.13 (d,
J=12.7 Hz, 1H), 2.26-2.35 (m, 3H), 3.60 (s, 1H), 4.11 (d, J=14.8 Hz, 1H), 4.25 (d, J=14.8 Hz, 1H), 7.17-7.20 (m, 1H), 7.51 (d, J=8.1 Hz, 1H), 7.67 (dt, J=1.7, 7.7 Hz, 1H), 8.54 (d, J=4.6 Hz, 1H).
IR (ATR); 2912, 1734, 1429, 1336, 774 cm⁻¹.
EI-MS m/z; 325 (M⁺).

Example 89

Preparation of 1-(cyclopropylmethyl)-4,4-dimethyl-2-(adamantan-2-yl)-1,2-diazetidin-3-one 2-(Adamantan-2-yl)-4,4-dimethyl-1,2-diazetidin-3-one and cyclopropylmethyl bromide were used for a similar reaction and treatment as Process 6 of Example 1, and the title compound was obtained as a colorless oil.

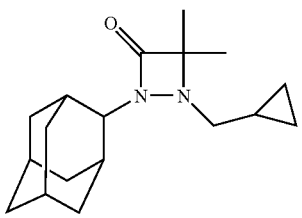

$^1$H-NMR (400 MHz, CDCl$_3$) δ; 0.143-0.271 (m, 2H), 0.527-0.589 (m, 2H), 0.730-0.783 (m, 1H), 1.38 (s, 3H), 1.46 (s, 3H), 1.55-1.74 (m, 6H), 182-1.87 (m, 4H), 2.08-2.11 (m, 1H), 2.20-2.23 (m, 1H), 2.37-2.44 (m, 3H), 2.90 (dd, J=12.7, 5.1 Hz, 1H), 3.61 (s, 1H).
IR (ATR); 2908, 1752, 1452, 1018, 772 cm$^{-1}$.
EI-MS m/z; 354 (M$^+$).

Example 90

Preparation of 4-[2-(4-fluorobenzyl)-3,3-dimethyl-4-oxo-1,2-diazetidin-1-yl]adamantane-1-carboxylic acid

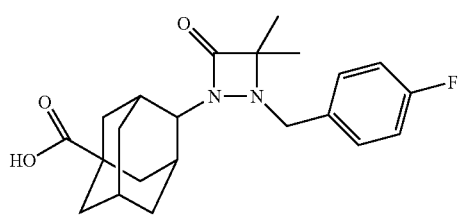

Process 1: Preparation of benzyl 2-(5-methoxycarbonyladamantan-2-ylidene)hydrazinecarboxylate Methyl 4-adamantanone-1-carboxylate prepared with the method described in US2006/0148871 was used for a similar reaction and treatment as Process 1 of Example 1, and benzyl 2-(5-methoxycarbonyladamantan-2-ylidene)hydrazinecarboxylate was obtained as a pale yellow oil.
$^1$H-NMR (400 MHz, CDCl$_3$) δ; 1.55-2.22 (m, 13H), 3.66 (s, 3H), 5.24 (s, 2H), 7.33-7.42 (m, 5H), 7.73 (s, 1H).

Process 2: Preparation of benzyl 2-(5-methoxycarbonyladamantan-2-yl)hydrazinecarboxylate Benzyl 2-(5-methoxycarbonyladamantan-2-ylidene)hydrazinecarboxylate was used for a similar reaction and treatment as Process 2 of Example 1, and benzyl 2-(5-methoxycarbonyladamantan-2-yl)hydrazinecarboxylate was obtained as a colorless oil.

$^1$H-NMR (400 MHz, CDCl$_3$) δ; 1.28-2.24 (m, 13H), 3.12 (s, 1H), 3.66 (s, 3H), 5.13 (s, 2H), 6.22 (s, 1H), 7.30-7.35 (m, 5H).

Process 3: Preparation of benzyl 2-(2-bromoisobutyryl)-2-(5-methoxycarbonyladamantan-2-yl)hydrazinecarboxylate Benzyl 2-(5-methoxycarbonyladamantan-2-yl)hydrazinecarboxylate and 2-bromoisobutyrylbromide were used for a similar reaction and treatment as Process 3 of Example 1, and benzyl 2-(2-bromoisobutyryl)-2-(5-methoxycarbonyladamantan-2-yl)hydrazinecarboxylate was obtained as a colorless oil.
$^1$H-NMR (400 MHz, CDCl$_3$) δ; 1.59-2.07 (m, 19H), 2.50 (s, 1H), 3.65 (s, 3H), 4.32 (s, 1H), 5.24 (s, 2H), 7.34-7.37 (m, 5H).

Process 4: Preparation of benzyl 2-(5-methoxycarbonyladamantan-2-yl)-4,4-dimethyl-3-oxo-1,2-diazetidine-1-carboxylate Benzyl 2-(2-bromoisobutyryl)-2-(5-methoxycarbonyladamantan-2-yl)hydrazinecarboxylate was used for a similar reaction and treatment as Process 4 of Example 1, and benzyl 2-(5-methoxycarbonyladamantan-2-yl)-4,4-dimethyl-3-oxo-1,2-diazetidine-1-carboxylate was obtained as a colorless oil.
$^1$H-NMR (400 MHz, CDCl$_3$) δ; 1.49-2.52 (m, 19H), 3.64 (s, 3H), 3.97-3.99 (m, 1H), 5.16 (s, 2H), 7.38-7.40 (m, 5H).

Process 5: Preparation of methyl 4-(3,3-dimethyl-4-oxo-1,2-diazetidin-1-yl)adamantane-1-carboxylate Benzyl 2-(5-methoxycarbonyladamantan-2-yl)-4,4-dimethyl-3-oxo-1,2-diazetidine-1-carboxylate was used for a similar reaction and treatment as Process 5 of Example 1, and methyl 4-(3,3-dimethyl-4-oxo-1,2-diazetidin-1-yl)adamantane-1-carboxylate was obtained as a colorless oil.
$^1$H-NMR (400 MHz, CDCl$_3$) δ; 1.40-2.42 (m, 19H), 3.68-3.70 (m, 4H).

Process 6: Preparation of methyl 4-[2-(4-fluorobenzyl)-3,3-dimethyl-4-oxo-1,2-diazetidin-1-yl]adamantane-1-carboxylate Methyl 4-(3,3-dimethyl-4-oxo-1,2-diazetidin-1-yl)adamantane-1-carboxylate and 4-fluorobenzyl bromide were used for a similar reaction and treatment as Process 6 of Example 1, and methyl 4-[2-(4-fluorobenzyl)-3,3-dimethyl-4-oxo-1,2-diazetidin-1-yl]adamantane-1-carboxylate was obtained as a colorless oil.
$^1$H-NMR (400 MHz, CDCl$_3$) δ; 1.23-2.47 (m, 19H), 3.50 (s, 1H), 3.59 (s, 3H), 3.89 (d, J=8.0 Hz, 1H), 4.02 (d, J=8.0 Hz, 1H), 6.97-6.99 (m, 2H), 7.31-7.34 (m, 2H).

Process 7: Preparation of 4-[2-(4-fluorobenzyl)-3,3-dimethyl-4-oxo-1,2-diazetidin-1-yl]adamantane-1-carboxylic acid A solution of methyl 4-[2-(4-fluorobenzyl)-3,3-dimethyl-4-oxo-1,2-diazetidin-1-yl]adamantane-1-carboxylate (40.0 mg, 0.100 mmol) in tetrahydrofuran-methanol (1:1, 1 mL) was added with 2M aqueous solution of sodium hydrate (1 mL) at room temperature, and the resultant was stirred at 80° C. for 30 minutes. The reaction solution was neutralized with 4M hydrochloric acid, and extracted with chloroform. The organic layer was dried over anhydrous sodium sulfate and concentrated in vacuo. The obtained residue was purified using Preparative Thin-Layer chromatography (hexane:ethyl acetate=1:2), and the title compound (24.5 mg, 63.4%) was obtained as a white crystalline powder.

$^1$H-NMR (400 MHz, CDCl$_3$) δ; 1.25-1.26 (m, 3H), 1.37-1.38 (m, 3H), 1.52-2.45 (m, 13H), 3.53 (s, 1H), 3.87 (d, J=13.8 Hz, 1H), 4.08 (d, J=13.8 Hz, 1H), 7.01 (t, J=8.9 Hz, 2H), 7.36 (dd, J=5.1, 8.9 Hz, 2H).

IR (ATR); 2920, 1722, 1694, 1609, 1222, 1080, 829 cm$^{-1}$.

EI-MS m/z; 386 (M$^+$).

Example 91

Preparation of 4-[2-(4-fluorobenzyl)-3,3-dimethyl-4-oxo-1,2-diazetidin-1-yl]adamantane-1-carboxamide

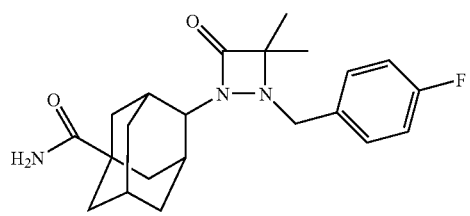

A solution of 4-[2-(4-fluorobenzyl)-3,3-dimethyl-4-oxo-1,2-diazetidin-1-yl]adamantane-1-carboxylic acid (20.0 mg, 0.0520 mmol) prepared in Example 90 in dichloromethane (1 mL) was added with hydroxybenzotriazole monohydrate (12.0 mg, 0.0890 mmol), WSC.HCl (20.0 mg, 0.100 mmol), 30% aqueous solution of ammonia (0.1 mL) at room temperature, and the resultant was stirred at the same temperature for 30 minutes. The reaction solution was added with water and extracted with chloroform. The organic layer was dried over anhydrous sodium sulfate and concentrated in vacuo. The obtained residue was purified using Preparative Thin-Layer chromatography (ethyl acetate), and the title compound (5.00 mg, 24.9%) was obtained as a white crystalline powder.

$^1$H-NMR (400 MHz, CDCl$_3$) δ; 1.27-1.28 (m, 3H), 1.37-1.38 (m, 3H), 1.52-2.55 (m, 13H), 3.36 (s, 0.4H), 3.55 (s, 0.6H), 3.86 (d, J=13.8 Hz, 1H), 4.00-4.08 (m, 1H), 6.98-7.05 (m, 2H), 7.33-7.38 (m, 2H).

IR (ATR); 3350, 2917, 2858, 1740, 1661, 1509, 1222, 755 cm$^{-1}$.

EI-MS m/z; 385 (M$^+$).

Example 92

Preparation of 1-(cyclohexa-2-ene-1-yl)-4,4-dimethyl-2-(adamantan-2-yl)-1,2-diazetidin-3-one 2-(Adamantan-2-yl)-4,4-dimethyl-1,2-diazetidin-3-one prepared in Process 3 of Example 12, and 3-bromocyclohexene were used for a similar reaction and treatment as Process 6 of Example 1, and the title compound was obtained as a colorless oil.

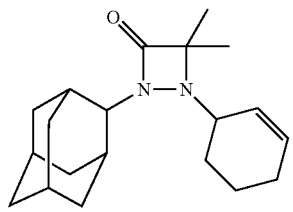

$^1$H-NMR (400 MHz, CDCl$_3$) δ; 1.45-2.51 (m, 26H), 3.49-3.63 (m, 2H), 5.79-5.85 (m, 2H).

EI-MS m/z; 314 (M$^+$).

Example 93

Preparation of 1-cyclohexyl-4,4-dimethyl-2-(adamantan-2-yl)-1,2-diazetidin-3-one

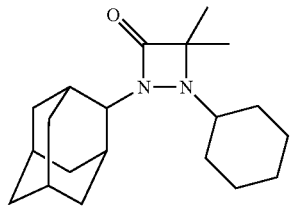

A solution of 1-(cyclohexa-2-ene-1-yl)-4,4-dimethyl-2-(adamantan-2-yl)-1,2-diazetidin-3-one (3.20 mg, 0.0100 mmol) in ethanol (2 mL) was added with 10% palladium carbon (catalyst amount), and under hydrogen atmosphere, the resultant was stirred at room temperature for 2 hours. The reaction solution was filtered using celite and concentrated in vacuo. The obtained residue was purified using Preparative Thin-Layer chromatography (hexane:ethyl acetate=3:1), and the title compound (3.2 mg, quant.) was obtained as a colorless oil.

$^1$H-NMR (400 MHz, CDCl$_3$) δ; 1.16-1.88 (m, 26H), 2.10-2.12 (m, 1H), 2.33-2.35 (m, 1H), 2.45 (s, 2H), 2.72 (s, 1H), 3.51 (s, 1H).

IR (ATR); 2907, 2854, 1758 cm$^{-1}$.

EI-MS m/z; 316 (M$^+$).

Example 94

Preparation of 4,4-dimethyl-1-[2-(methylsulfonyl)benzyl]-2-(adamantan-2-yl)-1,2-diazetidin-3-one

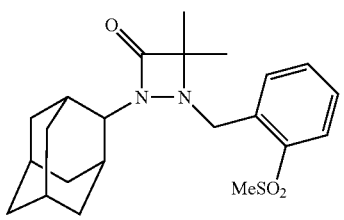

A solution of 4,4-dimethyl-1-[2-(methylthio)benzyl]-2-(adamantan-2-yl)-1,2-diazetidin-3-one (7.20 mg, 0.0186 mmol) prepared in Example 60 in methanol was added sequentially with tantalum pentachloride (3.30 mg, 0.00930 mmol) and hydrogen peroxide water (5.70 mg, 0.0558 mmol) at room temperature, and the resultant was stirred at the same temperature for 36.5 hours. The reaction solution was added with water and extracted with diethyl ether. The organic layer was dried over anhydrous sodium sulfate and concentrated in vacuo. The obtained residue was purified using Preparative Thin-Layer chromatography (hexane:ethyl acetate=1:5), and the title compound (2.40 mg, 32.0%) was obtained as a white crystalline powder.

$^1$H-NMR (270 MHz, CDCl$_3$) δ; 1.43 (s, 3H), 1.53 (s, 3H), 1.58-2.47 (m, 14H), 3.31 (s, 3H), 3.48 (s, 1H), 3.94 (d, J=20.8 Hz, 1H), 4.97 (d, J=20.8 Hz, 1H), 7.47-7.61 (m, 3H), 8.10 (d, J=10.4 Hz, 1H).

IR (ATR); 2909, 1747, 1307, 1151, 750 cm$^{-1}$.
EI-MS m/z; 402 (M$^+$).

Example 95

Preparation of 4-[2-(2-chlorobenzyl)-3,3-dimethyl-4-oxo-1,2-diazetidin-1-yl]adamantane-1-carboxamide

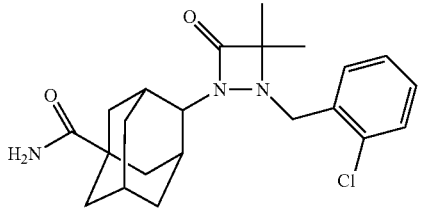

Process 1: Preparation of methyl 4-[2-(2-chlorobenzyl)-3,3-dimethyl-4-oxo-1,2-diazetidin-1-yl]adamantane-1-carboxylate Methyl 4-(3,3-dimethyl-4-oxo-1,2-diazetidin-1-yl)adamantane-1-carboxylate prepared in Process 5 of Example 90, and 2-chlorobenzyl bromide were used for a similar reaction and treatment as Process 6 of Example 1, and methyl 4-[2-(2-chlorobenzyl)-3,3-dimethyl-4-oxo-1,2-diazetidin-1-yl]adamantane-1-carboxylate was obtained as a pale yellow oil.

$^1$H-NMR (400 MHz, CDCl$_3$) δ; 1.46-2.55 (m, 19H), 3.58 (s, 1H), 4.06 (d, J=16.0 Hz, 1H), 4.16 (d, J=16.0 Hz, 1H), 7.20-7.65 (m, 4H).

Process 2: Preparation of 4-[2-(2-chlorobenzyl)-3,3-dimethyl-4-oxo-1,2-diazetidin-1-yl]adamantane-1-carboxylic acid Methyl 4-[2-(2-chlorobenzyl)-3,3-dimethyl-4-oxo-1,2-diazetidin-1-yl]adamantane-1-carboxylate was used for a similar reaction and treatment as Process 7 of Example 90 and 4-[2-(2-chlorobenzyl)-3,3-dimethyl-4-oxo-1,2-diazetidin-1-yl]adamantane-1-carboxylic acid was obtained as a colorless oil.

$^1$H-NMR (400 MHz, CDCl$_3$) δ; 1.42 (s, 6H), 1.56-2.58 (m, 13H), 3.58 (s, 1H), 4.06 (d, J=14.8 Hz, 1H), 4.14 (d, J=14.8 Hz, 1H), 7.19-7.37 (m, 3H), 7.62-7.64 (m, 1H).

Process 3: Preparation of 4-[2-(2-chlorobenzyl)-3,3-dimethyl-4-oxo-1,2-diazetidin-1-yl]adamantane-1-carboxamide 4-[2-(2-chlorobenzyl)-3,3-dimethyl-4-oxo-1,2-diazetidin-1-yl]adamantane-1-carboxylic acid was used for a similar reaction and treatment as Example 91, and the title compound was obtained as a colorless amorphous solid.

$^1$H-NMR (400 MHz, CDCl$_3$) δ; 1.29-1.26 (m, 3H), 1.47-1.44 (m, 3H), 2.58-1.50 (m, 13H), 3.61-3.42 (m, 1H), 4.18-3.95 (m, 2H), 5.29 (br, 2H), 7.30-7.18 (m, 2H), 7.38-7.34 (m, 1H), 7.64-7.60 (m, 1H).

Example 96

Preparation of 4,4-dimethyl-1-(phenylcarbonyl)-2-(adamantan-2-yl)-1,2-diazetidin-3-one

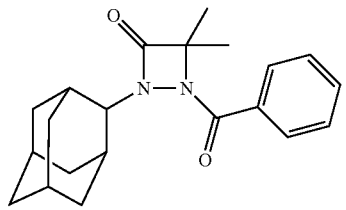

A solution of 2-(adamantan-2-yl)-4,4-dimethyl-1,2-diazetidin-3-one (33.6 mg, 0.140 mmol) prepared in Process 3 of Example 12 in dichloromethane (2 mL) was added sequentially with benzoyl chloride (40.0 mg, 0.280 mmol), triethylamine (56.6 mg, 0.560 mmol), and DMAP (catalyst amount) at room temperature, and the resultant was stirred at the same temperature for 1.5 hours. The reaction solution was added with water and extracted with chloroform. The organic layer was dried over anhydrous sodium sulfate and concentrated in vacuo. The obtained residue was purified using Preparative Thin-Layer chromatography (hexane:ethyl acetate=3:1), and the title compound (40.4 mg, 85.3%) was obtained as a white crystalline powder.

$^1$H-NMR (400 MHz, CDCl$_3$) δ; 1.40 (s, 6H), 1.69-1.92 (m, 10H), 2.07-2.10 (m, 2H), 2.43 (s, 2H), 4.34 (s, 1H), 7.47 (t, J=7.3 Hz, 2H), 7.58 (t, J=7.3 Hz, 1H), 7.77 (d, J=7.3 Hz, 2H).

IR (ATR); 2915, 1770, 1675, 1397, 1310, 1306, 1264, 698 cm$^{-1}$.
EI-MS m/z; 338 (M$^+$).

Example 97

Preparation of 1-[(2-methylphenyl)carbonyl]-4-(propan-2-yl)-2-(adamantan-2-yl)-1,2-diazetidin-3-one 2-(Adamantan-2-yl)-4-(propan-2-yl)-1,2-diazetidin-3-one prepared in Process 3 of Example 10 and 2-methylbenzoyl chloride were used for a similar reaction and treatment as Example 96, and the title compound was obtained as a colorless oil.

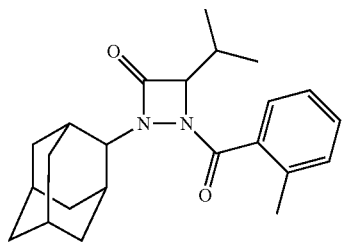

$^1$H-NMR (400 MHz, CDCl$_3$) δ; 0.93 (d, J=6.8 Hz, 3H), 1.06 (d, J=6.8 Hz, 3H), 1.62-1.91 (m, 13H), 2.14 (s, 1H), 2.27 (s, 1H), 2.43 (s, 3H), 4.32 (d, J=4.6 Hz, 1H), 4.43 (s, 1H), 7.19-7.42 (m, 4H).
EI-MS m/z; 366 (M$^+$).

Example 98

Preparation of 1-[(3-fluorophenyl)carbonyl]-4,4-dimethyl-2-(adamantan-2-yl)-1,2-diazetidin-3-one 3-Fluorobenzoyl chloride was used in place of benzoyl chloride for a similar reaction and treatment as Example 96, and the title compound was obtained as a white crystalline powder.

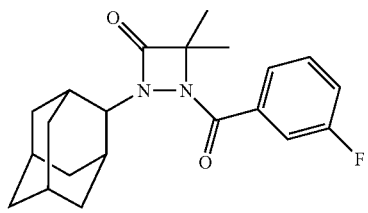

$^1$H-NMR (400 MHz, CDCl$_3$) δ; 1.42 (s, 6H), 1.68-1.89 (m, 10H), 2.03-2.08 (m, 2H), 2.40 (s, 2H), 4.32 (s, 1H), 7.26-7.32 (m, 1H), 7.42-7.48 (m, 2H), 7.55-7.57 (m, 1H).
IR (ATR); 2910, 1773, 1679, 1588, 1442, 1307, 1263, 768 cm$^{-1}$.
EI-MS m/z; 356 (M$^+$).

Example 99

Preparation of 1-[(3,4-dichlorophenyl)carbonyl]-4,4-dimethyl-2-(adamantan-2-yl)-1,2-diazetidin-3-one 3,4-Dichlorobenzoyl chloride was used in place of benzoyl chloride for a similar reaction and treatment as Example 96, and the title compound was obtained as a white crystalline powder.

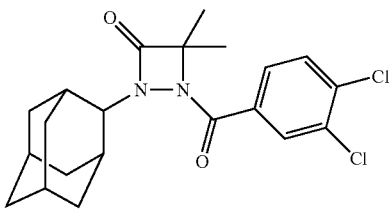

$^1$H-NMR (400 MHz, CDCl$_3$) δ; 1.43 (s, 6H), 1.64-2.07 (m, 12H), 2.38 (s, 2H), 4.30 (s, 1H), 7.55 (d, J=8.1 Hz, 1H), 7.61 (d, J=8.1 Hz, 1H), 7.85 (s, 1H).
IR (ATR); 2912, 1774, 1678, 1306, 1032, 762 cm$^{-1}$.
EI-MS m/z; 407 (M$^+$).

Example 100

Preparation of 4,4-dimethyl-2-(adamantan-2-yl)-1-{[2-(trifluoromethyl)phenyl]carbonyl}-1,2-diazetidin-3-one 2-(Trifluoromethyl)benzoyl chloride was used in place of benzoyl chloride for a similar reaction and treatment as Example 96, and the title compound was obtained as a white crystalline powder.

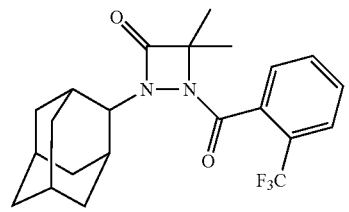

$^1$H-NMR (400 MHz, CDCl$_3$) δ; 1.38 (s, 6H), 1.70-1.90 (m, 10H), 2.04-2.09 (m, 2H), 2.45 (s, 2H), 4.46 (s, 1H), 7.63-7.84 (m, 4H).
IR (ATR); 2910, 1776, 1680, 1311, 1164, 1143, 772, 681 cm$^{-1}$.
EI-MS m/z; 406 (M$^+$).

Example 101

Preparation of 1-[(2-methoxyphenyl)carbonyl]-4,4-dimethyl-2-(adamantan-2-yl)-1,2-diazetidin-3-one 2-Methoxybenzoyl chloride was used in place of benzoyl chloride for a similar reaction and treatment as Example 96, and the title compound was obtained as a white crystalline powder.

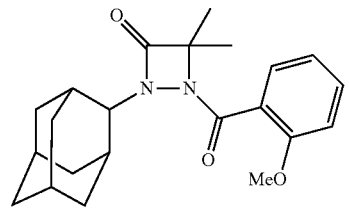

$^1$H-NMR (400 MHz, CDCl$_3$) δ; 1.35 (s, 6H), 1.69-1.90 (m, 10H), 2.08 (d, J=12.9 Hz, 2H), 2.45 (s, 2H), 3.87 (s, 3H), 4.42 (s, 1H), 6.96-7.00 (m, 2H), 7.44-7.48 (m, 2H).
IR (ATR); 2923, 1780, 1667, 1280, 1018, 942, 769 cm$^{-1}$.
FAB-MS m/z; 369 (M+H)$^+$.

Example 102

Preparation of 1-[(3-methoxyphenyl)carbonyl]-4,4-dimethyl-2-(adamantan-2-yl)-1,2-diazetidin-3-one 3-Methoxybenzoyl chloride was used in place of benzoyl chloride for a similar reaction and treatment as Example 96, and the title compound was obtained as a white crystalline powder.

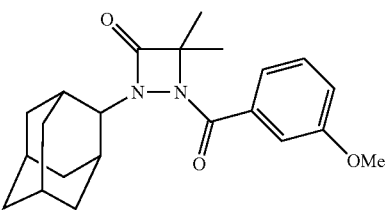

¹H-NMR (400 MHz, CDCl₃) δ; 1.42 (s, 6H), 1.68-1.92 (m, 10H), 2.07 (d, J=12.4 Hz, 2H), 2.42 (s, 2H), 3.88 (s, 3H), 4.33 (s, 1H), 7.11 (dt, J=2.4, 7.1 Hz, 1H), 7.27-7.39 (m, 3H).
IR (ATR); 2908, 1773, 1669, 1298, 1264, 1039, 774 cm⁻¹.
FAB-MS m/z; 369 (M+H)⁺.

Example 103

Preparation of 1-[(4-chlorophenyl)carbonyl]-4,4-dimethyl-2-(adamantan-2-yl)-1,2-diazetidin-3-one 4-Chlorobenzoyl chloride was used in place of benzoyl chloride for a similar reaction and treatment as Example 96, and the title compound was obtained as a white crystalline powder.

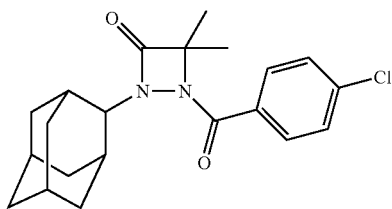

¹H-NMR (400 MHz, CDCl₃) δ; 1.41 (s, 6H), 1.68-1.92 (m, 10H), 2.06 (d, J=12.9 Hz, 2H), 2.40 (s, 2H), 4.31 (s, 1H), 7.44-7.47 (m, 2H), 7.71-7.74 (m, 2H).
IR (ATR); 2929, 1777, 1668, 1306, 1087, 852, 776 cm⁻¹.
FAB-MS m/z; 373 (M+H)⁺.

Example 104

Preparation of 1-[(4-fluorophenyl)carbonyl]-4,4-dimethyl-2-(adamantan-2-yl)-1,2-diazetidin-3-one 4-Fluorobenzoyl chloride was used in place of benzoyl chloride for a similar reaction and treatment as Example 96, and the title compound was obtained as a white crystalline powder.

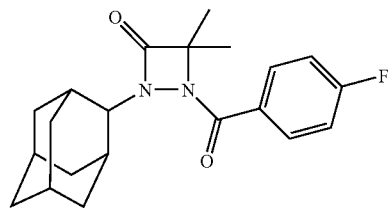

¹H-NMR (400 MHz, CDCl₃) δ; 1.41 (s, 6H), 1.68-1.89 (m, 10H), 2.04-2.09 (m, 2H), 2.40 (s, 2H), 4.31 (s, 1H), 7.16 (t, J=8.6 Hz, 2H), 7.80 (dd, J=5.7, 8.6 Hz, 2H).
EI-MS m/z; 356 (M⁺).

Example 105

Preparation of 1-[(4-t-butylphenyl)carbonyl]-4,4-dimethyl-2-(adamantan-2-yl)-1,2-diazetidin-3-one 4-t-Butylbenzoyl chloride was used in place of benzoyl chloride for a similar reaction and treatment as Example 96, and the title compound was obtained as a white crystalline powder.

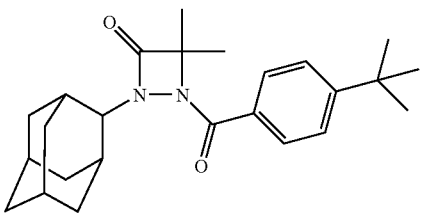

¹H-NMR (400 MHz, CDCl₃) δ; 1.34 (s, 9H), 1.42 (s, 6H), 1.68-1.91 (m, 10H), 2.06-2.10 (m, 2H), 2.41 (s, 2H), 4.32 (s, 1H), 7.47 (d, J=8.6 Hz, 2H), 7.72 (d, J=8.6 Hz, 2H).
IR (ATR); 2912, 1764, 1673, 1314, 702 cm⁻¹.
EI-MS m/z; 394 (M⁺).

Example 106

Preparation of 1-[(4-bromophenyl)carbonyl]-4,4-dimethyl-2-(adamantan-2-yl)-1,2-diazetidin-3-one 4-Bromobenzoyl chloride was used in place of benzoyl chloride for a similar reaction and treatment as Example 96, and the title compound was obtained as a white crystalline powder.

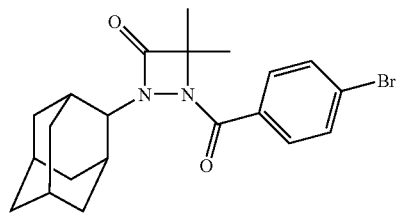

¹H-NMR (400 MHz, CDCl₃) δ; 1.40 (s, 6H), 1.68-1.92 (m, 10H), 2.05-2.07 (m, 2H), 2.40 (s, 2H), 4.31 (s, 1H), 7.60-7.66 (m, 4H).
IR (ATR); 2923, 1777, 1672, 1395, 1318, 1260, 773 cm⁻¹.
EI-MS m/z; 416 (M⁺).

Example 107

Preparation of 4,4-dimethyl-1-[(4-nitrophenyl)carbonyl]-2-(adamantan-2-yl)-1,2-diazetidin-3-one 4-Nitrobenzoyl chloride was used in place of benzoyl chloride for a similar reaction and treatment as Example 96, and the title compound was obtained as a yellow crystalline powder.

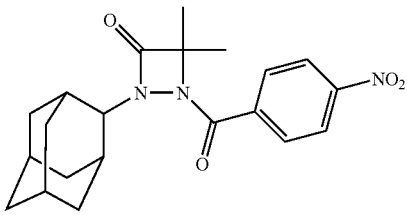

¹H-NMR (400 MHz, CDCl₃) δ; 1.42 (s, 6H), 1.71-1.94 (m, 10H), 2.05-2.08 (m, 2H), 2.41 (s, 2H), 4.34 (s, 1H), 7.94 (d, J=8.8 Hz, 2H), 8.34 (d, J=8.8 Hz, 2H).

IR (ATR); 2928, 1778, 1673, 1603, 1522, 1346, 1305, 1260, 743 cm$^{-1}$.
EI-MS m/z; 383 (M$^+$).

Example 108

Preparation of 4,4-dimethyl-1-[(3-nitrophenyl)carbonyl]-2-(adamantan-2-yl)-1,2-diazetidin-3-one 3-Nitrobenzoyl chloride was used in place of benzoyl chloride for a similar reaction and treatment as Example 96, and the title compound was obtained as a white crystalline powder.

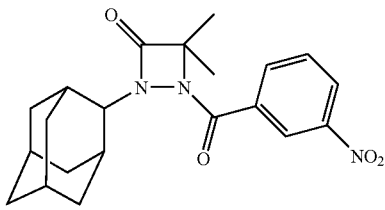

$^1$H-NMR (270 MHz, CDCl$_3$) δ; 1.45 (s, 6H), 1.62-1.94 (m, 10H), 2.07 (d, J=13.0 Hz, 2H), 2.40 (s, 2H), 4.34 (s, 1H), 7.71 (t, J=7.8 Hz, 1H), 8.13 (d, J=7.8 Hz, 1H), 8.45 (d, J=7.8 Hz, 1H), 8.60 (s, 1H).
IR (ATR); 2913, 1775, 1678, 1531, 1347, 963, 714 cm$^{-1}$.

Example 109

Preparation of 4,4-dimethyl-1-[(3-methylphenyl)carbonyl]-2-(adamantan-2-yl)-1,2-diazetidin-3-one 3-Methylbenzoyl chloride was used in place of benzoyl chloride for a similar reaction and treatment as Example 96, and the title compound was obtained as a white crystalline powder.

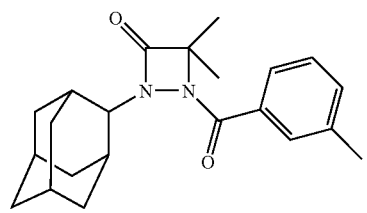

$^1$H-NMR (270 MHz, CDCl$_3$) δ; 1.39 (s, 6H), 1.67-1.88 (m, 10H), 2.07 (d, J=13.0 Hz, 2H), 2.41 (s, 5H), 4.33 (s, 1H), 7.30-7.40 (m, 2H), 7.54-7.57 (m, 2H).
IR (ATR); 2911, 1774, 1666, 1308, 963, 770 cm$^{-1}$.

Example 110

Preparation of 1-{[3,5-bis(trifluoromethyl)phenyl]carbonyl}-4,4-dimethyl-2-(adamantan-2-yl)-1,2-diazetidin-3-one 3,5-bis(Trifluoromethyl)benzoyl chloride was used in place of benzoyl chloride for a similar reaction and treatment as Example 96, and the title compound was obtained as a white crystalline powder.

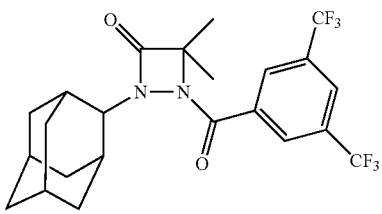

$^1$H-NMR (270 MHz, CDCl$_3$) δ; 1.43 (s, 6H), 1.61-1.91 (m, 10H), 2.06 (d, J=12.7 Hz, 2H), 2.40 (s, 2H), 4.34 (s, 1H), 8.09 (s, 1H), 8.22 (s, 2H).
IR (ATR); 2913, 1777, 1680, 1280, 1178, 1134, 908 cm$^{-1}$.

Example 111

Preparation of 1-[(2,4-dichlorophenyl)carbonyl]-4,4-dimethyl-2-(adamantan-2-yl)-1,2-diazetidin-3-one 2,4-Dichlorobenzoyl chloride was used in place of benzoyl chloride for a similar reaction and treatment as Example 96, and the title compound was obtained as a white crystalline powder.

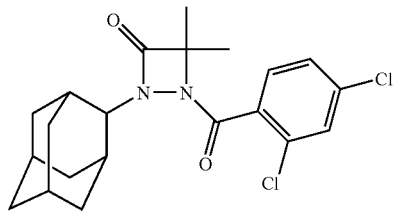

$^1$H-NMR (400 MHz, CDCl$_3$) δ; 1.38 (s, 6H), 1.70-1.91 (m, 10H), 2.03-2.07 (m, 2H), 2.43 (s, 2H), 4.40 (s, 1H), 7.32-7.34 (m, 1H), 7.47-7.53 (m, 2H).
IR (ATR); 2917, 1781, 1683, 1307, 945 cm$^{-1}$.
EI-MS m/z; 407 (M$^+$).

Example 112

Preparation of 1-[(4-iodophenyl)carbonyl]-4,4-dimethyl-2-(adamantan-2-yl)-1,2-diazetidin-3-one 4-Iodobenzoyl chloride was used in place of benzoyl chloride for a similar reaction and treatment as Example 96, and the title compound was obtained as a white crystalline powder.

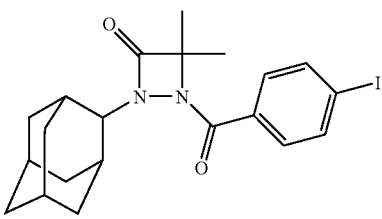

$^1$H-NMR (400 MHz, CDCl$_3$) δ; 1.40 (s, 6H), 1.68-1.91 (m, 10H), 2.04-2.07 (m, 2H), 2.39 (s, 2H), 4.31 (s, 1H), 7.49 (d, J=8.6 Hz, 2H), 7.83 (d, J=8.6 Hz, 2H).
IR (ATR); 2907, 1670, 1581, 1305, 772 cm$^{-1}$.
FAB-MS m/z; 464 (M$^+$).

Example 113

Preparation of 1-[(3-bromophenyl)carbonyl]-4,4-dimethyl-2-(adamantan-2-yl)-1,2-diazetidin-3-one 3-Bromobenzoyl chloride was used in place of benzoyl chloride for a similar reaction and treatment as Example 96, and the title compound was obtained as a white crystalline powder.

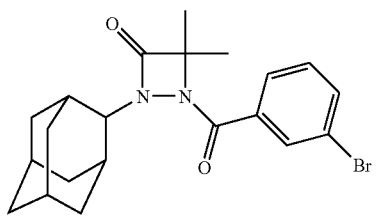

$^1$H-NMR (400 MHz, CDCl$_3$) δ; 1.41 (s, 6H), 1.69-1.92 (m, 10H), 2.05-2.08 (m, 2H), 2.40 (s, 2H), 4.32 (s, 1H), 7.36 (t, J=7.8 Hz, 1H), 7.70-7.73 (m, 2H), 7.90-7.91 (m, 1H).
IR (ATR); 2916, 1779, 1660, 1312, 720 cm$^{-1}$.
FAB-MS m/z; 417 (M$^+$).

Example 114

Preparation of 4,4-dimethyl-1-[(4-methylphenyl)carbonyl]-2-(adamantan-2-yl)-1,2-diazetidin-3-one 4-Methylbenzoyl chloride was used in place of benzoyl chloride for a similar reaction and treatment as Example 96, and the title compound was obtained as a white crystalline powder.

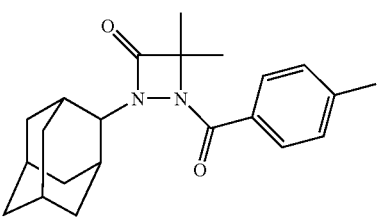

$^1$H-NMR (270 MHz, CDCl$_3$) δ; 1.39 (s, 6H), 1.63-1.90 (m, 10H), 2.05-2.10 (m, 2H), 2.42 (m, 5H), 4.32 (s, 1H), 7.25 (d, J=10.8 Hz, 2H), 7.66 (d, J=12.4 Hz, 2H).
IR (ATR); 2923, 1769, 1668, 1607, 1454, 1397, 1313, 766 cm$^{-1}$.
FAB-MS m/z; 352 (M$^+$).

Example 115

Preparation of 4,4-dimethyl-2-(adamantan-2-yl)-1-{[4-(trifluoromethyl)phenyl]carbonyl}-1,2-diazetidin-3-one 4-(Trifluoromethyl)benzoyl chloride was used in place of benzoyl chloride for a similar reaction and treatment as Example 96, and the title compound was obtained as a white crystalline powder.

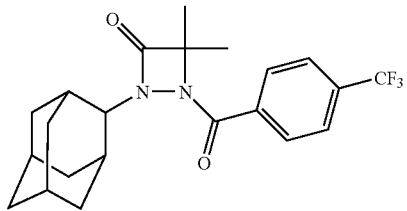

$^1$H-NMR (400 MHz, CDCl$_3$) δ; 1.42 (s, 6H), 1.70-1.93 (m, 10H), 2.05-2.09 (m, 2H), 2.42 (s, 2H), 4.34 (s, 1H), 7.74 (d, J=8.0 Hz, 2H), 7.89 (d, J=8.0 Hz, 2H).
IR (ATR); 2923, 1770, 1672, 1325, 1168, 1128, 1065, 865 cm$^{-1}$.
FAB-MS m/z; 406 (M$^+$).

Example 116

Preparation of 4,4-dimethyl-1-[(2-methylphenyl)carbonyl]-2-(adamantan-2-yl)-1,2-diazetidin-3-one 2-Methylbenzoyl chloride was used in place of benzoyl chloride for a similar reaction and treatment as Example 96, and the title compound was obtained as a white crystalline powder.

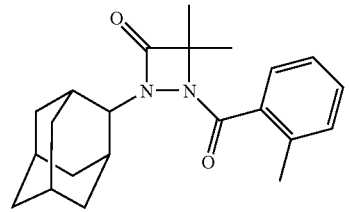

$^1$H-NMR (400 MHz, CDCl$_3$) δ; 1.33 (s, 6H), 1.61-1.92 (m, 10H), 2.06 (d, J=8.3 Hz, 2H), 2.45-2.47 (m, 5H), 4.38 (s, 1H), 7.22-7.29 (m, 2H), 7.38-7.42 (m, 1H), 7.54 (d, J=6.6 Hz, 1H).
IR (ATR); 2911, 1770, 1671, 1454, 1398, 1321, 752 cm$^{-1}$.
EI-MS m/z; 352 (M$^+$).

Example 117

Preparation of 1-[(3,5-dichlorophenyl)carbonyl]-4,4-dimethyl-2-(adamantan-2-yl)-1,2-diazetidin-3-one 3,5-Dichlorobenzoyl chloride was used in place of benzoyl chloride for a similar reaction and treatment as Example 96, and the title compound was obtained as a white crystalline powder.

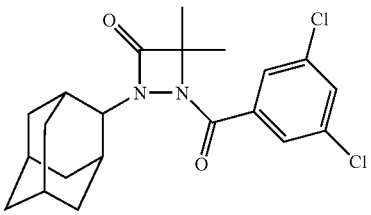

$^1$H-NMR (400 MHz, CDCl$_3$) δ; 1.44 (s, 6H), 1.70-1.93 (m, 10H), 2.05 (m, 2H), 2.38 (s, 2H), 4.31 (s, 1H), 7.57 (t, J=2.0 Hz, 1H), 7.64 (d, J=2.0 Hz, 2H).

Example 118

Preparation of 1-[(2-chlorophenyl)carbonyl]-4,4-dimethyl-2-(adamantan-2-yl)-1,2-diazetidin-3-one 2-Chlorobenzoyl chloride was used in place of benzoyl chloride for a similar reaction and treatment as Example 96, and the title compound was obtained as a white crystalline powder.

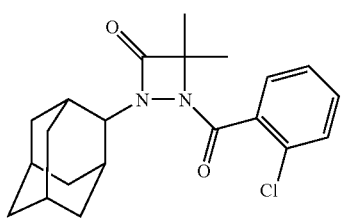

$^1$H-NMR (400 MHz, CDCl$_3$) δ; 1.37 (s, 6H), 1.70-1.92 (m, 10H), 2.05-2.09 (m, 2H), 2.46 (s, 2H), 4.43 (s, 1H), 7.32-7.36 (m, 1H), 7.42-7.55 (m, 3H).
IR (ATR); 2912, 1774, 1678, 1319, 756 cm$^{-1}$.
FAB-MS m/z; 372 (M$^+$).

Example 119

Preparation of 1-[(2-fluorophenyl)carbonyl]-4,4-dimethyl-2-(adamantan-2-yl)-1,2-diazetidin-3-one 2-Fluorobenzoyl chloride was used in place of benzoyl chloride for a similar reaction and treatment as Example 96, and the title compound was obtained as a white crystalline powder.

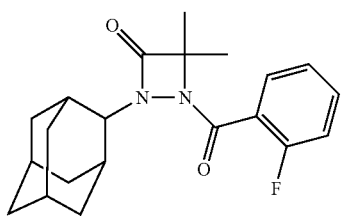

$^1$H-NMR (400 MHz, CDCl$_3$) δ; 1.40 (s, 6H), 1.66-1.92 (m, 10H), 2.05-2.09 (m, 2H), 2.45 (s, 2H), 4.37 (s, 1H), 7.15-7.27 (m, 2H), 7.50-7.53 (m, 1H), 7.58-7.62 (m, 1H).
IR (ATR); 2916, 1773, 1678, 1320, 775, 762 cm$^{-1}$.
FAB-MS m/z; 356 (M$^+$).

Example 120

Preparation of 1-[(2-bromophenyl)carbonyl]-4,4-dimethyl-2-(adamantan-2-yl)-1,2-diazetidin-3-one 2-Bromobenzoyl chloride was used in place of benzoyl chloride for a similar reaction and treatment as Example 96, and the title compound was obtained as a white crystalline powder.

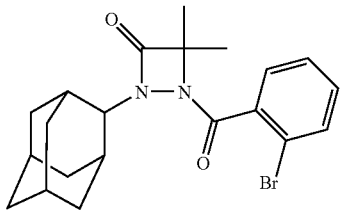

$^1$H-NMR (400 MHz, CDCl$_3$) δ; 1.40 (s, 6H), 1.67-1.91 (m, 10H), 2.06-2.09 (m, 2H), 2.46 (s, 2H), 4.45 (s, 1H), 7.34-7.41 (m, 2H), 7.52-7.55 (m, 1H), 7.69-7.71 (m, 1H).
IR (ATR); 2913, 1772, 1670, 1314, 785, 758 cm$^{-1}$.
FAB-MS m/z; 416 (M$^+$).

Example 121

Preparation of 1-[(2-iodophenyl)carbonyl]-4,4-dimethyl-2-(adamantan-2-yl)-1,2-diazetidin-3-one 2-Iodobenzoyl chloride was used in place of benzoyl chloride for a similar reaction and treatment as Example 96, and the title compound was obtained as a white crystalline powder.

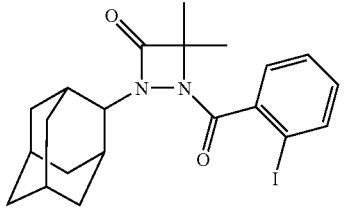

$^1$H-NMR (400 MHz, CDCl$_3$) δ; 1.40 (s, 6H), 1.65-1.92 (m, 10H), 2.05-2.09 (m, 2H), 2.45 (s, 2H), 4.46 (s, 1H), 7.20 (dt, J=7.8, 1.7 Hz, 1H), 7.42 (dt, J=7.8, 1.2 Hz, 1H), 7.52 (dd, 7.8, 1.7 Hz, 1H), 8.01 (dd, J=7.8, 1.2 Hz, 1H).
IR (ATR); 2912, 1771, 1658, 1314, 754 cm$^{-1}$.
FAB-MS m/z; 464 (M$^+$).

Example 122

Preparation of 1-[(2,5-dichlorophenyl)carbonyl]-4,4-dimethyl-2-(adamantan-2-yl)-1,2-diazetidin-3-one 2,5-Dichlorobenzoyl chloride was used in place of benzoyl chloride for a similar reaction and treatment as Example 96, and the title compound was obtained as a white crystalline powder.

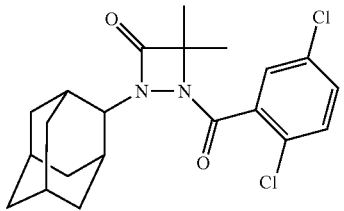

$^1$H-NMR (400 MHz, CDCl$_3$) δ; 1.41 (s, 6H), 1.72-1.93 (m, 10H), 2.05-2.07 (m, 2H), 2.44 (s, 2H), 4.42 (s, 1H), 7.41-7.43 (m, 2H), 7.50 (d, J=1.5 Hz, 1H).
IR (ATR); 2908, 1771, 1661, 1395, 1102, 817 cm$^{-1}$.

Example 123

Preparation of 1-[(2,6-dichlorophenyl)carbonyl]-4,4-dimethyl-2-(adamantan-2-yl)-1,2-diazetidin-3-one 2,6-Dichlorobenzoyl chloride was used in place of benzoyl chloride for a similar reaction and treatment as Example 96, and the title compound was obtained as a white crystalline powder.

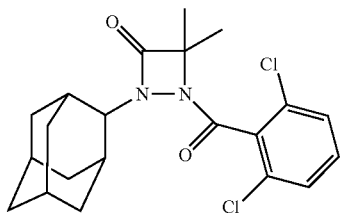

$^1$H-NMR (270 MHz, CDCl$_3$) δ; 1.45 (s, 6H), 1.69-1.93 (m, 10H), 2.08-2.12 (m, 2H), 2.53 (s, 2H), 4.56 (s, 1H), 7.27-7.41 (m, 3H).

IR (ATR); 2908, 1774, 1658, 1430, 795 cm$^{-1}$.

Example 124

Preparation of 4,4-dimethyl-1-[(2-nitrophenyl)carbonyl]-2-(adamantan-2-yl)-1,2-diazetidin-3-one 2-Nitrobenzoyl chloride was used in place of benzoyl chloride for a similar reaction and treatment as Example 96, and the title compound was obtained as a white crystalline powder.

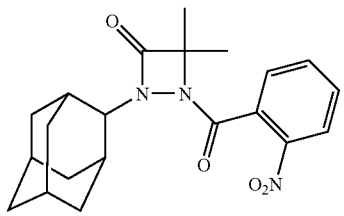

$^1$H-NMR (400 MHz, CDCl$_3$) δ; 1.40 (s, 6H), 1.71-1.91 (m, 10H), 2.02-2.05 (m, 2H), 2.44 (s, 2H), 4.41 (s, 1H), 7.64-7.73 (m, 3H), 7.93-7.96 (m, 1H).

IR (ATR); 2907, 1777, 1674, 1538, 1360, 1320, 789, 742 cm$^{-1}$.

FAB-MS m/z; 383 (M$^+$).

Example 125

Preparation of 1-[(5-fluoro-2-methylphenyl)carbonyl]-4,4-dimethyl-2-(adamantan-2-yl)-1,2-diazetidin-3-one 5-Fluoro-2-methylbenzoyl chloride was used in place of benzoyl chloride for a similar reaction and treatment as Example 96, and the title compound was obtained as a white crystalline powder.

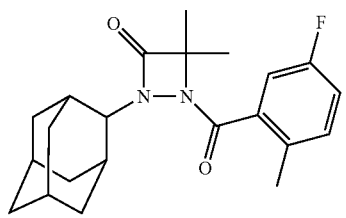

$^1$H-NMR (400 MHz, CDCl$_3$) δ; 1.36 (s, 6H), 1.71-1.93 (m, 10H), 2.06 (d, J=14.2 Hz, 2H), 2.44 (m, 5H), 4.37 (s, 1H), 7.12 (dt, J=8.3 2.7 Hz, 1H), 7.23-7.27 (m, 2H).

IR (ATR); 2917, 1772, 1674, 1498, 1398, 1225, 830, 789 cm$^{-1}$.

EI-MS m/z; 370 (M$^+$).

Example 126

Preparation of 1-[(2-ethylphenyl)carbonyl]-4,4-dimethyl-2-(adamantan-2-yl)-1,2-diazetidin-3-one 2-Ethylbenzoyl chloride was used in place of benzoyl chloride for a similar reaction and treatment as Example 96, and the title compound was obtained as a white crystalline powder.

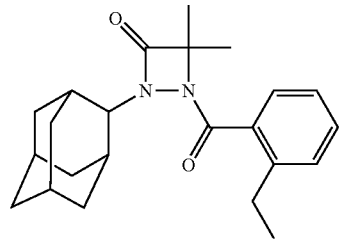

$^1$H-NMR (400 MHz, CDCl$_3$) δ; 1.29 (t, J=7.6 Hz, 3H), 1.32 (s, 6H), 1.71-1.91 (m, 10H), 2.08 (d, J=12.7 Hz, 2H), 2.46 (s, 2H), 2.82 (q, J=7.6 Hz, 2H), 4.39 (s, 1H), 7.23 (t, J=6.5 Hz, 1H), 7.35 (d, J=7.8 Hz, 1H), 7.43-7.47 (m, 1H), 7.53 (d, J=6.5 Hz, 1H).

IR (ATR); 2913, 1770, 1664, 1315, 944, 758 cm$^{-1}$.

FAB-MS m/z; 366 (M$^+$).

Example 127

Preparation of 1-[(2,3-difluorophenyl)carbonyl]-4,4-dimethyl-2-(adamantan-2-yl)-1,2-diazetidin-3-one 2,3-Difluorobenzoyl chloride was used in place of benzoyl chloride for a similar reaction and treatment as Example 96, and the title compound was obtained as a white crystalline powder.

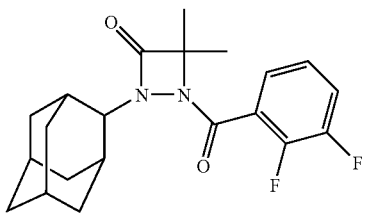

¹H-NMR (400 MHz, CDCl₃) δ; 1.42 (s, 6H), 1.70-1.91 (m, 10H), 2.05-2.08 (m, 2H), 2.43 (s, 2H), 4.36 (s, 1H), 7.16-7.22 (m, 1H), 7.32-7.39 (m, 2H).
IR (ATR); 2913, 1775, 1670, 1480, 1323, 1271, 756 cm⁻¹.
FAB-MS m/z; 374 (M⁺).

Example 128

Preparation of 1-[(3-chlorophenyl)carbonyl]-4,4-dimethyl-2-(adamantan-2-yl)-1,2-diazetidin-3-one 3-Chlorobenzoyl chloride was used in place of benzoyl chloride for a similar reaction and treatment as Example 96, and the title compound was obtained as a white crystalline powder.

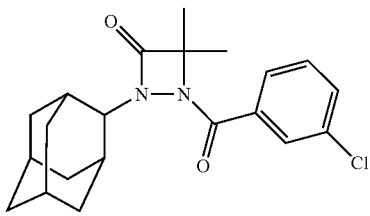

¹H-NMR (270 MHz, CDCl₃) δ; 1.41 (s, 6H), 1.62-1.89 (m, 10H), 2.03-2.08 (m, 2H), 2.40 (s, 2H), 4.31 (s, 1H), 7.41 (t, J=11.6 Hz, 1H), 7.56 (d, J=11.6 Hz, 1H), 7.65 (d, J=11.6 Hz, 1H), 7.74 (s, 1H).
IR (ATR); 2916, 1780, 1663, 1313, 768, 742 cm⁻¹.
FAB-MS m/z; 372 (M⁺).

Example 129

Preparation of 4,4-dimethyl-2-(adamantan-2-yl)-1-{[3-(trifluoromethyl)phenyl]carbonyl}-1,2-diazetidin-3-one 3-(Trifluoromethyl)benzoyl chloride was used in place of benzoyl chloride for a similar reaction and treatment as Example 96, and the title compound was obtained as a white crystalline powder.

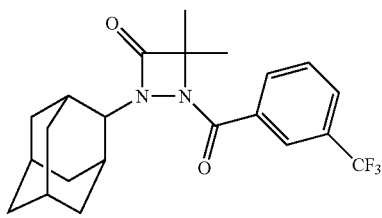

¹H-NMR (270 MHz, CDCl₃) δ; 1.41 (s, 6H), 1.67-1.90 (m, 10H), 2.04-2.09 (m, 2H), 2.41 (m, 2H), 4.34 (s, 1H), 7.64 (t, J=11.6 Hz, 1H), 7.85 (d, J=11.6 Hz, 1H), 7.98 (d, J=11.6 Hz, 1H), 8.02 (s, 1H).
IR (ATR); 2986, 1774, 1666, 1344, 1312, 1164, 1132, 1071, 758, 707 cm⁻¹.
FAB-MS m/z; 406 (M⁺).

Example 130

Preparation of 1-[(2,4-difluorophenyl)carbonyl]-4,4-dimethyl-2-(adamantan-2-yl)-1,2-diazetidin-3-one 2,4-Difluorobenzoyl chloride was used in place of benzoyl chloride for a similar reaction and treatment as Example 96, and the title compound was obtained as a white crystalline powder.

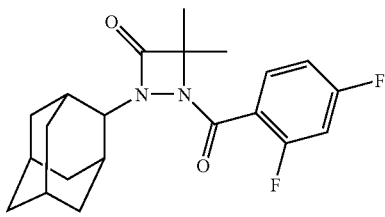

¹H-NMR (270 MHz, CDCl₃) δ; 1.40 (s, 6H), 1.73-1.90 (m, 10H), 2.03-2.07 (m, 2H), 2.42 (s, 2H), 4.34 (s, 1H), 6.90-7.00 (m, 2H), 7.59-7.67 (m, 1H).
IR (ATR); 2917, 1774, 1666, 1618, 972, 854, 773 cm⁻¹.
FAB-MS m/z; 374 (M⁺).

Example 131

Preparation of 1-[(2,5-difluorophenyl)carbonyl]-4,4-dimethyl-2-(adamantan-2-yl)-1,2-diazetidin-3-one 2,5-Difluorobenzoyl chloride was used in place of benzoyl chloride for a similar reaction and treatment as Example 96, and the title compound was obtained as a white crystalline powder.

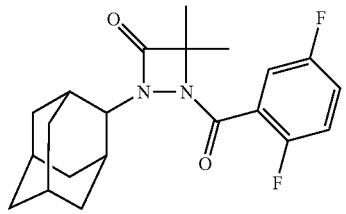

¹H-NMR (270 MHz, CDCl₃) δ; 1.43 (s, 6H), 1.67-1.92 (m, 10H), 2.05-2.08 (m, 2H), 2.43 (s, 2H), 4.35 (s, 1H), 7.13-7.25 (m, 2H), 7.28-7.34 (m, 1H).
IR (ATR); 2919, 1775, 1686, 1494, 1321, 844, 758 cm⁻¹.
FAB-MS m/z; 374 (M⁺).

Example 132

Preparation of 1-[(4-fluoro-2-trifluoromethylphenyl)carbonyl]-4,4-dimethyl-2-(adamantan-2-yl)-1,2-diazetidin-3-one 4-Fluoro-2-(trifluoromethyl)benzoyl chloride was used in place of benzoyl chloride for a similar reaction and treatment as Example 96, and the title compound was obtained as a white crystalline powder.

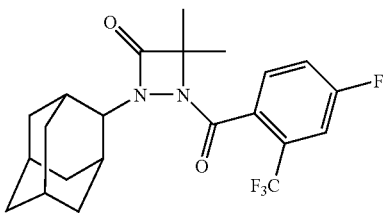

¹H-NMR (400 MHz, CDCl₃) δ; 1.39 (s, 6H), 1.71-1.92 (m, 10H), 2.05 (d, J=13.0 Hz, 2H), 2.42 (s, 2H), 4.43 (s, 1H), 7.33 (dt, J=8.1, 2.7 Hz, 1H), 7.55 (dd, J=8.8, 2.7 Hz, 1H), 7.73-7.77 (m, 1H).
IR (ATR); 2919, 1779, 1677, 1307, 1265, 1189, 1164, 862 cm⁻¹.
EI-MS m/z; 424 (M⁺).

Example 133

Preparation of 1-[(2-chloro-4-fluorophenyl)carbonyl]-4,4-dimethyl-2-(adamantan-2-yl)-1,2-diazetidin-3-one 2-Chloro-4-fluorobenzoyl chloride was used in place of benzoyl chloride for a similar reaction and treatment as Example 96, and the title compound was obtained as a white crystalline powder.

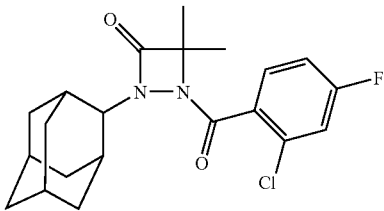

¹H-NMR (400 MHz, CDCl₃) δ; 1.38 (s, 6H), 1.70-1.91 (m, 10H), 2.05-2.07 (m, 2H), 2.43 (s, 2H), 4.40 (s, 1H), 7.04-7.08 (m, 1H), 7.24-7.27 (m, 1H), 7.54-7.58 (m, 1H).
IR (ATR); 2909, 1775, 1674, 1601, 1318, 1263, 1219 cm⁻¹.
FAB-MS m/z; 390 (M⁺).

Example 134

Preparation of 1-(1,3-benzodioxol-4-ylcarbonyl)-4,4-dimethyl-2-(adamantan-2-yl)-1,2-diazetidin-3-one 2,3-Methylenedioxybenzoyl chloride was used in place of benzoyl chloride for a similar reaction and treatment as Example 96, and the title compound was obtained as a white crystalline powder.

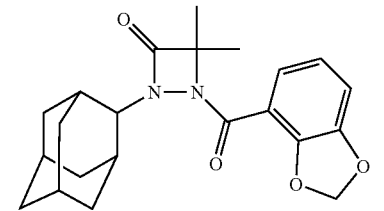

¹H-NMR (400 MHz, CDCl₃) δ; 1.45 (s, 6H), 1.68-1.90 (m, 10H), 2.05-2.08 (m, 2H), 2.42 (s, 2H), 4.34 (s, 1H), 6.09 (s, 2H), 6.85-6.90 (m, 1H), 6.96-6.98 (m, 1H), 7.09-7.11 (m, 1H).
IR (ATR); 2916, 1776, 1670, 1450, 1302, 1253, 1051, 931, 765 cm⁻¹.
FAB-MS m/z; 382 (M⁺).

Example 135

Preparation of 1-(1,3-benzodioxol-5-ylcarbonyl)-4,4-dimethyl-2-(adamantan-2-yl)-1,2-diazetidin-3-one 3,4-Methylenedioxybenzoyl chloride was used in place of benzoyl chloride for a similar reaction and treatment as Example 96, and the title compound was obtained as a white crystalline powder.

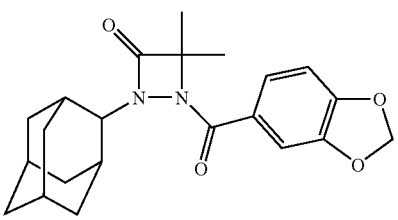

¹H-NMR (270 MHz, CDCl₃) δ; 1.42 (s, 6H), 1.58-1.90 (m, 10H), 2.04-2.09 (m, 2H), 2.39 (s, 2H), 4.29 (s, 1H), 6.07 (s, 2H), 6.87 (d, J=12.0 Hz, 1H), 7.23 (d, J=2.4 Hz, 1H), 7.37 (dd, J=12.0, 2.4 Hz, 1H).
IR (ATR); 2919, 1772, 1670, 1487, 1439, 1359, 1298, 1096, 1038 cm⁻¹.

Example 136

Preparation of 1-[(2-aminophenyl)carbonyl]-4,4-dimethyl-2-(adamantan-2-yl)-1,2-diazetidin-3-one

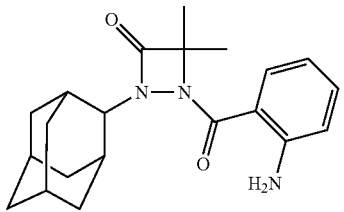

A solution of 4,4-dimethyl-1-[(2-nitrophenyl)carbonyl]-2-(adamantan-2-yl)-1,2-diazetidin-3-one (16.7 mg, 0.0436 mmol) prepared in Example 124 in ethanol-tetrahydrofuran was added with 10% palladium carbon (catalyst amount), and under a hydrogen atmosphere, the resultant was stirred at room temperature for 1 hour. The reaction solution was filtered using celite and concentrated in vacuo. The obtained residue was purified using Preparative Thin-Layer chromatography (hexane:ethyl acetate=2:1), and the title compound (14.8 mg, 96.1%) was obtained as a white crystalline solid.
¹H-NMR (400 MHz, CDCl₃) δ; 1.40 (s, 6H), 1.68-1.92 (m, 10H), 2.06-2.09 (m, 2H), 2.42 (s, 2H), 4.26 (s, 1H), 5.42 (s, 2H), 6.64-6.70 (m, 2H), 7.55 (dd, J=6.6 1.5 Hz, 1H), 7.28 (m, 1H).

IR (ATR); 3363, 2922, 1771, 1618, 1453, 1397, 1321, 1263, 750 cm$^{-1}$.
FAB-MS m/z; 353 (M$^+$).

Example 137

Preparation of 2-{[4,4-dimethyl-3-oxo-2-(adamantan-2-yl)-1,2-diazetidin-1-yl]carbonyl}phenyl acetate O-acetylsalicyloyl chloride was used in place of benzoyl chloride for a similar reaction and treatment as Example 96, and the title compound was obtained as a white crystalline powder.

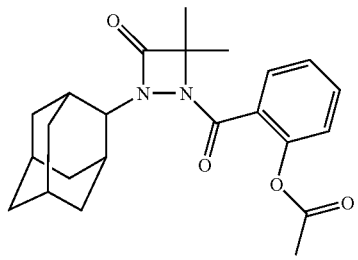

$^1$H-NMR (400 MHz, CDCl$_3$) δ; 1.37 (s, 6H), 1.69-1.91 (m, 10H), 2.03-2.06 (m, 2H), 2.32 (s, 3H), 2.42 (s, 2H), 4.33 (s, 1H), 7.18 (dd, J=7.8, 1.0 Hz, 1H), 7.32 (dt, J=7.8, 1.0 Hz, 1H), 7.56 (dt, J=7.8, 1.7 Hz, 1H), 7.66 (dd, J=7.8, 1.7 Hz, 1H).
IR (ATR); 2921, 1769, 1679, 1183, 1168, 906, 754 cm$^{-1}$.
FAB-MS m/z; 396 (M$^+$).

Example 138

Preparation of 1-[(2-hydroxyphenyl)carbonyl]-4,4-dimethyl-2-(adamantan-2-yl)-1,2-diazetidin-3-one

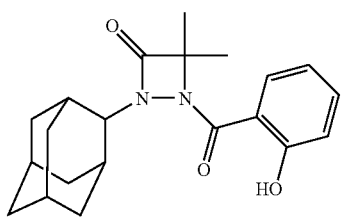

A solution of 2-{[4,4-dimethyl-3-oxo-2-(adamantan-2-yl)-1,2-diazetidin-1-yl]carbonyl}phenyl acetate (15.0 mg, 0.0378 mmol) prepared in Example 137 in methanol-tetrahydrofuran was dropped with saturated sodium bicarbonate water (0.5 mL), and the resultant was stirred at room temperature for 4.5 hours. The reaction solution was added with water and extracted with ethyl acetate. The organic layer was dried over anhydrous sodium sulfate and concentrated in vacuo. The obtained residue was purified using Preparative Thin-Layer chromatography (hexane:ethyl acetate=2:1), and the title compound (9.80 mg, 73.7%) was obtained as a white crystalline powder.
$^1$H-NMR (400 MHz, CDCl$_3$) δ; 1.48 (s, 6H), 1.66-1.91 (m, 10H), 2.03-2.06 (m, 2H), 2.40 (s, 2H), 4.26 (s, 1H), 6.91 (dt, J=8.3, 1.2 Hz, 1H), 7.02 (dd, J=8.3, 1.0 Hz, 1H), 7.48 (dt, J=7.8, 1.7 Hz, 1H), 7.58 (dd, J=7.8, 1.2 Hz, 1H), 10.73 (s, 1H).

IR (ATR); 2918, 1770, 1645, 1603, 1480, 1255, 761 cm$^{-1}$.
FAB-MS m/z; 354 (M$^+$).

Example 139

Preparation of 1-[(4-aminophenyl)carbonyl]-4,4-dimethyl-2-(adamantan-2-yl)-1,2-diazetidin-3-one 4,4-Dimethyl-1-[(4-nitrophenyl)carbonyl]-2-(adamantan-2-yl)-1,2-diazetidin-3-one prepared in Example 107 was used for a similar reaction and treatment as Example 136, and the title compound was obtained as a white crystalline powder.

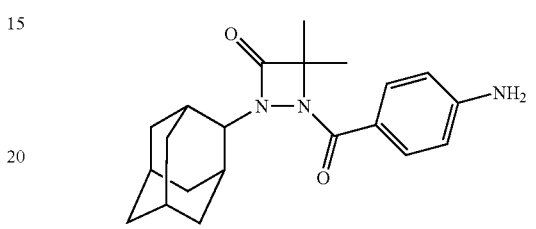

$^1$H-NMR (270 MHz, CDCl$_3$) δ; 1.41 (s, 6H), 1.61-1.89 (m, 10H), 2.05-2.09 (m, 2H), 2.40 (s, 2H), 4.11 (m, 2H), 4.28 (s, 1H), 6.67 (d, J=12.4 Hz, 2H), 7.62 (d, J=12.4 Hz, 2H).
IR (ATR); 3352, 2910, 1760, 1602, 1311, 1177, 769 cm$^{-1}$.

Example 140

Preparation of 1-[(4-(4-fluorobenzene sulfonylaminophenyl)carbonyl)-4,4-dimethyl-2-(adamantan-2-yl)-1,2-diazetidin-3-one

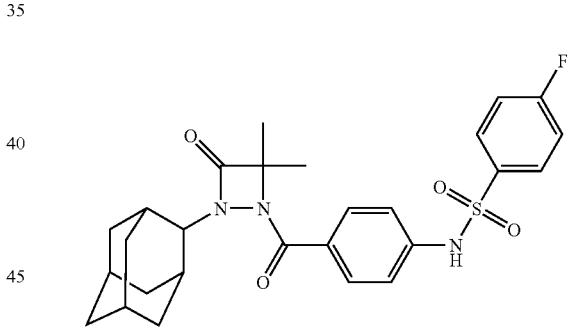

A solution of 1-[(4-aminophenyl)carbonyl]-4,4-dimethyl-2-(adamantan-2-yl)-1,2-diazetidin-3-one (5.00 mg, 0.0141 mmol) prepared in Example 139 in dichloromethane was added sequentially with 4-fluorobenzene sulfonyl chloride (3.30 mg, 0.0169 mmol) and triethylamine (2.90 mg, 0.0282 mmol) at room temperature, and the resultant was stirred at 50° C. for 1 hour. The reaction solution was added with water and extracted with chloroform. The organic layer was dried over anhydrous sodium sulfate and concentrated in vacuo. The obtained residue was purified using Preparative Thin-Layer chromatography (hexane:ethyl acetate=2:1), and the title compound (3.30 mg, 45.8%) was obtained as a white crystalline powder.
$^1$H-NMR (270 MHz, CDCl$_3$) δ; 1.42 (s, 6H), 1.68-1.90 (m, 10H), 2.03-2.08 (m, 2H), 2.40 (s, 2H), 4.33 (s, 1H), 7.13 (d, J=12.8 Hz, 2H), 7.78 (d, J=12.8 Hz, 2H), 7.92-7.97 (m, 4H).
IR (ATR); 2925, 1770, 1675, 1592, 1492, 1380, 1242, 1175, 1154, 1083, 914, 835 cm$^{-1}$
FAB-MS m/z; 511 (M$^+$).

Example 141

Preparation of 4,4-dimethyl-1-(naphthalen-1-ylcarbonyl)-2-(adamantan-2-yl)-1,2-diazetidin-3-one 1-Naphthoyl chloride was used in place of benzoyl chloride for a similar reaction and treatment as Example 96, and the title compound was obtained as a white crystalline powder.

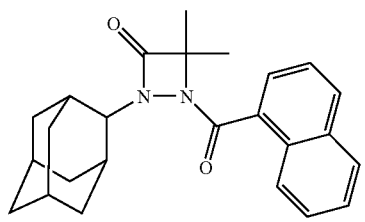

$^1$H-NMR (270 MHz, CDCl$_3$) δ; 1.29 (s, 6H), 1.61-1.92 (m, 10H), 2.11-2.16 (m, 2H), 2.52 (s, 2H), 4.47 (s, 1H), 7.48-7.59 (m, 3H), 7.81-7.89 (m, 2H), 8.01 (d, 12.2 Hz, 1H), 8.45 (d, J=11.2 Hz, 1H).
IR (ATR); 2916, 1779, 1657, 1307, 813, 787 cm$^{-1}$.
FAB-MS m/z; 388 (M$^+$).

Example 142

Preparation of 4,4-dimethyl-1-(naphthalen-2-ylcarbonyl)-2-(adamantan-2-yl)-1,2-diazetidin-3-one 2-Naphthoyl chloride was used in place of benzoyl chloride for a similar reaction and treatment as Example 96, and the title compound was obtained as a white crystalline powder.

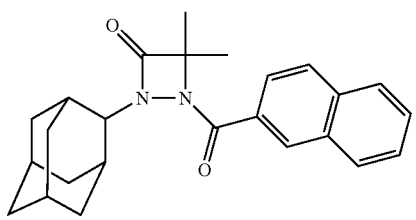

$^1$H-NMR (400 MHz, CDCl$_3$) δ; 1.43 (s, 6H), 1.72-1.95 (m, 10H), 2.11-2.14 (m, 2H), 2.47 (s, 2H), 4.38 (s, 1H), 7.56-7.64 (m, 2H), 7.81 (dd, J=8.5, 2.7 Hz, 1H), 7.90-7.97 (m, 3H), 8.31 (s, 1H).
IR (ATR); 3363, 2922, 1771, 1618, 750 cm$^{-1}$.
FAB-MS m/z; 388 (M$^+$).

Example 143

Preparation of 4,4-dimethyl-1-(quinoxalin-2-ylcarbonyl)-2-(adamantan-2-yl)-1,2-diazetidin-3-one 2-quinoxaloyl chloride was used in place of benzoyl chloride for a similar reaction and treatment as Example 96, and the title compound was obtained as a yellow crystalline powder.

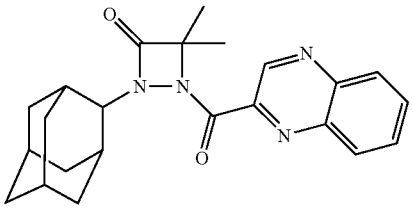

$^1$H-NMR (400 MHz, CDCl$_3$) δ; 1.53 (d, J=13.4 Hz, 1H), 1.70 (s, 6H), 1.73-1.92 (m, 9H), 2.11-2.15 (m, 2H), 2.47 (s, 2H), 4.49 (s, 1H), 7.88-7.94 (m, 2H), 8.16-8.21 (m, 2H).
IR (ATR); 2912, 1771, 1654, 1392, 1364, 942, 788 cm$^{-1}$.
EI-MS m/z; 390 (M$^+$).

Example 144

Preparation of 1-(cyclohexylcarbonyl)-4,4-dimethyl-2-(adamantan-2-yl)-1,2-diazetidin-3-one Cyclohexanecarbonyl chloride was used in place of benzoyl chloride for a similar reaction and treatment as Example 96, and the title compound was obtained as a yellow crystalline powder.

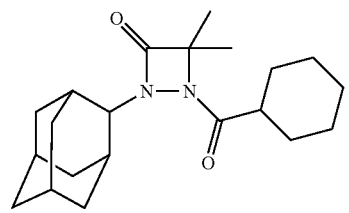

$^1$H-NMR (270 MHz, CDCl$_3$) δ; 1.15-1.34 (m, 3H), 1.51-2.04 (m, 26H), 2.28 (s, 2H), 4.21 (s, 1H).
IR (ATR); 2907, 1770, 1692, 1088, 765 cm$^{-1}$.

Example 145

Preparation of 4,4-dimethyl-1-(pyridin-3-ylcarbonyl)-2-(adamantan-2-yl)-1,2-diazetidin-3-one Nicotinoyl chloride hydrochloride was used in place of benzoyl chloride for a similar reaction and treatment as Example 96, and the title compound was obtained as a yellow crystalline powder.

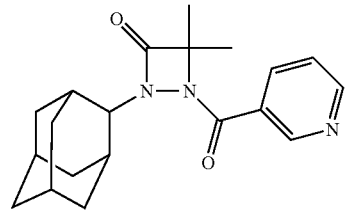

$^1$H-NMR (400 MHz, CDCl$_3$) δ; 1.44 (s, 6H), 1.70-1.90 (m, 10H), 2.05-2.09 (m, 2H), 2.41 (s, 2H), 4.33 (s, 1H), 7.43-7.46 (m, 1H), 8.06-8.10 (m, 1H), 8.82 (dd, J=4.9, 1.9 Hz, 1H), 8.99 (d, J=1.9 Hz, 1H).
IR (ATR); 2903, 1791, 1682, 1584, 1302, 1235, 747 cm$^{-1}$.
FAB-MS m/z; 339 (M$^+$).

Example 146

Preparation of 4,4-dimethyl-1-(pyridin-4-ylcarbonyl)-2-(adamantan-2-yl)-1,2-diazetidin-3-one Isonicotinoyl chloride hydrochloride was used in place of benzoyl chloride for a similar reaction and treatment as Example 96, and the title compound was obtained as a yellow crystalline powder.

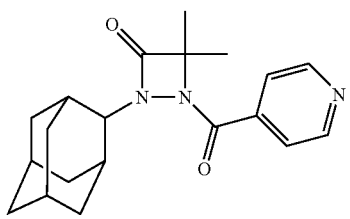

$^1$H-NMR (400 MHz, CDCl$_3$) δ; 1.44 (s, 6H), 1.70-1.93 (m, 10H), 2.04-2.07 (m, 2H), 2.41 (s, 2H), 4.34 (s, 1H), 7.60 (dd, J=4.4, 1.7 Hz, 2H), 8.80 (dd, J=4.4, 1.7 Hz, 2H).
IR (ATR); 2914, 1774, 1675, 1561, 1317 cm$^{-1}$.
FAB-MS m/z; 339 (M$^+$).

Example 147

Preparation of 2-cyclohexyl-4,4-dimethyl-1-[(2-methylphenyl)carbonyl]-1,2-diazetidin-3-one 2-Cyclohexyl-4,4-dimethyl-1,2-diazetidin-3-one prepared in Process 5 of Example 68 and 2-methylbenzoyl chloride were used for a similar reaction and treatment as Example 96, and the title compound was obtained as a colorless oil.

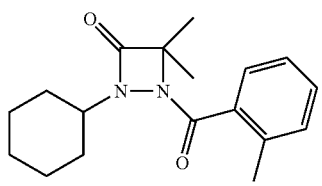

$^1$H-NMR (400 MHz, CDCl$_3$) δ; 1.21-1.35 (m, 3H), 1.29 (s, 6H), 1.63-1.67 (m, 2H), 1.74-1.85 (m, 3H), 2.18 (d, J=11.2 Hz, 2H), 2.47 (s, 2H), 3.75-3.86 (m, 1H), 7.23 (t, J=7.6 Hz, 1H), 7.28 (d, J=7.8 Hz, 1H), 7.39 (d, J=7.6 Hz, 1H), 7.48 (d, J=7.8 Hz, 1H).
IR (ATR); 2932, 1782, 1673, 1308, 948, 750 cm$^{-1}$.
EI-MS m/z; 300 (M$^+$).

Example 148

Preparation of 2-cyclohexyl-1-[(2,4-dimethylphenyl)carbonyl]-4,4-dimethyl-1,2-diazetidin-3-one 2-Cyclohexyl-4,4-dimethyl-1,2-diazetidin-3-one and 2,4-dimethylbenzoyl chloride were used for a similar reaction and treatment as Example 96, and the title compound was obtained as a colorless oil.

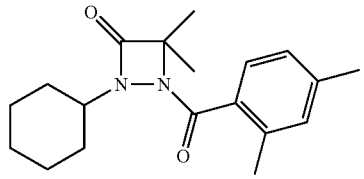

$^1$H-NMR (400 MHz, CDCl$_3$) δ; 1.16-1.35 (m, 3H), 1.29 (s, 6H), 1.63-1.66 (m, 2H), 1.73-1.85 (m, 3H), 2.18 (d, J=12.0 Hz, 2H), 2.36 (s, 3H), 2.43 (s, 3H), 3.72-3.83 (m, 1H), 7.02 (d, J=7.8 Hz, 1H), 7.09 (s, 1H), 7.39 (d, J=7.8 Hz, 1H).
IR (ATR); 2930, 1781, 1674, 1307, 956, 776 cm$^{-1}$.
FAB-MS m/z; 315 (M+H)$^+$.

Example 149

Preparation of 2-cyclohexyl-1-[(2,5-dimethylphenyl)carbonyl]-4,4-dimethyl-1,2-diazetidin-3-one 2-Cyclohexyl-4,4-dimethyl-1,2-diazetidin-3-one and 2,5-dimethylbenzoyl chloride were used for a similar reaction and treatment as Example 96, and the title compound was obtained as a white crystalline powder.

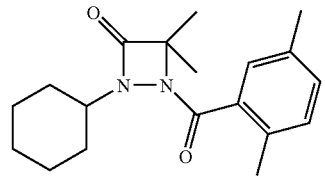

$^1$H-NMR (400 MHz, CDCl$_3$) δ; 1.20-1.31 (m, 3H), 1.28 (s, 6H), 1.61-1.67 (m, 2H), 1.74-1.85 (m, 3H), 2.19 (d, J=11.5 Hz, 2H), 2.35 (s, 3H), 2.41 (s, 3H), 3.72-3.83 (m, 1H), 7.15-7.21 (m, 2H), 7.29 (s, 1H).
IR (ATR); 2927, 1773, 1662, 1317, 1047, 962, 836 cm$^{-1}$.
EI-MS m/z; 314 (M$^+$).

Example 150

Preparation of 1-[(3-chlorophenyl)carbonyl]-2-cyclooctyl-4,4-dimethyl-1,2-diazetidin-3-one 2-Cyclooctyl-4,4-dimethyl-1,2-diazetidin-3-one prepared in Process 5 of Example 73 and 3-chlorobenzoyl chloride were used for a similar reaction and treatment as Example 96, and the title compound was obtained as a white crystalline powder.

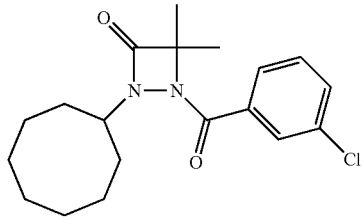

$^1$H-NMR (270 MHz, CDCl$_3$) δ; 1.37 (s, 6H), 1.49-1.64 (m, 8H), 1.73-1.80 (m, 2H), 2.03-2.18 (m, 4H), 3.90-4.00 (m,

1H), 7.41 (t, J=11.6 Hz, 1H), 7.53-7.57 (m, 1H), 7.60-7.64 (m, 1H), 7.70 (t, J=2.4 Hz, 1H).

IR (ATR); 2925, 1787, 1659, 1572, 1302, 1274, 1252, 777, 759 cm$^{-1}$.

FAB-MS m/z; 348 (M$^+$).

Example 151

Preparation of 2-cyclooctyl-4,4-dimethyl-1-[(3-methylphenyl)carbonyl]-1,2-diazetidin-3-one 2-Cyclooctyl-4,4-dimethyl-1,2-diazetidin-3-one and 3-methylbenzoyl chloride were used for a similar reaction and treatment as Example 96, and the title compound was obtained as a colorless oil.

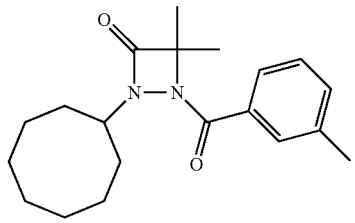

$^1$H-NMR (270 MHz, CDCl$_3$) δ; 1.29-1.77 (m, 16H), 1.98-2.21 (m, 4H), 2.41 (s, 3H), 3.94 (br, 1H), 7.25-7.54 (m, 4H).

IR (ATR); 2922, 1775, 1676, 1311, 755 cm$^{-1}$.

FAB-MS m/z; 328 (M$^+$).

Example 152

Preparation of 2-cyclooctyl-4,4-dimethyl-1-[(2-methylphenyl)carbonyl]-1,2-diazetidin-3-one 2-Cyclooctyl-4,4-dimethyl-1,2-diazetidin-3-one and 2-methylbenzoyl chloride were used for a similar reaction and treatment as Example 96, and the title compound was obtained as a white crystalline powder.

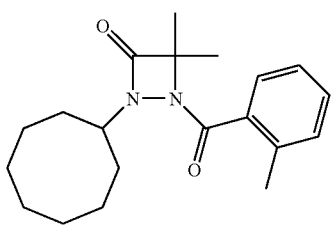

$^1$H-NMR (270 MHz, CDCl$_3$) δ; 1.29 (s, 6H), 1.57-1.79 (m, 10H), 2.01-2.24 (m, 4H), 2.47 (s, 3H), 4.06 (br, 1H), 7.20-7.29 (m, 2H), 7.37-7.42 (m, 1H), 7.49 (d, J=11.2 Hz, 1H).

IR (ATR); 2926, 1771, 1670, 1388, 1313, 751 cm$^{-1}$.

FAB-MS m/z; 328 (M$^+$).

Example 153

Preparation of 1-[(2-aminophenyl)carbonyl]-2-cyclooctyl-4,4-dimethyl-1,2-diazetidin-3-one

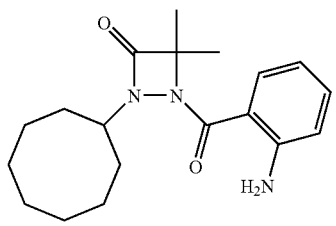

Process 1: Preparation of 2-cyclooctyl-4,4-dimethyl-1-[(2-nitrophenyl)carbonyl]-1,2-diazetidin-3-one 2-Cyclooctyl-4,4-dimethyl-1,2-diazetidin-3-one prepared in Process 5 of Example 73 and 2-nitorbenzoyl chloride were used for a similar reaction and treatment as Example 96, and 2-cyclooctyl-4,4-dimethyl-1-[(2-nitrophenyl)carbonyl]-1,2-diazetidin-3-one was obtained as a pale yellow oil.

$^1$H-NMR (270 MHz, CDCl$_3$) δ; 1.25-2.09 (m, 20H), 4.19 (s, 1H), 7.52-7.82 (m, 4H).

Process 2: Preparation of 1-[(2-aminophenyl)carbonyl]-2-cyclooctyl-4,4-dimethyl-1,2-diazetidin-3-one A solution of 2-cyclooctyl-4,4-dimethyl-1-[(2-nitrophenyl)carbonyl]-1,2-diazetidin-3-one (22.3 mg, 0.0620 mmol) in methanol was added with 10% palladium carbon (catalyst amount), and under a hydrogen atmosphere, the resultant was stirred at room temperature for 30 minutes. The reaction solution was filtered using celite, concentrated in vacuo, and the obtained residue was purified using Preparative Thin-Layer chromatography (hexane:ethyl acetate=2:1), and the title compound (14.7 mg, 72.1%) was obtained as a colorless oil.

$^1$H-NMR (270 MHz, CDCl$_3$) δ; 1.37 (s, 6H), 1.47-1.59 (m, 8H), 1.74-1.82 (m, 2H), 2.05-2.20 (m, 4H), 3.81-3.91 (m, 1H), 5.35 (br, 2H), 6.63-6.70 (m, 2H), 7.24-7.31 (m, 1H), 7.51 (dd, J=11.6, 2.4 Hz, 1H).

IR (ATR); 3460, 3350, 2925, 1754, 1659, 1617, 1301, 1247, 752 cm$^{-1}$.

Example 154

Preparation of 2-cyclooctyl-4,4-dimethyl-1-(naphthalen-1-ylcarbonyl)-1,2-diazetidin-3-one 2-Cyclooctyl-4,4-dimethyl-1,2-diazetidin-3-one and 1-naphtoyl chloride were used for a similar reaction and treatment as Example 96, and the title compound was obtained as a colorless oil.

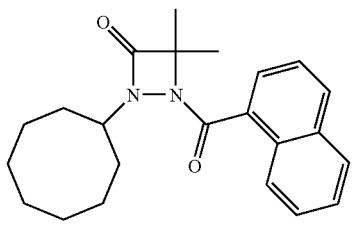

¹H-NMR (400 MHz, CDCl₃) δ; 1.24 (s, 6H), 1.45-1.73 (m, 8H), 1.75-1.89 (m, 2H), 2.11-2.27 (m, 4H), 4.15 (br, 1H), 7.47-7.62 (m, 3H), 7.77 (d, J=6.6 Hz, 1H), 7.89-7.91 (m, 1H), 8.01 (d, J=8.3 Hz, 1H), 8.39 (d, J=8.0 Hz, 1H).

IR (ATR); 2925, 1777, 1669, 1299, 1252, 786, 753 cm⁻¹.

Example 155

Preparation of trans-1-[(4-fluorophenyl)carbonyl]-2-(5-hydroxyadamantan-2-yl)-4,4-dimethyl-1,2-diazetidin-3-one trans-2-(5-Hydroxyadamantan-2-yl)-4,4-dimethyl-1,2-diazetidin-3-one prepared in Process 5 of Example 65 and 4-fluorobenzoyl chloride were used for a similar reaction and treatment as Example 96, and the title compound was obtained as a white crystalline powder.

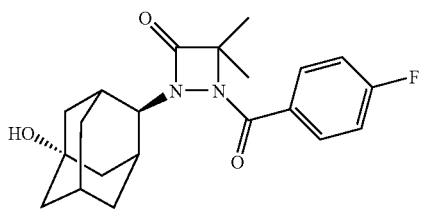

¹H-NMR (270 MHz, CDCl₃) δ; 1.40 (s, 6H), 1.56 (d, J=12.7 Hz, 2H), 1.79-1.85 (m, 6H), 1.98 (d, J=13.2 Hz, 2H), 2.20 (s, 1H), 2.60 (s, 2H), 3.21 (br, 1H), 7.09-7.18 (m, 2H), 7.76-7.82 (m, 2H).

IR (ATR); 3440, 2925, 1767, 1663, 1229, 1117, 860 cm⁻¹.
EI-MS m/z; 372 (M⁺).

Example 156

Preparation of 1-[(4-fluorophenyl)carbonyl]-2-(5-fluoroadamantan-2-yl)-4,4-dimethyl-1,2-diazetidin-3-one

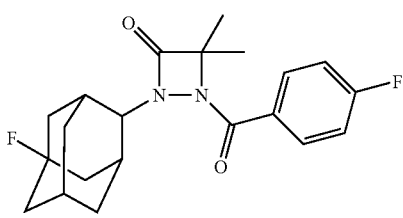

Under an argon atmosphere, a solution of trans-1-[(4-fluorophenyl)carbonyl]-2-(5-hydroxyadamantan-2-yl)-4,4-dimethyl-1,2-diazetidin-3-one (4.00 mg, 0.0100 mmol) prepared in Example 155 in dichloromethane (1 mL) was added with (diethylamino)sulfur trifluoride (24.2 mg, 0.150 mmol) at 0° C., and the resultant was stirred at the same temperature for 1 hour. The reaction solution was added with water and extracted with chloroform. The organic layer was dried over anhydrous sodium sulfate, concentrated in vacuo, and the title compound (4.20 mg, quant.) was obtained as a colorless oil.

¹H-NMR (400 MHz, CDCl₃) δ; 1.41 (s, 6H), 1.72 (s, 4H), 1.84-1.92 (m, 4H), 2.20-2.26 (m, 3H), 2.95-3.00 (m, 2H), 4.18 (s, 1H), 7.17 (t, J=8.8 Hz, 2H), 7.80 (dd, J=5.4, 8.8 Hz, 2H).

IR (ATR); 2931, 1772, 1677, 1602, 1507, 1308, 1297, 1230, 779 cm⁻¹.

EI-MS m/z; 374 (M⁺).

Example 157

Preparation of 1-[(3-fluoro-2-methylphenyl)carbonyl]-4,4-dimethyl-2-(adamantan-2-yl)-1,2-diazetidin-3-one

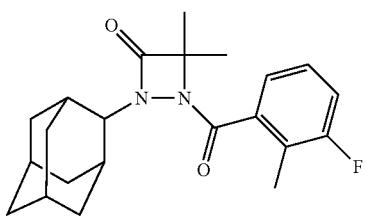

A solution of 2-(adamantan-2-yl)-4,4-dimethyl-1,2-diazetidin-3-one (50.0 mg, 0.213 mmol) prepared in Process 3 of Example 12 in dichloromethane was added with 3-fluoro-2-methylbenzoic acid (32.8 mg, 0.213 mmol), diisopropylethylamine (82.6 mg, 0.639 mmol) and PyBOP (133 mg, 0.256 mmol) at room temperature, and the resultant was stirred at the same temperature for 18 hours. The reaction solution was added with water and extracted with chloroform. The organic layer was dried over anhydrous sodium sulfate, concentrated in vacuo, the obtained residue was purified using Preparative Thin-Layer chromatography (hexane:ethyl acetate=2:1), and the title compound (6.90 mg, 8.70%) was obtained as a white crystalline solid.

¹H-NMR (400 MHz, CDCl₃) δ; 1.35 (s, 6H), 1.71-1.92 (m, 10H), 2.06 (d, J=13.2 Hz, 2H), 2.38-2.44 (m, 5H), 4.38 (s, 1H), 7.16-7.25 (m, 3H), 7.33 (dd, J=7.1, 1.5 Hz, 1H).

IR (ATR); 2915, 1771, 1671, 1317, 760 cm⁻¹.

FAB-MS m/z; 370 (M⁺).

Example 158

Preparation of 1-[(4-fluoro-2-methylphenyl)carbonyl]-4,4-dimethyl-2-(adamantan-2-yl)-1,2-diazetidin-3-one 4-Fluoro-2-methylbenzoic acid was used in place of 3-fluoro-2-methylbenzoic acid for a similar reaction and treatment as Example 157, and the title compound was obtained as a white crystalline powder.

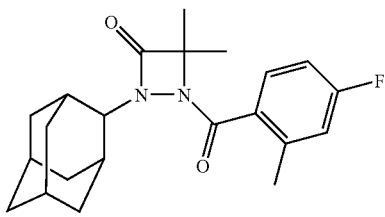

¹H-NMR (400 MHz, CDCl₃) δ; 1.35 (s, 6H), 1.71-1.91 (m, 10H), 2.05-2.08 (m, 2H), 2.43 (s, 2H), 2.49 (s, 3H), 4.36 (s, 1H), 6.93 (dt, J=8.6, 2.4 Hz, 1H), 7.00 (dd, J=9.5, 2.4 Hz, 1H), 7.55-7.58 (m, 1H).
IR (ATR); 2918, 1772, 1677, 1312, 1238, 964, 772 cm⁻¹.

Example 159

Preparation of 1-[(2,3-dimethylphenyl)carbonyl]-4,4-dimethyl-2-(adamantan-2-yl)-1,2-diazetidin-3-one 2,3-Dimethylbenzoic acid was used in place of 3-fluoro-2-methylbenzoic acid for a similar reaction and treatment as Example 157, and the title compound was obtained as a white crystalline powder.

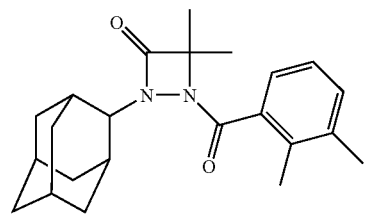

¹H-NMR (400 MHz, CDCl₃) δ; 1.33 (s, 6H), 1.68-1.91 (m, 10H), 2.07-2.10 (m, 2H), 2.32 (s, 3H), 2.36 (s, 3H), 2.46 (s, 2H), 4.40 (s, 1H), 7.13 (t, J=7.6 Hz, 1H), 7.29 (d, J=7.6 Hz, 1H), 7.36 (d, J=7.6 Hz, 1H).
IR (ATR); 2912, 1777, 1666, 1317, 960, 769 cm⁻¹.
FAB-MS m/z; 366 (M⁺).

Example 160

Preparation of 1-[(2,4-dimethylphenyl)carbonyl]-4,4-dimethyl-2-(adamantan-2-yl)-1,2-diazetidin-3-one 2,4-Dimethylbenzoic acid was used in place of 3-fluoro-2-methylbenzoic acid for a similar reaction and treatment as Example 157, and the title compound was obtained as a white crystalline powder.

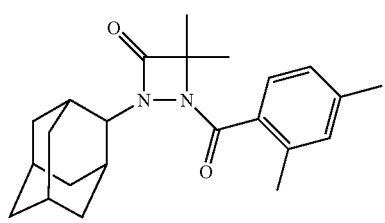

¹H-NMR (400 MHz, CDCl₃) δ; 1.33 (s, 6H), 1.67-1.92 (m, 10H), 2.06-2.09 (m, 2H), 2.36 (s, 3H), 2.45 (m, 5H), 4.36 (s, 1H), 7.03 (d, J=7.8 Hz, 1H), 7.09 (s, 1H), 7.45 (d, J=7.8 Hz, 1H).

IR (ATR); 2919, 1770, 1670, 1396, 1310 cm⁻¹.
FAB-MS m/z; 366 (M⁺).

Example 161

Preparation of 1-[(2,5-dimethylphenyl)carbonyl]-4,4-dimethyl-2-(adamantan-2-yl)-1,2-diazetidin-3-one 2,5-Dimethylbenzoic acid was used in place of 3-fluoro-2-methylbenzoic acid for a similar reaction and treatment as Example 157, and the title compound was obtained as a white crystalline powder.

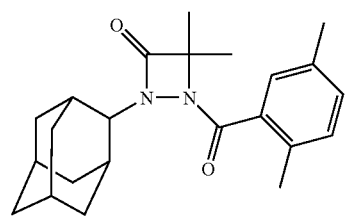

¹H-NMR (400 MHz, CDCl₃) δ; 1.33 (s, 6H), 1.68-1.93 (m, 10H), 2.08-2.11 (m, 2H), 2.35 (s, 3H), 2.43 (s, 3H), 2.46 (s, 2H), 4.38 (s, 1H), 7.16 (d, J=7.8 Hz, 1H), 7.21 (d, J=8.1 Hz, 1H), 7.33 (s, 1H).
IR (ATR); 2922, 1771, 1318, 783 cm⁻¹.
FAB-MS m/z; 366 (M⁺).

Example 162

Preparation of 1-[(2-bromo-5-fluorophenyl)carbonyl]-4,4-dimethyl-2-(adamantan-2-yl)-1,2-diazetidin-3-one 2-Bromo-5-fluorobenzoic acid was used in place of 3-fluoro-2-methylbenzoic acid for a similar reaction and treatment as Example 157, and the title compound was obtained as a white crystalline powder.

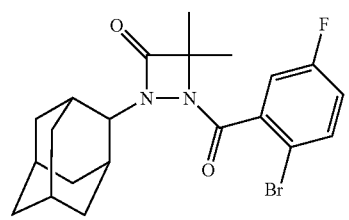

¹H-NMR (400 MHz, CDCl₃) δ; 1.42 (s, 6H), 1.72-1.92 (m, 10H), 2.04-2.08 (m, 2H), 2.44 (s, 2H), 4.43 (s, 1H), 7.08-7.13 (m, 1H), 7.24-7.27 (m, 1H), 7.65-7.68 (m, 1H).
IR (ATR); 2916, 1773, 1655, 1261, 828 cm⁻¹.
FAB-MS m/z; 434 (M⁺).

Example 163

Preparation of 1-[(2-bromo-5-chlorophenyl)carbonyl]-4,4-dimethyl-2-(adamantan-2-yl)-1,2-diazetidin-3-one 2-Bromo-5-chlorobenzoic acid was used in place of 3-fluoro-2-methylbenzoic acid for a similar reaction and

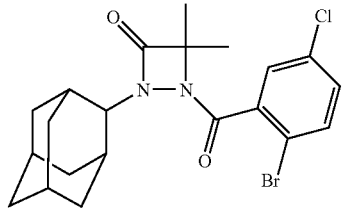

¹H-NMR (400 MHz, CDCl₃) δ; 1.42 (s, 6H), 1.72-1.90 (m, 10H), 2.05-2.08 (m, 2H), 2.44 (s, 2H), 4.43 (s, 1H), 7.34 (dd, J=8.6, 2.7 Hz, 1H), 7.48 (d, J=2.7 Hz, 1H), 7.63 (d, J=8.6 Hz, 1H).

IR (ATR); 2908, 1772, 1660, 1101, 815 cm⁻¹.

FAB-MS m/z; 450 (M⁺).

Example 164

Preparation of 1-[(3-chloro-2-fluorophenyl)carbonyl]-4,4-dimethyl-2-(adamantan-2-yl)-1,2-diazetidin-3-one 3-Chloro-2-fluorobenzoic acid was used in place of 3-fluoro-2-methylbenzoic acid for a similar reaction and treatment as Example 157, and the title compound was obtained as a white crystalline powder.

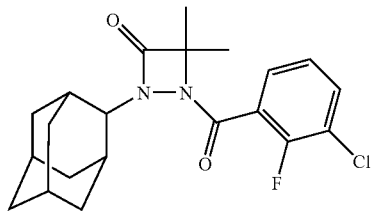

¹H-NMR (400 MHz, CDCl₃) δ; 1.40 (s, 6H), 1.70-1.91 (m, 10H), 2.05-2.08 (m, 2H), 2.43 (s, 2H), 4.36 (s, 1H), 7.19 (dt, J=7.8, 1.2 Hz, 1H), 7.47-7.51 (m, 1H), 7.57-7.60 (m, 1H).

IR (ATR); 2913, 1775, 1663, 1454, 1323, 749 cm⁻¹.

FAB-MS m/z; 391 (M⁺).

Example 165

Preparation of 4,4-dimethyl-1-{[2-(methylthio)phenyl]carbonyl}-2-(adamantan-2-yl)-1,2-diazetidin-3-one 2-(Methylthio)benzoic acid was used in place of 3-fluoro-2-methylbenzoic acid for a similar reaction and treatment as Example 157, and the title compound was obtained as a white crystalline powder.

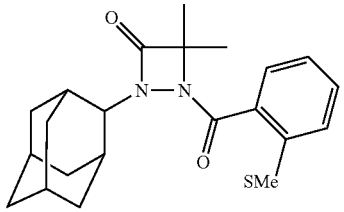

¹H-NMR (400 MHz, CDCl₃) δ; 1.38 (s, 6H), 1.69-1.91 (m, 10H), 2.07-2.09 (m, 2H), 2.42-2.49 (m, 5H), 4.42 (s, 1H), 7.14-7.18 (m, 1H), 7.32 (d, J=8.1 Hz, 1H), 7.59 (dd, J=7.6, 1.2 Hz, 1H), 7.45-7.49 (m, 1H).

IR (ATR); 2912, 1762, 1671, 1312, 1258, 945, 796, 770 cm⁻¹.

FAB-MS m/z; 384 (M⁺).

Example 166

Preparation of 1-[(5-chloro-2-fluorophenyl)carbonyl]-4,4-dimethyl-2-(adamantan-2-yl)-1,2-diazetidin-3-one 5-Chloro-2-fluorobenzoic acid was used in place of 3-fluoro-2-methylbenzoic acid for a similar reaction and treatment as Example 157, and the title compound was obtained as a white crystalline powder.

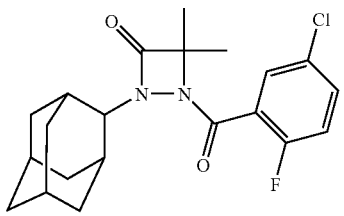

¹H-NMR (400 MHz, CDCl₃) δ; 1.42 (s, 6H), 1.70-1.92 (m, 10H), 2.05-2.08 (m, 2H), 2.42 (s, 2H), 4.35 (s, 1H), 7.14 (t, J=9.0 Hz, 1H), 7.46-7.50 (m, 1H), 7.54-7.56 (m, 1H).

IR (ATR); 2917, 1774, 1686, 1482, 1397, 1307, 1260, 962, 843, 743 cm⁻¹.

FAB-MS m/z; 390 (M⁺).

Example 167

Preparation of 4,4-dimethyl-1-[(2-methylpyridin-3-yl)carbonyl]-2-(adamantan-2-yl)-1,2-diazetidin-3-one 2-Methylnicotinic acid was used in place of 3-fluoro-2-methylbenzoic acid for a similar reaction and treatment as Example 157, and the title compound was obtained as a white crystalline powder.

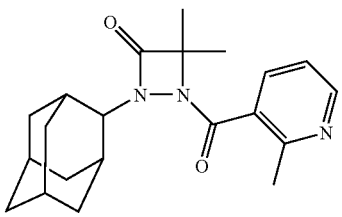

$^1$H-NMR (400 MHz, CDCl$_3$) δ; 1.34 (s, 6H), 1.71-1.92 (m, 10H), 2.05-2.09 (m, 2H), 2.44-2.50 (m, 5H), 4.39 (s, 1H), 7.19 (t, J=7.8 Hz, 1H), 7.42 (d, J=7.8 Hz, 1H), 7.51 (d, J=7.8 Hz, 1H).
IR (ATR); 2913, 1770, 1668, 1316, 736 cm$^{-1}$.

Example 168

Preparation of 2-cyclooctyl-4,4-dimethyl-1-{[2-(methylthio)phenyl]carbonyl}-1,2-diazetidin-3-one 2-Cyclooctyl-4,4-dimethyl-1,2-diazetidin-3-one prepared in Process 5 of Example 73 and 2-methylthiobenzoic acid were used for a similar reaction and treatment as Example 157, and the title compound was obtained as a colorless oil.

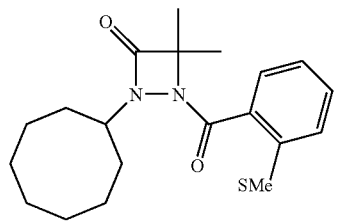

$^1$H-NMR (270 MHz, CDCl$_3$) δ; 1.33 (s, 6H), 1.43-1.67 (m, 8H), 1.70-1.86 (m, 2H), 1.98-2.23 (m, 4H), 2.46 (s, 3H), 4.03 (br, 1H), 7.14-7.20 (m, 1H), 7.32 (d, J=11.2 Hz, 1H), 7.43-7.54 (m, 2H).
IR (ATR); 2923, 1777, 1672, 1435, 1311, 1252, 751 cm$^{-1}$.

Example 169

Preparation of 1-[(4-methylphenyl)sulfonyl]-2-(adamantan-2-yl)-1,2-diazetidin-3-one

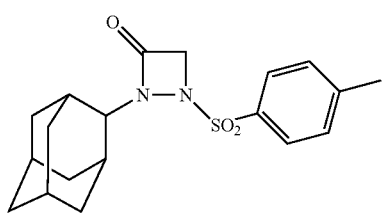

A solution of 2-(adamantan-2-yl)-1,2-diazetidin-3-one (5.00 mg, 0.0240 mmol) prepared in Process 5 of Example 1 in dichloromethane (1 mL) was added with diisopropylethylamine (9.30 mg, 0.0720 mmol) and p-toluenesulfonyl chloride (6.80 mg, 0.0360 mmol) at room temperature, and the resultant was stirred at the same temperature for 12 hours. The reaction solution was added with water and extracted with chloroform. The organic layer was dried over anhydrous sodium sulfate, concentrated in vacuo, the obtained residue was purified using Preparative Thin-Layer chromatography (hexane:ethyl acetate=2:1), and the title compound (7.40 mg, 83.3%) was obtained as a white crystalline powder.
$^1$H-NMR (400 MHz, CDCl$_3$) δ; 1.62-2.03 (m, 12H), 2.52 (s, 3H), 2.62 (s, 2H), 3.96 (s, 1H), 4.27 (s, 2H), 7.45 (d, J=12.8 Hz, 2H), 7.79 (d, J=12.8 Hz, 2H).
IR (ATR); 2903, 1782, 1352, 1164, 604 cm$^{-1}$.
EI-MS m/z; 360 (M$^+$).

Example 170

Preparation of 1-(phenylsulfonyl)-2-(adamantan-2-yl)-1,2-diazetidin-3-one

Benzenesulfonyl chloride was used in place of p-toluenesulfonyl chloride for a similar reaction and treatment as Example 169, and the title compound was obtained as a white crystalline powder.

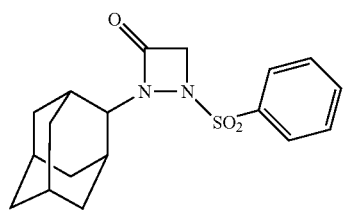

$^1$H-NMR (400 MHz, CDCl$_3$) δ; 1.53-2.00 (m, 12H), 2.57 (s, 2H), 3.93 (s, 1H), 4.25 (br, 2H), 7.65 (t, J=7.6 Hz, 2H), 7.76 (t, J=7.6 Hz, 1H), 7.89 (d, J=7.6 Hz, 2H).
IR (ATR); 2010, 1780, 1349, 1325, 1173, 1087, 760, 735, 691 cm$^{-1}$.

Example 171

Preparation of 1-[(4-chlorophenyl)sulfonyl]-2-(adamantan-2-yl)-1,2-diazetidin-3-one 4-Chlorobenzene sulfonyl chloride was used in place of p-toluenesulfonyl chloride for a similar reaction and treatment as Example 169, and the title compound was obtained as a white crystalline powder.

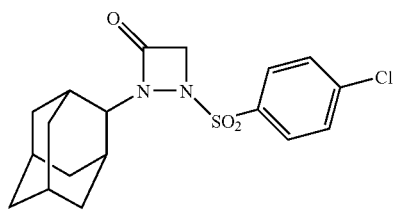

$^1$H-NMR (400 MHz, CDCl$_3$) δ; 1.52-2.00 (m, 12H), 2.57 (s, 2H), 3.91 (s, 1H), 4.25 (br, 2H), 7.62 (d, J=8.3 Hz, 2H), 7.81 (d, J=8.3 Hz, 2H).
IR (ATR); 2908, 1778, 1362, 1179, 1165, 1088, 759 cm$^{-1}$.

Example 172

Preparation of 1-[(4-methoxyphenyl)sulfonyl]-2-(adamantan-2-yl)-1,2-diazetidin-3-one 4-Methoxybenzene sulfonyl chloride was used in place of p-toluenesulfonyl chloride for a similar reaction and treatment as Example 169, and the title compound was obtained as a white crystalline powder.

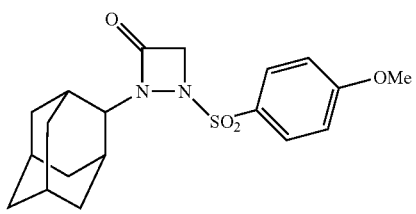

¹H-NMR (400 MHz, CDCl₃) δ; 1.52-2.00 (m, 12H), 2.59 (s, 2H), 3.91 (s, 4H), 4.21 (br, 2H), 7.07 (d, J=8.9 Hz, 2H), 7.80 (d, J=8.9 Hz, 2H).
IR (ATR); 2905, 1777, 1596, 1356, 1266, 1161, 1089, 1019, 697 cm⁻¹.

Example 173

Preparation of 1-[(4-chlorophenyl)sulfonyl]-4,4-dimethyl-2-(adamantan-2-yl)-1,2-diazetidin-3-one 2-(Adamantan-2-yl)-4,4-dimethyl-1,2-diazetidin-3-one prepared in Process 5 of Example 12 and 4-chlorobenzene sulfonyl chloride were used for a similar reaction and treatment as Example 169, and the title compound was obtained as a colorless crystalline powder.

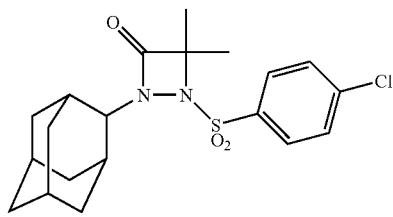

¹H-NMR (400 MHz, CDCl₃) δ; 1.39-1.42 (m, 2H), 1.57 (s, 3H), 1.59-1.84 (m, 8H), 1.65 (s, 3H), 2.08-2.11 (m, 4H), 3.53 (s, 1H), 7.54-7.56 (m, 2H), 7.87-7.90 (m, 2H).

Example 174

Preparation of 4,4-dimethyl-1-(phenylsulfonyl)-2-(adamantan-2-yl)-1,2-diazetidin-3-one 2-(Adamantan-2-yl)-4,4-dimethyl-1,2-diazetidin-3-one and benzene sulfonyl chloride were used for a similar reaction and treatment as Example 169, and the title compound was obtained as a colorless crystalline powder.

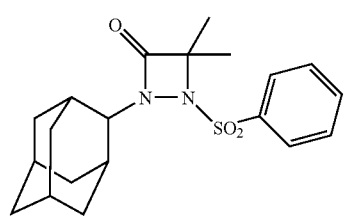

¹H-NMR (400 MHz, CDCl₃) δ; 1.28-1.37 (m, 2H), 1.53-1.85 (m, 14H), 2.03-2.09 (m, 4H), 3.51 (s, 1H), 7.54-7.67 (m, 3H), 7.94 (d, J=7.6 Hz, 2H).

Example 175

Preparation of 4,4-dimethyl-1-[(2-methylphenyl)sulfonyl]-2-(adamantan-2-yl)-1,2-diazetidin-3-one 2-(Adamantan-2-yl)-4,4-dimethyl-1,2-diazetidin-3-one and o-toluenesulfonyl chloride were used for a similar reaction and treatment as Example 169, and the title compound was obtained as a white crystalline powder.

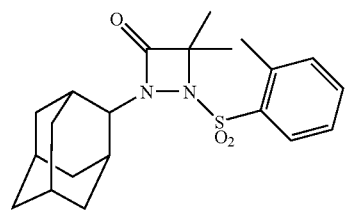

¹H-NMR (400 MHz, CDCl₃) δ; 1.07 (d, J=12.0 Hz, 2H), 1.48-1.79 (m, 16H), 2.03-2.07 (m, 2H), 2.73 (s, 3H), 3.22 (s, 1H), 7.34-7.39 (m, 2H), 7.54 (t, J=7.8 Hz, 1H), 8.05 (d, J=7.8 Hz, 1H).
IR (ATR); 2908, 1770, 1333, 1160, 761 cm⁻¹.
FAB-MS m/z; 388 (M⁺).

Example 176

Preparation of 1-[(2-chlorophenyl)sulfonyl]-4,4-dimethyl-2-(adamantan-2-yl)-1,2-diazetidin-3-one 2-(Adamantan-2-yl)-4,4-dimethyl-1,2-diazetidin-3-one and 2-chlorobenzene sulfonyl chloride were used for a similar reaction and treatment as Example 169, and the title compound was obtained as a white crystalline powder.

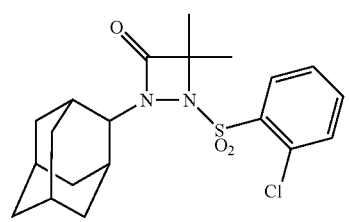

¹H-NMR (400 MHz, CDCl₃) δ; 1.09 (d, J=11.9 Hz, 2H), 1.53-1.69 (m, 7H), 1.80-1.86 (m, 9H), 2.08 (d, J=11.9 Hz, 2H), 3.24 (s, 1H), 7.44-7.49 (m, 1H), 7.58-7.61 (m, 2H), 8.13-8.15 (m, 1H).
IR (ATR); 2905, 1774, 1342, 1158, 1045, 769 cm⁻¹.
FAB-MS m/z; 408 (M⁺).

Example 177

Preparation of 1-(benzylsulfonyl)-2-(adamantan-2-yl)-1,2-diazetidin-3-one

Benzylsulfonyl chloride was used in place of p-toluenesulfonyl chloride for a similar reaction and treatment as Example 169, and the title compound was obtained as a white crystalline powder.

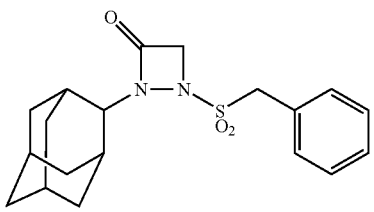

¹H-NMR (400 MHz, CDCl₃) δ; 1.52-2.00 (m, 12H), 2.46 (s, 2H), 3.64 (s, 1H), 4.33 (s, 2H), 4.43 (s, 2H), 7.41-7.43 (m, 5H).
IR (ATR); 2901, 1773, 1349, 1158, 773, 695 cm⁻¹.

Example 178

Preparation of 1-[(3-chlorophenyl)sulfonyl]-4,4-dimethyl-2-(adamantan-2-yl)-1,2-diazetidin-3-one 2-(Adamantan-2-yl)-4,4-dimethyl-1,2-diazetidin-3-one prepared in Process 5 of Example 12 and 3-chlorobenzen sulfonyl chloride were used for a similar reaction and treatment as Example 169, and the title compound was obtained as a white crystalline powder.

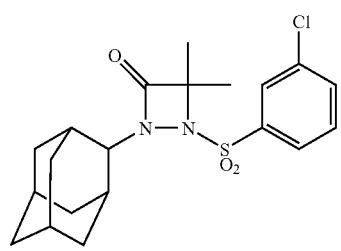

¹H-NMR (400 MHz, CDCl₃) δ; 1.39 (d, J=12.9 Hz, 2H), 1.56-1.59 (m, 3H), 1.78-1.84 (m, 11H), 2.08-2.12 (m, 4H), 3.51 (s, 1H), 7.52 (t, J=7.8 Hz, 1H), 7.63-7.65 (m, 1H), 7.83-7.84 (m, 1H), 7.93 (t, J=1.7 Hz, 1H).
IR (ATR); 2910, 1773, 1352, 1164, 792 cm⁻¹.
FAB-MS m/z; 408 (M⁺).

Example 179

Preparation of 1-[(2-fluorophenyl)sulfonyl]-4,4-dimethyl-2-(adamantan-2-yl)-1,2-diazetidin-3-one 2-(Adamantan-2-yl)-4,4-dimethyl-1,2-diazetidin-3-one and 2-fluorobenzenesulfonyl chloride were used for a similar reaction and treatment as Example 169, and the title compound was obtained as a white crystalline powder.

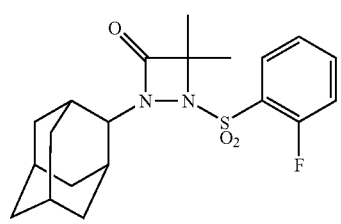

¹H-NMR (400 MHz, CDCl₃) δ; 1.25 (d, J=7.1 Hz, 2H), 1.56 (d, J=11.7 Hz, 2H), 1.63-1.78 (m, 11H), 1.83 (s, 1H), 2.08-2.13 (m, 4H), 3.51 (s, 1H), 7.23-7.28 (m, 1H), 7.31-7.42 (m, 1H), 7.65-7.71 (m, 1H), 7.92-8.00 (m, 1H).
IR (ATR); 2909, 1767, 1596, 1476, 1167, 1155, 767, 701 cm⁻¹.
FAB-MS m/z; 392 (M⁺).

Example 180

Preparation of 1-(2-nitrophenyl)-2-(adamantan-2-yl)-1,2-diazetidin-3-one

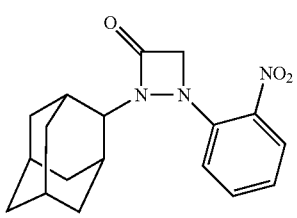

Process 1: Preparation of 1-(adamantan-2-ylidene)-2-(2-nitrophenyl)hydrazine

2-Nitrophenylhydrazine was used in place of benzylcarbazate for a similar reaction and treatment as Process 1 of Example 1, and 1-(adamantan-2-ylidene)-2-(2-nitrophenyl)hydrazine was obtained as a brown crystalline powder.
¹H-NMR (400 MHz, CDCl₃) δ; 1.71-2.10 (m, 12H), 2.75 (s, 1H), 3.21 (s, 1H), 6.73 (t, J=8.1 Hz, 1H), 7.48 (t, J=8.1 Hz, 1H), 7.89 (d, J=8.1 Hz, 1H), 8.13 (d, J=8.1 Hz, 1H), 10.83 (s, 1H).

Process 2: Preparation of 1-(adamantan-2-yl)-2-(2-nitrophenyl)hydrazine 1-(Adamantan-2-ylidene)-2-(2-nitrophenyl)hydrazine was used for a similar reaction and treatment as Process 2 of Example 1, and 1-(adamantan-2-yl)-2-(2-nitrophenyl)hydrazine was obtained as a yellow oil.
¹H-NMR (400 MHz, CDCl₃) δ; 1.39-2.12 (m, 14H), 3.07 (s, 1H), 3.87 (s, 1H), 6.63 (t, J=8.1 Hz, 1H), 7.43 (t, J=8.1 Hz, 1H), 7.77 (d, J=8.1 Hz, 1H), 8.09 (d, J=8.1 Hz, 1H), 8.80 (s, 1H).

Process 3: Preparation of 1-(2-bromoacetyl)-1-(adamantan-2-yl)-2-(2-nitrophenyl)hydrazine 1-(Adamantan-2-yl)-2-(2-nitrophenyl)hydrazine and bromoacetyl bromide were used for a similar reaction and treatment as Process 3 of Example 1, and 1-(2-bromoacetyl)-1-(adamantan-2-yl)-2-(2-nitrophenyl)hydrazine was obtained as a yellow oil.
¹H-NMR (400 MHz, CDCl₃) δ; 1.56-1.90 (m, 13H), 2.54 (s, 1H), 3.71 (d, J=11.0 Hz, 1H), 3.90 (d, J=11.0 Hz, 1H), 4.51 (s, 1H), 6.89-6.94 (m, 2H), 7.55 (t, J=8.1 Hz, 1H), 8.24 (d, J=8.1 Hz, 1H), 9.59 (s, 1H).

Process 4: Preparation of 1-(2-nitrophenyl)-2-(adamantan-2-yl)-1,2-diazetidin-3-one 1-(2-Bromoacetyl)-1-(adamantan-2-yl)-2-(2-nitrophenyl)hydrazine was used for a similar reaction and treatment as Process 4 of Example 1, and the title compound was obtained as a pale yellow oil.

¹H-NMR (400 MHz, CDCl₃) δ; 1.57-2.52 (m, 14H), 3.71 (s, 1H), 4.12 (br, 1H), 5.10 (br, 1H), 7.31 (t, J=8.1 Hz, 1H), 7.95 (d, J=8.1 Hz, 1H), 7.58-7.67 (m, 2H).
IR (ATR); 2907, 2360, 2342, 1761, 1603, 1513, 1344, 752 cm⁻¹.
EI-MS m/z; 327 (M⁺).

Example 181

Preparation of 4,4-dimethyl-1-phenyl-2-(adamantan-2-yl)-1,2-diazetidin-3-one

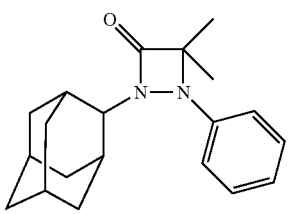

Under an argon atmosphere, a solution of 2-(adamantan-2-yl)-4,4-dimethyl-1,2-diazetidin-3-one (50.0 mg, 0.213 mmol) prepared in Process 3 of Example 12 in toluene (1 mL) was added with palladium acetate (II) (1.00 mg, 0.00445 mmol), tri-t-butylphosphine (0.700 mg, 0.00346 mmol), sodium t-butoxide (30.8 mg, 0.320 mmol) and bromobenzene (67.0 mg, 0.427 mmol) sequentially at room temperature, and the resultant was stirred under microwave irradiation at 110° C. for 1 hour. The reaction solution was added with water and extracted with ethyl acetate. The organic layer was dried over anhydrous sodium sulfate, concentrated in vacuo, the obtained residue was purified using Preparative Thin-Layer chromatography (hexane:ethyl acetate=5:1), and the title compound (42.0 mg, 64.4%) was obtained as a pale yellow amorphous solid.
¹H-NMR (400 MHz, CDCl₃) δ; 0.80-1.95 (m, 18H), 2.24 (d, J=12.2 Hz, 2H), 3.77 (s, 1H), 7.00 (d, J=7.6 Hz, 2H), 7.12 (t, J=7.6 Hz, 1H), 7.33 (d, J=7.6 Hz, 2H).
IR (ATR); 2923, 1754, 1323, 775 cm⁻¹.
EI-MS m/z; 310 (M⁺).

Example 182

Preparation of 4,4-dimethyl-1-(4-nitrophenyl)-2-(adamantan-2-yl)-1,2-diazetidin-3-one

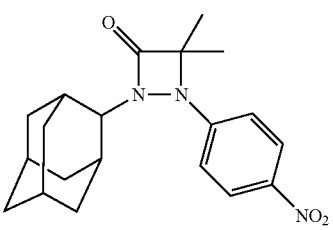

Process 1: Preparation of 1-(adamantan-2-ylidene)-2-(4-nitrophenyl)hydrazine

4-Nitrophenylhydrazine was used in place of benzylcarbazate for a similar reaction and treatment as Process 1 of Example 1, and 1-(adamantan-2-ylidene)-2-(2-nitrophenyl)hydrazine was obtained as a brown crystalline powder.
¹H-NMR (400 MHz, CDCl₃) δ; 1.84-2.17 (m, 12H), 2.70 (s, 1H), 3.09 (s, 1H), 7.02 (d, J=9.0 Hz, 2H), 7.56 (s, 1H), 8.13 (d, J=9.1 Hz, 2H).

Process 2: Preparation of 1-(adamantan-2-yl)-2-(4-nitrophenyl)hydrazine 1-(Adamantan-2-ylidene)-2-(4-nitrophenyl)hydrazine was used for a similar reaction and treatment as Process 2 of Example 1, and 1-(adamantan-2-yl)-2-(4-nitrophenyl)hydrazine was obtained as a yellow oil.
¹H-NMR (400 MHz, CDCl₃) δ; 1.51-2.27 (m, 14H), 2.98 (s, 1H), 3.75 (s, 1H), 5.64 (s, 1H), 6.87 (d, J=9.0 Hz, 2H), 8.08 (d, J=9.0 Hz, 2H).

Process 3: Preparation of 2-bromo-N-(adamantan-2-yl)-2-methyl-N'-(4-nitrophenyl)propane hydrazide 1-(Adamantan-2-yl)-2-(4-nitrophenyl)hydrazine and 2-bromoisobutyrylbromide were used for a similar reaction and treatment as Process 3 of Example 1, and 2-bromo-N-(adamantan-2-yl)-2-methyl-N'-(4-nitrophenyl)propane hydrazide was obtained as a yellow oil.
¹H-NMR (400 MHz, CDCl₃) δ; 1.46-1.90 (m, 13H), 2.46 (s, 1H), 4.51 (s, 1H), 6.60 (s, 1H), 6.68 (d, J=9.0 Hz, 2H), 8.22 (d, J=9.0 Hz, 2H).

Process 4: Preparation of 4,4-dimethyl-1-(4-nitrophenyl)-2-(adamantan-2-yl)-1,2-diazetidin-3-one 2-Bromo-N-(adamantan-2-yl)-2-methyl-N'-(4-nitrophenyl)propane hydrazide was used for a similar reaction and treatment as Process 4 of Example 1, and the title compound was obtained as a pale yellow oil.
¹H-NMR (400 MHz, CDCl₃) δ; 1.35 (s, 6H), 1.64-1.89 (m, 10H), 2.15-2.18 (m, 2H), 2.35 (s, 1H), 3.81 (s, 1H), 7.03 (d, J=8.3 Hz, 2H), 8.22 (d, J=8.3 Hz, 2H).
IR (ATR); 2913, 1764, 1591, 1514, 1341, 1110, 754 cm⁻¹.
EI-MS m/z; 355 (M⁺).

Example 183

Preparation of 1-(4-aminophenyl)-4,4-dimethyl-2-(adamantan-2-yl)-1,2-diazetidin-3-one

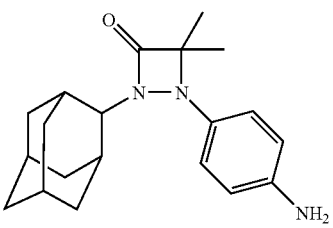

A solution of 4,4-dimethyl-1-(4-nitrophenyl)-2-(adamantan-2-yl)-1,2-diazetidin-3-one (15.3 mg, 0.0430 mmol) prepared in Example 182 in ethanol (2 mL) was added with 10% palladium carbon (catalyst amount), and under a hydrogen atmosphere the resultant was stirred at room temperature for 20 minutes. The reaction solution was filtered using celite, concentrated in vacuo, the obtained residue was purified using Preparative Thin-Layer chromatography (hexane:ethyl acetate=1:1), and the title compound (14.2 m, quant.) was obtained as a colorless oil.

$^1$H-NMR (400 MHz, CDCl$_3$) δ; 0.87 (br, 3H), 1.43-1.89 (m, 14H), 2.17-2.28 (m, 2H), 2.61 (br, 1H), 3.69 (s, 1H), 6.65 (d, J=8.8 Hz, 2H), 6.87 (d, J=8.8 Hz, 2H).

IR (ATR); 3342, 2908, 2853, 2359, 1744, 1655, 1545, 1508, 1221, 750 cm$^{-1}$.

EI-MS m/z; 325 (M$^+$).

Example 184

Preparation of N-{4-[4,4-dimethyl-3-oxo-2-(adamantan-2-yl)-1,2-diazetidin-1-yl]phenyl}methanesulfonamide

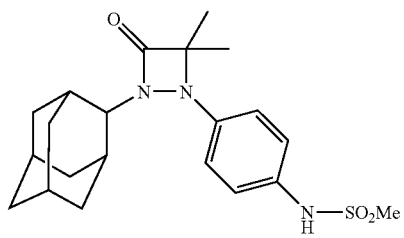

Under an argon atmosphere, a solution of 1-(4-aminophenyl)-4,4-dimethyl-2-(adamantan-2-yl)-1,2-diazetidin-3-one (30.0 mg, 0.0920 mmol) prepared in Example 183 in dichloromethane (1 mL) was added with triethylamine (18.6 mg, 0.184 mmol) and methanesulfonyl chloride (15.8 mg, 0.138 mmol) at room temperature, and the resultant was stirred at the same temperature for 3 hours. The reaction solution was added with water and extracted with chloroform. The organic layer was dried over anhydrous sodium sulfate, concentrated in vacuo, the obtained residue was purified using Preparative Thin-Layer chromatography (hexane:ethyl acetate=1:1), and the title compound (6.80 mg, 18.3%) was obtained as a brown amorphous solid.

$^1$H-NMR (400 MHz, CDCl$_3$) δ; 1.33 (s, 6H), 1.52-1.84 (m, 12H), 2.19-2.23 (m, 2H), 3.02 (s, 3H), 3.73 (s, 1H), 6.44 (s, 1H), 7.00 (d, J=8.8 Hz, 2H), 7.20 (d, J=8.8 Hz, 2H).

IR (ATR); 2912, 2360, 2342, 1740, 1505, 1328, 1155, 968, 754 cm$^{-1}$.

EI-MS m/z; 403 (M$^+$).

Example 185

Preparation of 1-[(N,N-bismethanesulfonyl)-4-aminophenyl]-4,4-dimethyl-2-(adamantan-2-yl)-1,2-diazetidin-3-one The same reaction and treatment were conducted as Example 184 except that an excessive amount of methane sulfonyl chloride was used, and the title compound was obtained as a brown amorphous solid.

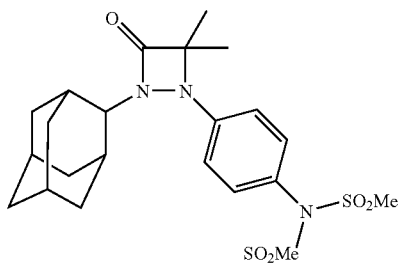

$^1$H-NMR (400 MHz, CDCl$_3$) δ; 1.26 (s, 6H), 1.54-1.84 (m, 11H), 2.19-2.36 (m, 3H), 3.41 (s, 6H), 3.74 (s, 1H), 7.02 (d, J=8.5 Hz, 2H), 7.30 (d, J=8.5 Hz, 2H).

IR (ATR); 2912, 1757, 1500, 1368, 1353, 1161, 977, 904, 758 cm$^{-1}$.

EI-MS m/z; 481 (M$^+$).

Example 186

Preparation of N-{4-[4,4-dimethyl-3-oxo-2-(adamantan-2-yl)-1,2-diazetidin-1-yl]phenyl}benzamide Benzoyl chloride was used in place of methanesulfonyl chloride for a similar reaction and treatment as Example 184, and the title compound was obtained as a yellow amorphous solid.

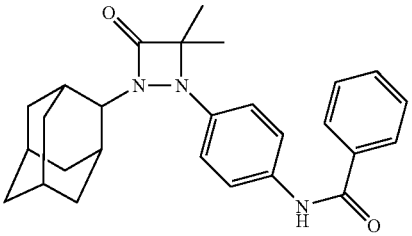

$^1$H-NMR (400 MHz, CDCl$_3$) δ; 1.23 (br, 6H), 1.62-2.25 (m, 14H), 3.76 (s, 1H), 7.03 (d, J=8.6 Hz, 2H), 7.45-7.57 (m, 3H), 7.62 (d, J=8.6 Hz, 2H), 7.87 (d, J=7.3 Hz, 2H), 7.95 (s, 1H).

IR (ATR); 3308, 2912, 2855, 1740, 1652, 1602, 1530, 1506, 1407, 1316, 846, 754, 706 cm$^{-1}$.

EI-MS m/z; 429 (M$^+$).

Example 187

Preparation of N-{4-[4,4-dimethyl-3-oxo-2-(adamantan-2-yl)-1,2-diazetidin-1-yl]phenyl}acetoamide Acetyl chloride was used in place of methanesulfonyl chloride for a similar reaction and treatment as Example 184, and the title compound was obtained as a yellow amorphous solid.

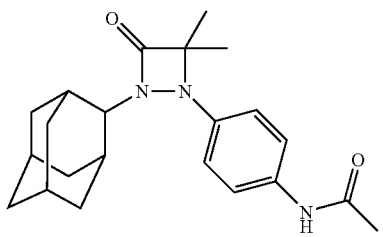

¹H-NMR (400 MHz, CDCl₃) δ; 1.31 (br, 6H), 1.51-2.08 (m, 14H), 2.18 (s, 3H), 3.73 (s, 1H), 6.97 (d, J=8.6 Hz, 2H), 7.43 (s, 1H), 7.47 (d, J=8.6 Hz, 2H).

IR (ATR); 3309, 2911, 2855, 1742, 1668, 1540, 1507, 1314, 848, 752 cm⁻¹.

EI-MS m/z; 367 (M⁺).

Example 188

Preparation of 4,4-dimethyl-1-(2-nitrophenyl)-2-(adamantan-2-yl)-1,2-diazetidin-3-one

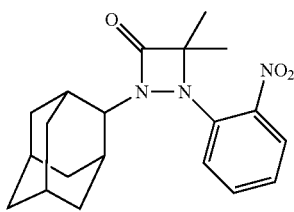

Process 1: Preparation of 2-bromo-N-(adamantan-2-yl)-2-methyl-N'-(2-nitrophenyl)propane hydrazide 1-(Adamantan-2-yl)-2-(2-nitrophenyl)hydrazine prepared in Processes 1 and 2 in Example 180 and 2-bromoisobutyryl bromide were used for a similar reaction and treatment as Process 3 of Example 1, and 2-bromo-N-(adamantan-2-yl)-2-methyl-N'-(2-nitrophenyl)propane hydrazide was obtained as a yellow oil.

¹H-NMR (400 MHz, CDCl₃) δ; 1.56-1.98 (m, 19H), 2.54 (s, 1H), 4.49 (s, 1H), 6.86-6.89 (m, 2H), 7.50 (t, J=8.1 Hz, 1H), 8.21 (d, J=8.1 Hz, 1H), 9.78 (s, 1H).

Process 2: Preparation of 4,4-dimethyl-1-(2-nitrophenyl)-2-(adamantan-2-yl)-1,2-diazetidin-3-one 2-Bromo-N-(adamantan-2-yl)-2-methyl-N'-(2-nitrophenyl)propane hydrazide was used for a similar reaction and treatment as Process 4 of Example 1, and the title compound was obtained as a pale yellow oil.

¹H-NMR (400 MHz, CDCl₃) δ; 1.09 (s, 3H), 1.50-1.55 (m, 2H), 1.56 (s, 3H), 1.60-1.88 (m, 9H), 2.03-2.06 (m, 1H), 2.17-2.23 (m, 1H), 2.64 (s, 1H), 3.60 (s, 1H), 7.29 (t, J=8.0 Hz, 1H), 7.48 (d, J=8.0 Hz, 1H), 7.62 (t, J=8.0 Hz, 1H), 7.81 (d, J=8.0 Hz, 1H).

IR (ATR); 2911, 2856, 1762, 1530, 1381, 1361, 1100, 764 cm⁻¹.

EI-MS m/z; 355 (M⁺).

Example 189

Preparation of 1-(2-chlorophenyl)-4,4-dimethyl-2-(adamantan-2-yl)-1,2-diazetidin-3-one 1-Bromo-2-chlorobenzene was used in place of bromobenzene for a similar reaction and treatment as Example 181, and the title compound was obtained as a pale yellow amorphous solid.

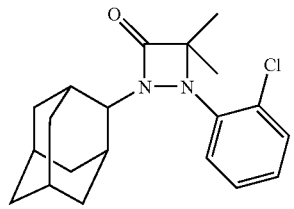

¹H-NMR (400 MHz, CDCl₃) δ; 0.99 (s, 3H), 1.55-1.93 (m, 11H), 1.79 (s, 3H), 2.20 (d, J=13.1 Hz, 1H), 2.32 (d, J=13.1 Hz, 1H), 2.69 (s, 1H), 3.71 (s, 1H), 7.06 (t, J=7.6 Hz, 1H), 7.20 (d, J=7.6 Hz, 1H), 7.27 (t, J=7.6 Hz, 1H), 7.38 (d, J=7.6 Hz, 1H).

IR (ATR); 2911, 1751, 1468, 1039, 767 cm⁻¹.

EI-MS m/z; 344 (M⁺).

Example 190

Preparation of 1-(3-chlorophenyl)-4,4-dimethyl-2-(adamantan-2-yl)-1,2-diazetidin-3-one 1-Bromo-3-chlorobenzene was used in place of bromobenzene for a similar reaction and treatment as Example 181, and the title compound was obtained as a pale yellow oil.

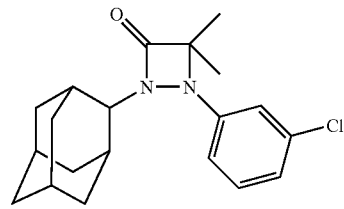

¹H-NMR (400 MHz, CDCl₃) δ; 1.05-2.55 (m, 20H), 3.74 (s, 1H), 6.89 (d, J=7.8 Hz, 1H), 7.00 (s, 1H), 7.10 (d, J=7.8 Hz, 1H), 7.26 (t, J=7.8 Hz, 1H).

IR (ATR); 2911, 1762, 1590, 1471, 1072, 752 cm⁻¹.

EI-MS m/z; 344 (M⁺).

Example 191

Preparation of 1-(4-chlorophenyl)-4,4-dimethyl-2-(adamantan-2-yl)-1,2-diazetidin-3-one 1-Bromo-4-chlorobenzene was used in place of bromobenzene for a similar reaction and treatment as Example 181, and the title compound was obtained as a pale yellow oil.

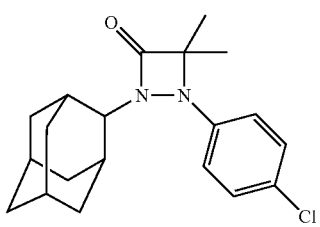

¹H-NMR (400 MHz, CDCl₃) δ; 0.80-2.52 (m, 20H), 3.73 (s, 1H), 6.95 (d, J=8.5 Hz, 2H), 7.30 (d, J=8.5 Hz, 2H).
IR (ATR); 2911, 1760, 1485, 1090, 842, 756 cm⁻¹.
EI-MS m/z; 344 (M⁺).

Example 192

Preparation of 4,4-dimethyl-1-(2-methylphenyl)-2-(adamantan-2-yl)-1,2-diazetidin-3-one 2-Bromotoluene was used in place of bromobenzene for a similar reaction and treatment as Example 181, and the title compound was obtained as a white crystalline powder.

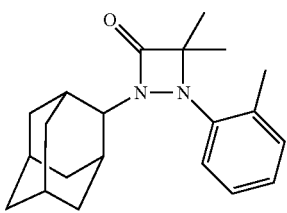

¹H-NMR (400 MHz, CDCl₃) δ; 0.89 (s, 3H), 1.47-1.90 (m, 11H), 1.70 (s, 3H), 2.18-2.32 (m, 2H), 2.28 (s, 3H), 2.72 (s, 1H), 3.69 (s, 1H), 7.05 (t, J=7.3 Hz, 1H), 7.13-7.22 (m, 3H).
IR (ATR); 2910, 1751, 1451, 1330, 773 cm⁻¹.
EI-MS m/z; 324 (M⁺).

Example 193

Preparation of 4,4-dimethyl-1-(3-methylphenyl)-2-(adamantan-2-yl)-1,2-diazetidin-3-one 3-Bromotoluene was used in place of bromobenzene for a similar reaction and treatment as Example 181, and the title compound was obtained as a colorless oil.

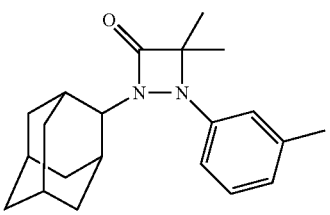

¹H-NMR (400 MHz, CDCl₃) δ; 0.85-2.51 (m, 20H), 2.35 (s, 3H), 3.75 (s, 1H), 6.80-6.82 (m, 2H), 6.93 (d, J=7.8 Hz, 1H), 7.21 (t, J=7.8 Hz, 1H).
IR (ATR); 2911, 1760, 1453, 1322, 787 cm⁻¹.
EI-MS m/z; 324 (M⁺).

Example 194

Preparation of 4,4-dimethyl-1-(4-methylphenyl)-2-(adamantan-2-yl)-1,2-diazetidin-3-one 4-Bromotoluene was used in place of bromobenzene for a similar reaction and treatment as Example 181, and the title compound was obtained as a colorless oil.

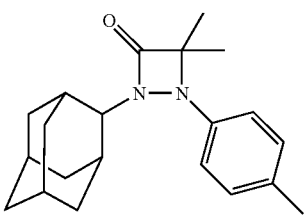

¹H-NMR (400 MHz, CDCl₃) δ; 0.85-2.75 (m, 20H), 2.32 (s, 3H), 3.74 (s, 1H), 6.91 (d, J=8.3 Hz, 1H), 7.13 (t, J=8.3 Hz, 2H).
IR (ATR); 2911, 1759, 1506, 1322, 837 cm⁻¹.
EI-MS m/z; 324 (M⁺).

Example 195

Preparation of 1-(2,4-difluorophenyl)-4,4-dimethyl-2-(adamantan-2-yl)-1,2-diazetidin-3-one 1-Bromo-2,4-difluorobenzene was used in place of bromobenzene for a similar reaction and treatment as Example 181, and the title compound was obtained as a colorless oil.

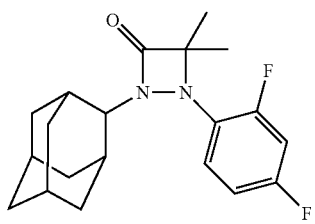

¹H-NMR (400 MHz, CDCl₃) δ; 1.00-2.32 (m, 19H), 2.55-2.64 (m, 1H), 3.72 (s, 1H), 6.83-6.88 (m, 2H), 7.06-7.12 (m, 1H).

Example 196

Preparation of 1-(2,5-difluorophenyl)-4,4-dimethyl-2-(adamantan-2-yl)-1,2-diazetidin-3-one 1-Bromo-2,5-difluorobenzene was used in place of bromobenzene for a similar reaction and treatment as Example 181, and the title compound was obtained as a colorless oil.

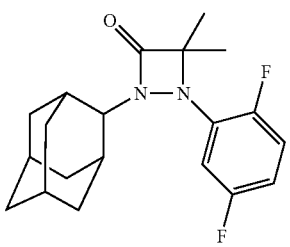

¹H-NMR (400 MHz, CDCl₃) δ; 1.06-2.27 (m, 19H), 2.65-2.70 (m, 1H), 3.74 (m, 1H), 6.70-6.76 (m, 1H), 6.81-6.86 (m, 1H), 6.99-7.05 (m, 1H).
IR (ATR); 2910, 1770, 1496, 1244, 1159, 1004, 762 cm⁻¹.
EI-MS m/z; 346 (M⁺).

Example 197

Preparation of 1-(2,3-difluorophenyl)-4,4-dimethyl-2-(adamantan-2-yl)-1,2-diazetidin-3-one 1-Bromo-2,3-difluorobenzene was used in place of bromobenzene for a similar reaction and treatment as Example 181, and the title compound was obtained as a pale yellow crystalline powder.

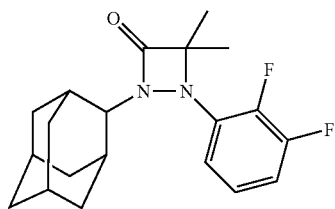

¹H-NMR (400 MHz, CDCl₃) δ; 1.02-2.55 (m, 20H), 3.71 (s, 1H), 6.75-6.77 (m, 1H), 6.85-6.89 (m, 1H), 7.13 (dd, J=8.8, 18.6 Hz, 1H).
IR (ATR); 2913, 1760, 1511, 1211, 1100, 772 cm⁻¹.
EI-MS m/z; 346 (M⁺).

Example 198

Preparation of 1-(3,5-difluorophenyl)-4,4-dimethyl-2-(adamantan-2-yl)-1,2-diazetidin-3-one 1-Bromo-3,5-difluorobenzene was used in place of bromobenzene for a similar reaction and treatment as Example 181, and the title compound was obtained as a pale yellow crystalline powder.

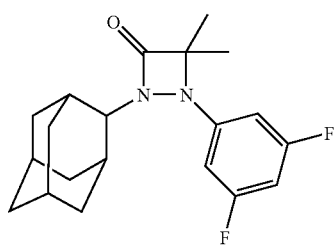

¹H-NMR (400 MHz, CDCl₃) δ; 1.26-1.91 (m, 18H), 2.18 (d, J=11.7 Hz, 1H), 2.34 (s, 1H), 3.73 (s, 1H), 6.52-6.60 (m, 3H).

IR (ATR); 2916, 1758, 1621, 1456, 1113, 821 cm⁻¹.
EI-MS m/z; 346 (M⁺).

Example 199

Preparation of 1-(1,3-benzodioxol-5-yl)-4,4-dimethyl-2-(adamantan-2-yl)-1,2-diazetidin-3-one 1-Bromo-3,4-(methylenedioxy)benzene was used in place of bromobenzene for a similar reaction and treatment as Example 181, and the title compound was obtained as a pale yellow amorphous solid.

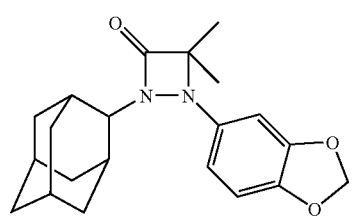

¹H-NMR (400 MHz, CDCl₃) δ; 0.92 (s, 3H), 1.57-1.90 (m, 14H), 2.04-2.20 (m, 2H), 2.50-2.65 (m, 1H), 3.69 (s, 1H), 5.96 (s, 2H), 6.52 (d, J=8.2 Hz, 1H), 6.59 (s, 1H), 6.76 (d, J=8.2 Hz, 1H).
IR (ATR); 2909, 1755, 1482, 1241, 1037, 755 cm⁻¹.
EI-MS m/z; 354 (M⁺).

Example 200

Preparation of 1-(3-fluorophenyl)-4,4-dimethyl-2-(adamantan-2-yl)-1,2-diazetidin-3-one 1-Bromo-3-fluorobenzene was used in place of bromobenzene for a similar reaction and treatment as Example 181, and the title compound was obtained as a white crystalline powder.

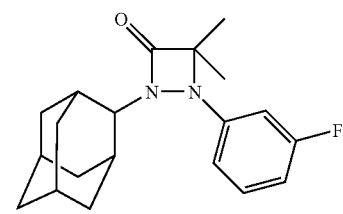

¹H-NMR (400 MHz, CDCl₃) δ; 1.15-1.50 (m, 3H), 1.56-1.91 (m, 14H), 2.20-2.54 (m, 3H), 3.75 (s, 1H), 6.71-6.84 (m, 3H), 7.25-7.31 (m, 1H).
IR (ATR); 2912, 1758, 1613, 1485, 1148, 862 cm⁻¹.
EI-MS m/z; 328 (M⁺).

Example 201

Preparation of 1-(4-fluorophenyl)-4,4-dimethyl-2-(adamantan-2-yl)-1,2-diazetidin-3-one 1-Bromo-4-fluorobenzene was used in place of bromobenzene for a similar reaction and treatment as Example 181, and the title compound was obtained as a pale yellow oil.

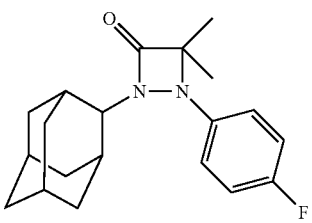

¹H-NMR (400 MHz, CDCl₃) δ; 0.85-1.20 (m, 3H), 1.42-1.90 (m, 14H), 2.02-2.30 (m, 3H), 3.71 (s, 1H), 6.98-7.05 (m, 4H).
IR (ATR); 2911, 1759, 1501, 1212, 1100, 845 cm⁻¹.
EI-MS m/z; 328 (M⁺).

Example 202

Preparation of 1-(3,5-dichlorophenyl)-4,4-dimethyl-2-(adamantyl)-1,2-diazetidin-3-one 1-Bromo-3,5-dichlorobenzene was used in place of bromobenzene for a similar reaction and treatment as Example 181, and the title compound was obtained as a white crystalline powder.

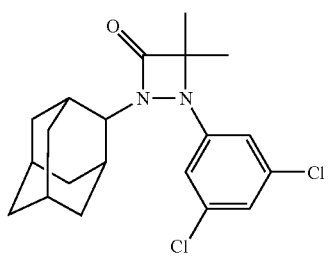

¹H-NMR (400 MHz, CDCl₃) δ; 1.21-2.32 (m, 24H), 3.72 (s, 1H), 6.89 (s, 2H), 7.12 (t, J=1.7 Hz, 1H).
IR (ATR); 2914, 1757, 1582, 1312, 843, 759 cm⁻¹.
EI-MS m/z; 379 (M⁺).

Example 203

Preparation of 1-(4-methoxyphenyl)-4,4-dimethyl-2-(adamantan-2-yl)-1,2-diazetidin-3-one 1-Bromo-4-methoxybenzene was used in place of bromobenzene for a similar reaction and treatment as Example 181, and the title compound was obtained as a yellow oil.

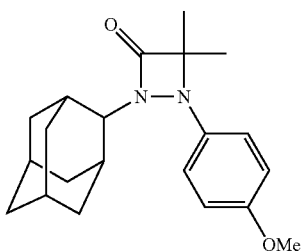

¹H-NMR (400 MHz, CDCl₃) δ; 0.69-1.12 (m, 3H), 1.59-1.90 (m, 14H), 2.04-2.22 (m, 2H), 2.63 (br, 1H), 3.71 (s, 1H), 3.80 (s, 3H), 6.87 (d, J=8.8 Hz, 2H), 6.98 (d, J=8.8 Hz, 2H).

IR (ATR); 2910, 1755, 1504, 1244, 1036, 841, 731 cm⁻¹.
EI-MS m/z; 340 (M⁺).

Example 204

Preparation of 1-(3-methoxyphenyl)-4,4-dimethyl-2-(adamantan-2-yl)-1,2-diazetidin-3-one 1-Bromo-3-methoxybenzene was used in place of bromobenzene for a similar reaction and treatment as Example 181, and the title compound was obtained as a yellow oil.

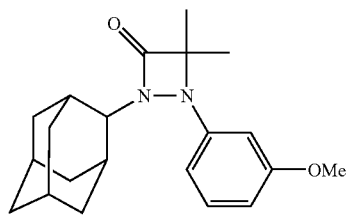

¹H-NMR (400 MHz, CDCl₃) δ; 1.22-1.91 (m, 18H), 2.23 (d, J=12.7 Hz, 2H), 3.76 (s, 1H), 3.81 (s, 3H), 6.55 (s, 1H), 6.60 (d, J=7.8 Hz, 1H), 6.67-6.68 (m, 1H), 7.23 (t, J=8.0 Hz, 1H).
IR (ATR); 2911, 1759, 1601, 1484, 1153, 1047, 753 cm⁻¹.
EI-MS m/z; 340 (M⁺).

Example 205

Preparation of 1-(2-methoxyphenyl)-4,4-dimethyl-2-(adamantan-2-yl)-1,2-diazetidin-3-one 1-Bromo-2-methoxybenzene was used in place of bromobenzene for a similar reaction and treatment as Example 181, and the title compound was obtained as a brown oil.

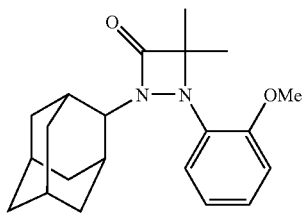

¹H-NMR (400 MHz, CDCl₃) δ; 0.94 (s, 3H), 1.57-1.78 (m, 10H), 2.11 (s, 1H), 2.24 (d, J=12.7 Hz, 1H), 2.38 (d, J=12.7 Hz, 1H), 2.67 (s, 1H), 3.75 (s, 1H), 3.84 (s, 6.88 (d, J=7.8 Hz, 1H), 6.94 (t, J=7.8 Hz, 1H), 7.01-7.07 (m, 2H).
IR (ATR); 2910, 1758, 1491, 1454, 1244, 753 cm⁻¹.
EI-MS m/z; 340 (M⁺).

Example 206

Preparation of 1-(2,3-dichlorophenyl)-4,4-dimethyl-2-(adamantan-2-yl)-1,2-diazetidin-3-one 1-Bromo-2,3-dichlorobenzene was used in place of bromobenzene for a similar reaction and treatment as Example 181, and the title compound was obtained as a colorless oil.

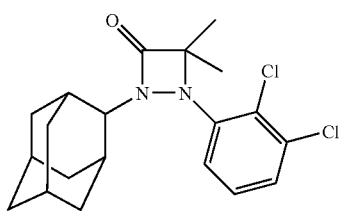

¹H-NMR (400 MHz, CDCl₃) δ; 1.00 (s, 3H), 1.55-1.61 (m, 2H), 1.69-1.77 (m, 5H), 1.81 (s, 3H), 1.87-1.91 (m, 3H), 2.69 (s, 1H), 3.69 (s, 1H), 7.12 (dd, J=1.9, 7.6 Hz, 1H), 7.19-7.26 (m, 2H).
IR (ATR); 2915, 1755, 1576, 1446, 1057, 753 cm⁻¹.
EI-MS m/z; 378 (M⁺).

Example 207

Preparation of 1-(2,3-dimethylphenyl)-4,4-dimethyl-2-(adamantan-2-yl)-1,2-diazetidin-3-one 3-Bromo-o-xylene was used in place of bromobenzene for a similar reaction and treatment as Example 181, and the title compound was obtained as a colorless oil.

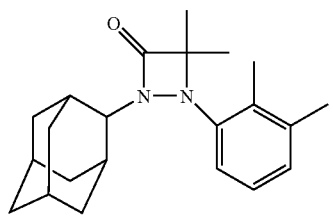

¹H-NMR (400 MHz, CDCl₃) δ; 0.86 (s, 3H), 1.59 (s, 3H), 1.66-1.76 (m, 7H), 1.84-1.90 (m, 4H), 2.19-2.22 (m, 4H), 2.27-2.31 (m, 4H), 2.73 (s, 1H), 3.69 (s, 1H), 6.96 (d, J=7.3 Hz, 1H), 7.01 (d, J=7.3 Hz, 1H), 7.10 (t, J=7.6 Hz, 1H).
IR (ATR); 2912, 1757, 754 cm⁻¹.
EI-MS m/z; 338 (M⁺).

Example 208

Preparation of 1-(2,4-dichlorophenyl)-4,4-dimethyl-2-(adamantan-2-yl)-1,2-diazetidin-3-one 1-Bromo-2,4-dichlorobenzene was used in place of bromobenzene for a similar reaction and treatment as Example 181, and the title compound was obtained as a colorless oil.

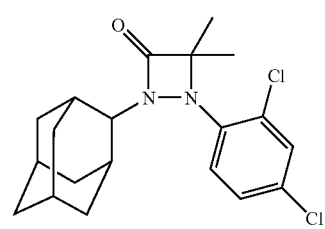

¹H-NMR (400 MHz, CDCl₃) δ; 1.00 (s, 3H), 1.56-1.62 (m, 3H), 1.68-1.74 (m, 5H), 1.78 (s, 3H), 1.87-1.91 (m, 3H), 2.14 (d, J=12.9 Hz, 1H), 2.27 (d, J=12.9 Hz, 1H), 2.66 (s, 1H), 3.67 (s, 1H), 7.14 (d, J=8.5 Hz, 1H), 7.25 (dd, J=2.4, 8.5 Hz, 1H), 7.40 (d, J=2.4 Hz, 1H).

IR (ATR); 2912, 2855, 1764, 1468, 1102, 756 cm⁻¹.
EI-MS m/z; 378 (M⁺).

Example 209

Preparation of 1-(2,5-dichlorophenyl)-4,4-dimethyl-2-(adamantan-2-yl)-1,2-diazetidin-3-one 1-Bromo-2,5-dichlorobenzene was used in place of bromobenzene for a similar reaction and treatment as Example 181, and the title compound was obtained as a colorless oil.

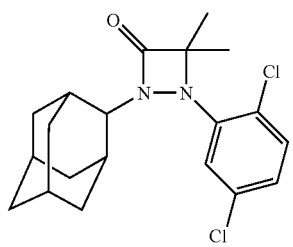

¹H-NMR (400 MHz, CDCl₃) δ; 1.02 (s, 3H), 1.50-1.76 (m, 8H), 1.79 (s, 3H), 1.87-1.91 (m, 3H), 2.14 (d, J=12.7 Hz, 1H), 2.27 (d, J=12.7 Hz, 1H), 2.66 (s, 1H), 3.69 (s, 1H), 7.04 (dd, J=2.2, 8.6 Hz, 1H), 7.19 (d, J=2.2 Hz, 1H), 7.30 (d, J=8.6 Hz, 1H).
IR (ATR); 2910, 2854, 1768, 1466, 806 cm⁻¹.
EI-MS m/z; 378 (M⁺).

Example 210

Preparation of 1-(1-benzothiophen-3-yl)-4,4-dimethyl-2-(adamantan-2-yl)-1,2-diazetidin-3-one 3-Bromobenzothiophene was used in place of bromobenzene for a similar reaction and treatment as Example 181, and the title compound was obtained as a red-brown oil.

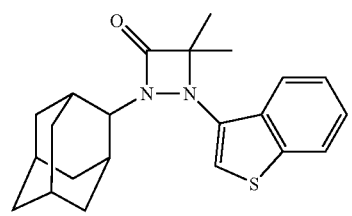

¹H-NMR (400 MHz, CDCl₃) δ; 1.00 (s, 3H), 1.56 (s, 3H), 1.72-1.91 (m, 10H), 2.10-2.34 (m, 3H), 2.70 (s, 1H), 3.81 (s, 1H), 6.89 (s, 1H), 7.36-7.40 (m, 2H), 7.73-7.75 (m, 1H), 7.79-7.82 (m, 1H).
IR (ATR); 2912, 1759, 755 cm⁻¹.
EI-MS m/z; 366 (M⁺).

Example 211

Preparation of 4,4-dimethyl-1-(pyridin-2-yl)-2-(adamantan-2-yl)-1,2-diazetidin-3-one 2-Bromopyridine was used in place of bromobenzene for a similar reaction and treatment as Example 181, and the title compound was obtained as a white crystalline powder.

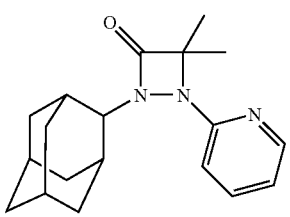

¹H-NMR (400 MHz, CDCl₃) δ; 1.36 (s, 6H), 1.63-1.92 (m, 10H), 2.19 (d, J=12.7 Hz, 2H), 2.38 (s, 2H), 4.11 (s, 1H).
IR (ATR); 2910, 1753, 1430, 1295, 796 cm⁻¹.
EI-MS m/z; 311 (M⁺).

Example 212

Preparation of 4,4-dimethyl-1-(naphthalen-1-yl)-2-(adamantan-2-yl)-1,2-diazetidin-3-one 1-Bromonaphtalene was used in place of bromobenzene for a similar reaction and treatment as Example 181, and the title compound was obtained as a yellow oil.

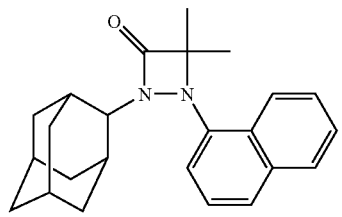

¹H-NMR (400 MHz, CDCl₃) δ; 0.81 (s, 3H), 1.53-1.57 (m, 3H), 1.64-1.93 (m, 11H), 2.28 (d, J=12.9 Hz, 1H), 2.37 (d, J=13.2 Hz, 1H), 2.79 (s, 1H), 3.82 (s, 1H), 7.25-7.27 (m, 1H), 7.43-7.53 (m, 3H), 7.64 (d, J=8.3 Hz, 1H), 7.82-7.86 (m, 1H), 8.26-8.29 (m, 1H).
IR (ATR); 2912, 1756, 1390, 775, 753 cm⁻¹.
EI-MS m/z; 360 (M⁺).

Example 213

Preparation of 4,4-dimethyl-1-(naphthalen-2-yl)-2-(adamantan-2-yl)-1,2-diazetidin-3-one 2-Bromonaphthalene was used in place of bromobenzene for a similar reaction and treatment as Example 181, and the title compound was obtained as a white crystalline powder.

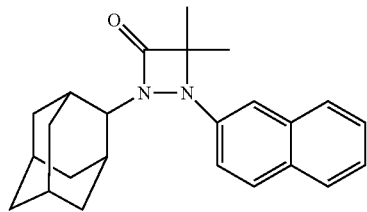

¹H-NMR (400 MHz, CDCl₃) δ; 1.46-2.31 (m, 20H), 3.89 (s, 1H), 7.14 (s, 1H), 7.40-7.44 (m, 2H), 7.48 (dt, J=6.8, 1.2 Hz, 1H), 7.78-7.82 (m, 3H).
IR (ATR); 2924, 1754, 860, 754 cm⁻¹.
EI-MS m/z; 360 (M⁺).

Example 214

Preparation of 1-[4-(methoxymethoxy)phenyl]-4,4-dimethyl-2-(adamantan-2-yl)-1,2-diazetidin-3-one 1-Bromo-4-(methoxymethoxy)benzene was used in place of bromobenzene for a similar reaction and treatment as Example 181, and the title compound was obtained as a white amorphous solid.

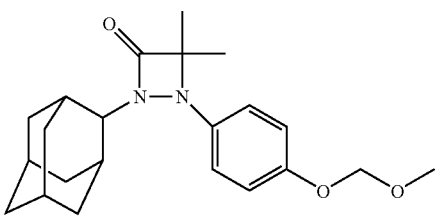

¹H-NMR (400 MHz, CDCl₃) δ; 0.89 (s, 3H), 1.61-2.31 (m, 17H), 3.50 (s, 3H), 3.87 (s, 1H), 5.15 (s, 2H), 6.97-7.21 (m, 4H).
IR (ATR); 2913, 1752, 1502, 1150, 1078, 991, 843 cm⁻¹.
EI-MS m/z; 370 (M⁺).

Example 215

Preparation of 4,4-dimethyl-1-(4-hydroxyphenyl)-2-(adamantan-2-yl)-1,2-diazetidin-3-one

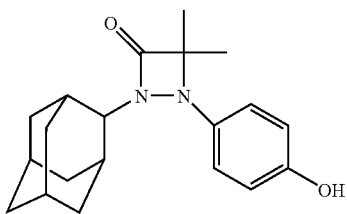

A solution of 1-[4-(methoxymethoxy)phenyl]-4,4-dimethyl-2-(adamantan-2-yl)-1,2-diazetidin-3-one (62.5 mg, 0.169 mmol) prepared in Example 214 in methanol was added with concentrated hydrochloric acid (0.3 mL) under ice-cold conditions, and the resultant was stirred at 50° C. for 30 minutes. The reaction solution was added under ice-cold conditions with a saturated aqueous solution of ammonium chloride, extracted with chloroform, and concentrated in vacuo. The obtained residue was purified using Preparatory Thin-Layer chromatography (chloroform:methanol=10:1), and the title compound (38.0 mg, 68.8%) was obtained as a white crystalline solid.

¹H-NMR (400 MHz, CDCl₃) δ; 0.85 (br, 3H), 1.59-1.93 (m, 14H), 2.01 (s, 1H), 2.17-2.32 (m, 1H), 2.66 (s, 1H), 3.72 (s, 1H), 6.67 (br, 1H), 6.83 (d, J=8.5 Hz, 2H), 6.91 (d, J=8.5 Hz, 2H).
IR (ATR); 3302, 2913, 1724, 1507, 1453, 1219, 843, 754 cm⁻¹.
EI-MS m/z; 326 (M⁺).

Example 216

Preparation of 1-[3-(methoxymethoxy)phenyl]-4,4-dimethyl-2-(adamantan-2-yl)-1,2-diazetidin-3-one 1-Bromo-3-(methoxymethoxy)benzene was used in place of bromobenzene for a similar reaction and treatment as Example 181, and the title compound was obtained as a red-brown oil.

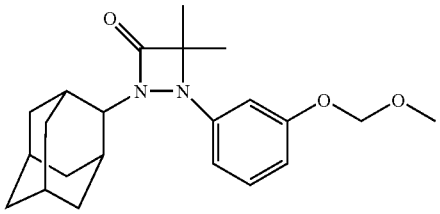

$^1$H-NMR (270 MHz, CDCl$_3$) δ; 1.26-2.31 (m, 20H), 3.48 (s, 3H), 3.77 (s, 1H), 5.17 (s, 2H), 6.62-6.69 (m, 2H), 6.78-6.81 (m, 1H), 7.22 (t, J=11.6 Hz, 1H).
IR (ATR); 2909, 1760, 1597, 1483, 1148, 1077, 1016, 755 cm$^{-1}$.
EI-MS m/z; 370 (M$^+$).

Example 217

Preparation of 1-(3-hydroxyphenyl)-4,4-dimethyl-2-(adamantan-2-yl)-1,2-diazetidin-3-one 1-[3-(Methoxymethoxy)phenyl]-4,4-dimethyl-2-(adamantan-2-yl)-1,2-diazetidin-3-one prepared in Example 216 was used for a similar reaction and treatment as Example 215, and the title compound was obtained as a white amorphous solid.

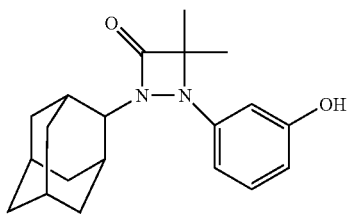

$^1$H-NMR (270 MHz, CDCl$_3$) δ; 1.73-2.31 (m, 20H), 3.80 (s, 1H), 6.48-6.65 (m, 3H), 7.06-7.34 (m, 2H).
IR (ATR); 2924, 1754, 860, 754 cm$^{-1}$.
EI-MS m/z; 326 (M$^+$).

Example 218

Preparation of 1-[2-(methoxymethoxy)phenyl]-4,4-dimethyl-2-(adamantan-2-yl)-1,2-diazetidin-3-one 1-Bromo-2-(methoxymethoxy)bezene was used in place of bromobenzene for a similar reaction and treatment as Example 181, and the title compound was obtained as a yellow oil.

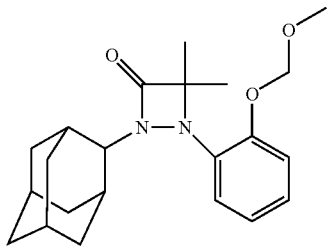

$^1$H-NMR (400 MHz, CDCl$_3$) δ; 0.99 (s, 3H), 1.57 (s, 3H), 1.70-1.78 (m, 7H), 1.86-1.91 (m, 3H), 2.00 (s, 1H), 2.22 (d, J=12.7 Hz, 1H), 2.31 (d, J=13.4 Hz, 1H), 2.75 (s, 1H), 3.53 (s, 3H), 3.76 (s, 1H), 5.18 (d, J=4.6 Hz, 2H), 7.00-7.10 (m, 4H).
IR (ATR); 2910, 1759, 1489, 1240, 1155, 993, 754 cm$^{-1}$.
EI-MS m/z; 370 (M$^+$).

Example 219

Preparation of 1-(2-hydroxyphenyl)-4,4-dimethyl-2-(adamantan-2-yl)-1,2-diazetidin-3-one 1-[2-(Methoxymethoxy)phenyl]-4,4-dimethyl-2-(adamantan-2-yl)-1,2-diazetidin-3-one prepared in Example 218 was used for a similar reaction and treatment as Example 215, and the title compound was obtained as a green amorphous solid.

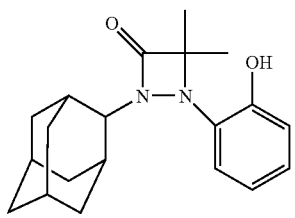

$^1$H-NMR (400 MHz, CDCl$_3$) δ; 1.00 (s, 3H), 1.54-1.97 (m, 14H), 2.10 (d, J=12.7 Hz, 1H), 2.23 (d, J=13.2 Hz, 1H), 2.56 (s, 1H), 3.64 (s, 1H), 6.36 (s, 1H), 6.89-6.96 (m, 2H), 7.09-7.13 (m, 1H), 7.18 (dd, J=7.8, 1.2 Hz, 1H).
IR (ATR); 3266, 2910, 1726, 1592, 1455, 758 cm$^{-1}$.
EI-MS m/z; 326 (M$^+$).

Example 220

Preparation of 2-cyclooctyl-1-(2-methoxyphenyl)-4,4-dimethyl-1,2-diazetidin-3-one 2-Cyclooctyl-4,4-dimethyl-1,2-diazetidin-3-one prepared in Process 5 of Example 73 and 1-bromo-2-methoxybenzene was used for a similar reaction and treatment as Example 181, and the title compound was obtained as a pale yellow oil.

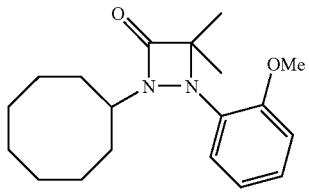

¹H-NMR (400 MHz, CDCl₃) δ; 0.98 (s, 3H), 1.43-1.65 (m, 14H), 1.77-1.86 (m, 1H), 1.95-2.16 (m, 1H), 2.18-2.35 (m, 1H), 3.22-3.28 (m, 1H), 3.85 (s, 3H), 6.89 (d, J=8.1 Hz, 1H), 6.96-6.99 (m, 2H), 7.04-7.09 (m, 1H).
IR (ATR); 2925, 1767, 1492, 1246, 1028, 745 cm⁻¹.
EI-MS m/z; 316 (M⁺).

Example 221

Preparation of 2-cyclooctyl-1-(2,3-dichlorophenyl)-4,4-dimethyl-1,2-diazetidin-3-one 2-Cyclooctyl-4,4-dimethyl-1,2-diazetidin-3-one and 1-bromo-2,3-dichlorobenzene were used for a similar reaction and treatment as Example 181, and the title compound was obtained as a pale yellow oil.

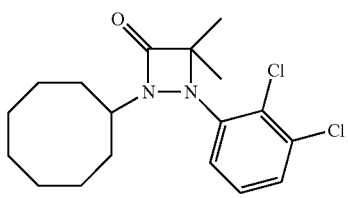

¹H-NMR (400 MHz, CDCl₃) δ; 1.04 (s, 3H), 1.41-1.65 (m, 8H), 1.73 (s, 1H), 1.74-1.85 (m, 2H), 1.90-2.07 (m, 2H), 2.15-2.20 (m, 1H), 2.25-2.34 (m, 1H), 3.18-3.25 (m, 1H), 7.07-7.12 (m, 1H), 7.20-7.25 (m, 2H).
IR (ATR); 2926, 1771, 1576, 1445, 1274, 1056, 788 cm⁻¹.
EI-MS m/z; 354 (M⁺).

Example 222

Preparation of 2-cyclooctyl-4,4-dimethyl-1-(naphthalen-1-yl)-1,2-diazetidin-3-one 2-Cyclooctyl-4,4-dimethyl-1,2-diazetidin-3-one and 1-bromonaphtalene were used for a similar reaction and treatment as Example 181, and the title compound was obtained as a pale yellow oil.

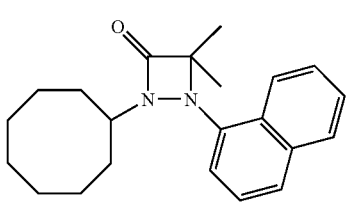

¹H-NMR (400 MHz, CDCl₃) δ; 0.82 (s, 3H), 1.40-1.62 (m, 8H), 1.71-1.90 (m, 2H), 1.79 (s, 3H), 1.97-2.11 (m, 2H), 2.23-2.41 (m, 2H), 3.35-3.41 (m, 1H), 7.25-7.27 (m, 1H), 7.45-7.53 (m, 3H), 7.63 (d, J=8.3 Hz, 1H), 7.84-7.86 (m, 1H), 8.22-8.24 (m, 1H).
IR (ATR); 2925, 1764, 1390, 1278, 775 cm⁻¹.
EI-MS m/z; 336 (M⁺).

Example 223

Preparation of 2-(bicyclo[2.2.1]heptan-2-yl)-1-(2-methoxyphenyl)-4,4-dimethyl-1,2-diazetidin-3-one 2-(Bicyclo[2.2.1]heptan-2-yl)-4,4-dimethyl-1,2-diazetidin-3-one prepared in Process 5 of Example 78 and 1-bromo-2-methoxybenzene were used for a similar reaction and treatment as Example 181, and the title compound was obtained as a pale yellow oil.

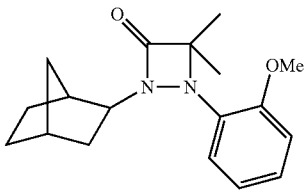

¹H-NMR (400 MHz, CDCl₃) δ; 0.95 (s, 3H), 1.27-1.34 (m, 2H), 1.55-1.91 (m, 8H), 2.03-2.28 (m, 2H), 2.60-2.75 (m, 1H), 3.63-3.75 (m, 1H), 3.85 (s, 3H), 6.89 (d, J=8.0 Hz, 1H), 6.96 (t, J=7.1 Hz, 1H), 7.10-7.09 (m, 2H).
IR (ATR); 2954, 1760, 1492, 1245, 1027, 748 cm⁻¹.
EI-MS m/z; 300 (M⁺).

Example 224

Preparation of 2-(bicyclo[2.2.1]heptan-2-yl)-1-(2,3-dichlorophenyl)-4,4-dimethyl-1,2-diazetidin-3-one 2-(Bicyclo[2.2.1]heptan-2-yl)-4,4-dimethyl-1,2-diazetidin-3-one and 1-bromo-2,3-dichlorobenzene were used for a similar reaction and treatment as Example 181, and the title compound was obtained as a pale yellow crystalline powder.

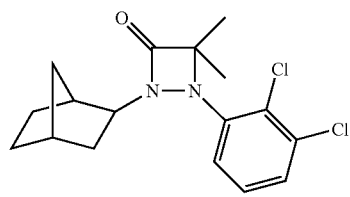

¹H-NMR (400 MHz, CDCl₃) δ; 1.01 (s, 3H), 1.26-1.35 (m, 2H), 1.51-1.61 (m, 4H), 1.73-2.01 (m, 5H), 2.20-2.30 (m, 1H), 2.54-2.71 (m, 1H), 3.50-3.78 (m, 1H), 7.06-7.14 (m, 1H), 7.18-7.26 (m, 2H).
IR (ATR); 2969, 1755, 1574, 1420, 1335, 1053, 784 cm⁻¹.
EI-MS m/z; 338 (M⁺).

Example 225

Preparation of 2-(bicyclo[2.2.1]heptan-2-yl)-4,4-dimethyl-1-(naphthalen-1-yl)-1,2-diazetidin-3-one 2-(Bicyclo[2.2.1]heptan-2-yl)-4,4-dimethyl-1,2-diazetidin-3-one and 1-bromonaphtalene were used for a similar reaction and treatment as Example 181, and the title compound was obtained as a pale yellow crystalline powder.

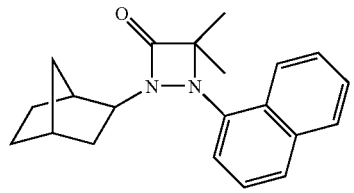

$^1$H-NMR (400 MHz, CDCl$_3$) δ; 0.81 (d, J=7.3 Hz, 3H), 1.24-1.32 (m, 2H), 1.47-1.65 (m, 4H), 1.86 (d, J=11.2 Hz, 3H), 1.92-1.97 (m, 1H), 1.99-1.97 (m, 1H), 2.31-2.36 (m, 1H), 2.51-2.81 (m, 1H), 3.64-3.92 (m, 1H), 7.20-7.27 (m, 2H), 7.42-7.51 (m, 3H) 7.62-7.65 (m, 1H), 7.83-7.86 (m, 1H).

IR (ATR) 2967, 1753, 1389, 808, 778 cm$^{-1}$.

EI-MS m/z; 320 (M$^+$).

Example 226

Preparation of trans-2-(5-hydroxyadamantan-2-yl)-4,4-dimethyl-1-phenyl-1,2-diazetidin-3-one trans-2-(5-Hydroxyadamantan-2-yl)-4,4-dimethyl-1,2-diazetidin-3-one prepared in Process 5 of Example 65 was used for a similar reaction and treatment as Example 181, and the title compound was obtained as a colorless oil.

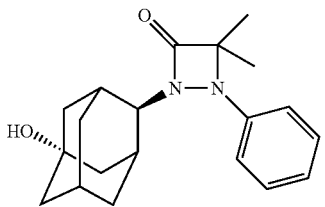

$^1$H-NMR (400 MHz, CDCl$_3$) δ; 0.77-1.95 (m, 17H), 2.16 (s, 1H), 2.19 (s, 2H), 3.70 (s, 1H), 7.00 (d, J=7.6 Hz, 2H), 7.14 (t, J=7.6 Hz, 1H), 7.34 (d, J=7.6 Hz, 2H).

EI-MS m/z; 326 (M$^+$).

Example 227

Preparation of trans-1-(2-chlorophenyl)-2-(5-hydroxyadamantan-2-yl)-4,4-dimethyl-1,2-diazetidin-3-one trans-2-(5-Hydroxyadamantan-2-yl)-4,4-dimethyl-1,2-diazetidin-3-one and 1-bromo-2-chlorobenzene were used for a similar reaction and treatment as Example 181, and the title compound was obtained as a pale yellow oil.

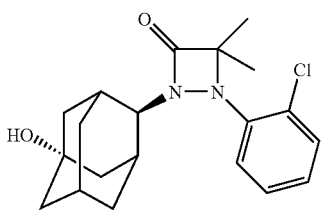

$^1$H-NMR (400 MHz, CDCl$_3$) δ; 0.99 (s, 3H), 1.42-1.79 (m, 12H), 2.11-2.25 (m, 4H), 2.89 (s, 1H), 3.65 (s, 1H), 7.09 (t, J=7.2 Hz, 1H), 7.18 (d, J=7.2 Hz, 1H), 7.28 (t, J=7.2 Hz, 1H), 7.39 (d, J=7.2 Hz, 1H).

EI-MS m/z; 360 (M$^+$).

Example 228

Preparation of trans-2-(5-hydroxyadamantan-2-yl)-1-(2-methoxyphenyl)-4,4-dimethyl-1,2-diazetidin-3-one trans-2-(5-Hydroxyadamantan-2-yl)-4,4-dimethyl-1,2-diazetidin-3-one and 1-bromo-2-methoxybenzene were used for a similar reaction and treatment as Example 181, and the title compound was obtained as a colorless oil.

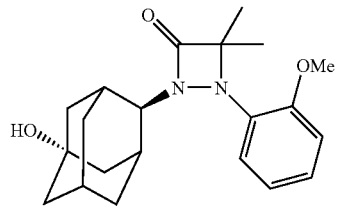

$^1$H-NMR (400 MHz, CDCl$_3$) δ; 0.95 (s, 3H), 1.39-1.80 (m, 12H), 2.16-2.32 (m, 4H), 2.85 (s, 1H), 3.69 (s, 1H), 3.84 (s, 3H), 6.88 (d, J=8.8 Hz, 1H), 6.97 (d, J=8.8 Hz, 1H), 7.00 (d, J=8.8 Hz, 1H), 7.07 (t, J=8.8 Hz, 1H).

IR (ATR); 3422, 2926, 2859, 2359, 2746, 1492, 1456, 1245, 1120, 1027, 754 cm$^{-1}$.

EI-MS m/z; 356 (M$^+$).

Example 229

Preparation of trans-2-(5-hydroxyadamantan-2-yl)-1-(3-methoxyphenyl)-4,4-dimethyl-1,2-diazetidin-3-one trans-2-(5-Hydroxyadamantan-2-yl)-4,4-dimethyl-1,2-diazetidin-3-one and 1-bromo-3-methoxybenzene were used for a similar reaction and treatment as Example 181, and the title compound was obtained as a colorless oil.

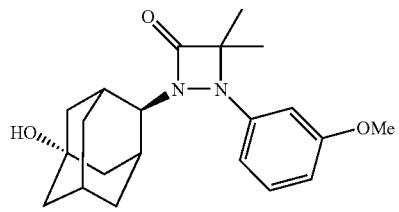

$^1$H-NMR (400 MHz, CDCl$_3$) δ; 0.99-1.86 (m, 15H), 2.12-2.30 (m, 4H), 2.60 (br, 1H), 3.70 (s, 1H), 3.81 (s, 3H), 6.55 (s, 1H), 6.60 (d, J=7.3 Hz, 1H), 6.68 (d, J=7.3 Hz, 1H), 7.24 (t, J=7.3 Hz, 1H).

IR (ATR); 3404, 2925, 2859, 1747, 1602, 1485, 1286, 1152, 753 cm$^{-1}$.

EI-MS m/z; 356 (M$^+$).

Example 230

Preparation of trans-2-(5-hydroxyadamantan-2-yl)-1-(4-methoxyphenyl)-4,4-dimethyl-1,2-diazetidin-3-one trans-2-(5-Hydroxyadamantan-2-yl)-4,4-dimethyl-1,2-diazetidin-3-one and 1-bromo-4-methoxybenzene were used for a similar reaction and treatment as Example 181, and the title compound was obtained as a colorless oil.

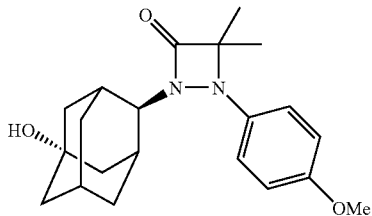

¹H-NMR (400 MHz, CDCl$_3$) δ; 0.87 (br, 3H), 1.46-1.71 (m, 12H), 2.08-2.32 (m, 4H), 2.81 (br, 1H), 3.65 (s, 1H), 3.80 (s, 3H), 6.87 (d, J=9.0 Hz, 2H), 6.98 (d, J=9.0 Hz, 2H).

IR (ATR) 3408, 2925, 2858, 1745, 1504, 1244, 1117, 1034, 844, 756 cm$^{-1}$.

EI-MS m/z; 356 (M$^+$).

Example 231

Preparation of trans-1-(2,3-dichlorophenyl)-2-(5-hydroxyadamantan-2-yl)-4,4-dimethyl-1,2-diazetidin-3-one trans-2-(5-Hydroxyadamantan-2-yl)-4,4-dimethyl-1,2-diazetidin-3-one and 1-bromo-2,3-dichlorobenzene were used for a similar reaction and treatment as Example 181, and the title compound was obtained as a colorless oil.

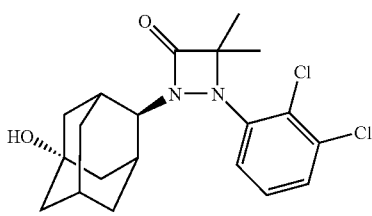

¹H-NMR (400 MHz, CDCl$_3$) δ; 1.01 (s, 3H), 1.43-1.75 (m, 9H), 1.81 (s, 3H), 2.11-2.20 (m, 4H), 2.88 (s, 1H), 3.63 (s, 1H), 7.10 (d, J=8.0 Hz, 1H), 7.23-7.28 (m, 2H).

IR (ATR); 3391, 2927, 2858, 1755, 1576, 1446, 1355, 1116, 754 cm$^{-1}$.

EI-MS m/z; 394 (M$^+$).

Example 232

Preparation of trans-2-(5-hydroxyadamantan-2-yl)-1-[2-(methoxymethoxy)phenyl]-4,4-dimethyl-1,2-diazetidin-3-one trans-2-(5-Hydroxyadamantan-2-yl)-4,4-dimethyl-1,2-diazetidin-3-one and 1-bromo-2-(methoxymethoxy)benzene were used for a similar reaction and treatment as Example 181, and the title compound was obtained as a colorless oil.

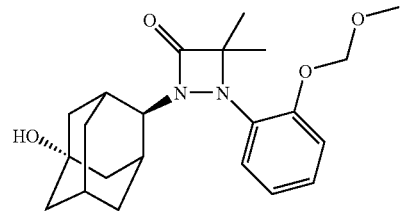

¹H-NMR (400 MHz, CDCl$_3$) δ; 0.99 (s, 3H), 1.41-1.44 (m, 1H), 1.56-1.59 (m, 1H), 1.70 (s, 3H), 1.73-1.80 (m, 7H), 2.13-2.25 (m, 4H), 2.93 (s, 1H), 3.52 (s, 3H), 3.70 (s, 1H), 5.19 (s, 2H), 7.02-7.10 (m, 4H).

IR (ATR); 3418, 2928, 1748, 1489, 1239, 1155, 1117, 1079, 993, 925, 750 cm$^{-1}$.

EI-MS m/z; 386 (M$^+$).

Example 233

Preparation of trans-1-(2-hydroxyphenyl)-2-(5-hydroxyadamantan-2-yl)-4,4-dimethyl-1,2-diazetidin-3-one trans-2-(5-Hydroxyadamantan-2-yl)-1-[2-(methoxymethoxy)phenyl]-4,4-dimethyl-1,2-diazetidin-3-one prepared in Example 232 was used for a similar reaction and treatment as Example 215, and the title compound was obtained as a green amorphous solid.

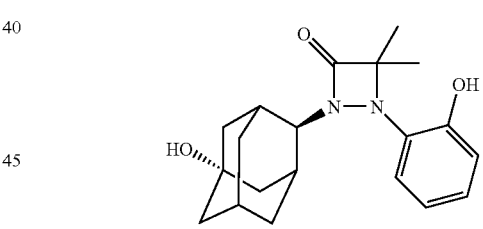

¹H-NMR (400 MHz, CDCl$_3$) δ; 1.01 (s, 3H), 1.47-1.65 (m, 5H), 1.69 (s, 3H), 1.73-1.77 (m, 4H), 2.02-2.20 (m, 4H), 2.72 (s, 1H), 3.57 (s, 1H), 6.25 (s, 1H), 6.91-6.97 (m, 2H), 7.13 (t, J=7.8 Hz, 1H), 7.18 (d, J=7.8 Hz, 1H).

EI-MS m/z; 342 (M$^+$).

Example 234

Preparation of trans-2-(5-hydroxyadamantan-2-yl)-4,4-dimethyl-1-(4-nitrophenyl)-1,2-diazetidin-3-one trans-2-(5-Hydroxyadamantan-2-yl)-4,4-dimethyl-1,2-diazetidin-3-one and 1-bromo-4-nitrobenzene were used for a similar reaction and treatment as Example 181, and the title compound was obtained as a yellow oil.

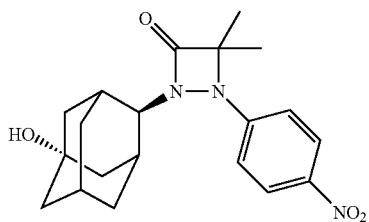

¹H-NMR (400 MHz, CDCl₃) δ; 1.35 (s, 6H), 1.51-1.55 (m, 1H), 1.69-1.86 (m, 7H), 2.09-2.25 (m, 4H), 2.55 (s, 2H), 3.85 (s, 1H), 7.04 (d, J=8.2 Hz, 2H), 8.23 (d, J=8.2 Hz, 2H).

IR (ATR); 3382, 2927, 2859, 1757, 1592, 1515, 1342, 1310, 1111, 752 cm⁻¹.

EI-MS m/z; 371 (M⁺).

Example 235

Preparation of trans-1-(4-aminophenyl)-2-(5-hydroxyadamantan-2-yl)-4,4-dimethyl-1,2-diazetidin-3-one trans-2-(5-Hydroxyadamantan-2-yl)-4,4-dimethyl-1-(4-nitrophenyl)-1,2-diazetidin-3-one prepared in Example 234 was used for a similar reaction and treatment as Example 183, and the title compound was obtained as a brown oil.

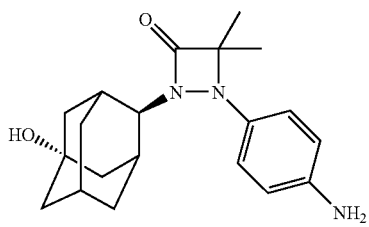

¹H-NMR (400 MHz, CDCl₃) δ; 0.88 (br, 3H), 1.25-1.76 (m, 12H), 2.09-2.26 (m, 4H), 2.80 (br, 1H), 3.63 (s, 1H), 3.28 (br, 2H), 6.66 (d, J=8.8 Hz, 2H), 6.87 (d, J=8.8 Hz, 2H).

IR (ATR); 3351, 2919, 2856, 2360, 2342, 1743, 1653, 1549, 1513, 1223, 1114, 1083, 752 cm⁻¹.

EI-MS m/z; 341 (M⁺).

Example 236

Preparation of trans-2-(5-hydroxyadamantan-2-yl)-4,4-dimethyl-1-(naphthalen-1-yl)-1,2-diazetidin-3-one trans-2-(5-Hydroxyadamantan-2-yl)-4,4-dimethyl-1,2-diazetidin-3-one prepared in Process 5 of Example 65 and 1-bromonaphtalene were used for a similar reaction and treatment as Example 181, and the title compound was obtained as a colorless oil.

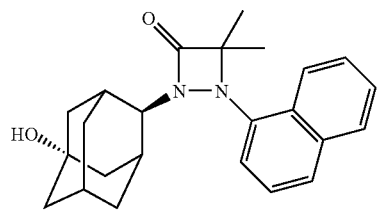

¹H-NMR (400 MHz, CDCl₃) δ; 0.80 (s, 3H), 1.37-1.83 (m, 9H), 1.86 (s, 3H), 2.22-2.31 (m, 4H), 2.98 (s, 1H), 3.75 (s, 1H), 7.22-7.24 (m, 1H), 7.45-7.52 (m, 3H), 7.65 (d, J=8.3 Hz, 1H), 7.84-7.87 (m, 1H), 8.25-8.27 (m, 1H).

IR (ATR); 3545, 2922, 1749, 1731, 1358, 1121, 804, 778 cm⁻¹.

EI-MS m/z; 376 (M⁺).

Example 237

Preparation of trans-2-(5-hydroxyadamantan-2-yl)-4,4-dimethyl-1-(naphthalen-2-yl)-1,2-diazetidin-3-one trans-2-(5-Hydroxyadamantan-2-yl)-4,4-dimethyl-1,2-diazetidin-3-one and 2-bromonaphthalene were used in place of bromobenzene for a similar reaction and treatment as Example 181, and the title compound was obtained as a colorless oil.

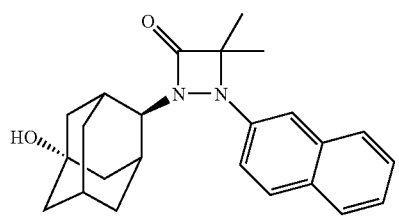

¹H-NMR (400 MHz, CDCl₃) δ; 0.83-1.80 (m, 15H), 2.12-2.30 (m, 4H), 2.88 (br, 1H), 3.70 (s, 1H), 7.14 (br, 1H), 7.41-7.51 (m, 3H), 7.79-7.82 (m, 3H).

IR (ATR); 3420, 2925, 2859, 1748, 1353, 1116, 750 cm⁻¹.

EI-MS m/z; 376 (M⁺).

Example 238

Preparation of trans-1-(4-fluoronaphthalen-1-yl)-2-(5-hydroxyadamantan-2-yl)-4,4-dimethyl-1,2-diazetidin-3-one trans-2-(5-Hydroxyadamantan-2-yl)-4,4-dimethyl-1,2-diazetidin-3-one and 1-bromo-4-fluoronaphthalene were used for a similar reaction and treatment as Example 181, and the title compound was obtained as a colorless oil.

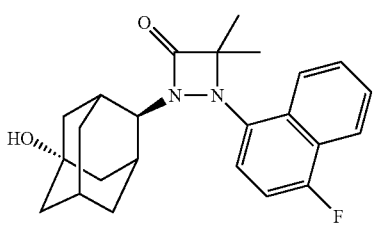

¹H-NMR (400 MHz, CDCl₃) δ; 0.81 (s, 3H), 1.44-1.45 (m, 1H), 1.55-1.62 (m, 1H), 1.70-1.81 (m, 7H), 1.84 (s, 3H), 2.13-2.28 (m, 4H), 2.94 (s, 1H), 3.71 (s, 1H), 7.12-7.20 (m, 2H), 7.55-7.61 (m, 2H), 8.09-8.13 (m, 1H), 8.26-8.28 (m, 1H).
IR (ATR); 3401, 2926, 2859, 1746, 1460, 1391, 754 cm⁻¹.
EI-MS m/z; 394 (M⁺).

Example 239

Preparation of cis-2-(5-hydroxyadamantan-2-yl)-1-(2-methoxyphenyl)-4,4-dimethyl-1,2-diazetidin-3-one

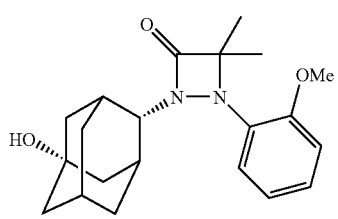

Process 1: Preparation of benzyl cis-2-(5-hydroxy-adamantan-2-yl)hydrazinecarboxylate Benzyl 2-(5-hydroxyadamantan-2-ylidene)hydrazinecarboxylate prepared in Process 1 of Example 65 was used for a similar reaction and treatment as Process 2 of Example 1, and the resultant two geometric isomers were separated using silica gel chromatography, and benzyl cis-2-(5-hydroxyadamantan-2-yl)hydrazinecarboxylate was obtained as a colorless amorphous solid.
¹H-NMR (400 MHz, CDCl₃) δ; 1.43 (d, J=11.2 Hz, 2H), 1.67-1.74 (m, 6H), 2.04-2.11 (m, 6H), 3.03 (s, 1H), 3.85 (br, 1H), 5.13 (s, 2H), 6.21 (s, 1H), 7.30-7.37 (m, 5H).

Process 2: Preparation of benzyl cis-2-(2-bromoisobutyryl)-2-(5-hydroxyadamantan-2-yl)hydrazinecarboxylate Benzyl cis-2-(5-hydroxyadamantan-2-yl)hydrazinecarboxylate and 2-bromoisobutyryl bromide were used for a similar reaction and treatment as Process 3 of Example 1, and benzyl cis-2-(2-bromoisobutyryl)-2-(5-hydroxyadamantan-2-yl)hydrazinecarboxylate was obtained as a colorless oil.
¹H-NMR (400 MHz, CDCl₃) δ; 1.50-2.22 (m, 20H), 2.61 (br, 1H), 4.03 (br, 0.25H), 4.23 (br, 0.75H), 5.07-5.28 (m, 2H), 7.34-7.38 (m, 5H).

Process 3: Preparation of benzyl cis-2-(5-hydroxy-adamantan-2-yl)-4,4-dimethyl-3-oxo-1,2-diazetidine-1-carboxylate Benzyl cis-2-(2-bromoisobutyryl)-2-(5-hydroxyadamantan-2-yl)hydrazinecarboxylate was used for a similar reaction and treatment as Process 4 of Example 1, and benzyl cis-2-(5-hydroxyadamantan-2-yl)-4,4-dimethyl-3-oxo-1,2-diazetidine-1-carboxylate was obtained as a colorless amorphous solid.
¹H-NMR (400 MHz, CDCl₃) δ; 1.49 (s, 6H), 1.60-2.01 (m, 12H), 2.13 (s, 1H), 2.64 (s, 1H), 3.87 (s, 1H), 5.19 (s, 2H), 7.35-7.39 (m, 5H).

Process 4: Preparation of cis-2-(5-hydroxyadamantan-2-yl)-4,4-dimethyl-1,2-diazetidin-3-one Benzyl cis-2-(5-hydroxyadamantan-2-yl)-4,4-dimethyl-3-oxo-1,2-diazetidine-1-carboxylate was used for a similar reaction and treatment as Process 5 of Example 1, and cis-2-(5-hydroxyadamantan-2-yl)-4,4-dimethyl-1,2-diazetidin-3-one was obtained as a pale yellow amorphous solid.
¹H-NMR (400 MHz, CDCl₃) δ; 1.49-1.75 (m, 18H), 1.99 (s, 1H), 2.15 (s, 1H), 2.38-2.76 (m, 1H), 3.58 (s, 1H), 3.87 (br, 1H).

Process 5: Preparation of cis-1-(2-chlorobenzyl)-2-(5-hydroxyadamantan-2-yl)-4,4-dimethyl-1,2-diazetidin-3-one cis-2-(5-Hydroxyadamantan-2-yl)-4,4-dimethyl-1,2-diazetidin-3-one and 1-bromo-2-methoxybenzene were used for a similar reaction and treatment as Example 181, and the title compound was obtained as a colorless oil.
¹H-NMR (400 MHz, CDCl₃) δ; 0.88 (s, 3H), 1.51-1.73 (m, 13H), 1.90-2.45 (m, 3H), 2.91 (s, 1H), 3.60 (s, 1H), 3.84 (s, 3H), 6.88 (d, J=8.1 Hz, 1H), 6.95 (t, J=8.1 Hz, 1H), 7.01 (d, J=8.1 Hz, 1H), 7.07 (t, J=8.1 Hz, 1H).
IR (ATR); 3413, 2919, 2857, 2360, 2342, 1755, 1492, 1454, 1246, 1120, 1099, 1027, 758 cm⁻¹.
EI-MS m/z; 356 (M⁺).

Example 240

Preparation of cis-2-(5-hydroxyadamantan-2-yl)-1-(4-methoxyphenyl)-4,4-dimethyl-1,2-diazetidin-3-one cis-2-(5-Hydroxyadamantan-2-yl)-4,4-dimethyl-1,2-diazetidin-3-one prepared in Process 4 of Example 239 and 1-bromo-4-methxoxybenzene were used for a similar reaction and treatment as Example 181, and the title compound was obtained as a colorless oil.

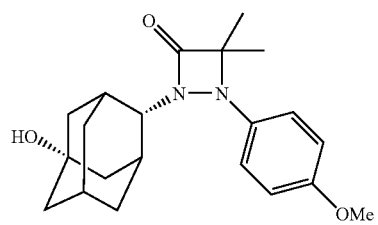

¹H-NMR (400 MHz, CDCl₃) δ; 0.87 (s, 3H), 1.51-1.75 (m, 13H), 2.10-2.33 (m, 3H), 2.86 (br, 1H), 3.56 (s, 1H), 3.84 (s, 3H), 6.87 (d, J=9.0 Hz, 2H), 6.98 (d, J=9.0 Hz, 2H).
IR (ATR); 3423, 2922, 2858, 2360, 1743, 1504, 1243, 1115, 1099, 1035, 834, 753 cm⁻¹.
EI-MS m/z; 356 (M⁺).

Example 241

Preparation of cis-2-(5-hydroxyadamantan-2-yl)-1-(3-methoxyphenyl)-4,4-dimethyl-1,2-diazetidin-3-one cis-2-(5-Hydroxyadamantan-2-yl)-4,4-dimethyl-1,2-diazetidin-3-one and 1-bromo-3-methoxybenzene were used for a similar reaction and treatment as Example 181, and the title compound was obtained as a colorless oil.

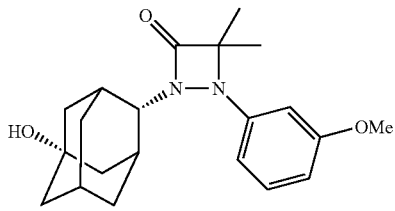

$^1$H-NMR (400 MHz, CDCl$_3$) δ; 1.21 (s, 3H), 1.25 (s, 3H), 1.54-2.35 (m, 13H), 2.67 (br, 1H), 3.61 (s, 1H), 3.81 (s, 3H), 6.55 (s, 1H), 6.60 (d, J=7.8 Hz, 1H), 6.68 (d, J=7.8 Hz, 1H), 7.24 (t, J=7.8 Hz, 1H).
IR (ATR); 3388, 2972, 2927, 2359, 2342, 1735, 1602, 1485, 1149, 1124, 982, 787 cm$^{-1}$.
EI-MS m/z; 356 (M$^+$).

Example 242

Preparation of cis-2-(5-hydroxyadamantan-2-yl)-4,4-dimethyl-1-(2-methylphenyl)-1,2-diazetidin-3-one cis-2-(5-Hydroxyadamantan-2-yl)-4,4-dimethyl-1,2-diazetidin-3-one and 2-bromotoluene were used for a similar reaction and treatment as Example 181, and the title compound was obtained as a pale yellow oil.

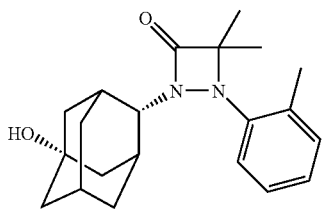

$^1$H-NMR (400 MHz, CDCl$_3$) δ; 0.90 (s, 3H), 1.44-1.68 (m, 9H), 1.70 (s, 3H), 2.10-2.27 (m, 4H), 2.29 (s, 3H), 2.98 (s, 1H), 3.54 (s, 1H), 7.06 (t, J=6.8 Hz, 1H), 7.13 (d, J=6.8 Hz, 1H), 7.18-7.23 (m, 2H).
IR (ATR); 3229, 2915, 2856, 2360, 1756, 1113, 1099, 768 cm$^{-1}$.
EI-MS m/z; 340 (M$^+$).

Example 243

Preparation of cis-2-(5-hydroxyadamantan-2-yl)-1-[2-(methoxymethoxy)phenyl]-4,4-dimethyl-1,2-diazetidin-3-one cis-2-(5-Hydroxyadamantan-2-yl)-4,4-dimethyl-1,2-diazetidin-3-one and 1-bromo-2-(methoxymethoxy)benzene were used for a similar reaction and treatment as Example 181, and the title compound was obtained as a colorless oil.

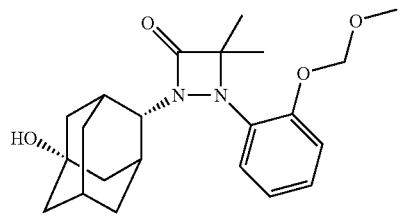

$^1$H-NMR (400 MHz, CDCl$_3$) δ; 0.83 (s, 3H), 1.54-2.20 (m, 14H), 2.29-2.33 (m, 2H), 2.99 (s, 1H), 3.52 (s, 3H), 3.60 (s, 1H), 5.20 (s, 2H), 7.03-7.11 (m, 4H).
IR (ATR); 3407, 2922, 2858, 1758, 1489, 1453, 1242, 1155, 1118, 1079, 987, 927, 758 cm$^{-1}$.
EI-MS m/z; 386 (M$^+$).

Example 244

Preparation of cis-1-(2-hydroxyphenyl)-2-(5-hydroxyadamantan-2-yl)-4,4-dimethyl-1,2-diazetidin-3-one cis-2-(5-Hydroxyadamantan-2-yl)-1-[2-(methoxymethoxy)phenyl]-4,4-dimethyl-1,2-diazetidin-3-one prepared in Example 243 was used for a similar reaction and treatment as Example 215, and the title compound was obtained as a colorless oil.

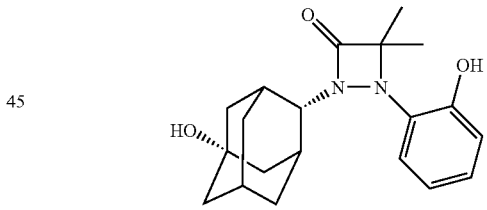

$^1$H-NMR (400 MHz, CDCl$_3$) δ; 1.00 (s, 3H), 1.46-1.49 (m, 1H), 1.59-1.65 (m, 8H), 1.70 (s, 3H), 2.07-2.29 (m, 4H), 2.77 (s, 1H), 3.56 (s, 1H), 6.27 (s, 1H), 6.91-6.97 (m, 2H), 7.13 (t, J=8.0 Hz, 1H), 7.18 (d, J=8.0 Hz, 1H).
EI-MS m/z; 342 (M$^+$).

Example 245

Preparation of cis-2-(5-hydroxyadamantan-2-yl)-4,4-dimethyl-1-(4-nitrophenyl)-1,2-diazetidin-3-one cis-2-(5-Hydroxyadamantan-2-yl)-4,4-dimethyl-1,2-diazetidin-3-one and 1-bromo-4-nitrobenzene were used for a similar reaction and treatment as Example 181, and the title compound was obtained as a yellow oil.

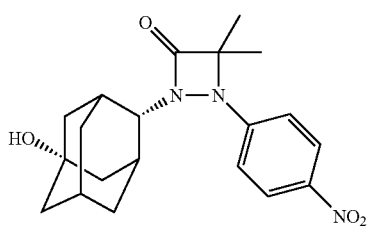

¹H-NMR (400 MHz, CDCl₃) δ; 1.35 (s, 6H), 1.61-1.73 (m, 9H), 2.14 (s, 1H), 2.17 (s, 2H), 2.62 (s, 2H), 3.65 (s, 1H), 7.05 (d, J=8.3 Hz, 2H), 8.23 (d, J=8.3 Hz, 2H).
IR (ATR); 3400, 2923, 2859, 1758, 1591, 1513, 1340, 1111, 1099, 851, 755 cm⁻¹.
EI-MS m/z; 371 (M⁺).

Example 246

Preparation of cis-1-(4-aminophenyl)-2-(5-hydroxy-adamantan-2-yl)-4,4-dimethyl-1,2-diazetidin-3-one cis-2-(5-Hydroxyadamantan-2-yl)-4,4-dimethyl-1-(4-nitrophenyl)-1,2-diazetidin-3-one prepared in Example 245 was used for a similar reaction and treatment as Example 183, and the title compound was obtained as a brown oil.

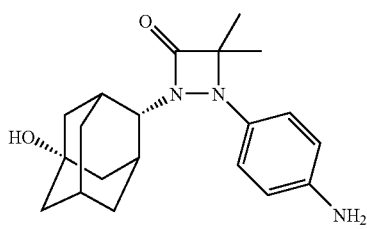

¹H-NMR (400 MHz, CDCl₃) δ; 0.87 (br, 3H), 1.42-1.77 (m, 11H), 2.10-2.33 (m, 5H), 2.85 (s, 1H), 3.54 (s, 1H), 3.60 (br, 2H), 6.66 (d, J=8.8 Hz, 2H), 6.88 (d, J=8.8 Hz, 2H).
IR (ATR); 3333, 2918, 2857, 2360, 2341, 1741, 1652, 1509, 1113, 754 cm⁻¹.
EI-MS m/z; 341 (M⁺).

Example 247

Preparation of cis-2-(5-hydroxyadamantan-2-yl)-4,4-dimethyl-1-(naphthalen-1-yl)-1,2-diazetidin-3-one cis-2-(5-Hydroxyadamantan-2-yl)-4,4-dimethyl-1,2-diazetidin-3-one prepared in Process 4 of Example 239 and 1-bromonaphtalene were used for a similar reaction and treatment as Example 181, and the title compound was obtained as a pale yellow oil.

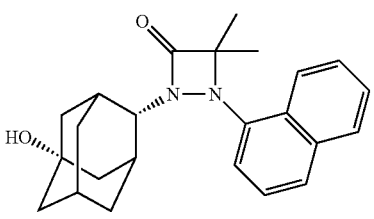

¹H-NMR (400 MHz, CDCl₃) δ; 0.80 (s, 3H), 1.43-1.80 (m, 9H), 1.87 (s, 3H), 2.10-2.36 (m, 4H), 3.05 (s, 1H), 3.66 (s, 1H), 7.24 (d, J=7.1 Hz, 1H), 7.44-7.54 (m, 3H), 7.64 (d, J=8.3 Hz, 1H), 7.84-7.87 (m, 1H), 8.26-8.28 (m, 1H).
IR (ATR); 3409, 2923, 2858, 1744, 1390, 1115, 776, 752 cm⁻¹.
EI-MS m/z; 376 (M⁺).

Example 248

Preparation of cis-2-(5-hydroxyadamantan-2-yl)-4,4-dimethyl-1-(naphthalen-2-yl)-1,2-diazetidin-3-one cis-2-(5-Hydroxyadamantan-2-yl)-4,4-dimethyl-1,2-diazetidin-3-one and 2-bromonaphthalene were used for a similar reaction and treatment as Example 181, and the title compound was obtained as a colorless oil.

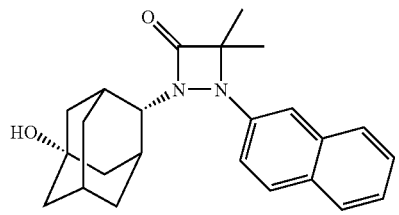

¹H-NMR (400 MHz, CDCl₃) δ; 1.21 (s, 3H), 1.25 (s, 3H), 1.50-2.20 (m, 13H), 2.80 (br, 1H), 3.72 (s, 1H), 7.14 (br, 1H), 7.41-7.52 (m, 3H), 7.91-7.83 (m, 3H).
IR (ATR); 3401, 2921, 2859, 1751, 1629, 1454, 1217, 1119, 1097, 980, 821, 751 cm⁻¹.
EI-MS m/z; 376 (M⁺).

Example 249

Preparation of cis-1-(4-fluoronaphthalen-1-yl)-2-(5-hydroxyadamantan-2-yl)-4,4-dimethyl-1,2-diazetidin-3-one cis-2-(5-Hydroxyadamantan-2-yl)-4,4-dimethyl-1,2-diazetidin-3-one and 1-bromo-4-fluoronaphthalene were used for a similar reaction and treatment as Example 181, and the title compound was obtained as a colorless oil.

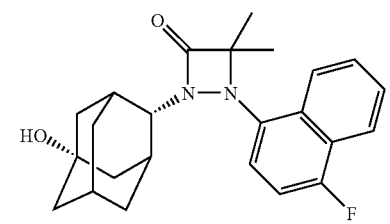

¹H-NMR (400 MHz, CDCl₃) δ; 0.81 (s, 3H), 1.42-1.53 (m, 2H), 1.68-1.73 (m, 5H), 1.85 (s, 3H), 2.10-2.12 (m, 1H), 2.20-2.24 (m, 2H), 2.31-2.34 (m, 1H), 3.01 (s, 1H), 3.62 (s, 1H), 7.11-7.20 (m, 2H), 7.55-7.62 (m, 2H), 8.09-8.12 (m, 1H), 8.26-8.29 (m, 1H).

IR (ATR); 3398, 2920, 2861, 1752, 1601, 1461, 1391, 983, 753 cm$^{-1}$.
EI-MS m/z; 394 (M$^+$).

Example 250

Preparation of trans-2-(5-chloroadamantan-2-yl)-1-(2-methoxyphenyl)-4,4-dimethyl-1,2-diazetidin-3-one

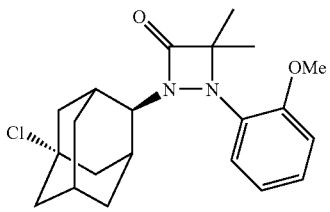

Process 1: Preparation of benzyl 2-(5-chloroadamantan-2-ylidene)hydrazinecarboxylate 5-Chloro-2-adamantanone was used in place of 2-adamantanone for a similar reaction and treatment as Process 1 of Example 1, and benzyl 2-(5-chloroadamantan-2-ylidene)hydrazinecarboxylate was obtained as a white crystalline powder.

$^1$H-NMR (400 MHz, CDCl$_3$) δ; 1.72-1.75 (m, 1H), 1.84-1.91 (m, 3H), 2.16-2.29 (m, 7H), 2.93 (s, 1H), 3.03 (s, 1H), 5.24 (s, 2H), 7.34-7.42 (m, 5H), 7.65 (s, 1H).

Process 2: Preparation of benzyl trans-2-(5-chloroadamantan-2-yl)hydrazinecarboxylate Benzyl 2-(5-chloroadamantan-2-ylidene)hydrazinecarboxylate was used for a similar reaction and treatment as Process 2 of Example 1, the resultant two geometric isomers were separated using silica gel chromatography, and benzyl trans-2-(5-chloroadamantan-2-yl)hydrazinecarboxylate was obtained as a colorless amorphous solid.

$^1$H-NMR (400 MHz, CDCl$_3$) δ; 1.37-2.70 (m, 12H), 3.16 (s, 1H), 3.95 (br, 1H), 5.12 (s, 2H), 5.24 (s, 1H), 6.28 (s, 1H), 7.32-7.38 (m, 5H).

Process 3: Preparation of benzyl trans-2-(2-bromoisobutyryl)-2-(5-chloroadamantan-2-yl)hydrazinecarboxylate Benzyl trans-2-(5-chloroadamantan-2-yl)hydrazinecarboxylate and 2-bromoisobutyryl bromide were used for a similar reaction and treatment as Process 3 of Example 1, and benzyl trans-2-(2-bromoisobutyryl)-2-(5-chloroadamantan-2-yl)hydrazinecarboxylate was obtained as a colorless amorphous solid.

$^1$H-NMR (400 MHz, CDCl$_3$) δ; 1.54-2.27 (m, 18H), 2.60 (s, 1H), 4.13-4.35 (m, 1H), 5.07-5.30 (m, 2H), 6.81-7.09 (m, 1H), 7.34-7.37 (m, 5H).

Process 4: Preparation of benzyl trans-2-(5-chloroadamantan-2-yl)-4,4-dimethyl-3-oxo-1,2-diazetidine-1-carboxylate Benzyl trans-2-(2-bromoisobutyryl)-2-(5-chloroadamantan-2-yl)hydrazinecarboxylate was used for a similar reaction and treatment as Process 4 of Example 1, and benzyl trans-2-(5-chloroadamantan-2-yl)-4,4-dimethyl-3-oxo-1,2-diazetidine-1-carboxylate was obtained as a colorless oil.

$^1$H-NMR (400 MHz, CDCl$_3$) δ; 1.48 (s, 6H), 1.54-2.27 (m, 12H), 2.58 (s, 1H), 3.99 (s, 1H), 5.18 (s, 2H), 7.37-7.41 (m, 5H).

Process 5: Preparation of trans-2-(5-chloroadamantan-2-yl)-4,4-dimethyl-1,2-diazetidin-3-one Benzyl trans-2-(5-chloroadamantan-2-yl)-4,4-dimethyl-3-oxo-1,2-diazetidine-1-carboxylate was used for a similar reaction and treatment as Process 5 of Example 1, and trans-2-(5-chloroadamantan-2-yl)-4,4-dimethyl-1,2-diazetidin-3-one was obtained as a white crystalline powder.

$^1$H-NMR (400 MHz, CDCl$_3$) δ; 1.44-2.18 (m, 18H), 2.76 (s, 1H), 3.69 (s, 1H), 3.84 (s, 1H).

Process 6: Preparation of trans-2-(5-chloroadamantan-2-yl)-1-(2-methoxyphenyl)-4,4-dimethyl-1,2-diazetidin-3-one trans-2-(5-Chloroadamantan-2-yl)-4,4-dimethyl-1,2-diazetidin-3-one and 1-bromo-2-methoxybenzene were used for a similar reaction and treatment as Example 181, and the title compound was obtained as a colorless oil.

$^1$H-NMR (400 MHz, CDCl$_3$) δ; 0.95 (s, 3H), 1.53-1.63 (m, 2H), 1.67 (s, 3H), 2.08-2.36 (m, 10H), 2.85 (s, 1H), 3.74 (s, 1H), 3.83 (s, 3H), 6.88 (d, J=8.0 Hz, 1H), 6.94-7.00 (m, 2H), 7.07 (t, J=8.0 Hz, 1H).

IR (ATR); 2935, 1759, 1589, 1492, 1246, 1027, 829, 755 cm$^{-1}$.

EI-MS m/z; 374 (M$^+$).

Example 251

Preparation of trans-2-(5-chloroadamantan-2-yl)-1-(2,3-dichlorophenyl)-4,4-dimethyl-1,2-diazetidin-3-one trans-2-(5-Chloroadamantan-2-yl)-4,4-dimethyl-1,2-diazetidin-3-one prepared in Process 5 of Example 250 and 1-bromo-2,3-dichlorobenzene were used for a similar reaction and treatment as Example 181, and the title compound was obtained as a colorless oil.

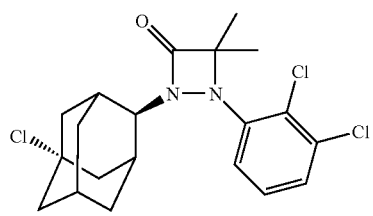

$^1$H-NMR (400 MHz, CDCl$_3$) δ; 1.01 (s, 3H), 1.51-1.54 (m, 1H), 1.63-1.66 (m, 1H), 1.80 (s, 3H), 1.99-2.26 (m, 10H), 2.87 (s, 1H), 3.68 (s, 1H), 7.09 (dd, J=2.0, 8.0 Hz, 1H), 7.23 (t, J=8.0 Hz, 1H), 7.26 (dd, J=2.0, 8.0 Hz, 1H).

IR (ATR); 2935, 1763, 1576, 1446, 1421, 1029, 830, 754 cm$^{-1}$.

EI-MS m/z; 414 (M$^+$).

Example 252

Preparation of trans-2-(5-chloroadamantan-2-yl)-1-[2-(methoxymethoxy)phenyl]-4,4-dimethyl-1,2-diazetidin-3-one trans-2-(5-Chloroadamantan-2-yl)-4,4-dimethyl-1,2-diazetidin-3-one and 1-bromo-2-(methoxymethoxy)benzene were used for a similar reaction and treatment as Example 181, and the title compound was obtained as a colorless oil.

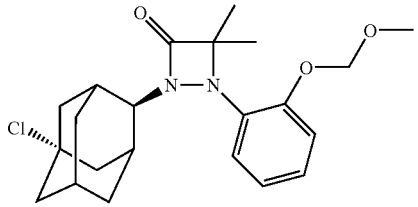

$^1$H-NMR (400 MHz, CDCl$_3$) δ; 0.99 (s, 3H), 1.49-1.54 (m, 1H), 1.64-1.67 (m, 1H), 1.69 (s, 1H), 2.07-2.30 (m, 10H), 2.91 (s, 1H), 3.58 (s, 3H), 3.76 (s, 1H), 5.18 (s, 2H), 7.01-7.14 (m, 4H).
IR (ATR); 2935, 2864, 1761, 1489, 1155, 994, 759 cm$^{-1}$.
EI-MS m/z; 404 (M$^+$).

Example 253

Preparation of trans-2-(5-chloroadamantan-2-yl)-1-(2-hydroxyphenyl)-4,4-dimethyl-1,2-diazetidin-3-one trans-2-(5-Chloroadamantan-2-yl)-1-[2-(methoxymethoxy)phenyl]-4,4-dimethyl-1,2-diazetidin-3-one prepared in Example 252 was used for a similar reaction and treatment as Example 215, and the title compound was obtained as a white crystalline powder.

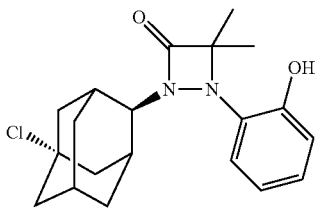

$^1$H-NMR (400 MHz, CDCl$_3$) δ; 1.01 (s, 3H), 1.56-1.58 (m, 2H), 1.59 (s, 3H), 1.98-2.22 (m, 10H), 2.68 (s, 1H), 3.63 (s, 1H), 6.21 (s, 1H), 6.91 (t, J=7.6 Hz, 1H), 6.95 (d, J=7.6 Hz, 1H), 7.13 (t, J=7.6 Hz, 1H), 7.17 (d, J=7.6 Hz, 1H).
IR (ATR); 3417, 2922, 2359, 1744, 1488, 1255, 1031, 829, 750 cm$^{-1}$.
EI-MS m/z; 360 (M$^+$).

Example 254

Preparation of trans-2-(5-chloroadamantan-2-yl)-4,4-dimethyl-1-(naphthalen-1-yl)-1,2-diazetidin-3-one trans-2-(5-Chloroadamantan-2-yl)-4,4-dimethyl-1,2-diazetidin-3-one prepared in Process 5 of Example 250 and 1-bromonaphtalene were used for a similar reaction and treatment as Example 181, and the title compound was obtained as a pale yellow oil.

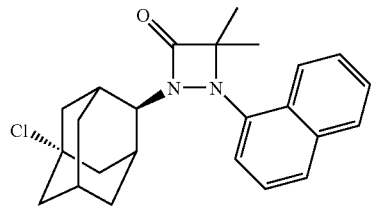

$^1$H-NMR (400 MHz, CDCl$_3$) δ; 0.80 (s, 3H), 1.48-1.51 (m, 1H), 1.59-1.61 (m, 1H), 1.85 (s, 3H), 2.00-2.37 (m, 10H), 2.97 (s, 1H), 3.81 (s, 1H), 7.23 (d, J=7.4 Hz, 1H), 7.46-7.52 (m, 3H), 7.65 (d, J=8.1 Hz, 1H), 7.84-7.86 (m, 1H), 8.23-8.26 (m, 1H).
IR (ATR); 2935, 2863, 1756, 1390, 1025, 776, 755 cm$^{-1}$.
EI-MS m/z; 394 (M$^+$).

Example 255

Preparation of trans-2-(5-chloroadamantan-2-yl)-1-(4-fluoronaphthalen-1-yl)-4,4-dimethyl-1,2-diazetidin-3-one trans-2-(5-Chloroadamantan-2-yl)-4,4-dimethyl-1,2-diazetidin-3-one and 1-bromo-4-fluoronaphthalene were used for a similar reaction and treatment as Example 181, and the title compound was obtained as a colorless oil.

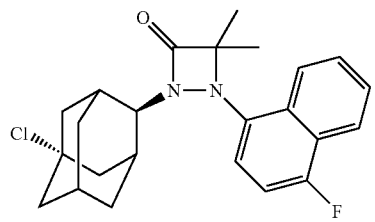

$^1$H-NMR (400 MHz, CDCl$_3$) δ; 0.81 (s, 3H), 1.50-1.53 (m, 1H), 1.66-1.69 (m, 1H), 1.83 (s, 3H), 2.00-2.38 (m, 10H), 2.92 (s, 1H), 3.77 (s, 1H), 7.11-7.19 (m, 2H), 7.52-7.61 (m, 1H), 8.09-8.12 (m, 1H), 8.24-8.27 (m, 1H).
IR (ATR); 2936, 2864, 1758, 1391, 1262, 763 cm$^{-1}$.
EI-MS m/z; 412 (M$^+$).

Example 256

Preparation of cis-2-(5-chloroadamantan-2-yl)-1-(2,3-dichlorophenyl)-4,4-dimethyl-1,2-diazetidin-3-one

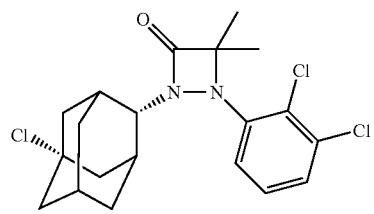

Process 1: Preparation of benzyl cis-2-(5-chloroadamantan-2-yl)hydrazinecarboxylate Benzyl 2-(5-chloroadamantan-2-ylidene)hydrazinecarboxylate prepared in Process 1 of Example 250 was used for a similar reaction and treatment as Process 2 of Example 1, the resultant two geometric isomers were separated using silica gel chromatography, and benzyl cis-2-(5-chloroadamantan-2-yl)hydrazinecarboxylate was obtained as a colorless amorphous solid.

$^1$H-NMR (400 MHz, CDCl$_3$) δ; 1.62 (d, J=11.7 Hz, 2H), 1.75 (d, J=12.7 Hz, 2H), 1.84 (d, J=11.7 Hz, 2H), 2.05-2.18 (m, 5H), 2.48 (d, J=11.7 Hz, 2H), 3.09 (s, 1H), 3.88 (s, 1H), 5.12 (s, 2H), 6.26 (s, 1H), 7.32-7.39 (m, 5H).

Process 2: Preparation of benzyl cis-2-(2-bromoisobutyryl)-2-(5-chloroadamantan-2-yl)hydrazinecarboxylate Benzyl cis-2-(5-chloroadamantan-2-yl)hydrazinecarboxylate and 2-bromoisobutyryl bromide were used for a similar reaction and treatment as Process 3 of Example 1, and benzyl cis-2-(2-bromoisobutyryl)-2-(5-chloroadamantan-2-yl)hydrazinecarboxylate was obtained as a colorless amorphous solid.

$^1$H-NMR (400 MHz, CDCl$_3$) δ; 1.65-1.79 (m, 7H), 1.93-2.24 (m, 11H), 2.60 (s, 1H), 4.03-4.25 (m, 1H), 5.08-5.29 (m, 2H), 6.88-7.17 (m, 1H), 7.35-7.38 (m, 5H).

Process 3: Preparation of benzyl cis-2-(5-chloro adamantan-2-yl)-4,4-dimethyl-3-oxo-1,2-diazetidine-1-carboxylate Benzyl cis-2-(2-bromoisobutyryl)-2-(5-chloroadamantan-2-yl)hydrazinecarboxylate was used for a similar reaction and treatment as Process 4 of Example 1, and benzyl cis-2-(5-chloro adamantan-2-yl)-4,4-dimethyl-3-oxo-1,2-diazetidine-1-carboxylate was obtained as a colorless oil.

$^1$H-NMR (400 MHz, CDCl$_3$) δ; 1.50 (s, 6H), 1.63-2.42 (m, 11H), 2.64 (s, 2H), 3.89 (s, 1H), 5.19 (s, 2H), 7.30-7.38 (m, 5H).

Process 4: Preparation of cis-2-(5-chloroadamantan-2-yl)-4,4-dimethyl-1,2-diazetidin-3-one Benzyl cis-2-(5-chloro adamantan-2-yl)-4,4-dimethyl-3-oxo-1,2-diazetidine-1-carboxylate was used for a similar reaction and treatment as Process 5 of Example 1, and cis-2-(5-chloroadamantan-2-yl)-4,4-dimethyl-1,2-diazetidin-3-one was obtained as a colorless oil.

$^1$H-NMR (400 MHz, CDCl$_3$) δ; 1.51-2.56 (m, 19H), 3.61 (s, 1H), 3.88 (br, 1H).

Process 5: Preparation of cis-2-(5-chloroadamantan-2-yl)-1-(2,3-dichlorophenyl)-4,4-dimethyl-1,2-diazetidin-3-one cis-2-(5-Chloroadamantan-2-yl)-4,4-dimethyl-1,2-diazetidin-3-one and 1-bromo-2,3-dichlorobenzene were used for a similar reaction and treatment as Example 181, and the title compound was obtained as a colorless oil.

$^1$H-NMR (400 MHz, CDCl$_3$) δ; 1.01 (s, 3H), 1.51-1.81 (m, 4H), 1.83 (s, 3H), 1.95-1.98 (m, 1H), 2.05-2.12 (m, 5H), 2.56-2.63 (m, 2H), 32.95 (s, 1H), 3.58 (s, 1H), 7.10 (dd, J=1.7, 8.1 Hz, 1H), 7.22 (t, J=8.1 Hz, 1H), 7.26 (dd, J=1.7, 8.1 Hz, 1H).

IR (ATR); 2928, 2861, 1763, 1576, 1446, 1421, 1029, 754 cm$^{-1}$.

EI-MS m/z; 414 (M$^+$).

Example 257

Preparation of cis-2-(5-chloroadamantan-2-yl)-4,4-dimethyl-1-(naphthalen-1-yl)-1,2-diazetidin-3-one cis-2-(5-Chloroadamantan-2-yl)-4,4-dimethyl-1,2-diazetidin-3-one prepared in Process 4 of Example 256 and 1-bromonaphtalene were used for a similar reaction and treatment as Example 181, and the title compound was obtained as a colorless oil.

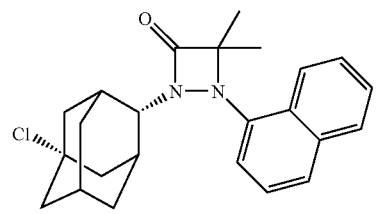

$^1$H-NMR (400 MHz, CDCl$_3$) δ; 0.81 (s, 3H), 1.47-1.50 (m, 1H), 1.58-1.72 (m, 2H), 1.81-1.84 (m, 1H), 1.89 (s, 3H), 1.94-1.97 (m, 1H), 2.06-2.16 (m, 5H), 2.68-2.7 (m, 2H), 3.08 (s, 1H), 3.72 (s, 1H), 7.23 (d, J=7.3 Hz, 1H), 7.46 (t, J=8.0 Hz, 1H), 7.51-7.54 (m, 2H), 7.65 (d, J=8.0 Hz, 1H), 7.83-7.87 (m, 1H), 8.25-8.28 (m, 1H).

IR (ATR); 2928, 2861, 1756, 1390, 800, 776 cm$^{-1}$.

EI-MS m/z; 394 (M$^+$).

Example 258

Preparation of 1-(1,3-benzodioxol-4-yl)-4,4-dimethyl-2-(adamantan-2-yl)-1,2-diazetidin-3-one 1-Bromo-2,3-(methylenedioxy)benzene was used in place of bromobenzene for a similar reaction and treatment as Example 181, and the title compound was obtained as a pale yellow amorphous.

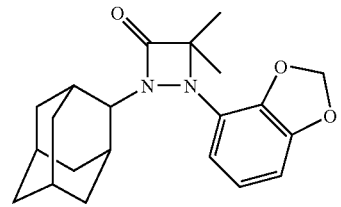

$^1$H-NMR (400 MHz, CDCl$_3$) δ; 1.07-2.62 (m, 14H), 3.76 (s, 1H), 5.96 (s, 2H), 6.64 (d, J=8.0 Hz, 2H), 6.82 (t, J=8.0 Hz, 1H).

IR (ATR); 2910, 2856, 1759, 1457, 774 cm$^{-1}$.

EI-MS m/z; 354 (M$^+$).

Example 259

Preparation of trans-1-(1,3-benzodioxol-4-yl)-2-(5-hydroxyadamantan-2-yl)-4,4-dimethyl-1,2-diazetidin-3-one trans-2-(5-Hydroxyadamantan-2-yl)-4,4-dimethyl-1,2-diazetidin-3-one prepared in Process 5 of Example 65 and 1-bromo-2,3-(methylenedioxy)benzene were used for a similar reaction and treatment as Example 181, and the title compound was obtained as a pale yellow amorphous.

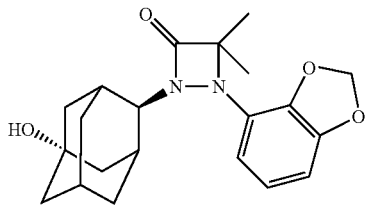

$^1$H-NMR (400 MHz, CDCl$_3$) δ; 1.07-2.20 (m, 13H), 2.81 (br, 1H), 3.69 (s, 1H), 5.97 (s, 2H), 6.64 (dd, J=8.0, 11.3 Hz, 2H), 6.83 (t, J=8.0 Hz, 1H).
IR (ATR); 3409, 2924, 2859, 1751, 1458, 1068, 774 cm$^{-1}$.
EI-MS m/z; 370 (M$^+$).

Example 260

Preparation of 4,4-dimethyl-1-[(2E)-3-phenylprop-2-en-1-yl]-2-(adamantan-2-yl)-1,2-diazetidin-3-one 2-(Adamantan-2-yl)-4,4-dimethyl-1,2-diazetidin-3-one prepared in Process 3 of Example 12 and cynnamylbromide were used for a similar reaction and treatment as Process 6 of Example 1, and the title compound was obtained as a colorless oil.

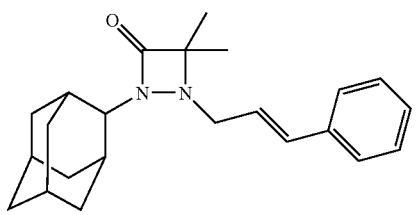

$^1$H-NMR (400 MHz, CDCl$_3$) δ; 1.41 (s, 3H), 1.47 (s, 3H), 1.58-1.82 (m, 10H), 2.10 (d, J=12.7 Hz, 1H), 2.23 (d, J=12.7 Hz, 1H), 2.40-2.43 (m, 2H), 3.57-3.68 (m, 3H), 6.19-6.27 (m, 1H), 6.58 (d, J=16.1 Hz, 1H), 7.25-7.37 (m, 5H).
IR (ATR); 2908, 2852, 1749, 1450, 1322, 968, 758, 734, 692 cm$^{-1}$.
EI-MS m/z; 350 (M$^+$).

Example 261

Preparation of 4,4-dimethyl-1-(3-phenylpropyl)-2-(adamantan-2-yl)-1,2-diazetidin-3-one

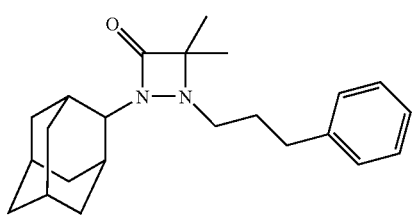

A solution of 4,4-dimethyl-1-[(2E)-3-phenylprop-2-en-1-yl]-2-(adamantan-2-yl)-1,2-diazetidin-3-one (30.0 mg, 0.0860 mmol) prepared in Example 260 in ethyl acetate (2 mL) was added with 10% palladium carbon (catalyst amount), and under a hydrogen atmosphere the resultant was stirred at room temperature for 1 hour. The reaction solution was filtered using celite, concentrated in vacuo, and the title compound (24.3 mg, 80.2%) was obtained as a colorless oil.
$^1$H-NMR (270 MHz, CDCl$_3$) δ; 1.33 (s, 3H), 1.43 (s, 3H), 1.54-1.83 (m, 12H), 2.04-2.05 (m, 1H), 2.10-2.11 (m, 1H), 2.29-2.33 (m, 2H), 2.62-2.84 (m, 4H), 3.54 (s, 1H), 7.16-7.31 (m, 5H).
IR (ATR); 2909, 2853, 1750, 1454, 1381, 1362, 1323, 1245, 700 cm$^{-1}$.
EI-MS m/z; 352 (M$^+$).

Example 262

Preparation of 4,4-dimethyl-1-(phenoxyactetyl)-2-(adamantan-2-yl)-1,2-diazetidin-3-one Phenoxyacetyl chloride was used in place of benzoyl chloride for a similar reaction and treatment as Example 96, and the title compound was obtained as a colorless oil.

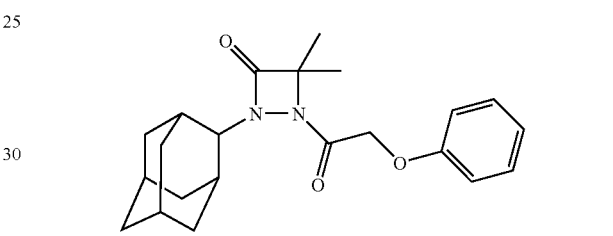

$^1$H-NMR (400 MHz, CDCl$_3$) δ; 1.58-1.63 (m, 2H), 1.69 (s, 6H), 1.73-1.88 (10H), 2.34 (s, 2H), 4.27 (s, 1H), 4.59 (s, 2H), 6.90 (d, J=7.3 Hz, 2H), 7.03 (t, J=7.3 Hz, 1H), 7.32 (t, J=7.3 Hz, 2H).
IR (ATR); 2916, 1760, 1676, 1491, 1227, 760 cm$^{-1}$.
EI-MS m/z; 368 (M$^+$).

Example 263

Preparation of 1-[(benzyloxy)acetyl]-4,4-dimethyl-2-(adamantan-2-yl)-1,2-diazetidin-3-one Benzyloxyacetyl chloride was used in place of benzoyl chloride for a similar reaction and treatment as Example 96, and the title compound was obtained as a colorless oil.

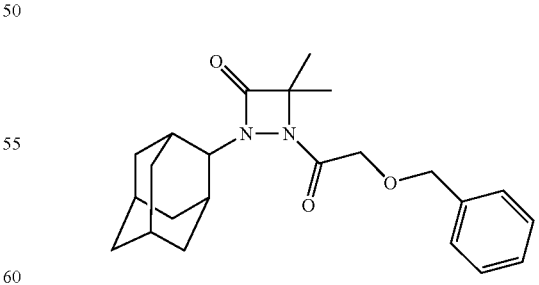

$^1$H-NMR (400 MHz, CDCl$_3$) δ; 1.56 (s, 6H), 1.66-2.02 (m, 12H), 2.36 (s, 2H), 4.10 (s, 2H), 4.27 (s, 1H), 4.59 (s, 2H), 7.33-7.37 (m, 5H).
IR (ATR); 2911, 1772, 1677, 1452, 1093, 987, 756, 708 cm$^{-1}$.
EI-MS m/z; 382 (M$^+$).

Example 264

Preparation of 4,4-dimethyl-1-[(phenylsulfanyl)acetyl]-2-(adamantan-2-yl)-1,2-diazetidin-3-one (Phenylthio)acetyl chloride was used in place of benzoyl chloride for a similar reaction and treatment as Example 96, and the title compound was obtained as a white amorphous solid.

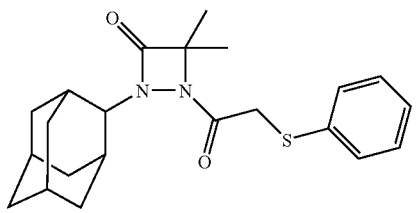

$^1$H-NMR (400 MHz, CDCl$_3$) δ; 1.54 (s, 6H), 1.58-1.86 (m, 12H), 2.19 (s, 2H), 3.55 (s, 2H), 4.22 (s, 1H), 7.25-7.33 (m, 3H), 7.45 (d, J=7.1 Hz, 2H).

IR (ATR); 2914, 1767, 1668, 1088, 745 cm$^{-1}$.

EI-MS m/z; 384 (M$^+$).

Example 265

Preparation of 4,4-dimethyl-1-[(E)-2-phenylethenyl]-2-(adamantan-2-yl)-1,2-diazetidin-3-one

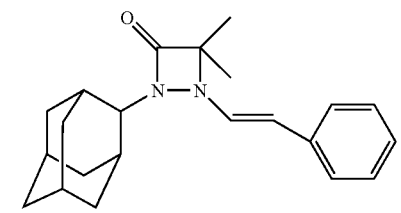

A solution of 2-(adamantan-2-yl)-4,4-dimethyl-1,2-diazetidin-3-one (50.0 mg, 0.213 mmol) prepared in Process 3 of Example 12 in chloroform (3 mL) was added sequentially with phenylacetaldehyde (25.6 mg, 0.213 mmol), sodium triacetoxyborohydride (67.8 mg, 0.320 mmol) and acetic acid (15.4 mg, 0.256 mmol) at room temperature, and the resultant was stirred at the same temperature for 2 hours. The reaction solution was added with water and extracted with chloroform. The organic layer was dried over anhydrous sodium sulfate, concentrated in vacuo, the obtained residue was purified using Preparatory Thin-Layer chromatography (hexane:ethyl acetate=4:1), and the title compound (3.70 mg, 5.20%) was obtained as a colorless oil.

$^1$H-NMR (400 MHz, CDCl$_3$) δ; 1.44 (s, 6H), 1.64-1.91 (m, 10H), 2.17 (d, J=12.0 Hz, 2H), 2.45 (s, 2H), 3.81 (s, 1H), 6.11 (d, J=14.0 Hz, 1H), 6.62 (d, J=14.0 Hz, 1H), 7.18-7.22 (m, 1H), 7.27-7.32 (m, 4H).

EI-MS m/z; 336 (M$^+$).

Example 266

Preparation of 4,4-dimethyl-1-(2-phenylethyl)-2-(adamantan-2-yl)-1,2-diazetidin-3-one

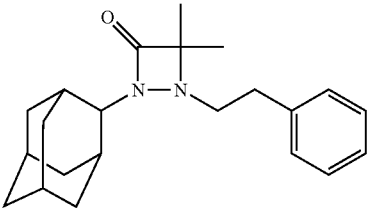

A solution of 4,4-dimethyl-1-[(E)-2-phenylethenyl]-2-(adamantan-2-yl)-1,2-diazetidin-3-one (38.4 mg, 0.103 mmol) prepared in Example 265 in methanol (2 mL) was added with 10% palladium carbon (catalyst amount), and the resultant was stirred at room temperature for 40 minutes under a hydrogen atmosphere. The reaction solution was filtered using celite, concentrated in vacuo, the obtained residue was purified using Preparatory Thin-Layer chromatography (hexane:ethyl acetate=2:1), and the title compound (1.80 mg, 5.20%) was obtained as a white crystalline powder.

$^1$H-NMR (400 MHz, CDCl$_3$) δ; 1.45 (s, 3H), 1.48 (s, 3H), 1.52-1.87 (m, 10H), 2.09 (d, J=12.9 Hz, 1H), 2.19 (d, J=12.6 Hz, 1H), 2.34 (m, 2H), 2.61-2.68 (m, 1H), 2.75-2.82 (m, 1H), 2.97-3.11 (m, 2H), 3.58 (s, 1H), 7.19-7.32 (m, 5H).

IR (ATR); 2913, 1763, 1250, 754, 700 cm$^{-1}$.

EI-MS m/z; 338 (M$^+$).

Example 267

Preparation of 4,4-dimethyl-2-(adamantan-2-yl)-1-{[2-(trifluoromethyl)phenoxy]acetyl}-1,2-diazetidin-3-one

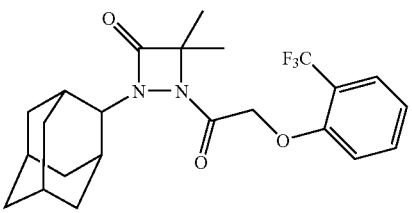

Process 1: Preparation of 2-trifluoromethyl phenoxyethyl acetate

A solution of 2-trifluoromethylphenol (300 mg, 1.85 mmol) in N,N-dimethylformamide (5 mL) was added with bromoethylacetate (340 mg, 2.04 mmol) and potassium carbonate (384 mg, 2.78 mmol) at room temperature, and the resultant was stirred at the same temperature for 15 hours. The reaction solution was added with water and extracted with ethyl acetate. The organic layer was washed with brine, dried with anhydrous sodium sulfate, concentrated in vacuo, the obtained residue was purified using silica gel chromatography (hexane:ethyl acetate=2:1), and 2-trifluoromethyl phenoxyehtyl acetate (430 mg, 100%) was obtained as a colorless oil.

¹H-NMR (400 MHz, CDCl₃) δ; 1.28 (t, J=7.1 Hz, 3H), 4.26 (q, J=7.1 Hz, 2H), 4.72 (s, 2H), 6.88 (d, J=7.8 Hz, 1H), 7.06 (t, J=7.8 Hz, 1H), 7.47 (t, J=7.8 Hz, 1H), 7.60 (d, J=7.8 Hz, 1H).

Process 2: Preparation of 2-trifluoromethyl phenoxyacetic acid

A solution of 2-trifluoromethylphenoxy ethyl acetate (429 mg, 1.85 mmol) in ethanol (4 mL) was added with an aqueous solution of 4N-sodium hydroxide (1 mL) at room temperature, and the resultant was stirred at the same temperature for 1.5 hours. The reaction solution was concentrated in vacuo, the residue was added with 2N-hydrochloric acid, and extrated with chloroform. The organic layer was dried over anhydrous sodium sulfate, concentrated in vacuo, 2-trifluoromethyl phenoxyacetic acid (376 mg, 92.3%) was obtained as a white crystalline powder.

¹H-NMR (400 MHz, CDCl₃) δ; 4.79 (s, 2H), 7.04-7.10 (m, 2H), 7.54 (t, J=7.8; H, 1H), 7.59 (d, J=7.8 Hz, 1H).

Process 3: Preparation of 4,4-dimethyl-2-(adamantan-2-yl)-1-{[2-(trifluoromethyl)phenoxy]acetyl}-1,2-diazetidin-3-one 2-Trifluoromethyl phenoxyacetic acid was used in place of 3-fluoro-2-methylbenzoic acid for a similar reaction and treatment as Example 157, and the title compound was obtained as a colorless oil.

¹H-NMR (400 MHz, CDCl₃) δ; 1.61 (s, 6H), 1.66-1.80 (m, 12H), 2.36 (s, 2H), 4.29 (s, 1H), 4.67 (s, 2H), 6.95 (d, J=8.3 Hz, 1H), 7.12 (t, J=8.3 Hz, 1H), 7.49 (t, J=8.3 Hz, 1H), 7.61 (d, J=8.3 Hz, 1H).

IR (ATR); 2914, 2855, 2360, 2342, 1775, 1684, 1496, 1461, 1321, 1132, 1119, 1039, 761 cm⁻¹.

EI-MS m/z; 436 (M⁺).

Example 268

Preparation of 4,4-dimethyl-2-(adamantan-2-yl)-1-{[2,2-dimethyl-2-(trifluoromethyl)phenoxy]acetyl}-1,2-diazetidin-3-one

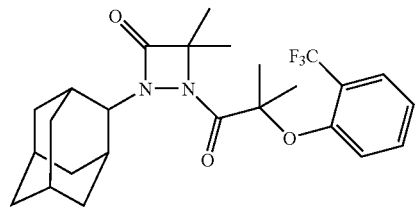

Process 1: Preparation of 2-methyl-2-[2-(trifluoromethyl)phenoxy]propionic acid A solution of 2-(trifluoromethyl)phenol (3.20 g, 20.0 mmol) in acetone (20 mL) was added with 1,1,1-trichloro-2-methyl-2-propanol 0.5 hydrate (7.82 g, 40.0 mmol) and sodium hydrate (3.20 g, 80.0 mmol) at 0° C., and the resultant was stirred at room temperature for 20 hours. The reaction solution was concentrated in vacuo, added with water, and washed with diethylether. The aqueous layer was neutralized with concentrated hydrochloric acid, and extracted with chloroform. The organic layer was dried over anhydrous sodium sulfate, concentrated in vacuo, and 2-methyl-2-[2-(trifluoromethyl)phenoxy]propionic acid (1.35 g, 27.2%) was obtained as a white amorphous solid.

¹H-NMR (400 MHz, CDCl₃) δ; 1.67 (s, 6H), 6.97 (d, J=8.3 Hz, 1H), 7.10 (t, J=8.3 Hz, 1H), 7.45 (t, J=8.3 Hz, 1H), 7.60 (d, J=8.3 Hz, 1H).

Process 2: Preparation of 4,4-dimethyl-2-(adamantan-2-yl)-1-{[2,2-dimethyl-2-(trifluoromethyl)phenoxy]acetyl}-1,2-diazetidin-3-one A solution of 2-methyl-2-[2-(trifluoromethyl)phenoxy] propionic acid (50.0 mg, 0.200 mmol) in dichloromethane (1 mL) was added with oxalyl chloride (50.3 mg, 0.400 mmol) and N,N-dimethylformamide (catalyst amount) at room temperature, and the resultant was stirred at the same temperature for 30 minutes. The reaction solution was concentrated in vacuo to make a solution of dichloromethane (1 mL), added with diisopropylethylamine (78.0 mg, 0.600 mmol), and 2-(adamantan-2-yl)-4,4-dimethyl-1,2-diazetidin-3-one (46.9 mg, 0.200 mmol) at room temperature, and the resultant was stirred at the same temperature for 20 hours. The reaction solution was added with water and extracted with chloroform. The organic layer was dried over anhydrous sodium sulfate, concentrated in vacuo, the obtained residue was purified using Preparatory Thin-Layer chromatography (hexane:ethyl acetate=4:1), and the title compound (38.9 mg, 83.7%) was obtained as a colorless oil.

¹H-NMR (400 MHz, CDCl₃) δ; 1.52 (s, 6H), 1.60 (s, 6H), 1.73-2.05 (m, 12H), 2.36 (s, 2H), 4.32 (s, 1H), 7.14 (t, J=7.8 Hz, 1H), 7.25 (d, J=7.8 Hz, 1H), 7.43 (t, J=7.8 Hz, 1H), 7.60 (d, J=7.8 Hz, 1H).

IR (ATR); 2912, 2856, 1775, 1675, 1491, 1319, 1156, 1132, 1113, 1056, 762 cm⁻¹.

Example 269

Preparation of N-(4-chlorophenyl)-4,4-dimethyl-3-oxo-2-(adamantan-2-yl)-1,2-diazetidine-1-carboxamide

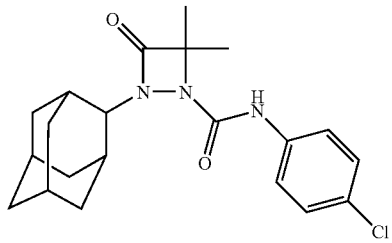

A solution of 2-(adamantan-2-yl)-4,4-dimethyl-1,2-diazetidin-3-one (30.0 mg, 0.128 mmol) prepared in Process 3 of Example 12 in dichloromethane (3 mL) was added sequentially with 4-chlorophenyl isocyanate (19.7 mg, 0.128 mmol), triethylamine (19.4 mg, 0.192 mmol), DMAP (catalyst amount) at room temperature, and the resultant was stirred at the same temperature for 1.5 hours. The reaction solution was filtered using celite, concentrated in vacuo, and the obtained residue was purified using Preparatory Thin-Layer chromatography (hexane:ethyl acetate=2:1), and the title compound (49.7 mg, 100%) was obtained as a white crystalline powder.

$^1$H-NMR (400 MHz, CD$_3$OD) δ; 1.54 (s, 6H), 1.67 (d, J=12.7 Hz, 2H), 1.78-1.91 (m, 8H), 2.09 (d, J=12.7 Hz, 2H), 2.33 (s, 2H), 4.04 (s, 1H), 7.27-7.31 (m, 2H), 7.45-7.50 (m, 2H).

IR (ATR); 3258, 2907, 1736, 1711, 1492, 1225, 823 cm$^{-1}$.

EI-MS m/z; 387 (M$^+$).

Example 270

Preparation of 1-{[(5-bromopyridin-2-yl)oxy]acetyl}-4,4-dimethyl-2-(adamantan-2-yl)-1,2-diazetidin-3-one

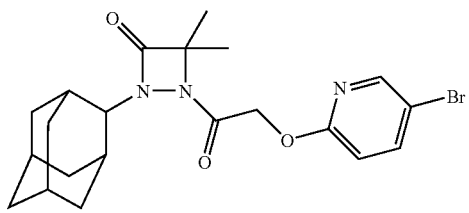

Process 1: Preparation of 4,4-dimethyl-1-(hydroxyacetyl)-2-(adamantan-2-yl)-1,2-diazetidin-3-one A solution of 1-[(benzyloxy)acetyl]-4,4-dimethyl-2-(adamantan-2-yl)-1,2-diazetidin-3-one (151 mg, 0.400 mmol) prepared in Example 263 in ethanol (3 mL) was added with 10% palladium carbon (catalyst amount), and under a hydrogen atmosphere the resultant was stirred at room temperature for 20 hours. The reaction solution was filtered using celite, concentrated in vacuo, the obtained residue was purified using silica gel chromatography (hexane:ethyl acetate=2:1), and 4,4-dimethyl-1-(hydroxyacetyl)-2-(adamantan-2-yl)-1,2-diazetidin-3-one (52.0 mg, 44.5%) was obtained as a white crystalline powder.

$^1$H-NMR (400 MHz, CDCl$_3$) δ; 1.62 (s, 6H), 1.65-1.88 (m, 10H), 1.98-2.01 (m, 2H), 2.35 (s, 2H), 4.09 (s, 2H), 4.26 (s, 1H).

Process 2: Preparation of 1-{[(5-bromopyridin-2-yl)oxy]acetyl}-4,4-dimethyl-2-(adamantan-2-yl)-1,2-diazetidin-3-one Under an argon atmosphere, a solution of 4,4-dimethyl-1-(hydroxyacetyl)-2-(adamantan-2-yl)-1,2-diazetidin-3-one (14.0 mg, 0.0480 mmol) in N,N-dimethylformamide (0.5 mL) was added with sodium hydroxide (excess amount) and 5-bromo-2-fluoropyridine (26.4 mg, 0.150 mmol) at room temperature, and the resultant was stirred at the same temperature for 1 hour. The reaction solution was added with water and extracted with diethyl ether. The organic layer was dried over anhydrous sodium sulfate, concentrated in vacuo, the obtained residue was purified using Preparatory Thin-Layer chromatography (hexane:ethyl acetate=2:1), and the title compound (2.20 mg, 10.2%) was obtained as a colorless oil.

$^1$H-NMR (400 MHz, CDCl$_3$) δ; 1.47-1.59 (m, 2H), 1.64 (s, 6H), 1.72-1.84 (m, 10H), 2.33 (s, 2H), 4.23 (s, 1H), 4.83 (s, 2H), 6.76 (d, J=8.6 Hz, 1H), 7.71 (dd, J=2.4 Hz, 1H), 8.14 (d, J=2.4 Hz, 1H).

EI-MS m/z; 448 (M$^+$).

Example 271

Preparation of 6-{2-[4,4-dimethyl-3-oxo-2-(adamantan-2-yl)-1,2-diazetidin-1-yl]ethoxy}pyridine-3-carbonitrile

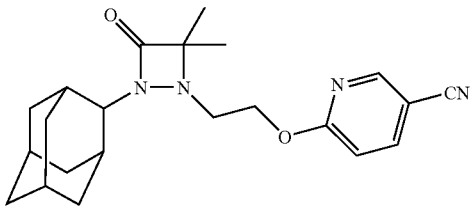

Process 1: Preparation of ethyl [4,4-dimethyl-3-oxo-2-(adamantan-2-yl)-1,2-diazetidin-1-yl]acetate Under an argon atmosphere, a solution of 2-(adamantan-2-yl)-4,4-dimethyl-1,2-diazetidin-3-one (234 mg, 1.00 mmol) prepared in Process 3 of Example 12 in N,N-dimethylformamide (2 mL) was added with potassium carbonate (277 mg, 2.00 mmol) and ethylbromoacetate (167 mg, 1.00 mmol) at room temperature, and the resultant was stirred at 80° C. for 20 hours. The reaction solution was added with water and extracted with diethyl ether. The organic layer was dried over anhydrous sodium sulfate, concentrated in vacuo, the obtained residue was purified using silica gel chromatography (hexane:ethyl acetate=2:1), and ethyl [4,4-dimethyl-3-oxo-2-(adamantan-2-yl)-1,2-diazetidin-1-yl]acetate (190 mg, 59.4%) was obtained as a colorless oil.

$^1$H-NMR (400 MHz, CDCl$_3$) δ; 1.28-1.86 (m, 19H), 2.11-2.50 (m, 4H), 3.58 (d, J=17.1 Hz, 1H), 3.78 (d, J=17.1 Hz, 1H), 4.18-4.24 (m, 3H).

Process 2: Preparation of 4,4-dimethyl-1-(2-hydroxyethyl)-2-(adamantan-2-yl)-1,2-diazetidin-3-one Under an argon atmosphere, a mixed solution of ethyl [4,4-dimethyl-3-oxo-2-(adamantan-2-yl)-1,2-diazetidin-1-yl]acetate (150 mg, 0.470 mmol) in tetrahydrofuran-methanol-water (10:1:1, 4 mL) was added with lithium borohydride (80.8 mg, 3.76 mmol) at room temperature, and the resultant was stirred at the same temperature for 1 hour. The reaction solution was added with a saturated aqueous solution of ammonium chloride, and extracted with chloroform. The organic layer was dried over anhydrous sodium sulfate, concentrated in vacuo, the obtained residue was purified using silica gel chromatography (hexane:ethyl acetate=2:1), and 4,4-dimethyl-1-(2-hydroxyethyl)-2-(adamantan-2-yl)-1,2-diazetidin-3-one (163 mg, 78.7%) was obtained as a colorless oil.

$^1$H-NMR (400 MHz, CDCl$_3$) δ; 1.38 (s, 3H), 1.46 (s, 3H), 1.59-1.89 (m, 10H), 2.06-2.09 (m, 1H), 2.20-2.23 (m, 1H), 2.39 (s, 2H), 2.45 (s, 1H), 2.98-3.08 (m, 2H), 3.58-2.66 (m, 3H).

Process 3: Preparation of 6-{2-[4,4-dimethyl-3-oxo-2-(adamantan-2-yl)-1,2-diazetidin-1-yl]ethoxy}pyridine-3-carbonitrile Under an argon atmosphere, a mixed solution of 4,4-dimethyl-1-(2-hydroxyethyl)-2-(adamantan-2-yl)-1,2-diazeti-

171 din-3-one (27.8 mg, 0.100 mmol) in tetrahydrofuran-N,N-dimethylformamide (2:1, 1 mL) was added with sodium hydride (10.0 mg, 0.200 mmol) and 6-chloro-3-pyridine carbonitrile (27.7 mg, 0.200 mmol), and the resultant was stirred at the same temperature for 1 hour. The reaction solution was added with water and extracted with diethyl ether. The organic layer was dried over anhydrous sodium sulfate, concentrated in vacuo, the obtained residue was purified using Preparatory Thin-Layer chromatography (hexane:ethyl acetate=1:1), and the title compound (38.1 mg, quant.) was obtained as a white crystalline powder.

$^1$H-NMR (400 MHz, CDCl$_3$) δ; 1.43 (s, 6H), 1.62-1.88 (m, 10H), 2.05-2.09 (m, 1H), 2.20-2.23 (m, 1H), 2.38 (s, 2H), 3.16-3.27 (m, 2H), 3.63 (s, 1H), 4.36-4.46 (m, 2H), 6.83 (d, J=8.8 Hz, 1H), 7.80 (dd, J=2.4, 8.8 Hz, 1H), 8.47 (d, J=2.4 Hz, 1H).

IR (ATR); 2916, 1742, 1601, 1489, 1403, 1290, 837 cm$^{-1}$.
EI-MS m/z; 380 (M$^+$).

Example 272

Preparation of cis-4-[2-(naphthalen-1-yl)-3,3-dimethyl-4-oxo-1,2-diazetidin-1-yl]adamantane-1-carboxylic acid

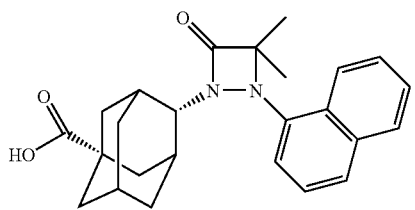

Process 1: Preparation of benzyl cis-2-(2-bromoisobutyryl)-2-(5-methoxycarbonyladamantan-2-yl)hydrazinecarboxylate Benzyl 2-(5-methoxycarbonyladamantan-2-yl)hydrazinecarboxylate prepared in Process 2 of Example 90 and 2-bromoisobutyryl bromide were used for a similar reaction and treatment as Process 3 of Example 1, the resultant two geometric isomers were separated using silica gel chromatography, and benzyl cis-2-(2-bromoisobutyryl)-2-(5-methoxycarbonyladamantan-2-yl)hydrazinecarboxylate was obtained as a colorless amorphous solid.

$^1$H-NMR (400 MHz, CDCl$_3$) δ; 1.66-2.09 (m, 18H), 2.50 (s, 1H), 3.65 (s, 3H), 4.11 (s, 0.3H), 4.31 (s, 0.7H), 5.08-5.25 (m, 2H), 7.11 (s, 0.3H), 7.18 (s, 0.7H), 7.34-7.37 (m, 5H).

Process 2: Preparation of benzyl cis-2-(5-methoxycarbonyladamantan-2-yl)-4,4-dimethyl-3-oxo-1,2-diazetidine-1-carboxylate Benzyl cis-2-(2-bromoisobutyryl)-2-(5-methoxycarbonyladamantan-2-yl)hydrazinecarboxylate was used for a similar reaction and treatment as Process 4 of Example 1, and benzyl cis-2-(5-methoxycarbonyladamantan-2-yl)-4,4-dimethyl-3-oxo-1,2-diazetidine-1-carboxylate was obtained as a colorless oil.

$^1$H-NMR (400 MHz, CDCl$_3$) δ; 1.49 (s, 6H), 1.59-2.19 (m, 11H), 2.53 (s, 2H), 3.64 (s, 3H), 3.95 (s, 1H), 5.19 (s, 2H), 7.34-7.40 (m, 5H).

172

Process 3: Preparation of methyl cis-4-(3,3-dimethyl-4-oxo-1,2-diazetidin-1-yl)adamantane-1-carboxylate Benzyl cis-2-(5-methoxycarbonyladamantan-2-yl)-4,4-dimethyl-3-oxo-1,2-diazetidine-1-carboxylate was used for a similar reaction and treatment as Process 5 of Example 1, and methyl cis-4-(3,3-dimethyl-4-oxo-1,2-diazetidin-1-yl)adamantane-1-carboxylate was obtained as a colorless oil.

$^1$H-NMR (400 MHz, CDCl$_3$) δ; 1.49 (s, 6H), 1.71-2.15 (m, 11H), 2.45 (s, 2H), 3.66 (s, 3H), 3.84 (br, 1H).

Process 4: Preparation of methyl cis-4-[2-(naphthalen-1-yl)-3,3-dimethyl-4-oxo-1,2-diazetidin-1-yl]adamantane-1-carboxylate Methyl cis-4-(3,3-dimethyl-4-oxo-1,2-diazetidin-1-yl)adamantane-1-carboxylate and 1-bromonaphtalene were used for a similar reaction and treatment as Example 181, and methyl cis-4-[2-(naphthalen-1-yl)-3,3-dimethyl-4-oxo-1,2-diazetidin-1-yl]adamantane-1-carboxylate was obtained as a pale yellow oil.

$^1$H-NMR (400 MHz, CDCl$_3$) δ; 0.80 (s, 3H), 1.54-2.04 (m, 10H), 1.87 (s, 3H), 2.46-2.50 (m, 2H), 2.96 (s, 1H), 3.67 (s, 3H), 3.79 (s, 1H), 7.24 (s, 1H), 7.46 (t, J=7.8 Hz, 1H), 7.50-7.53 (m, 2H), 7.64 (d, J=8.4 Hz, 1H), 7.83-7.86 (m, 1H), 8.26-8.29 (m, 1H).

Process 5: Preparation of cis-4-[2-(naphthalen-1-yl)-3,3-dimethyl-4-oxo-1,2-diazetidin-1-yl]adamantane-1-carboxylic acid A solution of methyl cis-4-[2-(naphthalen-1-yl)-3,3-dimethyl-4-oxo-1,2-diazetidin-1-yl]adamantane-1-carboxylate (49.0 mg, 0.117 mmol) in methanol (2 mL) was added with an aqueous solution of 4N-sodium hydroxide (0.5 mL) at room temperature, and the resultant was stirred at the same temperature for 13 hours. The reaction solution was concentrated in vacuo, the obtained residue was dissolved in water, and washed with diethylether. The aqueous layer was adjusted to pH=1.0 with 4N-hydrochlorid acid, and extracted with chloroform. The organic layer was dried over anhydrous sodium sulfate, concentrated in vacuo, the obtained residue was purified using Preparatory Thin-Layer chromatography (hexane:ethyl acetate=1:1), and the title compound (32.9 mg, 67.8%) was obtained as a pale yellow oil.

$^1$H-NMR (400 MHz, CDCl$_3$) δ; 0.80 (s, 3H), 1.52-2.09 (m, 10H), 1.89 (s, 3H), 2.48-2.57 (m, 2H), 3.00 (s, 1H), 3.00 (s, 3H), 3.79 (s, 1H), 7.24 (s, 1H), 7.46 (t, J=7.8 Hz, 1H), 7.50-7.53 (m, 2H), 7.65 (d, J=8.0 Hz, 1H), 7.83-7.86 (m, 1H), 8.26-8.29 (m, 1H).

Example 273

Preparation of cis-4-[2-(naphthalen-1-yl)-3,3-dimethyl-4-oxo-1,2-diazetidin-1-yl]adamantane-1-carboxamide cis-4-[2-(Naphthalen-1-yl)-3,3-dimethyl-4-oxo-1,2-diazetidin-1-yl]adamantane-1-carboxylic acid prepared in Example 272 was used for a similar reaction and treatment as Example 91, and the title compound was obtained as a pale yellow amorphous solid.

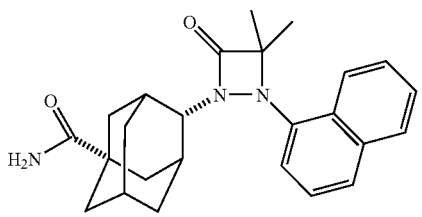

¹H-NMR (400 MHz, CDCl₃) δ; 0.82 (s, 3H), 1.54-1.58 (m, 1H), 1.66-1.77 (m, 4H), 1.84-1.93 (m, 3H), 1.86 (s, 3H), 2.02-2.04 (m, 1H), 2.24 (s, 1H), 2.39-2.42 (m, 1H), 2.69-2.72 (m, 1H), 2.84 (s, 1H), 3.67 (s, 1H), 5.33 (br, 1H), 5.85 (br, 1H), 7.25 (d, J=1.0, 7.3 Hz, 1H), 7.47 (t, J=7.8 Hz, 1H), 7.50-7.53 (m, 2H), 7.66 (d, J=8.3 Hz, 1H), 7.84-7.87 (m, 1H), 8.23-8.26 (m, 1H).
IR (ATR); 3344, 2918, 1748, 1666, 1390, 752 cm⁻¹.
EI-MS m/z; 403 (M⁺).

Example 274

Preparation of trans-4-[2-(naphthalen-1-yl)-3,3-dimethyl-4-oxo-1,2-diazetidin-1-yl]adamantane-1-carboxylic acid

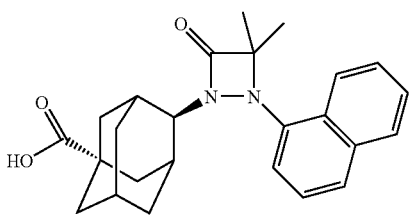

Process 1: Preparation of benzyl trans-2-(2-bromoisobutyryl)-2-(5-methoxycarbonyladamantan-2-yl)hydrazinecarboxylate Benzyl 2-(5-methoxycarbonyladamantan-2-yl)hydrazinecarboxylate prepared in Process 2 of Example 90 and 2-bromoisobutyryl bromide were used for a similar reaction and treatment as Process 3 of Example 1, and the resultant two geometric isomers were separated using silica gel chromatography, and benzyl trans-2-(2-bromoisobutyryl)-2-(5-methoxycarbonyladamantan-2-yl)hydrazinecarboxylate was obtained as a colorless amorphous solid.
¹H-NMR (400 MHz, CDCl₃) δ; 1.55-1.59 (m, 2H), 1.76-2.06 (m, 16H), 2.51 (s, 1H), 3.65 (s, 3H), 4.13 (s, 0.3H), 4.33 (s, 0.7H), 5.09-5.27 (m, 2H), 6.87 (s, 0.3H), 7.11 (s, 0.7H), 7.34-7.37 (m, 5H).

Process 2: Preparation of benzyl trans-2-(5-methoxycarbonyladamantan-2-yl)-4,4-dimethyl-3-oxo-1,2-diazetidine-1-carboxylate Benzyl trans-2-(2-bromoisobutyryl)-2-(5-methoxycarbonyladamantan-2-yl)hydrazinecarboxylate was used for a similar reaction and treatment as Process 4 of Example 1, and benzyl trans-2-(5-methoxycarbonyladamantan-2-yl)-4,4-dimethyl-3-oxo-1,2-diazetidine-1-carboxylate was obtained as a colorless oil.

¹H-NMR (400 MHz, CDCl₃) δ; 1.49 (s, 6H), 1.57-1.61 (m, 2H), 1.76-2.04 (m, 9H), 2.49 (s, 2H), 3.66 (s, 3H), 3.98 (s, 1H), 5.19 (s, 2H), 7.34-7.40 (m, 5H).

Process 3: Preparation of methyl trans-4-(3,3-dimethyl-4-oxo-1,2-diazetidin-1-yl)adamantane-1-carboxylate Benzyl trans-2-(5-methoxycarbonyladamantan-2-yl)-4,4-dimethyl-3-oxo-1,2-diazetidine-1-carboxylate was used for a similar reaction and treatment as Process 5 of Example 1, and methyl trans-4-(3,3-dimethyl-4-oxo-1,2-diazetidin-1-yl)adamantane-1-carboxylate was obtained as a colorless oil.
¹H-NMR (400 MHz, CDCl₃) δ; 1.50 (s, 6H), 1.60 (d, J=13.4 Hz, 2H), 1.89-2.02 (m, 9H), 2.42 (s, 2H), 3.66 (s, 3H), 3.84 (br, 1H).

Process 4: Preparation of methyl trans-4-[2-(naphthalen-1-yl)-3,3-dimethyl-4-oxo-1,2-diazetidin-1-yl]adamantane-1-carboxylate Methyl trans-4-(3,3-dimethyl-4-oxo-1,2-diazetidin-1-yl)adamantane-1-carboxylate and 1-bromonaphtalene were used for a similar reaction and treatment as Example 181, and methyl trans-4-[2-(naphthalen-1-yl)-3,3-dimethyl-4-oxo-1,2-diazetidin-1-yl]adamantane-1-carboxylate was obtained as a pale yellow oil.
¹H-NMR (400 MHz, CDCl₃) δ; 0.80 (s, 3H), 1.45-1.53 (m, 1H), 1.69-2.07 (m, 9H), 1.87 (s, 3H), 2.26-2.37 (m, 2H), 2.91 (s, 1H), 3.62 (s, 3H), 3.81 (s, 1H), 7.24 (d, J=7.3 Hz, 1H), 7.45 (t, J=7.8 Hz, 1H), 7.48-7.53 (m, 2H), 7.64 (d, J=8.3 Hz, 1H), 7.83-7.86 (m, 1H), 8.25-8.28 (m, 1H).

Process 5: Preparation of trans-4-[2-(naphthalen-1-yl)-3,3-dimethyl-4-oxo-1,2-diazetidin-1-yl]adamantane-1-carboxylic acid Methyl trans-4-[2-(naphthalen-1-yl)-3,3-dimethyl-4-oxo-1,2-diazetidin-1-yl]adamantane-1-carboxylate was used in place of methyl cis-4-[2-(naphthalen-1-yl)-3,3-dimethyl-4-oxo-1,2-diazetidin-1-yl]adamantane-1-carboxylate for a similar reaction and treatment as Process 2 of Example 272, and the title compound was obtained as a pale yellow amorphous solid.
¹H-NMR (400 MHz, CDCl₃) δ; 0.80 (s, 3H), 1.49-1.52 (m, 1H), 1.68-2.08 (m, 9H), 1.86 (s, 3H), 2.25-2.36 (m, 2H), 2.91 (s, 1H), 3.80 (s, 1H), 7.23 (d, J=7.3 Hz, 1H), 7.45 (t, J=7.8 Hz, 1H), 7.48-7.53 (m, 2H), 7.64 (d, J=8.1 Hz, 1H), 7.83-7.86 (m, 1H), 8.24-8.27 (m, 1H).

Example 275

Preparation of trans-4-[2-(naphthalen-1-yl)-3,3-dimethyl-4-oxo-1,2-diazetidin-1-yl]adamantane-1-carboxamide trans-4-[2-(Naphthalen-1-yl)-3,3-dimethyl-4-oxo-1,2-diazetidin-1-yl]adamantane-1-carboxylic acid prepared in Example 274 was used for a similar reaction and treatment as Example 91, and the title compound was obtained as a pale yellow oil.

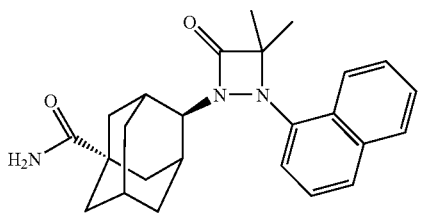

¹H-NMR (400 MHz, CDCl₃) δ; 0.81 (s, 3H), 1.50-1.75 (m, 7H), 1.87 (s, 3H), 1.99 (s, 1H), 2.08-2.11 (m, 2H), 2.28-2.40 (m, 2H), 2.93 (s, 1H), 3.82 (s, 1H), 5.23 (br, 1H), 5.51 (br, 1H), 7.24 (d, J=7.3 Hz, 1H), 7.45 (t, J=7.8 Hz, 1H), 7.50-7.52 (m, 2H), 7.65 (d, J=8.1 Hz, 1H), 7.84-7.86 (m, 1H), 8.24-8.27 (m, 1H).

Example 276

Preparation of cis-4-[2-(2,3-dichlorophenyl)-3,3-dimethyl-4-oxo-1,2-diazetidin-1-yl]adamantane-1-carboxamide

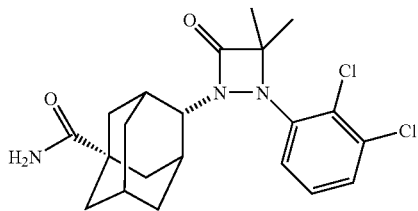

Process 1: Preparation of methyl cis-4-[2-(2,3-dichlorophenyl)-3,3-dimethyl-4-oxo-1,2-diazetidin-1-yl]adamantane-1-carboxylate Methyl cis-4-(3,3-dimethyl-4-oxo-1,2-diazetidin-1-yl)adamantane-1-carboxylate prepared in Process 3 of Example 272 and 1-bromo-2,3-dichlorobenzene were used for a similar reaction and treatment as Example 181, and methyl cis-4-[2-(2,3-dichlorophenyl)-3,3-dimethyl-4-oxo-1,2-diazetidin-1-yl]adamantane-1-carboxylate was obtained as a pale yellow oil.

¹H-NMR (400 MHz, CDCl₃) δ; 0.90 (s, 3H), 1.52-2.05 (m, 10H), 1.82 (s, 3H), 2.33-2.42 (m, 2H), 2.84 (s, 1H), 3.66 (s, 1H), 3.67 (s, 3H), 7.12 (dd, J=2.0, 7.8 Hz, 1H), 7.22 (t, J=7.8 Hz, 1H), 7.24-7.27 (m, 1H).

Process 2: Preparation of cis-4-[2-(2,3-dichlorophenyl)-3,3-dimethyl-4-oxo-1,2-diazetidin-1-yl]adamantane-1-carboxylic acid Methyl cis-4-[2-(2,3-dichlorophenyl)-3,3-dimethyl-4-oxo-1,2-diazetidin-1-yl]adamantane-1-carboxylate was used for a similar reaction and treatment as Process 5 of Example 272, and cis-4-[2-(2,3-dichlorophenyl)-3,3-dimethyl-4-oxo-1,2-diazetidin-1-yl]adamantane-1-carboxylic acid was obtained as a white crystalline powder.

¹H-NMR (400 MHz, CDCl₃) δ; 1.01 (s, 3H), 1.57-2.02 (m, 10H), 1.83 (s, 3H), 2.40-2.44 (m, 2H), 2.87 (s, 1H), 3.66 (s, 1H), 7.11 (dd, J=1.8, 7.8 Hz, 1H), 7.22 (t, J=7.8 Hz, 1H), 7.24-7.27 (m, 1H).

Process 3: Preparation of cis-4-[2-(2,3-dichlorophenyl)-3,3-dimethyl-4-oxo-1,2-diazetidin-1-yl]adamantane-1-carboxamide cis-4-[2-(2,3-Dichlorophenyl)-3,3-dimethyl-4-oxo-1,2-diazetidin-1-yl]adamantane-1-carboxylic acid was used for a similar reaction and treatment as Example 91, and the title compound was obtained as a white crystalline powder.

¹H-NMR (400 MHz, CDCl₃) δ; 1.02 (s, 3H), 1.54-1.96 (m, 10H), 1.80 (s, 3H), 2.04-2.05 (m, 1H), 2.23 (s, 1H), 2.29-2.32 (m, 1H), 3.52 (s, 1H), 5.30 (br, 1H), 5.86 (br, 1H), 7.10 (dd, J=1.7, 7.8 Hz, 1H), 7.23 (t, J=7.8 Hz, 1H), 7.26-7.30 (m, 1H).

IR (ATR); 3345, 2918, 1756, 1576, 1446, 752 cm⁻¹.

EI-MS m/z; 421 (M⁺).

Example 277

Preparation of trans-4-[2-(2,3-dichlorophenyl)-3,3-dimethyl-4-oxo-1,2-diazetidin-1-yl]adamantane-1-carboxamide

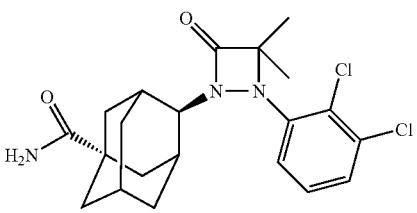

Process 1: Preparation of trans-4-[2-(2,3-dichlorophenyl)-3,3-dimethyl-4-oxo-1,2-diazetidin-1-yl]adamantane-1-carboxylic acid Methyl trans-4-[2-(2,3-dichlorophenyl)-3,3-dimethyl-4-oxo-1,2-diazetidin-1-yl]adamantane-1-carboxylate obtained by using methyl trans-4-(3,3-dimethyl-4-oxo-1,2-diazetidin-1-yl)adamantane-1-carboxylate prepared in Process 3 of Example 274 and 1-bromo-2,3-dichlorobenzene for a similar reaction and treatment as Example 181, was used for a similar reaction and treatment as Process 5 of Example 272, and trans-4-[2-(2,3-dichlorophenyl)-3,3-dimethyl-4-oxo-1,2-diazetidin-1-yl]adamantane-1-carboxylic acid was obtained as a colorless oil.

¹H-NMR (400 MHz, CDCl₃) δ; 1.01 (s, 3H), 1.52-2.26 (m, 11H), 1.81 (s, 3H), 2.61 (s, 1H), 2.81 (s, 1H), 3.67 (s, 1H), 7.11 (dd, J=1.8, 7.8 Hz, 1H), 7.22 (t, J=7.8 Hz, 1H), 7.25-7.27 (m, 1H).

Process 2: Preparation of trans-4-[2-(2,3-dichlorophenyl)-3,3-dimethyl-4-oxo-1,2-diazetidin-1-yl]adamantane-1-carboxamide trans-4-[2-(2,3-Dichlorophenyl)-3,3-dimethyl-4-oxo-1,2-diazetidin-1-yl]adamantane-1-carboxylic acid was used for a similar reaction and treatment as Example 91, and the title compound was obtained as a pale yellow crystalline powder.

¹H-NMR (400 MHz, CDCl₃) δ; 1.02 (s, 3H), 1.53-2.32 (m, 12H), 1.81 (s, 3H), 2.84 (s, 1H), 3.70 (s, 1H), 5.29 (br, 1H), 5.54 (br, 1H), 7.10 (dd, J=1.7, 7.8 Hz, 1H), 7.22 (t, J=8.1 Hz, 1H), 7.25-7.27 (m, 1H).

Test Example 1

Human 11β-HSD1-, human 11β-HSD2- and mouse 11β-HSD1-inhibitory effect

1. Human 11β-HSD1-, Human 11β-HSD2- and Mouse 11β-HSD1-Gene Clonings and Establishment of Stably Expressing Cells Human 11β-HSD1-, human 11β-HSD2-, and mouse 11β-HSD1-gene clonings were conducted using as a template a reverse transcription product of human-liver RNA, human-kidney RNA (CELL APPLICATIONS), and mouse-kidney RNA respectively, by means of PCR cloning with reference to nucleotide sequences of Genbank Accession Nos. NM_005525, NM_000196, and NM_008288. The obtained PCR products of about 0.9 kbp, 1.2 kbp, and 0.9 kbp were subcloned into an expression vector pcDNA3.1+/Zeo (Invitrogen).

Human 11β-HSD1- and human 11β-HSD2-expressing vectors were transfected into human kidney-derived cell line, HEK293 cells, using a transfection reagent, jet PEI (Funakoshi). Mouse 11β-HSD1 was transfected to Chinese hamster ovary-derived cell line, CHO-K1 cells. Selection was conducted with 200-400 μg/mL of zeocine (Invitrogen) to provide stably expressing-cell clones. The stably expressing cells were suspended in buffer solution A (20 mmol/L Tris-HCl, pH 7.4, 250 mmol/L sucrose, 1 mmol/L EGTA, 1 mmol/L EDTA, 1 mmol/L $MgCl_2$), sonicated, and then stored at −80° C.

2. Assay of Enzyme Inhibitory Activity

An enzymatic reaction was conducted using a polystyrene 96-well plate. Each well was added with 1 μL of a test agent dissolved in DMSO and then diluted (0.003 to 3 mmol/L), and further added with 10 μL of cell lysate diluted to a concentration of 0.1 mg/mL to 0.4 mg/mL. Next, 90 μL of buffer solution A containing substrate (100 nmol/L cortisone or cortisol) and coenzyme (400 μmol/L NADPH or NAD+) was added and the mixture was incubated at 37° C. for 1 hour. The enzymatic reaction was stopped by treating at 95° C. for 3 minutes. Cortisol that was present in the reaction solution was determined by a competitive ELISA shown below.

Anti-rabbit IgG antibody (Chemi-con) diluted to 2 μg/mL with carbonate buffer solution (pH 9.6) was added in 100 μL each to a 96-well immuno plate (Nunc) and immobilized by an incubation at 4° C. overnight. 50 μL of enzymatic reaction solution was put onto the plates, and further, anti-cortisol antibody (Cosmo Bio) and HRP-labeled cortisol (Cosmo Bio), diluted with buffer solution B (25 mmol/L Tris-HCl pH 7.4, 137 mmol/L NaCl, 2.68 mmol/L KCl), were added in 50 μL respectively and incubated at 4° C. overnight. After washed three times with buffer solution B containing 0.05% Tween 20, the plates were allowed to develop color by adding 100 μL of color reagent, TMB (Moss). The color reaction was stopped by 25 μL of 1 mol/L sulfuric acid and the absorbance was determined at 450 nm with a microplate reader (Molecular Device, VersaMax).

The values of human 11β-HSD1, human 11β-HSD2, and mouse 11β-HSD1 activities were subtracted from 100, and the resultant values were regarded as the respective 11β-HSD inhibition rates of example compounds. For each example compound, the value of 50% inhibitory concentration ($IC_{50}$) was calculated from 11β-HSD inhibition rates at plural concentrations, for 11β-HSD1 and 11β-HSD2 activities. The comparison of human 11β-HSD1 and human 11β-HSD2 inhibiting activities is shown in Table 1, and the comparison of human 11β-HSD1 and mouse 11β-HSD1 inhibiting activities is shown in Table 2.

TABLE 1

Enzyme inhibitory selectivity 1 of human 11β-HSD1 and human 11β-HSD2

| No. | h HSD1 | h HSD2 |
|---|---|---|
| | in vitro assay (IC50 uM) | |
| 39 | 0.015 | 3.0 |
| 40 | 0.012 | 10 |
| 41 | 0.023 | 3.2 |
| 42 | 0.025 | 30 |
| 48 | 0.031 | >30 |
| 49 | 0.80 | NA |
| 50 | 0.042 | 6.6 |
| 52 | 0.078 | 9.5 |
| 60 | 0.0082 | 1.1 |
| 66 | 0.09 | NA |
| 74 | 0.046 | 3-30 |
| 76 | 0.031 | 4.8 |
| 77 | 0.016 | 2.0 |
| 116 | 0.13 | 30 |
| 119 | 0.72 | >30 |
| 120 | 0.27 | >30 |
| 121 | 0.07 | NA |
| 122 | 0.32 | NA |
| 125 | 0.47 | NA |
| 126 | 0.11 | NA |
| 128 | 0.50 | NA |
| 132 | 0.66 | NA |
| 136 | 0.14 | NA |
| 138 | 0.22 | 30 |
| 139 | 0.79 | NA |
| 141 | 0.071 | 14 |
| 149 | 0.90 | NA |
| 150 | 0.84 | NA |
| 151 | 0.81 | NA |
| 152 | 0.23 | NA |
| 153 | 0.14 | NA |
| 154 | 0.036 | NA |
| 157 | 0.44 | 30 |
| 160 | 0.52 | 30 |
| 161 | 0.50 | >30 |
| 163 | 0.72 | NA |
| 165 | 0.096 | 30 |
| 168 | 0.11 | NA |
| 181 | 0.062 | 3-30 |
| 188 | 0.082 | >30 |
| 189 | 0.022 | 3-30 |
| 190 | 0.093 | 3-30 |
| 203 | 0.026 | >30 |
| 204 | 0.16 | 30 |
| 205 | 0.10 | 30 |
| 206 | 0.0061 | 3-30 |
| 208 | 0.02 | 3-30 |
| 212 | 0.032 | 3-30 |
| 214 | 0.041 | NA |
| 215 | 0.023 | 4.5 |
| 218 | 0.81 | >30 |
| 220 | 0.056 | NA |
| 221 | 0.023 | 3-30 |
| 222 | 0.019 | 5.5 |
| 223 | 0.68 | NA |
| 224 | 0.044 | NA |
| 225 | 0.036 | NA |
| 226 | 0.95 | 30 |
| 227 | 0.023 | 3-30 |
| 230 | 0.54 | NA |
| 231 | 0.088 | >30 |
| 236 | 0.095 | NA |
| 238 | 0.020 | NA |
| 240 | 0.32 | NA |
| 242 | 0.076 | NA |
| 244 | 0.81 | NA |
| 247 | 0.027 | NA |
| 248 | 0.028 | 3-30 |
| 249 | 0.013 | NA |
| 250 | 0.042 | >30 |
| 251 | 0.030 | 3-30 |
| 252 | 0.034 | NA |
| 253 | 0.013 | 3-30 |

TABLE 1-continued

Enzyme inhibitory selectivity 1 of human 11β-HSD1 and human 11β-HSD2

| | in vitro assay (IC50 uM) | |
|---|---|---|
| No. | h HSD1 | h HSD2 |
| 254 | 0.012 | NA |
| 255 | 0.003 | 30 |
| 256 | 0.26 | NA |
| 257 | 0.24 | NA |
| 265 | 0.036 | 19 |
| 272 | 0.050 | >30 |
| 273 | 0.020 | NA |
| 274 | 0.011 | NA |
| 275 | 0.011 | NA |
| 276 | 0.007 | NA |
| 277 | 0.007 | NA |

Note)
hHSD1 and hHSD2 denote human HSD1 and HSD2, respectively.

As it is shown in Table 1, it has been confirmed that the compound of the present invention has an activity to strongly and selectively inhibit human 11β-HSD1.

TABLE 2

Enzyme inhibitory activity of human 11β-HSD1 and mouse 11β-HSD1

| | in vitro assay (IC50 uM) | |
|---|---|---|
| No. | h HSD1 | m HSD1 |
| 8 | 0.79 | 0.18 |
| 9 | 0.68 | 0.24 |
| 12 | 0.047 | 0.023 |
| 13 | 0.058 | 0.025 |
| 14 | 0.84 | 0.088 |
| 15 | 0.36 | 0.084 |
| 16 | 0.80 | 0.10 |
| 17 | 0.71 | 0.23 |
| 19 | 0.47 | 0.27 |
| 20 | 0.35 | 0.20 |
| 22 | 0.64 | 0.079 |
| 27 | 0.03 | 0.094 |
| 28 | 0.44 | 0.073 |
| 29 | 0.60 | 0.37 |
| 30 | 0.047 | 0.10 |
| 31 | 0.96 | 0.30 |
| 32 | 0.25 | 0.054 |
| 33 | 0.38 | 0.086 |
| 35 | 0.44 | 0.15 |
| 36 | 0.69 | 0.21 |
| 38 | 0.26 | 0.10 |
| 39 | 0.015 | 0.04 |
| 40 | 0.012 | 0.084 |
| 41 | 0.023 | 0.13 |
| 42 | 0.025 | 0.24 |
| 43 | 0.072 | 0.074 |
| 44 | 0.044 | 0.073 |
| 45 | 0.079 | 0.14 |
| 46 | 0.23 | 0.45 |
| 47 | 0.20 | 0.58 |
| 48 | 0.031 | 0.50 |
| 49 | 0.80 | 0.31 |
| 50 | 0.042 | 0.16 |
| 51 | 0.082 | 0.58 |
| 52 | 0.078 | 0.16 |
| 53 | 0.35 | 0.06 |
| 54 | 0.30 | 0.036 |
| 55 | 0.067 | 0.069 |
| 56 | 0.054 | 0.052 |
| 58 | 0.026 | 0.061 |
| 59 | 0.25 | 0.064 |
| 60 | 0.0082 | 0.15 |
| 61 | 0.23 | 0.30 |
| 63 | 0.015 | 0.41 |

TABLE 2-continued

Enzyme inhibitory activity of human 11β-HSD1 and mouse 11β-HSD1

| | in vitro assay (IC50 uM) | |
|---|---|---|
| No. | h HSD1 | m HSD1 |
| 64 | 0.60 | 0.041 |
| 65 | 0.50 | 0.47 |
| 66 | 0.09 | 0.57 |
| 67 | 0.12 | 0.29 |
| 73 | 0.021 | 0.11 |
| 74 | 0.046 | 0.13 |
| 75 | 0.038 | 0.15 |
| 76 | 0.031 | 0.14 |
| 77 | 0.016 | 0.092 |
| 78 | 0.15 | 0.64 |
| 79 | 0.22 | 0.36 |
| 80 | 0.13 | 0.39 |
| 83 | 0.092 | 0.66 |
| 84 | 0.13 | 0.61 |
| 85 | 0.053 | 0.37 |
| 86 | 0.14 | 0.49 |
| 87 | 0.10 | 0.85 |
| 95 | 0.13 | 0.35 |
| 96 | 0.80 | 0.22 |
| 106 | 0.75 | 0.17 |
| 109 | 0.75 | 0.20 |
| 113 | 0.42 | 0.12 |
| 114 | 0.54 | 0.11 |
| 116 | 0.13 | 0.15 |
| 117 | 0.98 | 0.39 |
| 125 | 0.47 | 0.42 |
| 128 | 0.50 | 0.10 |
| 135 | 0.76 | 0.11 |
| 138 | 0.22 | 0.24 |
| 139 | 0.79 | 0.36 |
| 150 | 0.84 | 0.43 |
| 151 | 0.81 | 0.30 |
| 152 | 0.23 | 0.54 |
| 153 | 0.14 | 0.032 |
| 157 | 0.44 | 0.15 |
| 160 | 0.52 | 0.16 |
| 161 | 0.50 | 0.23 |
| 183 | 0.057 | 0.76 |
| 188 | 0.082 | 0.76 |
| 192 | 0.49 | 0.03 |
| 193 | 0.86 | 0.36 |
| 204 | 0.16 | 0.42 |
| 205 | 0.10 | 0.20 |
| 206 | 0.0061 | 0.44 |
| 207 | 0.61 | 0.054 |
| 210 | 0.44 | 0.16 |
| 212 | 0.032 | 0.089 |
| 215 | 0.023 | 0.54 |
| 218 | 0.81 | 0.57 |
| 219 | 0.56 | 0.23 |
| 220 | 0.056 | 0.088 |
| 221 | 0.023 | 0.29 |
| 222 | 0.019 | 0.087 |
| 224 | 0.044 | 0.34 |
| 225 | 0.036 | 0.012 |
| 227 | 0.023 | 0.95 |
| 233 | 0.18 | 0.27 |
| 235 | 0.056 | 0.75 |
| 236 | 0.095 | 0.31 |
| 238 | 0.02 | 0.38 |
| 247 | 0.027 | 0.26 |
| 249 | 0.013 | 0.78 |
| 250 | 0.042 | 0.13 |
| 251 | 0.03 | 0.61 |
| 252 | 0.034 | 0.24 |
| 253 | 0.013 | 0.15 |
| 254 | 0.012 | 0.075 |
| 255 | 0.003 | 0.18 |
| 257 | 0.24 | 0.24 |
| 261 | 0.45 | 0.70 |
| 266 | 0.55 | 0.47 |
| 272 | 0.05 | 0.90 |
| 273 | 0.02 | 0.10 |

TABLE 2-continued

Enzyme inhibitory activity of human
11β-HSD1 and mouse 11β-HSD1

| | in vitro assay (IC50 uM) | |
|---|---|---|
| No. | h HSD1 | m HSD1 |
| 274 | 0.011 | 0.25 |
| 275 | 0.011 | 0.25 |
| 276 | 0.007 | 0.40 |
| 277 | 0.007 | 0.40 |

Note)
mHSD1 denotes mouse HSD1.

For medicine development, it is required to make a dosage selection for clinical experiments by extrapolating data which have been accumulated with animal models to human. Sometimes, the difference of enzyme species becomes an issue for evaluating an inhibitor targeting a certain enzyme, such as the compound of the present invention. Specifically, as rodents such as mouse are generally used as an animal model, a compound having an inhibitory activity to mouse type enzyme as well as human type enzyme, has an advantageous property for evaluating usefulness as medicine. As it is shown in Table 2, the compound of the present invention has been confirmed to have an inhibitory effect to mouse 11β-HSD1 as well.

The invention claimed is:

1. A 1,2-diazetidin-3-one derivative represented by the following general formula (I) or salt thereof:

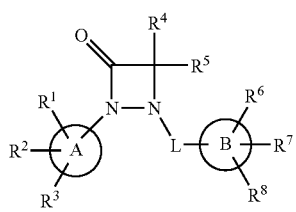

wherein A ring represents a saturated $C_{3-10}$ carbocyclic group, wherein B ring represents a $C_{3-8}$ cycloalkyl group, $C_{3-8}$ cycloalkenyl group, $C_{6-14}$ aryl group or a 5- to 14-membered heteroaryl group, wherein $R^1$, $R^2$ and $R^3$ are the same or different and represent a hydrogen atom, halogen atom, hydroxyl group, carboxyl group, carbamoyl group or $C_{1-6}$ alkyl group, wherein $R^4$ and $R^5$ are the same or different and represent a hydrogen atom or $C_{1-6}$ alkyl group, wherein $R^6$, $R^7$ and $R^8$ are the same or different and represent a hydrogen atom, halogen atom, hydroxyl group, nitro group, cyano group, amino group which may be substituted with a sulfonyl group or acyl group, $C_{1-6}$ alkyl group, halo $C_{1-6}$ alkyl group, $C_{1-6}$ alkoxy group which may be substituted with a $C_{1-6}$ alkoxy group, $C_{6-10}$ aryl group, $C_{2-6}$ alkanoyloxy group, $C_{1-6}$ alkylthio group, $C_{1-6}$ alkylsulfinyl group or $C_{1-6}$ alkylsulfonyl group, or $R^6$ and $R^7$ may together form a $C_{1-3}$ alkylenedioxy group, wherein L represents a single bond, $C_{1-6}$ alkylene chain, $C_{2-6}$ alkenylene chain, —($C_{1-6}$ alkylene)-O—, —CO—X— or —SO$_2$—Y—, wherein X represents a single bond, —N(R$^9$)—, —O—($C_{1-6}$ alkylene)-, —($C_{1-6}$ alkylene)-O—, —($C_{1-6}$ alkylene)-O—($C_{1-6}$ alkylene)- or —($C_{1-6}$ alkylene)-S—, wherein $R^9$ represents a hydrogen atom, $C_{1-6}$ alkyl group or acyl group, and wherein Y represents a single bond or $C_{1-6}$ alkylene chain.

2. The 1,2-diazetidin-3-one derivative or salt thereof, according to claim 1, wherein the saturated $C_{3-10}$ carbocyclic group in the A ring of general formula (I) is a $C_{3-8}$ cycloalkyl group or $C_{4-10}$ cross-linked cyclic hydrocarbon group.

3. The 1,2-diazetidin-3-one derivative or salt thereof, according to claim 1, wherein the compound represented by general formula (I) is:

1-benzyl-4-methyl-2-(adamantan-2-yl)-1,2-diazetidin-3-one, 1-(4-chlorobenzyl)-4-methyl-2-(adamantan-2-yl)-1,2-diazetidin-3-one, 1-benzyl-4,4-dimethyl-2-(adamantan-2-yl)-1,2-diazetidin-3-one, 1-(4-chlorobenzyl)-4,4-dimethyl-2-(adamantan-2-yl)-1,2-diazetidin-3-one, 4,4-dimethyl-1-(4-methylbenzyl)-2-(adamantan-2-yl)-1,2-diazetidin-3-one, 1-(4-fluorobenzyl)-4,4-dimethyl-2-(adamantan-2-yl)-1,2-diazetidin-3-one, 1-(3,4-difluorobenzyl)-4,4-dimethyl-2-(adamantan-2-yl)-1,2-diazetidin-3-one, 1-(2,4-difluorobenzyl)-4,4-dimethyl-2-(adamantan-2-yl)-1,2-diazetidin-3-one, 1-(3,5-difluorobenzyl)-4,4-dimethyl-2-(adamantan-2-yl)-1,2-diazetidin-3-one, 1-(2,3-difluorobenzyl)-4,4-dimethyl-2-(adamantan-2-yl)-1,2-diazetidin-3-one, 1-(2,5-difluorobenzyl)-4,4-dimethyl-2-(adamantan-2-yl)-1,2-diazetidin-3-one, 1-(3-fluorobenzyl)-4,4-dimethyl-2-(adamantan-2-yl)-1,2-diazetidin-3-one, 1-(3,5-dimethoxybenzyl)-4,4-dimethyl-2-(adamantan-2-yl)-1,2-diazetidin-3-one, 1-(2-chlorobenzyl)-4,4-dimethyl-2-(adamantan-2-yl)-1,2-diazetidin-3-one, 1-(3-chlorobenzyl)-4,4-dimethyl-2-(adamantan-2-yl)-1,2-diazetidin-3-one, 4,4-dimethyl-1-(3-nitrobenzyl)-2-(adamantan-2-yl)-1,2-diazetidin-3-one, 4,4-dimethyl-1-(2-methylbenzyl)-2-(adamantan-2-yl)-1,2-diazetidin-3-one, 4,4-dimethyl-1-(4-nitrobenzyl)-2-(adamantan-2-yl)-1,2-diazetidin-3-one, 4,4-dimethyl-1-(3-methylbenzyl)-2-(adamantan-2-yl)-1,2-diazetidin-3-one, 1-(3-bromobenzyl)-4,4-dimethyl-2-(adamantan-2-yl)-1,2-diazetidin-3-one, 1-(3-iodobenzyl)-4,4-dimethyl-2-(adamantan-2-yl)-1,2-diazetidin-3-one, 4,4-dimethyl-2-(adamantan-2-yl)-1-[4-(trifluoromethyl)benzyl]-1,2-diazetidin-3-one, 1-(2,6-dichlorobenzyl)-4,4-dimethyl-2-(adamantan-2-yl)-1,2-diazetidin-3-one, 1-(2-fluorobenzyl)-4,4-dimethyl-2-(adamantan-2-yl)-1,2-diazetidin-3-one, 1-(2-bromobenzyl)-4,4-dimethyl-2-(adamantan-2-yl)-1,2-diazetidin-3-one, 1-(2-iodobenzyl)-4,4-dimethyl-2-(adamantan-2-yl)-1,2-diazetidin-3-one, 1-(2-chloro-5-fluorobenzyl)-4,4-dimethyl-2-(adamantan-2-yl)-1,2-diazetidin-3-one, 4,4-dimethyl-2-(adamantan-2-yl)-1-[2-(trifluoromethyl)benzyl]-1,2-diazetidin-3-one,
1-(2,3-dichlorobenzyl)-4,4-dimethyl-2-(adamantan-2-yl)-1,2-diazetidin-3-one,
1-(2,5-dichlorobenzyl)-4,4-dimethyl-2-(adamantan-2-yl)-1,2-diazetidin-3-one,
1-(2-chloro-4-fluorobenzyl)-4,4-dimethyl-2-(adamantan-2-yl)-1,2-diazetidin-3-one,
1-(2-chloro-6-fluorobenzyl)-4,4-dimethyl-2-(adamantan-2-yl)-1,2-diazetidin-3-one,
4,4-dimethyl-1-(2-nitrobenzyl)-2-(adamantan-2-yl)-1,2-diazetidin-3-one,
1-[4-fluoro-2-(trifluoromethyl)benzyl]-4,4-dimethyl-2-(adamantan-2-yl)-1,2-diazetidin-3-one,
1-(biphenyl-2-ylmethyl)-4,4-dimethyl-2-(adamantan-2-yl)-1,2-diazetidin-3-one,
1-(2-ethylbenzyl)-4,4-dimethyl-2-(adamantan-2-yl)-1,2-diazetidin-3-one,
1-(2-methoxybenzyl)-4,4-dimethyl-2-(adamantan-2-yl)-1,2-diazetidin-3-one,
1-(2,4-dichlorobenzyl)-4,4-dimethyl-2-(adamantan-2-yl)-1,2-diazetidin-3-one,
1-(4-bromobenzyl)-4,4-dimethyl-2-(adamantan-2-yl)-1,2-diazetidin-3-one,
1-(3-methoxybenzyl)-4,4-dimethyl-2-(adamantan-2-yl)-1,2-diazetidin-3-one,
1-(2,4-dimethylbenzyl)-4,4-dimethyl-2-(adamantan-2-yl)-1,2-diazetidin-3-one,
1-(2,5-dimethylbenzyl)-4,4-dimethyl-2-(adamantan-2-yl)-1,2-diazetidin-3-one,
1-(3-fluoro-2-methylbenzyl)-4,4-dimethyl-2-(adamantan-2-yl)-1,2-diazetidin-3-one,
1-(3-chloro-2-fluorobenzyl)-4,4-dimethyl-2-(adamantan-2-yl)-1,2-diazetidin-3-one,
4,4-dimethyl-1-[2-(methylthio)benzyl]-2-(adamantan-2-yl)-1,2-diazetidin-3-one,
1-(1,3-benzodioxol-4-ylmethyl)-4,4-dimethyl-2-(adamantan-2-yl)-1,2-diazetidin-3-one,
4,4-dimethyl-1-(naphthalen-1-ylmethyl)-2-(adamantan-2-yl)-1,2-diazetidin-3-one,
4,4-dimethyl-1-(naphthalen-2-ylmethyl)-2-(adamantan-2-yl)-1,2-diazetidin-3-one,
trans-1-(2-chlorobenzyl)-2-(5-hydroxyadamantan-2-yl)-4,4-dimethyl-1,2-diazetidin-3-one,
trans-2-(5-hydroxyadamantan-2-yl)-4,4-dimethyl-1-[2-(trifluoromethyl)benzyl]-1,2-diazetidin-3-one,
trans-1-(2-chloro-5-fluorobenzyl)-2-(5-hydroxyadamantan-2-yl)-4,4-dimethyl-1,2-diazetidin-3-one,
1-(2-chlorobenzyl)-2-cyclohexyl-4,4-dimethyl-1,2-diazetidin-3-one,
2-cyclohexyl-1-(2,3-dichlorobenzyl)-4,4-dimethyl-1,2-diazetidin-3-one,
2-cyclohexyl-1-(2,5-dichlorobenzyl)-4,4-dimethyl-1,2-diazetidin-3-one,
1-(2-chloro-5-fluorobenzyl)-2-cyclohexyl-4,4-dimethyl-1,2-diazetidin-3-one,
1-(2-chloro-4-fluorobenzyl)-2-cyclohexyl-4,4-dimethyl-1,2-diazetidin-3-one,
1-(2-chlorobenzyl)-2-cyclooctyl-4,4-dimethyl-1,2-diazetidin-3-one,
2-cyclooctyl-1-(2,3-dichlorobenzyl)-4,4-dimethyl-1,2-diazetidin-3-one,
2-cyclooctyl-1-(2,5-dichlorobenzyl)-4,4-dimethyl-1,2-diazetidin-3-one,
1-(2-chloro-4-fluorobenzyl)-2-cyclooctyl-4,4-dimethyl-1,2-diazetidin-3-one,
1-(2-chloro-5-fluorobenzyl)-2-cyclooctyl-4,4-dimethyl-1,2-diazetidin-3-one,
2-(bicyclo[2.2.1]heptan-2-yl)-1-(2-chlorobenzyl)-4,4-dimethyl-1,2-diazetidin-3-one,
2-(bicyclo[2.2.1]heptan-2-yl)-1-(2,3-dichlorobenzyl)-4,4-dimethyl-1,2-diazetidin-3-one,
2-(bicyclo[2.2.1]heptan-2-yl)-1-(2,5-dichlorobenzyl)-4,4-dimethyl-1,2-diazetidin-3-one,
2-(bicyclo[2.2.1]heptan-2-yl)-1-(2-chloro-4-fluorobenzyl)-4,4-dimethyl-1,2-diazetidin-3-one,
2-(bicyclo[2.2.1]heptan-2-yl)-1-(2-chloro-5-fluorobenzyl)-4,4-dimethyl-1,2-diazetidin-3-one,
1-(2-chlorobenzyl)-2-cycloheptyl-4,4-dimethyl-1,2-diazetidin-3-one,
2-cycloheptyl-1-(2,3-dichlorobenzyl)-4,4-dimethyl-1,2-diazetidin-3-one,
2-cycloheptyl-1-(2,5-dichlorobenzyl)-4,4-dimethyl-1,2-diazetidin-3-one,
1-(2-chloro-4-fluorobenzyl)-2-cycloheptyl-4,4-dimethyl-1,2-diazetidin-3-one,
1-(2-chloro-5-fluorobenzyl)-2-cycloheptyl-4,4-dimethyl-1,2-diazetidin-3-one,
1-(cyclohexa-2-en-1-yl)-4,4-dimethyl-2-(adamantan-2-yl)-1,2-diazetidin-3-one,
1-cyclohexyl-4,4-dimethyl-2-(adamantan-2-yl)-1,2-diazetidin-3-one,
4-[2-(2-chlorobenzyl)-3,3-dimethyl-4-oxo-1,2-diazetidin-1-yl]adamantane-1-carboxamide,
4,4-dimethyl-1-(phenylcarbonyl)-2-(adamantan-2-yl)-1,2-diazetidin-3-one,
4,4-dimethyl-2-(adamantan-2-yl)-1-{[2-(trifluoromethyl)phenyl]carbonyl}-1,2-diazetidin-3-one,
1-[(4-bromophenyl)carbonyl]-4,4-dimethyl-2-(adamantan-2-yl)-1,2-diazetidin-3-one,
4,4-dimethyl-1-[(3-methylphenyl)carbonyl]-2-(adamantan-2-yl)-1,2-diazetidin-3-one,
1-[(3-bromophenyl)carbonyl]-4,4-dimethyl-2-(adamantan-2-yl)-1,2-diazetidin-3-one,
4,4-dimethyl-1-[(4-methylphenyl)carbonyl]-2-(adamantan-2-yl)-1,2-diazetidin-3-one,
4,4-dimethyl-1-[(2-methylphenyl)carbonyl]-2-(adamantan-2-yl)-1,2-diazetidin-3-one,
1-[(3,5-dichlorophenyl)carbonyl]-4,4-dimethyl-2-(adamantan-2-yl)-1,2-diazetidin-3-one,
1-[(2-fluorophenyl)carbonyl]-4,4-dimethyl-2-(adamantan-2-yl)-1,2-diazetidin-3-one,
1-[(2-bromophenyl)carbonyl]-4,4-dimethyl-2-(adamantan-2-yl)-1,2-diazetidin-3-one,
1-[(2-iodophenyl)carbonyl]-4,4-dimethyl-2-(adamantan-2-yl)-1,2-diazetidin-3-one,
1-[(2,5-dichlorophenyl)carbonyl]-4,4-dimethyl-2-(adamantan-2-yl)-1,2-diazetidin-3-one,
1-[(5-fluoro-2-methylphenyl)carbonyl]-4,4-dimethyl-2-(adamantan-2-yl)-1,2-diazetidin-3-one,
1-[(2-ethylphenyl)carbonyl]-4,4-dimethyl-2-(adamantan-2-yl)-1,2-diazetidin-3-one,
1-[(3-chlorophenyl)carbonyl]-4,4-dimethyl-2-(adamantan-2-yl)-1,2-diazetidin-3-one,
1-[(4-fluoro-2-trifluoromethylphenyl)carbonyl]-4,4-dimethyl-2-(adamantan-2-yl)-1,2-diazetidin-3-one,
1-(1,3-benzodioxol-5-ylcarbonyl)-4,4-dimethyl-2-(adamantan-2-yl)-1,2-diazetidin-3-one,
1-[(2-aminophenyl)carbonyl]-4,4-dimethyl-2-(adamantan-2-yl)-1,2-diazetidin-3-one,
1-[(2-hydroxyphenyl)carbonyl]-4,4-dimethyl-2-(adamantan-2-yl)-1,2-diazetidin-3-one, 1-[(4-aminophenyl)carbonyl]-4,4-dimethyl-2-(adamantan-2-yl)-1,2-diazetidin-3-one,
4,4-dimethyl-1-(naphthalen-1-ylcarbonyl)-2-(adamantan-2-yl)-1,2-diazetidin-3-one,
2-cyclohexyl-1-[(2,5-dimethylphenyl)carbonyl]-4,4-dimethyl-1,2-diazetidin-3-one,
1-[(3-chlorophenyl)carbonyl]-2-cyclooctyl-4,4-dimethyl-1,2-diazetidin-3-one,
2-cyclooctyl-4,4-dimethyl-1-[(3-methylphenyl)carbonyl]-1,2-diazetidin-3-one,
2-cyclooctyl-4,4-dimethyl-1-[(2-methylphenyl)carbonyl]-1,2-diazetidin-3-one,
1-[(2-aminophenyl)carbonyl]-2-cyclooctyl-4,4-dimethyl-1,2-diazetidin-3-one,
2-cyclooctyl-4,4-dimethyl-1-(naphthalen-1-ylcarbonyl)-1,2-diazetidin-3-one,
1-[(3-fluoro-2-methylphenyl)carbonyl]-4,4-dimethyl-2-(adamantan-2-yl)-1,2-diazetidin-3-one,
1-[(2,4-dimethylphenyl)carbonyl]-4,4-dimethyl-2-(adamantan-2-yl)-1,2-diazetidin-3-one,
1-[(2,5-dimethylphenyl)carbonyl]-4,4-dimethyl-2-(adamantan-2-yl)-1,2-diazetidin-3-one,
1-[(2-bromo-5-chlorophenyl)carbonyl]-4,4-dimethyl-2-(adamantan-2-yl)-1,2-diazetidin-3-one,
4,4-dimethyl-1-{[2-(methylthio)phenyl]carbonyl}-2-(adamantan-2-yl)-1,2-diazetidin-3-one,
2-cyclooctyl-4,4-dimethyl-1-{[2-(methylthio)phenyl]carbonyl}-1,2-diazetidin-3-one,
4,4-dimethyl-1-phenyl-2-(adamantan-2-yl)-1,2-diazetidin-3-one,
1-(4-aminophenyl)-4,4-dimethyl-2-(adamantan-2-yl)-1,2-diazetidin-3-one,
4,4-dimethyl-1-(2-nitrophenyl)-2-(adamantan-2-yl)-1,2-diazetidin-3-one,
1-(2-chlorophenyl)-4,4-dimethyl-2-(adamantan-2-yl)-1,2-diazetidin-3-one,
1-(3-chlorophenyl)-4,4-dimethyl-2-(adamantan-2-yl)-1,2-diazetidin-3-one,
4,4-dimethyl-1-(2-methylphenyl)-2-(adamantan-2-yl)-1,2-diazetidin-3-one,
4,4-dimethyl-1-(3-methylphenyl)-2-(adamantan-2-yl)-1,2-diazetidin-3-one,
1-(3,5-difluorophenyl)-4,4-dimethyl-2-(adamantan-2-yl)-1,2-diazetidin-3-one,
1-(1,3-benzodioxol-5-yl)-4,4-dimethyl-2-(adamantan-2-yl)-1,2-diazetidin-3-one,
1-(3-fluorophenyl)-4,4-dimethyl-2-(adamantan-2-yl)-1,2-diazetidin-3-one,
1-(4-fluorophenyl)-4,4-dimethyl-2-(adamantan-2-yl)-1,2-diazetidin-3-one,
1-(3,5-dichlorophenyl)-4,4-dimethyl-2-(adamantyl)-1,2-diazetidin-3-one,
1-(4-methoxyphenyl)-4,4-dimethyl-2-(adamantan-2-yl)-1,2-diazetidin-3-one,
1-(3-methoxyphenyl)-4,4-dimethyl-2-(adamantan-2-yl)-1,2-diazetidin-3-one,
1-(2-methoxyphenyl)-4,4-dimethyl-2-(adamantan-2-yl)-1,2-diazetidin-3-one,
1-(2,3-dichlorophenyl)-4,4-dimethyl-2-(adamantan-2-yl)-1,2-diazetidin-3-one,
1-(2,3-dimethylphenyl)-4,4-dimethyl-2-(adamantan-2-yl)-1,2-diazetidin-3-one,
1-(2,4-dichlorophenyl)-4,4-dimethyl-2-(adamantan-2-yl)-1,2-diazetidin-3-one,
1-(2,5-dichlorophenyl)-4,4-dimethyl-2-(adamantan-2-yl)-1,2-diazetidin-3-one,
1-(1-benzothiophen-3-yl)-4,4-dimethyl-2-(adamantan-2-yl)-1,2-diazetidin-3-one,
4,4-dimethyl-1-(naphthalen-1-yl)-2-(adamantan-2-yl)-1,2-diazetidin-3-one,
1-[4-(methoxymethoxy)phenyl]-4,4-dimethyl-2-(adamantan-2-yl)-1,2-diazetidin-3-one,
4,4-dimethyl-1-(4-hydroxyphenyl)-2-(adamantan-2-yl)-1,2-diazetidin-3-one,
1-[3-(methoxymethoxy)phenyl]-4,4-dimethyl-2-(adamantan-2-yl)-1,2-diazetidin-3-one,
1-[2-(methoxymethoxy)phenyl]-4,4-dimethyl-2-(adamantan-2-yl)-1,2-diazetidin-3-one,
1-(2-hydroxyphenyl)-4,4-dimethyl-2-(adamantan-2-yl)-1,2-diazetidin-3-one,
2-cyclooctyl-1-(2-methoxyphenyl)-4,4-dimethyl-1,2-diazetidin-3-one,
2-cyclooctyl-1-(2,3-dichlorophenyl)-4,4-dimethyl-1,2-diazetidin-3-one,
2-cyclooctyl-4,4-dimethyl-1-(naphthalen-1-yl)-1,2-diazetidin-3-one,
2-(bicyclo[2.2.1]heptan-2-yl)-1-(2-methoxyphenyl)-4,4-dimethyl-1,2-diazetidin-3-one,
2-(bicyclo[2.2.1]heptan-2-yl)-1-(2,3-dichlorophenyl)-4,4-dimethyl-1,2-diazetidin-3-one,
2-(bicyclo[2.2.1]heptan-2-yl)-4,4-dimethyl-1-(naphthalen-1-yl)-1,2-diazetidin-3-one,
trans-2-(5-hydroxyadamantan-2-yl)-4,4-dimethyl-1-phenyl-1,2-diazetidin-3-one,
trans-1-(2-chlorophenyl)-2-(5-hydroxyadamantan-2-yl)-4,4-dimethyl-1,2-diazetidin-3-one,
trans-2-(5-hydroxyadamantan-2-yl)-1-(4-methoxyphenyl)-4,4-dimethyl-1,2-diazetidin-3-one,
trans-1-(2,3-dichlorophenyl)-2-(5-hydroxyadamantan-2-yl)-4,4-dimethyl-1,2-diazetidin-3-one,
trans-1-(2-hydroxyphenyl)-2-(5-hydroxyadamantan-2-yl)-4,4-dimethyl-1,2-diazetidin-3-one,
trans-1-(4-aminophenyl)-2-(5-hydroxyadamantan-2-yl)-4,4-dimethyl-1,2-diazetidin-3-one,
trans-2-(5-hydroxyadamantan-2-yl)-4,4-dimethyl-1-(naphthalen-1-yl)-1,2-diazetidin-3-one,
trans-1-(4-fluoronaphthalen-1-yl)-2-(5-hydroxyadamantan-2-yl)-4,4-dimethyl-1,2-diazetidin-3-one,
cis-2-(5-hydroxyadamantan-2-yl)-1-(4-methoxyphenyl)-4,4-dimethyl-1,2-diazetidin-3-one,
cis-2-(5-hydroxyadamantan-2-yl)-4,4-dimethyl-1-(2-methylphenyl)-1,2-diazetidin-3-one,
cis-1-(2-hydroxyphenyl)-2-(5-hydroxyadamantan-2-yl)-4,4-dimethyl-1,2-diazetidin-3-one,
cis-1-(4-aminophenyl)-2-(5-hydroxyadamantan-2-yl)-4,4-dimethyl-1,2-diazetidin-3-one,
cis-2-(5-hydroxyadamantan-2-yl)-4,4-dimethyl-1-(naphthalen-1-yl)-1,2-diazetidin-3-one,
cis-2-(5-hydroxyadamantan-2-yl)-4,4-dimethyl-1-(naphthalen-2-yl)-1,2-diazetidin-3-one,
cis-1-(4-fluoronaphthalen-1-yl)-2-(5-hydroxyadamantan-2-yl)-4,4-dimethyl-1,2-diazetidin-3-one,
trans-2-(5-chloroadamantan-2-yl)-1-(2-methoxyphenyl)-4,4-dimethyl-1,2-diazetidin-3-one,
trans-2-(5-chloroadamantan-2-yl)-1-(2,3-dichlorophenyl)-4,4-dimethyl-1,2-diazetidin-3-one,
trans-2-(5-chloroadamantan-2-yl)-1-[2-(methoxymethoxy)phenyl]-4,4-dimethyl-1,2-diazetidin-3-one,
trans-2-(5-chloroadamantan-2-yl)-1-(2-hydroxyphenyl)-4,4-dimethyl-1,2-diazetidin-3-one,
trans-2-(5-chloroadamantan-2-yl)-4,4-dimethyl-1-(naphthalen-1-yl)-1,2-diazetidin-3-one, trans-2-(5-chloroadamantan-2-yl)-1-(4-fluoronaphthalen-1-yl)-4,4-dimethyl-1,2-diazetidin-3-one, cis-2-(5-chloroadamantan-2-yl)-1-(2,3-dichlorophenyl)-4,4-dimethyl-1,2-diazetidin-3-one, cis-2-(5-chloroadamantan-2-yl)-4,4-dimethyl-1-(naphthalen-1-yl)-1,2-diazetidin-3-one, 1-(1,3-benzodioxol-4-yl)-4,4-dimethyl-2-(adamantan-2-yl)-1,2-diazetidin-3-one, 4,4-dimethyl-1-(3-phenylpropyl)-2-(adamantan-2-yl)-1,2-diazetidin-3-one, 4,4-dimethyl-1-[(E)-2-phenylethenyl]-2-(adamantan-2-yl)-1,2-diazetidin-3-one, 4,4-dimethyl-1-(2-phenylethyl)-2-(adamantan-2-yl)-1,2-diazetidin-3-one, trans-4-[2-(naphthalen-1-yl)-3,3-dimethyl-4-oxo-1,2-diazetidin-1-yl]adamantane-1-carboxylic acid, trans-4-[2-(naphthalen-1-yl)-3,3-dimethyl-4-oxo-1,2-diazetidin-1-yl] adamantane-1-carboxamide, cis-4-[2-(naphthalen-1-yl)-3,3-dimethyl-4-oxo-1,2-diazetidin-1-yl] adamantane-1-carboxylic acid, cis-4-[2-(naphthalen-1-yl)-3,3-dimethyl-4-oxo-1,2-diazetidin-1-yl]adamantane-1-carboxamide, trans-4-[2-(2,3-dichlorophenyl)-3,3-dimethyl-4-oxo-1,2-diazetidin-1-yl]adamantane-1-carboxamide, or cis-4-[2-(2,3-dichlorophenyl)-3,3-dimethyl-4-oxo-1,2-diazetidin-1-yl]adamantane-1-carboxamide.

4. A pharmaceutical composition, comprising:

the 1,2-diazetidin-3-one derivative or salt thereof according to claim 1, and a pharmaceutically acceptable carrier.

* * * * *